(12) United States Patent
Burns et al.

(10) Patent No.: US 11,660,353 B2
(45) Date of Patent: May 30, 2023

(54) COMPOSITIONS AND METHODS FOR TREATING SENSORINEURAL HEARING LOSS USING OTOFERLIN DUAL VECTOR SYSTEMS

(71) Applicant: Decibel Therapeutics, Inc., Boston, MA (US)

(72) Inventors: Joseph Burns, Newton, MA (US); Kathryn Ellis, Arlington, MA (US); Adam Palermo, Cambridge, MA (US); Martin Schwander, Auburndale, MA (US); Jonathon Whitton, Cambridge, MA (US)

(73) Assignee: Decibel Therapeutics, Inc., Boston, MA (US)

(*) Notice: Subject to any disclaimer, the term of this patent is extended or adjusted under 35 U.S.C. 154(b) by 795 days.

(21) Appl. No.: 16/395,999

(22) Filed: Apr. 26, 2019

(65) Prior Publication Data
US 2020/0155705 A1    May 21, 2020

Related U.S. Application Data

(60) Provisional application No. 62/663,739, filed on Apr. 27, 2018.

(51) Int. Cl.
| | |
|---|---|
| *A61K 48/00* | (2006.01) |
| *C12N 15/09* | (2006.01) |
| *C07K 14/47* | (2006.01) |
| *C12N 15/86* | (2006.01) |
| *A61K 9/00* | (2006.01) |

(52) U.S. Cl.
CPC ........ *A61K 48/005* (2013.01); *A61K 48/0075* (2013.01); *C07K 14/47* (2013.01); *C12N 15/86* (2013.01); *A61K 9/0048* (2013.01); *C12N 2750/14143* (2013.01)

(58) Field of Classification Search
CPC ................................ A61K 48/00; C12N 15/09
See application file for complete search history.

(56) References Cited

U.S. PATENT DOCUMENTS

| | | | |
|---|---|---|---|
| 6,436,392 | B1 | 8/2002 | Engelhardt et al. |
| 6,544,786 | B1 | 4/2003 | Xiao et al. |
| 6,808,922 | B1 | 10/2004 | Bebbington et al. |
| 6,897,045 | B2 | 5/2005 | Engelhardt et al. |
| 7,803,622 | B2 | 9/2010 | Engelhardt et al. |
| 8,236,557 | B2 | 8/2012 | Dongsheng et al. |
| 8,298,818 | B2 | 10/2012 | Boye et al. |
| 2003/0219741 | A1 | 11/2003 | Isogai et al. |
| 2004/0072154 | A1 | 4/2004 | Morris et al. |
| 2007/0161031 | A1 | 7/2007 | Trinklein et al. |
| 2008/0249052 | A1 | 10/2008 | Duan et al. |
| 2010/0003218 | A1 | 1/2010 | Duan et al. |
| 2010/0266551 | A1 | 10/2010 | Richard et al. |
| 2012/0003190 | A1 | 1/2012 | Yamoah et al. |
| 2013/0210895 | A1 | 8/2013 | Boye et al. |
| 2014/0256802 | A1 | 9/2014 | Boye et al. |
| 2016/0076054 | A1* | 3/2016 | Auricchio et al. ..... C12N 15/86 |
| 2018/0055908 | A1* | 3/2018 | Petit et al. ......... A61K 38/1709 |
| 2018/0327779 | A1 | 11/2018 | Colella et al. |
| 2019/0002916 | A1 | 1/2019 | Kalatzis et al. |
| 2019/0153050 | A1 | 5/2019 | Boye et al. |
| 2019/0185864 | A1 | 6/2019 | Simons et al. |
| 2020/0157573 | A1 | 5/2020 | Boye et al. |
| 2021/0236654 | A1 | 8/2021 | Burns et al. |
| 2021/0388045 | A1 | 12/2021 | Burns et al. |
| 2021/0395781 | A1 | 12/2021 | Burns et al. |

FOREIGN PATENT DOCUMENTS

| | | | |
|---|---|---|---|
| WO | WO-200125465 A1 | 4/2001 | |
| WO | WO-2013075008 A1 | 5/2013 | |
| WO | WO-2017/100791 | 6/2017 | |
| WO | WO-2018/039375 | 3/2018 | |
| WO | WO2018039375 A1 * | 3/2018 | ............. C12N 15/85 |
| WO | WO-2018/145111 | 8/2018 | |
| WO | WO-2018/204734 | 11/2018 | |
| WO | WO-2019/162396 A1 | 8/2019 | |
| WO | WO-2019165292 A1 | 8/2019 | |
| WO | WO-2020093018 A1 | 5/2020 | |

(Continued)

OTHER PUBLICATIONS

Trapani et al. (2015) "Improved dual AAV vectors with reduced expression of truncated proteins are safe and effective in the retina of a mouse model of Stargardt disease" Human Molecular Genetics vol. 24, No. 23, pp. 6811-6825. (Year: 2015).*

Alemi, Aurash (2012) "Progress Report: AOS Research Grant: Restoration of Hearing in the Otoferlin Knockout Mouse using Viral Gene Therapy" Program and Abstracts of the One Hundred Forty-Fifth Annual Meeting of the American Otological Society, Inc., p. 68. (Year: 2012).*

Higashimoto et al. (2007) "The woodchuck hepatitis virus post-transcriptional regulatory element reduces readthrough transcription from retroviral vectors" Gene Therapy 14, 1298-1304. (Year: 2007).*

Akil et al. "Dual AAV gene therapy restores hearing in a mouse model for human genetic Deafness," International Symposium on Inner Ear Therapies 2017. Abstract only.

(Continued)

*Primary Examiner* — James D Schultz
*Assistant Examiner* — James Joseph Graber
(74) *Attorney, Agent, or Firm* — Clark & Elbing LLP

(57) ABSTRACT

The disclosure features compositions and methods for the treatment of sensorineural hearing loss and auditory neuropathy, particularly forms of the disease that are associated with mutations in otoferlin (OTOF), by way of OTOF gene therapy. The disclosure provides a variety of compositions that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of OTOF in a subject, such as a human subject suffering from sensorineural hearing loss.

11 Claims, 38 Drawing Sheets

Specification includes a Sequence Listing.

(56) References Cited

FOREIGN PATENT DOCUMENTS

| WO | WO-2020097372 A1 | 5/2020 |
| WO | WO-2020148458 A1 | 7/2020 |
| WO | WO-2020163743 | 8/2020 |
| WO | WO-2021/087296 A1 | 5/2021 |

OTHER PUBLICATIONS

Alemi, "Progress Report: AOS Research Grant: Restoration of Hearing in the Otoferlin Knockout Mouse using Viral Gene Therapy," 145th Annual Meeting of the American Otological Society, Inc. 68 (2012). Abstract only.

Choi et al., "Identities and frequencies of mutations of the otoferlin gene (OTOF) causing DFNB9 deafness in Pakistan," Clin Genet. 75(3):237-243 (2009).

Duan et al. "Expanding AAV Packaging Capacity with Trans-splicing or Overlapping Vectors: A Quantitative Comparison," Mol Ther. 4(4):383-391 (2001).

McClements et al. "Adeno-associated Virus (AAV) Dual Vector Strategies for Gene Therapy Encoding Large Transgenes," Yale J Biol Med. 90:611-623 (2017).

Trapani et al. "Effective delivery of large genes to the retina by dual AAV vectors," EMBO Mol Med. 6(2):194-211 (2014).

Trapani et al., "Improved dual AAV vectors with reduced expression of truncated proteins are safe and effective in the retina of a mouse model of Stargardt disease," Human Molecular Genetics. 24(23):6811-6825 (2015).

Yasunaga et al. "OTOF Encodes Multiple Long and Short Isoforms: Genetic Evidence That the Long Ones Underlie Recessive Deafness DFNB9," Am J Hum Genet. 67:591-600 (2000).

International Search Report and Written Opinion for International Application No. PCT/US2020/017257, dated Apr. 29, 2020 (22 pages).

Belyantseva et al., "Myosin XVa localizes to the tips of inner ear sensory cell stereocilia and is essential for staircase formation of the hair bundle," Proc Natl Acad Sci U S A. 100(24):13958-63 (2003).

Boëda et al., "A specific promoter of the sensory cells of the inner ear defined by transgenesis," Hum Mol Genet. 10(15):1581-1589 (2001).

Caberlotto et al., "Usher type 1G protein sans is a critical component of the tip-link complex, a structure controlling actin polymerization in stereocilia," Proc Natl Acad Sci U S A. 108(14):5825-30 (2011) (14 pages).

GenBank Accession No. JN953192.1, "Mus musculus targeted KO-first, conditional ready, lacZ-tagged mutant allele Myo15:tm1a(EUCOMM)Wtsi; transgenic," retrieved from <https://www.ncbi.nlm.nih.gov/nuccore/JN953192>, dated Nov. 5, 2011 (11 pages).

International Search Report and Written Opinion for International Application No. PCT/US2019/029366, dated Sep. 10, 2019 (17 pages).

International Search Report and Written Opinion for International Application No. PCT/US2020/017292, dated Jun. 26, 2020 (18 pages).

Schlabach et al., "Synthetic design of strong promoters," Proc Natl Acad Sci U S A. 107(6):2538-43 (2010).

GenBank Accession No. JN957158.1, "Mus musculus targeted non-conditional, lacZ-tagged mutant allele Myo15:tm1e(EUCOMM)Wtsi; transgenic," retrieved from <https://www.ncbi.nlm.nih.gov/nucleotide/JN957158.1>, dated Nov. 5, 2011 (12 pages).

International Search Report and Written Opinion for International Application No. PCT/US2020/058265, dated Feb. 8, 2021 (15 pages).

Michalski et al., "Genetics of auditory mechano-electrical transduction," Pflugers Arch. 467(1):49-72 (2015).

Skarnes et al., "A conditional knockout resource for the genome-wide study of mouse gene function," available in PMC Feb. 14, 2013, published in final edited form as: Nature. 474(7351):337-342 (2011) (18 pages).

Xu et al. "Trans-Splicing Adeno-Associated Viral Vector-Mediated Gene Therapy Is Limited by the Accumulation of Spliced mRNA but Not by Dual Vector Coinfection Efficiency," Hum Gene Ther. 15(9): 896-905 (2004).

Ghosh et al. "A Hybrid Vector System Expands Adeno-associated Viral Vector Packaging Capacity in a Transgene-independent Manner," The American Society of Gene Therapy. 16(1):124-130 (2008).

Ghosh et al., "Efficient Transgene Reconstitution with Hybrid Dual AAV Vectors Carrying the Minimized Bridging Sequences," Hum Gene Ther. 22(1):77-88 (2011).

Akil et al., "Dual AAV-mediated gene therapy restores hearing in a DFNB9 mouse model," Proc Natl Acad Sci U S A. 116(10):4496-4501 (Published Feb. 19, 2019).

Al-Moyed et al., "A dual AAV viral vector approach partially restores exocytosis and rescues hearing in deaf otoferlin knock-out mice," ARO Abstracts, Abstract PS 134. 41:76 (Published Feb. 9, 2018) (Abstract only).

Al-Moyed et al., "A dual-AAV approach restores fast exocytosis and partially rescues auditory function in deaf otoferlin knock-out mice," EMBO Molecular Medicine. 11(1):e9396 (Published Dec. 3, 2018) (13 pages).

Boye et al., "Transduction and Tropism of an Abbreviated Form of CMV-Chicken β-Actin Promoter (CBA) With AAV in Mouse Retina," ARVO Annual Meeting Abstract May 2006, published in: Investigative Opthalmology & Visual Science. 47: 852 (2006) (2 pages) (Abstract only).

Skarnes et al., "A conditional knockout resource for the genome-wide study of mouse gene function," Nature. 474(7351):337-42 (2011).

International Search Report and Written Opinion for International Patent Application No. PCT/US2020/058265, dated Feb. 9, 2021 (15 pages).

Lovell, "Mouse DNA sequence from clone RP23-135F6 on chromosome 11," European Nucleotide Archive, EMBL-EBI. (2012) (15 pages).

Wang, Aihui, Dissertation: "Molecular Cloning of an Unconventional Myosin MYO15 and the Identification of Mutations of MYO15 Responsible for Human Nonsyndromic Deafness DFNB3," Doctor of Philosophy, Graduate Program in Genetics, Michigan State University (1999) (140 pages).

* cited by examiner

SEQUENCE LISTING

<160> NUMBER OF SEQ ID NOS: 44

<210> SEQ ID NO 1
<211> LENGTH: 1997
<212> TYPE: PRT
<213> ORGANISM: Homo sapiens

<400> SEQUENCE: 1

```
Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
            260                 265                 270

Pro Val Val Cys Val Glu Val Gly Asp Asp Lys Lys Tyr Thr Ser Met
        275                 280                 285

Lys Glu Ser Thr Asn Cys Pro Tyr Tyr Asn Glu Tyr Phe Val Phe Asp
    290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Ile Ser Ser Gly
        355                 360                 365

Leu Lys Gly Tyr Val Lys Cys Asp Val Ala Val Gly Lys Gly Asp
    370                 375                 380

Asn Ile Lys Thr Pro His Lys Ala Asn Glu Thr Asp Glu Asp Asp Ile
385                 390                 395                 400

Glu Gly Asn Leu Leu Pro Glu Gly Val Pro Pro Glu Arg Gln Trp
                405                 410                 415
```

```
Ala Arg Phe Tyr Val Lys Ile Tyr Arg Ala Glu Gly Leu Pro Arg Met
                420                 425                 430

Asn Thr Ser Leu Met Ala Asn Val Lys Lys Ala Phe Ile Gly Glu Asn
            435                 440                 445

Lys Asp Leu Val Asp Pro Tyr Val Gln Val Phe Phe Ala Gly Gln Lys
        450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
        515                 520                 525

Leu Pro Thr Leu Gly Pro Ala Trp Val Asn Met Tyr Gly Ser Thr Arg
    530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Gly Leu Ala Val Glu
                565                 570                 575

Ile Val Asp Thr Ser Asn Pro Glu Leu Thr Ser Ser Thr Glu Val Gln
            580                 585                 590

Val Glu Gln Ala Thr Pro Ile Ser Glu Ser Cys Ala Gly Lys Met Glu
        595                 600                 605

Glu Phe Phe Leu Phe Gly Ala Phe Leu Glu Ala Ser Met Ile Asp Arg
    610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Val Asp Leu Ile Gln Asn Ala Ser
            660                 665                 670

Asp Asp Glu Ala Gly Asp Ala Gly Asp Leu Ala Ser Val Ser Ser Thr
        675                 680                 685

Pro Pro Met Arg Pro Gln Val Thr Asp Arg Asn Tyr Phe His Leu Pro
    690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
            740                 745                 750

Lys Ser Tyr Pro Glu Arg Arg Leu Arg Gly Val Leu Glu Glu Leu Ser
        755                 760                 765

Cys Gly Cys Cys Arg Phe Leu Ser Leu Ala Asp Lys Asp Gln Gly His
    770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
            820                 825                 830
```

```
Gln Lys Leu Arg Phe Leu Ala Asp Glu Pro Gln His Ser Ile Pro Asp
        835                 840                 845

Ile Phe Ile Trp Met Met Ser Asn Asn Lys Arg Val Ala Tyr Ala Arg
850                 855                 860

Val Pro Ser Lys Asp Leu Leu Phe Ser Ile Val Glu Glu Thr Gly
865                 870                 875                 880

Lys Asp Cys Ala Lys Val Lys Thr Leu Phe Leu Lys Leu Pro Gly Lys
                885                 890                 895

Arg Gly Phe Gly Ser Ala Gly Trp Thr Val Gln Ala Lys Val Glu Leu
            900                 905                 910

Tyr Leu Trp Leu Gly Leu Ser Lys Gln Arg Lys Glu Phe Leu Cys Gly
        915                 920                 925

Leu Pro Cys Gly Phe Gln Glu Val Lys Ala Ala Gln Gly Leu Gly Leu
    930                 935                 940

His Ala Phe Pro Pro Val Ser Leu Val Tyr Thr Lys Lys Gln Ala Phe
945                 950                 955                 960

Gln Leu Arg Ala His Met Tyr Gln Ala Arg Ser Leu Phe Ala Ala Asp
                965                 970                 975

Ser Ser Gly Leu Ser Asp Pro Phe Ala Arg Val Phe Phe Ile Asn Gln
            980                 985                 990

Ser Gln Cys Thr Glu Val Leu Asn Glu Thr Leu Cys Pro Thr Trp Asp
        995                 1000                1005

Gln Met Leu Val Phe Asp Asn Leu Glu Leu Tyr Gly Glu Ala His
    1010                1015                1020

Glu Leu Arg Asp Asp Pro Pro Ile Ile Val Ile Glu Ile Tyr Asp
    1025                1030                1035

Gln Asp Ser Met Gly Lys Ala Asp Phe Met Gly Arg Thr Phe Ala
    1040                1045                1050

Lys Pro Leu Val Lys Met Ala Asp Glu Ala Tyr Cys Pro Pro Arg
    1055                1060                1065

Phe Pro Pro Gln Leu Glu Tyr Tyr Gln Ile Tyr Arg Gly Asn Ala
    1070                1075                1080

Thr Ala Gly Asp Leu Leu Ala Ala Phe Glu Leu Leu Gln Ile Gly
    1085                1090                1095

Pro Ala Gly Lys Ala Asp Leu Pro Pro Ile Asn Gly Pro Val Asp
    1100                1105                1110

Val Asp Arg Gly Pro Ile Met Pro Val Pro Met Gly Ile Arg Pro
    1115                1120                1125

Val Leu Ser Lys Tyr Arg Val Glu Val Leu Phe Trp Gly Leu Arg
    1130                1135                1140

Asp Leu Lys Arg Val Asn Leu Ala Gln Val Asp Arg Pro Arg Val
    1145                1150                1155

Asp Ile Glu Cys Ala Gly Lys Gly Val Gln Ser Ser Leu Ile His
    1160                1165                1170

Asn Tyr Lys Lys Asn Pro Asn Phe Asn Thr Leu Val Lys Trp Phe
    1175                1180                1185

Glu Val Asp Leu Pro Glu Asn Glu Leu Leu His Pro Pro Leu Asn
    1190                1195                1200

Ile Arg Val Val Asp Cys Arg Ala Phe Gly Arg Tyr Thr Leu Val
    1205                1210                1215

Gly Ser His Ala Val Ser Ser Leu Arg Arg Phe Ile Tyr Arg Pro
    1220                1225                1230

Pro Asp Arg Ser Ala Pro Ser Trp Asn Thr Thr Val Arg Leu Leu
```

-continued

```
                1235                1240                1245

Arg  Arg  Cys  Arg  Val  Leu  Cys  Asn  Gly  Gly  Ser  Ser  Ser  His  Ser
          1250                1255                1260

Thr  Gly  Glu  Val  Val  Val  Thr  Met  Glu  Pro  Glu  Val  Pro  Ile  Lys
          1265                1270                1275

Lys  Leu  Glu  Thr  Met  Val  Lys  Leu  Asp  Ala  Thr  Ser  Glu  Ala  Val
          1280                1285                1290

Val  Lys  Val  Asp  Val  Ala  Glu  Glu  Lys  Glu  Lys  Lys  Lys
          1295                1300                1305

Lys  Lys  Gly  Thr  Ala  Glu  Glu  Pro  Glu  Glu  Glu  Pro  Asp  Glu
          1310                1315                1320

Ser  Met  Leu  Asp  Trp  Trp  Ser  Lys  Tyr  Phe  Ala  Ser  Ile  Asp  Thr
          1325                1330                1335

Met  Lys  Glu  Gln  Leu  Arg  Gln  Gln  Glu  Pro  Ser  Gly  Ile  Asp  Leu
          1340                1345                1350

Glu  Glu  Lys  Glu  Glu  Val  Asp  Asn  Thr  Glu  Gly  Leu  Lys  Gly  Ser
          1355                1360                1365

Met  Lys  Gly  Lys  Glu  Lys  Ala  Arg  Ala  Ala  Lys  Glu  Glu  Lys  Lys
          1370                1375                1380

Lys  Lys  Thr  Gln  Ser  Ser  Gly  Ser  Gly  Gln  Gly  Ser  Glu  Ala  Pro
          1385                1390                1395

Glu  Lys  Lys  Pro  Lys  Ile  Asp  Glu  Leu  Lys  Val  Tyr  Pro  Lys
          1400                1405                1410

Glu  Leu  Glu  Ser  Glu  Phe  Asp  Asn  Phe  Glu  Asp  Trp  Leu  His  Thr
          1415                1420                1425

Phe  Asn  Leu  Leu  Arg  Gly  Lys  Thr  Gly  Asp  Asp  Glu  Asp  Gly  Ser
          1430                1435                1440

Thr  Glu  Glu  Glu  Arg  Ile  Val  Gly  Arg  Phe  Lys  Gly  Ser  Leu  Cys
          1445                1450                1455

Val  Tyr  Lys  Val  Pro  Leu  Pro  Glu  Asp  Val  Ser  Arg  Glu  Ala  Gly
          1460                1465                1470

Tyr  Asp  Ser  Thr  Tyr  Gly  Met  Phe  Gln  Gly  Ile  Pro  Ser  Asn  Asp
          1475                1480                1485

Pro  Ile  Asn  Val  Leu  Val  Arg  Val  Tyr  Val  Val  Arg  Ala  Thr  Asp
          1490                1495                1500

Leu  His  Pro  Ala  Asp  Ile  Asn  Gly  Lys  Ala  Asp  Pro  Tyr  Ile  Ala
          1505                1510                1515

Ile  Arg  Leu  Gly  Lys  Thr  Asp  Ile  Arg  Asp  Lys  Glu  Asn  Tyr  Ile
          1520                1525                1530

Ser  Lys  Gln  Leu  Asn  Pro  Val  Phe  Gly  Lys  Ser  Phe  Asp  Ile  Glu
          1535                1540                1545

Ala  Ser  Phe  Pro  Met  Glu  Ser  Met  Leu  Thr  Val  Ala  Val  Tyr  Asp
          1550                1555                1560

Trp  Asp  Leu  Val  Gly  Thr  Asp  Asp  Leu  Ile  Gly  Glu  Thr  Lys  Ile
          1565                1570                1575

Asp  Leu  Glu  Asn  Arg  Phe  Tyr  Ser  Lys  His  Arg  Ala  Thr  Cys  Gly
          1580                1585                1590

Ile  Ala  Gln  Thr  Tyr  Ser  Thr  His  Gly  Tyr  Asn  Ile  Trp  Arg  Asp
          1595                1600                1605

Pro  Met  Lys  Pro  Ser  Gln  Ile  Leu  Thr  Arg  Leu  Cys  Lys  Asp  Gly
          1610                1615                1620

Lys  Val  Asp  Gly  Pro  His  Phe  Gly  Pro  Pro  Gly  Arg  Val  Lys  Val
          1625                1630                1635
```

-continued

```
Ala Asn Arg Val Phe Thr Gly Pro Ser Glu Ile Glu Asp Glu Asn
    1640                1645                1650

Gly Gln Arg Lys Pro Thr Asp Glu His Val Ala Leu Leu Ala Leu
    1655                1660                1665

Arg His Trp Glu Asp Ile Pro Arg Ala Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Ile Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Ile Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
    1835                1840                1845

Leu Asp Leu Asn Arg Phe Pro Arg Gly Ala Lys Thr Ala Lys Gln
    1850                1855                1860

Cys Thr Met Glu Met Ala Thr Gly Glu Val Asp Val Pro Leu Val
    1865                1870                1875

Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
    1895                1900                1905

Ala Glu Leu His Leu Leu Thr Ala Glu Glu Ala Glu Lys Asn Pro
    1910                1915                1920

Val Gly Leu Ala Arg Asn Glu Pro Asp Pro Leu Glu Lys Pro Asn
    1925                1930                1935

Arg Pro Asp Thr Ser Phe Ile Trp Phe Leu Asn Pro Leu Lys Ser
    1940                1945                1950

Ala Arg Tyr Phe Leu Trp His Thr Tyr Arg Trp Leu Leu Leu Lys
    1955                1960                1965

Leu Leu Leu Leu Leu Leu Leu Leu Leu Leu Ala Leu Phe Leu
    1970                1975                1980

Tyr Ser Val Pro Gly Tyr Leu Val Lys Lys Ile Leu Gly Ala
    1985                1990                1995

<210> SEQ ID NO 2
<211> LENGTH: 1230
<212> TYPE: PRT
<213> ORGANISM: Homo sapiens
```

```
<400> SEQUENCE: 2

Met Ile Lys Thr Glu Lys Ser Tyr Pro Glu Arg Arg Leu Arg Gly Val
1               5                   10                  15

Leu Glu Glu Leu Ser Cys Gly Cys Arg Phe Leu Ser Leu Ala Asp
            20                  25                  30

Lys Asp Gln Gly His Ser Ser Arg Thr Arg Leu Asp Arg Glu Arg Leu
                35                  40                  45

Lys Ser Cys Met Arg Glu Leu Glu Asn Met Gly Gln Gln Ala Arg Met
        50                  55                  60

Leu Arg Ala Gln Val Lys Arg His Thr Val Arg Asp Lys Leu Arg Leu
65                  70                  75                  80

Cys Gln Asn Phe Leu Gln Lys Leu Arg Phe Leu Ala Asp Glu Pro Gln
                85                  90                  95

His Ser Ile Pro Asp Ile Phe Ile Trp Met Met Ser Asn Asn Lys Arg
                100                 105                 110

Val Ala Tyr Ala Arg Val Pro Ser Lys Asp Leu Leu Phe Ser Ile Val
            115                 120                 125

Glu Glu Glu Thr Gly Lys Asp Cys Ala Lys Val Lys Thr Leu Phe Leu
130                 135                 140

Lys Leu Pro Gly Lys Arg Gly Phe Gly Ser Ala Gly Trp Thr Val Gln
145                 150                 155                 160

Ala Lys Val Glu Leu Tyr Leu Trp Leu Gly Leu Ser Lys Gln Arg Lys
                165                 170                 175

Glu Phe Leu Cys Gly Leu Pro Cys Gly Phe Gln Glu Val Lys Ala Ala
                180                 185                 190

Gln Gly Leu Gly Leu His Ala Phe Pro Pro Val Ser Leu Val Tyr Thr
            195                 200                 205

Lys Lys Gln Ala Phe Gln Leu Arg Ala His Met Tyr Gln Ala Arg Ser
210                 215                 220

Leu Phe Ala Ala Asp Ser Ser Gly Leu Ser Asp Pro Phe Ala Arg Val
225                 230                 235                 240

Phe Phe Ile Asn Gln Ser Gln Cys Thr Glu Val Leu Asn Glu Thr Leu
                245                 250                 255

Cys Pro Thr Trp Asp Gln Met Leu Val Phe Asp Asn Leu Glu Leu Tyr
                260                 265                 270

Gly Glu Ala His Glu Leu Arg Asp Asp Pro Pro Ile Ile Val Ile Glu
            275                 280                 285

Ile Tyr Asp Gln Asp Ser Met Gly Lys Ala Asp Phe Met Gly Arg Thr
290                 295                 300

Phe Ala Lys Pro Leu Val Lys Met Ala Asp Glu Ala Tyr Cys Pro Pro
305                 310                 315                 320

Arg Phe Pro Pro Gln Leu Glu Tyr Tyr Gln Ile Tyr Arg Gly Asn Ala
                325                 330                 335

Thr Ala Gly Asp Leu Leu Ala Ala Phe Glu Leu Leu Gln Ile Gly Pro
            340                 345                 350

Ala Gly Lys Ala Asp Leu Pro Pro Ile Asn Gly Pro Val Asp Val Asp
            355                 360                 365

Arg Gly Pro Ile Met Pro Val Pro Met Gly Ile Arg Pro Val Leu Ser
            370                 375                 380

Lys Tyr Arg Val Glu Val Leu Phe Trp Gly Leu Arg Asp Leu Lys Arg
385                 390                 395                 400

Val Asn Leu Ala Gln Val Asp Arg Pro Arg Val Asp Ile Glu Cys Ala
                405                 410                 415
```

```
Gly Lys Gly Val Gln Ser Ser Leu Ile His Asn Tyr Lys Lys Asn Pro
            420                 425                 430

Asn Phe Asn Thr Leu Val Lys Trp Phe Glu Val Asp Leu Pro Glu Asn
            435                 440                 445

Glu Leu Leu His Pro Pro Leu Asn Ile Arg Val Asp Cys Arg Ala
450                 455                 460

Phe Gly Arg Tyr Thr Leu Val Gly Ser His Ala Val Ser Ser Leu Arg
465                 470                 475                 480

Arg Phe Ile Tyr Arg Pro Pro Asp Arg Ser Ala Pro Ser Trp Asn Thr
            485                 490                 495

Thr Gly Glu Val Val Thr Met Glu Pro Glu Val Pro Ile Lys Lys
            500                 505                 510

Leu Glu Thr Met Val Lys Leu Asp Ala Thr Ser Glu Ala Val Val Lys
            515                 520                 525

Val Asp Val Ala Glu Glu Lys Glu Lys Lys Lys Lys Lys Gly
530                 535                 540

Thr Ala Glu Glu Pro Glu Glu Glu Pro Asp Glu Ser Met Leu Asp
545                 550                 555                 560

Trp Trp Ser Lys Tyr Phe Ala Ser Ile Asp Thr Met Lys Glu Gln Leu
            565                 570                 575

Arg Gln Gln Glu Pro Ser Gly Ile Asp Leu Glu Glu Lys Glu Glu Val
            580                 585                 590

Asp Asn Thr Glu Gly Leu Lys Gly Ser Met Lys Gly Lys Glu Lys Ala
            595                 600                 605

Arg Ala Ala Lys Glu Glu Lys Lys Lys Thr Gln Ser Ser Gly Ser
            610                 615                 620

Gly Gln Gly Ser Glu Ala Pro Glu Lys Lys Pro Lys Ile Asp Glu
625                 630                 635                 640

Leu Lys Val Tyr Pro Lys Glu Leu Glu Ser Glu Phe Asp Asn Phe Glu
            645                 650                 655

Asp Trp Leu His Thr Phe Asn Leu Leu Arg Gly Lys Thr Gly Asp Asp
            660                 665                 670

Glu Asp Gly Ser Thr Glu Glu Arg Ile Val Gly Arg Phe Lys Gly
            675                 680                 685

Ser Leu Cys Val Tyr Lys Val Pro Leu Pro Glu Asp Val Ser Arg Glu
690                 695                 700

Ala Gly Tyr Asp Ser Thr Tyr Gly Met Phe Gln Gly Ile Pro Ser Asn
705                 710                 715                 720

Asp Pro Ile Asn Val Leu Val Arg Val Tyr Val Arg Ala Thr Asp
            725                 730                 735

Leu His Pro Ala Asp Ile Asn Gly Lys Ala Asp Pro Tyr Ile Ala Ile
            740                 745                 750

Arg Leu Gly Lys Thr Asp Ile Arg Asp Lys Glu Asn Tyr Ile Ser Lys
            755                 760                 765

Gln Leu Asn Pro Val Phe Gly Lys Ser Phe Asp Ile Glu Ala Ser Phe
            770                 775                 780

Pro Met Glu Ser Met Leu Thr Val Ala Val Tyr Asp Trp Asp Leu Val
785                 790                 795                 800

Gly Thr Asp Asp Leu Ile Gly Glu Thr Lys Ile Asp Leu Glu Asn Arg
            805                 810                 815

Phe Tyr Ser Lys His Arg Ala Thr Cys Gly Ile Ala Gln Thr Tyr Ser
            820                 825                 830
```

-continued

```
Thr His Gly Tyr Asn Ile Trp Arg Asp Pro Met Lys Pro Ser Gln Ile
            835                 840                 845

Leu Thr Arg Leu Cys Lys Asp Gly Lys Val Asp Gly Pro His Phe Gly
850                 855                 860

Pro Pro Gly Arg Val Lys Val Ala Asn Arg Val Phe Thr Gly Pro Ser
865                 870                 875                 880

Glu Ile Glu Asp Glu Asn Gly Gln Arg Lys Pro Thr Asp Glu His Val
                885                 890                 895

Ala Leu Leu Ala Leu Arg His Trp Glu Asp Ile Pro Arg Ala Gly Cys
            900                 905                 910

Arg Leu Val Pro Glu His Val Glu Thr Arg Pro Leu Leu Asn Pro Asp
            915                 920                 925

Lys Pro Gly Ile Glu Gln Gly Arg Leu Glu Leu Trp Val Asp Met Phe
            930                 935                 940

Pro Met Asp Met Pro Ala Pro Gly Thr Pro Leu Asp Ile Ser Pro Arg
945                 950                 955                 960

Lys Pro Lys Lys Tyr Glu Leu Arg Val Ile Ile Trp Asn Thr Asp Glu
                965                 970                 975

Val Val Leu Glu Asp Asp Asp Phe Phe Thr Gly Glu Lys Ser Ser Asp
            980                 985                 990

Ile Phe Val Arg Gly Trp Leu Lys  Gly Gln Gln Glu Asp  Lys Gln Asp
            995                 1000                1005

Thr Asp  Val His Tyr His Ser  Leu Thr Gly Glu Gly  Asn Phe Asn
    1010                1015                1020

Trp Arg  Tyr Leu Phe Pro Phe  Asp Tyr Leu Ala Ala  Glu Glu Lys
    1025                1030                1035

Ile Val  Ile Ser Lys Lys Glu  Ser Met Phe Ser Trp  Asp Glu Thr
    1040                1045                1050

Glu Tyr  Lys Ile Pro Ala Arg  Leu Thr Leu Gln Ile  Trp Asp Ala
    1055                1060                1065

Asp His  Phe Ser Ala Asp Asp  Phe Leu Gly Ala Ile  Glu Leu Asp
    1070                1075                1080

Leu Asn  Arg Phe Pro Arg Gly  Ala Lys Thr Ala Lys  Gln Cys Thr
    1085                1090                1095

Met Glu  Met Ala Thr Gly Glu  Val Asp Val Pro Leu  Val Ser Ile
    1100                1105                1110

Phe Lys  Gln Lys Arg Val Lys  Gly Trp Trp Pro Leu  Leu Ala Arg
    1115                1120                1125

Asn Glu  Asn Asp Glu Phe Glu  Leu Thr Gly Lys Val  Glu Ala Glu
    1130                1135                1140

Leu His  Leu Leu Thr Ala Glu  Ala Glu Lys Asn  Pro Val Gly
    1145                1150                1155

Leu Ala  Arg Asn Glu Pro Asp  Pro Leu Glu Lys Pro  Asn Arg Pro
    1160                1165                1170

Asp Thr  Ser Phe Ile Trp Phe  Leu Asn Pro Leu Lys  Ser Ala Arg
    1175                1180                1185

Tyr Phe  Leu Trp His Thr Tyr  Arg Trp Leu Leu Leu  Lys Leu Leu
    1190                1195                1200

Leu Leu  Leu Leu Leu Leu Leu  Leu Leu Ala Leu Phe  Leu Tyr Ser
    1205                1210                1215

Val Pro  Gly Tyr Leu Val Lys  Lys Ile Leu Gly Ala
    1220                1225                1230
```

```
<210> SEQ ID NO 3
<211> LENGTH: 1230
<212> TYPE: PRT
<213> ORGANISM: Homo sapiens

<400> SEQUENCE: 3

Met Ile Lys Thr Glu Lys Ser Tyr Pro Glu Arg Arg Leu Arg Gly Val
1               5                   10                  15

Leu Glu Glu Leu Ser Cys Gly Cys Cys Arg Phe Leu Ser Leu Ala Asp
            20                  25                  30

Lys Asp Gln Gly His Ser Ser Arg Thr Arg Leu Asp Arg Glu Arg Leu
        35                  40                  45

Lys Ser Cys Met Arg Glu Leu Glu Asn Met Gly Gln Gln Ala Arg Met
    50                  55                  60

Leu Arg Ala Gln Val Lys Arg His Thr Val Arg Asp Lys Leu Arg Leu
65                  70                  75                  80

Cys Gln Asn Phe Leu Gln Lys Leu Arg Phe Leu Ala Asp Glu Pro Gln
                85                  90                  95

His Ser Ile Pro Asp Ile Phe Ile Trp Met Met Ser Asn Asn Lys Arg
            100                 105                 110

Val Ala Tyr Ala Arg Val Pro Ser Lys Asp Leu Leu Phe Ser Ile Val
        115                 120                 125

Glu Glu Glu Thr Gly Lys Asp Cys Ala Lys Val Lys Thr Leu Phe Leu
    130                 135                 140

Lys Leu Pro Gly Lys Arg Gly Phe Gly Ser Ala Gly Trp Thr Val Gln
145                 150                 155                 160

Ala Lys Val Glu Leu Tyr Leu Trp Leu Gly Leu Ser Lys Gln Arg Lys
                165                 170                 175

Glu Phe Leu Cys Gly Leu Pro Cys Gly Phe Gln Glu Val Lys Ala Ala
            180                 185                 190

Gln Gly Leu Gly Leu His Ala Phe Pro Pro Val Ser Leu Val Tyr Thr
        195                 200                 205

Lys Lys Gln Ala Phe Gln Leu Arg Ala His Met Tyr Gln Ala Arg Ser
    210                 215                 220

Leu Phe Ala Ala Asp Ser Ser Gly Leu Ser Asp Pro Phe Ala Arg Val
225                 230                 235                 240

Phe Phe Ile Asn Gln Ser Gln Cys Thr Glu Val Leu Asn Glu Thr Leu
                245                 250                 255

Cys Pro Thr Trp Asp Gln Met Leu Val Phe Asp Asn Leu Glu Leu Tyr
            260                 265                 270

Gly Glu Ala His Glu Leu Arg Asp Pro Pro Ile Val Ile Glu
        275                 280                 285

Ile Tyr Asp Gln Asp Ser Met Gly Lys Ala Asp Phe Met Gly Arg Thr
    290                 295                 300

Phe Ala Lys Pro Leu Val Lys Met Ala Asp Glu Ala Tyr Cys Pro Pro
305                 310                 315                 320

Arg Phe Pro Pro Gln Leu Glu Tyr Tyr Gln Ile Tyr Arg Gly Asn Ala
                325                 330                 335

Thr Ala Gly Asp Leu Leu Ala Ala Phe Glu Leu Leu Gln Ile Gly Pro
            340                 345                 350

Ala Gly Lys Ala Asp Leu Pro Pro Ile Asn Gly Pro Val Asp Val Asp
        355                 360                 365

Arg Gly Pro Ile Met Pro Val Pro Met Gly Ile Arg Pro Val Leu Ser
    370                 375                 380
```

```
Lys Tyr Arg Val Glu Val Leu Phe Trp Gly Leu Arg Asp Leu Lys Arg
385                 390                 395                 400

Val Asn Leu Ala Gln Val Asp Arg Pro Arg Val Asp Ile Glu Cys Ala
            405                 410                 415

Gly Lys Gly Val Gln Ser Ser Leu Ile His Asn Tyr Lys Lys Asn Pro
            420                 425                 430

Asn Phe Asn Thr Leu Val Lys Trp Phe Glu Val Asp Leu Pro Glu Asn
            435                 440                 445

Glu Leu Leu His Pro Pro Leu Asn Ile Arg Val Val Asp Cys Arg Ala
        450                 455                 460

Phe Gly Arg Tyr Thr Leu Val Gly Ser His Ala Val Ser Ser Leu Arg
465                 470                 475                 480

Arg Phe Ile Tyr Arg Pro Pro Asp Arg Ser Ala Pro Ser Trp Asn Thr
                485                 490                 495

Thr Gly Glu Val Val Val Thr Met Glu Pro Glu Val Pro Ile Lys Lys
                500                 505                 510

Leu Glu Thr Met Val Lys Leu Asp Ala Thr Ser Glu Ala Val Val Lys
            515                 520                 525

Val Asp Val Ala Glu Glu Lys Glu Lys Lys Lys Lys Lys Lys Lys Gly
        530                 535                 540

Thr Ala Glu Glu Pro Glu Glu Glu Pro Asp Glu Ser Met Leu Asp
545                 550                 555                 560

Trp Trp Ser Lys Tyr Phe Ala Ser Ile Asp Thr Met Lys Glu Gln Leu
                565                 570                 575

Arg Gln Gln Glu Pro Ser Gly Ile Asp Leu Glu Glu Lys Glu Glu Val
            580                 585                 590

Asp Asn Thr Glu Gly Leu Lys Gly Ser Met Lys Gly Lys Glu Lys Ala
            595                 600                 605

Arg Ala Ala Lys Glu Glu Lys Lys Lys Thr Gln Ser Ser Gly Ser
        610                 615                 620

Gly Gln Gly Ser Glu Ala Pro Glu Lys Lys Pro Lys Ile Asp Glu
625                 630                 635                 640

Leu Lys Val Tyr Pro Lys Glu Leu Glu Ser Glu Phe Asp Asn Phe Glu
                645                 650                 655

Asp Trp Leu His Thr Phe Asn Leu Leu Arg Gly Lys Thr Gly Asp Asp
                660                 665                 670

Glu Asp Gly Ser Thr Glu Glu Arg Ile Val Gly Arg Phe Lys Gly
            675                 680                 685

Ser Leu Cys Val Tyr Lys Val Pro Leu Pro Glu Asp Val Ser Arg Glu
        690                 695                 700

Ala Gly Tyr Asp Ser Thr Tyr Gly Met Phe Gln Gly Ile Pro Ser Asn
705                 710                 715                 720

Asp Pro Ile Asn Val Leu Val Arg Val Tyr Val Arg Ala Thr Asp
                725                 730                 735

Leu His Pro Ala Asp Ile Asn Gly Lys Ala Asp Pro Tyr Ile Ala Ile
            740                 745                 750

Arg Leu Gly Lys Thr Asp Ile Arg Asp Lys Glu Asn Tyr Ile Ser Lys
            755                 760                 765

Gln Leu Asn Pro Val Phe Gly Lys Ser Phe Asp Ile Glu Ala Ser Phe
        770                 775                 780

Pro Met Glu Ser Met Leu Thr Val Ala Val Tyr Asp Trp Asp Leu Val
785                 790                 795                 800

Gly Thr Asp Asp Leu Ile Gly Glu Thr Lys Ile Asp Leu Glu Asn Arg
```

-continued

```
                805                 810                 815
Phe Tyr Ser Lys His Arg Ala Thr Cys Gly Ile Ala Gln Thr Tyr Ser
                820                 825                 830
Thr His Gly Tyr Asn Ile Trp Arg Asp Pro Met Lys Pro Ser Gln Ile
                835                 840                 845
Leu Thr Arg Leu Cys Lys Asp Gly Lys Val Asp Gly Pro His Phe Gly
                850                 855                 860
Pro Pro Gly Arg Val Lys Val Ala Asn Arg Val Phe Thr Gly Pro Ser
865                 870                 875                 880
Glu Ile Glu Asp Glu Asn Gly Gln Arg Lys Pro Thr Asp Glu His Val
                885                 890                 895
Ala Leu Leu Ala Leu Arg His Trp Glu Asp Ile Pro Arg Ala Gly Cys
                900                 905                 910
Arg Leu Val Pro Glu His Val Glu Thr Arg Pro Leu Leu Asn Pro Asp
                915                 920                 925
Lys Pro Gly Ile Glu Gln Gly Arg Leu Glu Leu Trp Val Asp Met Phe
                930                 935                 940
Pro Met Asp Met Pro Ala Pro Gly Thr Pro Leu Asp Ile Ser Pro Arg
945                 950                 955                 960
Lys Pro Lys Lys Tyr Glu Leu Arg Val Ile Ile Trp Asn Thr Asp Glu
                965                 970                 975
Val Val Leu Glu Asp Asp Asp Phe Phe Thr Gly Glu Lys Ser Ser Asp
                980                 985                 990
Ile Phe Val Arg Gly Trp Leu Lys Gly Gln Gln Glu Asp Lys Gln Asp
                995                 1000                1005
Thr Asp Val His Tyr His Ser Leu Thr Gly Glu Gly Asn Phe Asn
    1010                1015                1020
Trp Arg Tyr Leu Phe Pro Phe Asp Tyr Leu Ala Ala Glu Glu Lys
    1025                1030                1035
Ile Val Ile Ser Lys Lys Glu Ser Met Phe Ser Trp Asp Glu Thr
    1040                1045                1050
Glu Tyr Lys Ile Pro Ala Arg Leu Thr Leu Gln Ile Trp Asp Ala
    1055                1060                1065
Asp His Phe Ser Ala Asp Asp Phe Leu Gly Ala Ile Glu Leu Asp
    1070                1075                1080
Leu Asn Arg Phe Pro Arg Gly Ala Lys Thr Ala Lys Gln Cys Thr
    1085                1090                1095
Met Glu Met Ala Thr Gly Glu Val Asp Val Pro Leu Val Ser Ile
    1100                1105                1110
Phe Lys Gln Lys Arg Val Lys Gly Trp Trp Pro Leu Leu Ala Arg
    1115                1120                1125
Asn Glu Asn Asp Glu Phe Glu Leu Thr Gly Lys Val Glu Ala Glu
    1130                1135                1140
Leu His Leu Leu Thr Ala Glu Ala Glu Lys Asn Pro Val Gly
    1145                1150                1155
Leu Ala Arg Asn Glu Pro Asp Pro Leu Glu Lys Pro Asn Arg Pro
    1160                1165                1170
Asp Thr Ala Phe Val Trp Phe Leu Asn Pro Leu Lys Ser Ile Lys
    1175                1180                1185
Tyr Leu Ile Cys Thr Arg Tyr Lys Trp Leu Ile Ile Lys Ile Val
    1190                1195                1200
Leu Ala Leu Leu Gly Leu Leu Met Leu Gly Leu Phe Leu Tyr Ser
    1205                1210                1215
```

```
Leu Pro Gly Tyr Met Val Lys  Lys Leu Leu Gly Ala
    1220            1225              1230

<210> SEQ ID NO 4
<211> LENGTH: 1307
<212> TYPE: PRT
<213> ORGANISM: Homo sapiens

<400> SEQUENCE: 4

Met Met Thr Asp Thr Gln Asp Gly Pro Ser Glu Ser Ser Gln Ile Met
1               5                   10                  15

Arg Ser Leu Thr Pro Leu Ile Asn Arg Glu Glu Ala Phe Gly Glu Ala
            20                  25                  30

Gly Glu Ala Gly Leu Trp Pro Ser Ile Thr His Thr Pro Asp Ser Gln
        35                  40                  45

Glu Glu Gly Leu Asn Asp Ile Gln Glu Met Ile Lys Thr Glu Lys Ser
    50                  55                  60

Tyr Pro Glu Arg Arg Leu Arg Gly Val Leu Glu Leu Ser Cys Gly
65                  70                  75                  80

Cys Cys Arg Phe Leu Ser Leu Ala Asp Lys Asp Gln Gly His Ser Ser
                85                  90                  95

Arg Thr Arg Leu Asp Arg Glu Arg Leu Lys Ser Cys Met Arg Glu Leu
            100                 105                 110

Glu Asn Met Gly Gln Gln Ala Arg Met Leu Arg Ala Gln Val Lys Arg
        115                 120                 125

His Thr Val Arg Asp Lys Leu Arg Leu Cys Gln Asn Phe Leu Gln Lys
    130                 135                 140

Leu Arg Phe Leu Ala Asp Glu Pro Gln His Ser Ile Pro Asp Ile Phe
145                 150                 155                 160

Ile Trp Met Met Ser Asn Asn Lys Arg Val Ala Tyr Ala Arg Val Pro
                165                 170                 175

Ser Lys Asp Leu Leu Phe Ser Ile Val Glu Glu Thr Gly Lys Asp
            180                 185                 190

Cys Ala Lys Val Lys Thr Leu Phe Leu Lys Leu Pro Gly Lys Arg Gly
        195                 200                 205

Phe Gly Ser Ala Gly Trp Thr Val Gln Ala Lys Val Glu Leu Tyr Leu
    210                 215                 220

Trp Leu Gly Leu Ser Lys Gln Arg Lys Glu Phe Leu Cys Gly Leu Pro
225                 230                 235                 240

Cys Gly Phe Gln Glu Val Lys Ala Ala Gln Gly Leu Gly Leu His Ala
                245                 250                 255

Phe Pro Pro Val Ser Leu Val Tyr Thr Lys Lys Gln Ala Phe Gln Leu
            260                 265                 270

Arg Ala His Met Tyr Gln Ala Arg Ser Leu Phe Ala Ala Asp Ser Ser
        275                 280                 285

Gly Leu Ser Asp Pro Phe Ala Arg Val Phe Phe Ile Asn Gln Ser Gln
    290                 295                 300

Cys Thr Glu Val Leu Asn Glu Thr Leu Cys Pro Thr Trp Asp Gln Met
305                 310                 315                 320

Leu Val Phe Asp Asn Leu Glu Leu Tyr Gly Glu Ala His Glu Leu Arg
                325                 330                 335

Asp Asp Pro Pro Ile Ile Val Ile Glu Ile Tyr Asp Gln Asp Ser Met
            340                 345                 350

Gly Lys Ala Asp Phe Met Gly Arg Thr Phe Ala Lys Pro Leu Val Lys
```

-continued

```
                355                 360                 365
Met Ala Asp Glu Ala Tyr Cys Pro Pro Arg Phe Pro Pro Gln Leu Glu
            370                 375                 380
Tyr Tyr Gln Ile Tyr Arg Gly Asn Ala Thr Ala Gly Asp Leu Leu Ala
385                 390                 395                 400
Ala Phe Glu Leu Leu Gln Ile Gly Pro Ala Gly Lys Ala Asp Leu Pro
                405                 410                 415
Pro Ile Asn Gly Pro Val Asp Val Asp Arg Gly Pro Ile Met Pro Val
            420                 425                 430
Pro Met Gly Ile Arg Pro Val Leu Ser Lys Tyr Arg Val Glu Val Leu
        435                 440                 445
Phe Trp Gly Leu Arg Asp Leu Lys Arg Val Asn Leu Ala Gln Val Asp
    450                 455                 460
Arg Pro Arg Val Asp Ile Glu Cys Ala Gly Lys Gly Val Gln Ser Ser
465                 470                 475                 480
Leu Ile His Asn Tyr Lys Lys Asn Pro Asn Phe Asn Thr Leu Val Lys
                485                 490                 495
Trp Phe Glu Val Asp Leu Pro Glu Asn Glu Leu Leu His Pro Pro Leu
            500                 505                 510
Asn Ile Arg Val Val Asp Cys Arg Ala Phe Gly Arg Tyr Thr Leu Val
        515                 520                 525
Gly Ser His Ala Val Ser Ser Leu Arg Arg Phe Ile Tyr Arg Pro Pro
    530                 535                 540
Asp Arg Ser Ala Pro Ser Trp Asn Thr Thr Val Arg Leu Leu Arg Arg
545                 550                 555                 560
Cys Arg Val Leu Cys Asn Gly Gly Ser Ser Ser His Ser Thr Gly Glu
                565                 570                 575
Val Val Val Thr Met Glu Pro Glu Val Pro Ile Lys Lys Leu Glu Thr
            580                 585                 590
Met Val Lys Leu Asp Ala Thr Ser Glu Ala Val Val Lys Val Asp Val
        595                 600                 605
Ala Glu Glu Glu Lys Glu Lys Lys Lys Lys Lys Gly Thr Ala Glu
    610                 615                 620
Glu Pro Glu Glu Glu Glu Pro Asp Glu Ser Met Leu Asp Trp Trp Ser
625                 630                 635                 640
Lys Tyr Phe Ala Ser Ile Asp Thr Met Lys Glu Gln Leu Arg Gln Gln
                645                 650                 655
Glu Pro Ser Gly Ile Asp Leu Glu Glu Lys Glu Glu Val Asp Asn Thr
            660                 665                 670
Glu Gly Leu Lys Gly Ser Met Lys Gly Lys Glu Lys Ala Arg Ala Ala
        675                 680                 685
Lys Glu Glu Lys Lys Lys Lys Thr Gln Ser Ser Gly Ser Gly Gln Gly
    690                 695                 700
Ser Glu Ala Pro Glu Lys Lys Pro Lys Ile Asp Glu Leu Lys Val
705                 710                 715                 720
Tyr Pro Lys Glu Leu Glu Ser Glu Phe Asp Asn Phe Glu Asp Trp Leu
                725                 730                 735
His Thr Phe Asn Leu Leu Arg Gly Lys Thr Gly Asp Asp Glu Asp Gly
            740                 745                 750
Ser Thr Glu Glu Glu Arg Ile Val Gly Arg Phe Lys Gly Ser Leu Cys
        755                 760                 765
Val Tyr Lys Val Pro Leu Pro Glu Asp Val Ser Arg Glu Ala Gly Tyr
    770                 775                 780
```

-continued

Asp Ser Thr Tyr Gly Met Phe Gln Gly Ile Pro Ser Asn Asp Pro Ile
785                 790                 795                 800

Asn Val Leu Val Arg Val Tyr Val Val Arg Ala Thr Asp Leu His Pro
            805                 810                 815

Ala Asp Ile Asn Gly Lys Ala Asp Pro Tyr Ile Ala Ile Arg Leu Gly
        820                 825                 830

Lys Thr Asp Ile Arg Asp Lys Glu Asn Tyr Ile Ser Lys Gln Leu Asn
        835                 840                 845

Pro Val Phe Gly Lys Ser Phe Asp Ile Glu Ala Ser Phe Pro Met Glu
    850                 855                 860

Ser Met Leu Thr Val Ala Val Tyr Asp Trp Asp Leu Val Gly Thr Asp
865                 870                 875                 880

Asp Leu Ile Gly Glu Thr Lys Ile Asp Leu Glu Asn Arg Phe Tyr Ser
            885                 890                 895

Lys His Arg Ala Thr Cys Gly Ile Ala Gln Thr Tyr Ser Thr His Gly
        900                 905                 910

Tyr Asn Ile Trp Arg Asp Pro Met Lys Pro Ser Gln Ile Leu Thr Arg
        915                 920                 925

Leu Cys Lys Asp Gly Lys Val Asp Gly Pro His Phe Gly Pro Pro Gly
    930                 935                 940

Arg Val Lys Val Ala Asn Arg Val Phe Thr Gly Pro Ser Glu Ile Glu
945                 950                 955                 960

Asp Glu Asn Gly Gln Arg Lys Pro Thr Asp Glu His Val Ala Leu Leu
            965                 970                 975

Ala Leu Arg His Trp Glu Asp Ile Pro Arg Ala Gly Cys Arg Leu Val
        980                 985                 990

Pro Glu His Val Glu Thr Arg Pro Leu Leu Asn Pro Asp Lys Pro Gly
        995                 1000                1005

Ile Glu Gln Gly Arg Leu Glu Leu Trp Val Asp Met Phe Pro Met
    1010                1015                1020

Asp Met Pro Ala Pro Gly Thr Pro Leu Asp Ile Ser Pro Arg Lys
    1025                1030                1035

Pro Lys Lys Tyr Glu Leu Arg Val Ile Ile Trp Asn Thr Asp Glu
    1040                1045                1050

Val Val Leu Glu Asp Asp Asp Phe Phe Thr Gly Glu Lys Ser Ser
    1055                1060                1065

Asp Ile Phe Val Arg Gly Trp Leu Lys Gly Gln Gln Glu Asp Lys
    1070                1075                1080

Gln Asp Thr Asp Val His Tyr His Ser Leu Thr Gly Glu Gly Asn
    1085                1090                1095

Phe Asn Trp Arg Tyr Leu Phe Pro Phe Asp Tyr Leu Ala Ala Glu
    1100                1105                1110

Glu Lys Ile Val Ile Ser Lys Lys Glu Ser Met Phe Ser Trp Asp
    1115                1120                1125

Glu Thr Glu Tyr Lys Ile Pro Ala Arg Leu Thr Leu Gln Ile Trp
    1130                1135                1140

Asp Ala Asp His Phe Ser Ala Asp Asp Phe Leu Gly Ala Ile Glu
    1145                1150                1155

Leu Asp Leu Asn Arg Phe Pro Arg Gly Ala Lys Thr Ala Lys Gln
    1160                1165                1170

Cys Thr Met Glu Met Ala Thr Gly Glu Val Asp Val Pro Leu Val
    1175                1180                1185

-continued

```
Ser Ile Phe Lys Gln Lys Arg Val Lys Gly Trp Trp Pro Leu Leu
    1190                1195                1200

Ala Arg Asn Glu Asn Asp Glu Phe Glu Leu Thr Gly Lys Val Glu
    1205                1210                1215

Ala Glu Leu His Leu Leu Thr Ala Glu Glu Ala Glu Lys Asn Pro
    1220                1225                1230

Val Gly Leu Ala Arg Asn Glu Pro Asp Pro Leu Glu Lys Pro Asn
    1235                1240                1245

Arg Pro Asp Thr Ser Phe Ile Trp Phe Leu Asn Pro Leu Lys Ser
    1250                1255                1260

Ala Arg Tyr Phe Leu Trp His Thr Tyr Arg Trp Leu Leu Leu Lys
    1265                1270                1275

Leu Leu Leu Leu Leu Leu Leu Leu Leu Leu Ala Leu Phe Leu
    1280                1285                1290

Tyr Ser Val Pro Gly Tyr Leu Val Lys Lys Ile Leu Gly Ala
    1295                1300                1305

<210> SEQ ID NO 5
<211> LENGTH: 1997
<212> TYPE: PRT
<213> ORGANISM: Homo sapiens

<400> SEQUENCE: 5

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
                165                 170                 175

Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
        195                 200                 205

Ala Ile Arg Leu Gly Asp Gly Leu Asp Pro Asp Ser Val Ser Leu Ala
    210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255
```

```
Ser Ile Thr Val Ile Glu Ala Arg Gln Leu Val Gly Leu Asn Met Asp
            260                 265                 270

Pro Val Val Cys Val Glu Val Gly Asp Asp Lys Lys Tyr Thr Ser Met
            275                 280                 285

Lys Glu Ser Thr Asn Cys Pro Tyr Tyr Asn Glu Tyr Phe Val Phe Asp
        290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Ile Ser Ser Gly
        355                 360                 365

Leu Lys Gly Tyr Val Lys Cys Asp Val Ala Val Gly Lys Gly Asp
    370                 375                 380

Asn Ile Lys Thr Pro His Lys Ala Asn Glu Thr Asp Glu Asp Ile
385                 390                 395                 400

Glu Gly Asn Leu Leu Pro Glu Gly Val Pro Pro Gly Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
            500                 505                 510

His Phe Ile Asp Leu Arg Lys Ile Ser Asn Asp Gly Asp Lys Gly Phe
        515                 520                 525

Leu Pro Thr Leu Gly Pro Ala Trp Val Asn Met Tyr Gly Ser Thr Arg
    530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Gly Leu Ala Val Glu
                565                 570                 575

Ile Val Asp Thr Ser Asn Pro Glu Leu Thr Ser Ser Thr Glu Val Gln
            580                 585                 590

Val Glu Gln Ala Thr Pro Ile Ser Glu Ser Cys Ala Gly Lys Met Glu
        595                 600                 605

Glu Phe Phe Leu Phe Gly Ala Phe Leu Glu Ala Ser Met Ile Asp Arg
    610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Val Asp Leu Ile Gln Asn Ala Ser
            660                 665                 670
```

```
Asp Asp Glu Ala Gly Asp Ala Gly Asp Leu Ala Ser Val Ser Ser Thr
            675                 680                 685

Pro Pro Met Arg Pro Gln Val Thr Asp Arg Asn Tyr Phe His Leu Pro
690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
            740                 745                 750

Lys Ser Tyr Pro Glu Arg Arg Leu Arg Gly Val Leu Glu Glu Leu Ser
        755                 760                 765

Cys Gly Cys Cys Arg Phe Leu Ser Leu Ala Asp Lys Asp Gln Gly His
770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
            820                 825                 830

Gln Lys Leu Arg Phe Leu Ala Asp Glu Pro Gln His Ser Ile Pro Asp
        835                 840                 845

Ile Phe Ile Trp Met Met Ser Asn Asn Lys Arg Val Ala Tyr Ala Arg
850                 855                 860

Val Pro Ser Lys Asp Leu Leu Phe Ser Ile Val Glu Glu Thr Gly
865                 870                 875                 880

Lys Asp Cys Ala Lys Val Lys Thr Leu Phe Leu Lys Leu Pro Gly Lys
                885                 890                 895

Arg Gly Phe Gly Ser Ala Gly Trp Thr Val Gln Ala Lys Val Glu Leu
            900                 905                 910

Tyr Leu Trp Leu Gly Leu Ser Lys Gln Arg Lys Glu Phe Leu Cys Gly
        915                 920                 925

Leu Pro Cys Gly Phe Gln Glu Val Lys Ala Ala Gln Gly Leu Gly Leu
930                 935                 940

His Ala Phe Pro Pro Val Ser Leu Val Tyr Thr Lys Lys Gln Ala Phe
945                 950                 955                 960

Gln Leu Arg Ala His Met Tyr Gln Ala Arg Ser Leu Phe Ala Ala Asp
                965                 970                 975

Ser Ser Gly Leu Ser Asp Pro Phe Ala Arg Val Phe Ile Asn Gln
            980                 985                 990

Ser Gln Cys Thr Glu Val Leu Asn Glu Thr Leu Cys Pro Thr Trp Asp
        995                 1000                1005

Gln Met Leu Val Phe Asp Asn Leu Glu Leu Tyr Gly Glu Ala His
    1010                1015                1020

Glu Leu Arg Asp Asp Pro Pro Ile Ile Val Ile Glu Ile Tyr Asp
    1025                1030                1035

Gln Asp Ser Met Gly Lys Ala Asp Phe Met Gly Arg Thr Phe Ala
    1040                1045                1050

Lys Pro Leu Val Lys Met Ala Asp Glu Ala Tyr Cys Pro Pro Arg
    1055                1060                1065

Phe Pro Pro Gln Leu Glu Tyr Tyr Gln Ile Tyr Arg Gly Asn Ala
    1070                1075                1080

Thr Ala Gly Asp Leu Leu Ala Ala Phe Glu Leu Leu Gln Ile Gly
```

-continued

```
            1085                1090                1095

Pro Ala Gly Lys Ala Asp Leu Pro Pro Ile Asn Gly Pro Val Asp
            1100                1105                1110

Val Asp Arg Gly Pro Ile Met Pro Val Pro Met Gly Ile Arg Pro
            1115                1120                1125

Val Leu Ser Lys Tyr Arg Val Glu Val Leu Phe Trp Gly Leu Arg
            1130                1135                1140

Asp Leu Lys Arg Val Asn Leu Ala Gln Val Asp Arg Pro Arg Val
            1145                1150                1155

Asp Ile Glu Cys Ala Gly Lys Gly Val Gln Ser Ser Leu Ile His
            1160                1165                1170

Asn Tyr Lys Lys Asn Pro Asn Phe Asn Thr Leu Val Lys Trp Phe
            1175                1180                1185

Glu Val Asp Leu Pro Glu Asn Glu Leu Leu His Pro Pro Leu Asn
            1190                1195                1200

Ile Arg Val Val Asp Cys Arg Ala Phe Gly Arg Tyr Thr Leu Val
            1205                1210                1215

Gly Ser His Ala Val Ser Ser Leu Arg Arg Phe Ile Tyr Arg Pro
            1220                1225                1230

Pro Asp Arg Ser Ala Pro Ser Trp Asn Thr Thr Val Arg Leu Leu
            1235                1240                1245

Arg Arg Cys Arg Val Leu Cys Asn Gly Gly Ser Ser Ser His Ser
            1250                1255                1260

Thr Gly Glu Val Val Val Thr Met Glu Pro Glu Val Pro Ile Lys
            1265                1270                1275

Lys Leu Glu Thr Met Val Lys Leu Asp Ala Thr Ser Glu Ala Val
            1280                1285                1290

Val Lys Val Asp Val Ala Glu Glu Lys Glu Lys Lys Lys
            1295                1300                1305

Lys Lys Gly Thr Ala Glu Glu Pro Glu Glu Glu Pro Asp Glu
            1310                1315                1320

Ser Met Leu Asp Trp Trp Ser Lys Tyr Phe Ala Ser Ile Asp Thr
            1325                1330                1335

Met Lys Glu Gln Leu Arg Gln Gln Glu Pro Ser Gly Ile Asp Leu
            1340                1345                1350

Glu Glu Lys Glu Glu Val Asp Asn Thr Glu Gly Leu Lys Gly Ser
            1355                1360                1365

Met Lys Gly Lys Glu Lys Ala Arg Ala Ala Lys Glu Glu Lys Lys
            1370                1375                1380

Lys Lys Thr Gln Ser Ser Gly Ser Gly Gln Ser Glu Ala Pro
            1385                1390                1395

Glu Lys Lys Lys Pro Lys Ile Asp Glu Leu Lys Val Tyr Pro Lys
            1400                1405                1410

Glu Leu Glu Ser Glu Phe Asp Asn Phe Glu Asp Trp Leu His Thr
            1415                1420                1425

Phe Asn Leu Leu Arg Gly Lys Thr Gly Asp Asp Glu Asp Gly Ser
            1430                1435                1440

Thr Glu Glu Glu Arg Ile Val Gly Arg Phe Lys Gly Ser Leu Cys
            1445                1450                1455

Val Tyr Lys Val Pro Leu Pro Glu Asp Val Ser Arg Glu Ala Gly
            1460                1465                1470

Tyr Asp Ser Thr Tyr Gly Met Phe Gln Gly Ile Pro Ser Asn Asp
            1475                1480                1485
```

```
Pro Ile Asn Val Leu Val Arg Val Tyr Val Val Arg Ala Thr Asp
    1490                1495                1500

Leu His Pro Ala Asp Ile Asn Gly Lys Ala Asp Pro Tyr Ile Ala
    1505                1510                1515

Ile Arg Leu Gly Lys Thr Asp Ile Arg Asp Lys Glu Asn Tyr Ile
    1520                1525                1530

Ser Lys Gln Leu Asn Pro Val Phe Gly Lys Ser Phe Asp Ile Glu
    1535                1540                1545

Ala Ser Phe Pro Met Glu Ser Met Leu Thr Val Ala Val Tyr Asp
    1550                1555                1560

Trp Asp Leu Val Gly Thr Asp Asp Leu Ile Gly Glu Thr Lys Ile
    1565                1570                1575

Asp Leu Glu Asn Arg Phe Tyr Ser Lys His Arg Ala Thr Cys Gly
    1580                1585                1590

Ile Ala Gln Thr Tyr Ser Thr His Gly Tyr Asn Ile Trp Arg Asp
    1595                1600                1605

Pro Met Lys Pro Ser Gln Ile Leu Thr Arg Leu Cys Lys Asp Gly
    1610                1615                1620

Lys Val Asp Gly Pro His Phe Gly Pro Pro Gly Arg Val Lys Val
    1625                1630                1635

Ala Asn Arg Val Phe Thr Gly Pro Ser Glu Ile Glu Asp Glu Asn
    1640                1645                1650

Gly Gln Arg Lys Pro Thr Asp Glu His Val Ala Leu Leu Ala Leu
    1655                1660                1665

Arg His Trp Glu Asp Ile Pro Arg Ala Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Ile Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Ile Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
    1835                1840                1845

Leu Asp Leu Asn Arg Phe Pro Arg Gly Ala Lys Thr Ala Lys Gln
    1850                1855                1860

Cys Thr Met Glu Met Ala Thr Gly Glu Val Asp Val Pro Leu Val
    1865                1870                1875
```

```
Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
    1895                1900                1905

Ala Glu Leu His Leu Leu Thr Ala Glu Glu Ala Glu Lys Asn Pro
    1910                1915                1920

Val Gly Leu Ala Arg Asn Glu Pro Asp Pro Leu Glu Lys Pro Asn
    1925                1930                1935

Arg Pro Asp Thr Ala Phe Val Trp Phe Leu Asn Pro Leu Lys Ser
    1940                1945                1950

Ile Lys Tyr Leu Ile Cys Thr Arg Tyr Lys Trp Leu Ile Ile Lys
    1955                1960                1965

Ile Val Leu Ala Leu Leu Gly Leu Leu Met Leu Gly Leu Phe Leu
    1970                1975                1980

Tyr Ser Leu Pro Gly Tyr Met Val Lys Lys Leu Leu Gly Ala
    1985                1990                1995

<210> SEQ ID NO 6
<211> LENGTH: 1997
<212> TYPE: PRT
<213> ORGANISM: Mus musculus

<400> SEQUENCE: 6

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Gly Val Ala Asp Phe Asp Glu Thr Phe
            35                  40                  45

Arg Trp Pro Val Ala Ser Ser Ile Asp Arg Asn Glu Val Leu Glu Ile
        50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Arg Ala Gly Arg Ser Val Phe Ser
                165                 170                 175

Ala Met Lys Leu Gly Lys Thr Arg Ser His Lys Glu Glu Pro Gln Arg
            180                 185                 190

Gln Asp Glu Pro Ala Val Leu Glu Met Glu Asp Leu Asp His Leu Ala
        195                 200                 205

Ile Gln Leu Gly Asp Gly Leu Asp Pro Asp Ser Val Ser Leu Ala Ser
    210                 215                 220

Val Thr Ala Leu Thr Ser Asn Val Ser Asn Lys Arg Ser Lys Pro Asp
225                 230                 235                 240

Ile Lys Met Glu Pro Ser Ala Gly Arg Pro Met Asp Tyr Gln Val Ser
                245                 250                 255
```

```
Ile Thr Val Ile Glu Ala Arg Gln Leu Val Gly Leu Asn Met Asp Pro
            260                 265                 270

Val Val Cys Val Glu Val Gly Asp Lys Lys Tyr Thr Ser Met Lys
            275                 280                 285

Glu Ser Thr Asn Cys Pro Tyr Tyr Asn Glu Tyr Phe Val Phe Asp Phe
290                 295                 300

His Val Ser Pro Asp Val Met Phe Asp Lys Ile Ile Lys Ile Ser Val
305                 310                 315                 320

Ile His Ser Lys Asn Leu Leu Arg Ser Gly Thr Leu Val Gly Ser Phe
            325                 330                 335

Lys Met Asp Val Gly Thr Val Tyr Ser Gln Pro Glu His Gln Phe His
            340                 345                 350

His Lys Trp Ala Ile Leu Ser Asp Pro Asp Asp Ile Ser Ala Gly Leu
            355                 360                 365

Lys Gly Tyr Val Lys Cys Asp Val Ala Val Val Gly Lys Gly Asp Asn
            370                 375                 380

Ile Lys Thr Pro His Lys Ala Asn Glu Thr Asp Glu Asp Asp Ile Glu
385                 390                 395                 400

Gly Asn Leu Leu Leu Pro Glu Gly Val Pro Pro Glu Arg Gln Trp Ala
            405                 410                 415

Arg Phe Tyr Val Lys Ile Tyr Arg Ala Glu Gly Leu Pro Arg Met Asn
            420                 425                 430

Thr Ser Leu Met Ala Asn Val Lys Lys Ala Phe Ile Gly Glu Asn Lys
            435                 440                 445

Asp Leu Val Asp Pro Tyr Val Gln Val Phe Phe Ala Gly Gln Lys Gly
            450                 455                 460

Lys Thr Ser Val Gln Lys Ser Ser Tyr Glu Pro Leu Trp Asn Glu Gln
465                 470                 475                 480

Val Val Phe Thr Asp Leu Phe Pro Pro Leu Cys Lys Arg Met Lys Val
            485                 490                 495

Gln Ile Arg Asp Ser Asp Lys Val Asn Asp Val Ala Ile Gly Thr His
            500                 505                 510

Phe Ile Asp Leu Arg Lys Ile Ser Asn Asp Gly Asp Lys Gly Phe Leu
            515                 520                 525

Pro Thr Leu Gly Pro Ala Trp Val Asn Met Tyr Gly Ser Thr Arg Asn
            530                 535                 540

Tyr Thr Leu Leu Asp Glu His Gln Asp Leu Asn Glu Gly Leu Gly Glu
545                 550                 555                 560

Gly Val Ser Phe Arg Ala Arg Leu Met Leu Gly Leu Ala Val Glu Ile
            565                 570                 575

Leu Asp Thr Ser Asn Pro Glu Leu Thr Ser Ser Thr Glu Val Gln Val
            580                 585                 590

Glu Gln Ala Thr Pro Val Ser Glu Ser Cys Thr Gly Arg Met Glu Glu
            595                 600                 605

Phe Phe Leu Phe Gly Ala Phe Leu Glu Ala Ser Met Ile Asp Arg Lys
            610                 615                 620

Asn Gly Asp Lys Pro Ile Thr Phe Glu Val Thr Ile Gly Asn Tyr Gly
625                 630                 635                 640

Asn Glu Val Asp Gly Met Ser Arg Pro Leu Arg Pro Arg Pro Arg Lys
            645                 650                 655

Glu Pro Gly Asp Glu Glu Glu Val Asp Leu Ile Gln Asn Ser Ser Asp
            660                 665                 670
```

```
Asp Glu Gly Asp Glu Ala Gly Asp Leu Ala Ser Val Ser Thr Pro
            675                 680                 685

Pro Met Arg Pro Gln Ile Thr Asp Arg Asn Tyr Phe His Leu Pro Tyr
        690                 695                 700

Leu Glu Arg Lys Pro Cys Ile Tyr Ile Lys Ser Trp Trp Pro Asp Gln
705                 710                 715                 720

Arg Arg Arg Leu Tyr Asn Ala Asn Ile Met Asp His Ile Ala Asp Lys
                725                 730                 735

Leu Glu Glu Gly Leu Asn Asp Val Gln Met Ile Lys Thr Glu Lys
                740                 745                 750

Ser Tyr Pro Glu Arg Arg Leu Arg Gly Val Leu Glu Glu Leu Ser Cys
        755                 760                 765

Gly Cys His Arg Phe Leu Ser Leu Ser Asp Lys Asp Gln Gly Arg Ser
        770                 775                 780

Ser Arg Thr Arg Leu Asp Arg Glu Arg Leu Lys Ser Cys Met Arg Glu
785                 790                 795                 800

Leu Glu Ser Met Gly Gln Gln Ala Lys Ser Leu Arg Ala Gln Val Lys
                805                 810                 815

Arg His Thr Val Arg Asp Lys Leu Arg Ser Cys Gln Asn Phe Leu Gln
            820                 825                 830

Lys Leu Arg Phe Leu Ala Asp Glu Pro Gln His Ser Ile Pro Asp Val
        835                 840                 845

Phe Ile Trp Met Met Ser Asn Asn Lys Arg Ile Ala Tyr Ala Arg Val
        850                 855                 860

Pro Ser Lys Asp Leu Leu Phe Ser Ile Val Glu Glu Leu Gly Lys
865                 870                 875                 880

Asp Cys Ala Lys Val Lys Thr Leu Phe Leu Lys Leu Pro Gly Lys Arg
                885                 890                 895

Gly Phe Gly Ser Ala Gly Trp Thr Val Gln Ala Lys Leu Glu Leu Tyr
                900                 905                 910

Leu Trp Leu Gly Leu Ser Lys Gln Arg Lys Asp Phe Leu Cys Gly Leu
        915                 920                 925

Pro Cys Gly Phe Glu Glu Val Lys Ala Ala Gln Gly Leu Gly Leu His
        930                 935                 940

Ser Phe Pro Pro Ile Ser Leu Val Tyr Thr Lys Lys Gln Ala Phe Gln
945                 950                 955                 960

Leu Arg Ala His Met Tyr Gln Ala Arg Ser Leu Phe Ala Ala Asp Ser
                965                 970                 975

Ser Gly Leu Ser Asp Pro Phe Ala Arg Val Phe Phe Ile Asn Gln Ser
                980                 985                 990

Gln Cys Thr Glu Val Leu Asn Glu Thr Leu Cys Pro Thr Trp Asp Gln
        995                 1000                1005

Met Leu Val Phe Asp Asn Leu Glu Leu Tyr Gly Glu Ala His Glu
    1010                1015                1020

Leu Arg Asp Asp Pro Pro Ile Ile Val Ile Glu Ile Tyr Asp Gln
    1025                1030                1035

Asp Ser Met Gly Lys Ala Asp Phe Met Gly Arg Thr Phe Ala Lys
    1040                1045                1050

Pro Leu Val Lys Met Ala Asp Glu Ala Tyr Cys Pro Pro Arg Phe
    1055                1060                1065

Pro Pro Gln Leu Glu Tyr Tyr Gln Ile Tyr Arg Gly Ser Ala Thr
    1070                1075                1080

Ala Gly Asp Leu Leu Ala Ala Phe Glu Leu Leu Gln Ile Gly Pro
```

```
                  1085                1090                1095

Ser Gly Lys Ala Asp Leu Pro Pro Ile Asn Gly Pro Val Asp Met
        1100                1105                1110

Asp Arg Gly Pro Ile Met Pro Val Pro Val Gly Ile Arg Pro Val
        1115                1120                1125

Leu Ser Lys Tyr Arg Val Glu Val Leu Phe Trp Gly Leu Arg Asp
        1130                1135                1140

Leu Lys Arg Val Asn Leu Ala Gln Val Asp Arg Pro Arg Val Asp
        1145                1150                1155

Ile Glu Cys Ala Gly Lys Gly Val Gln Ser Ser Leu Ile His Asn
        1160                1165                1170

Tyr Lys Lys Asn Pro Asn Phe Asn Thr Leu Val Lys Trp Phe Glu
        1175                1180                1185

Val Asp Leu Pro Glu Asn Glu Leu Leu His Pro Pro Leu Asn Ile
        1190                1195                1200

Arg Val Val Asp Cys Arg Ala Phe Gly Arg Tyr Thr Leu Val Gly
        1205                1210                1215

Ser His Ala Val Ser Ser Leu Arg Arg Phe Ile Tyr Arg Pro Pro
        1220                1225                1230

Asp Arg Ser Ala Pro Asn Trp Asn Thr Thr Val Arg Leu Leu Arg
        1235                1240                1245

Gly Cys His Arg Leu Arg Asn Gly Gly Pro Ser Ser Arg Pro Thr
        1250                1255                1260

Gly Glu Val Val Val Ser Met Glu Pro Glu Pro Val Lys Lys
        1265                1270                1275

Leu Glu Thr Met Val Lys Leu Asp Ala Thr Ser Asp Ala Val Val
        1280                1285                1290

Lys Val Asp Val Ala Glu Asp Glu Lys Glu Arg Lys Lys Lys Lys
        1295                1300                1305

Lys Lys Gly Pro Ser Glu Glu Pro Glu Glu Glu Pro Asp Glu
        1310                1315                1320

Ser Met Leu Asp Trp Trp Ser Lys Tyr Phe Ala Ser Ile Asp Thr
        1325                1330                1335

Met Lys Glu Gln Leu Arg Gln His Glu Thr Ser Gly Thr Asp Leu
        1340                1345                1350

Glu Glu Lys Glu Glu Met Glu Ser Ala Glu Gly Leu Lys Gly Pro
        1355                1360                1365

Met Lys Ser Lys Glu Lys Ser Arg Ala Ala Lys Glu Glu Lys Lys
        1370                1375                1380

Lys Lys Asn Gln Ser Pro Gly Pro Gly Gln Ser Glu Ala Pro
        1385                1390                1395

Glu Lys Lys Lys Ala Lys Ile Asp Glu Leu Lys Val Tyr Pro Lys
        1400                1405                1410

Glu Leu Glu Ser Glu Phe Asp Ser Phe Glu Asp Trp Leu His Thr
        1415                1420                1425

Phe Asn Leu Leu Arg Gly Lys Thr Gly Asp Asp Glu Asp Gly Ser
        1430                1435                1440

Thr Glu Glu Glu Arg Ile Val Gly Arg Phe Lys Gly Ser Leu Cys
        1445                1450                1455

Val Tyr Lys Val Pro Leu Pro Glu Asp Val Ser Arg Glu Ala Gly
        1460                1465                1470

Tyr Asp Pro Thr Tyr Gly Met Phe Gln Gly Ile Pro Ser Asn Asp
        1475                1480                1485
```

```
Pro Ile Asn Val Leu Val Arg Ile Tyr Val Val Arg Ala Thr Asp
    1490                1495                1500

Leu His Pro Ala Asp Ile Asn Gly Lys Ala Asp Pro Tyr Ile Ala
    1505                1510                1515

Ile Lys Leu Gly Lys Thr Asp Ile Arg Asp Lys Glu Asn Tyr Ile
    1520                1525                1530

Ser Lys Gln Leu Asn Pro Val Phe Gly Lys Ser Phe Asp Ile Glu
    1535                1540                1545

Ala Ser Phe Pro Met Glu Ser Met Leu Thr Val Ala Val Tyr Asp
    1550                1555                1560

Trp Asp Leu Val Gly Thr Asp Asp Leu Ile Gly Glu Thr Lys Ile
    1565                1570                1575

Asp Leu Glu Asn Arg Phe Tyr Ser Lys His Arg Ala Thr Cys Gly
    1580                1585                1590

Ile Ala Gln Thr Tyr Ser Ile His Gly Tyr Asn Ile Trp Arg Asp
    1595                1600                1605

Pro Met Lys Pro Ser Gln Ile Leu Thr Arg Leu Cys Lys Glu Gly
    1610                1615                1620

Lys Val Asp Gly Pro His Phe Gly Pro His Gly Arg Val Arg Val
    1625                1630                1635

Ala Asn Arg Val Phe Thr Gly Pro Ser Glu Ile Glu Asp Glu Asn
    1640                1645                1650

Gly Gln Arg Lys Pro Thr Asp Glu His Val Ala Leu Ser Ala Leu
    1655                1660                1665

Arg His Trp Glu Asp Ile Pro Arg Val Gly Cys Arg Leu Val Pro
    1670                1675                1680

Glu His Val Glu Thr Arg Pro Leu Leu Asn Pro Asp Lys Pro Gly
    1685                1690                1695

Ile Glu Gln Gly Arg Leu Glu Leu Trp Val Asp Met Phe Pro Met
    1700                1705                1710

Asp Met Pro Ala Pro Gly Thr Pro Leu Asp Ile Ser Pro Arg Lys
    1715                1720                1725

Pro Lys Lys Tyr Glu Leu Arg Val Ile Val Trp Asn Thr Asp Glu
    1730                1735                1740

Val Val Leu Glu Asp Asp Asp Phe Phe Thr Gly Glu Lys Ser Ser
    1745                1750                1755

Asp Ile Phe Val Arg Gly Trp Leu Lys Gly Gln Gln Glu Asp Lys
    1760                1765                1770

Gln Asp Thr Asp Val His Tyr His Ser Leu Thr Gly Glu Gly Asn
    1775                1780                1785

Phe Asn Trp Arg Tyr Leu Phe Pro Phe Asp Tyr Leu Ala Ala Glu
    1790                1795                1800

Glu Lys Ile Val Met Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
    1835                1840                1845

Leu Asp Leu Asn Arg Phe Pro Arg Gly Ala Lys Thr Ala Lys Gln
    1850                1855                1860

Cys Thr Met Glu Met Ala Thr Gly Glu Val Asp Val Pro Leu Val
    1865                1870                1875
```

Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
    1895                1900                1905

Ala Glu Leu His Leu Leu Thr Ala Glu Glu Ala Glu Lys Asn Pro
    1910                1915                1920

Val Gly Leu Ala Arg Asn Glu Pro Asp Pro Leu Glu Lys Pro Asn
    1925                1930                1935

Arg Pro Asp Thr Ser Phe Ile Trp Phe Leu Asn Pro Leu Lys Ser
    1940                1945                1950

Ala Arg Tyr Phe Leu Trp His Thr Tyr Arg Trp Leu Leu Leu Lys
    1955                1960                1965

Phe Leu Leu Leu Phe Leu Leu Leu Leu Phe Ala Leu Phe Leu
    1970                1975                1980

Tyr Ser Leu Pro Gly Tyr Leu Ala Lys Lys Ile Leu Gly Ala
    1985                1990                1995

<210> SEQ ID NO 7
<211> LENGTH: 1977
<212> TYPE: PRT
<213> ORGANISM: Mus musculus

<400> SEQUENCE: 7

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Gly Val Ala Asp Phe Asp Glu Thr Phe
        35                  40                  45

Arg Trp Pro Val Ala Ser Ser Ile Asp Arg Asn Glu Val Leu Glu Ile
    50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
                100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Arg Ala Gly Arg Ser Val Phe Ser
                165                 170                 175

Ala Met Lys Leu Gly Lys Thr Arg Ser His Lys Glu Glu Pro Gln Arg
        180                 185                 190

Gln Asp Glu Pro Ala Val Leu Glu Met Glu Asp Leu Asp His Leu Ala
    195                 200                 205

Ile Gln Leu Gly Asp Gly Leu Asp Pro Asp Ser Val Ser Leu Ala Ser
    210                 215                 220

Val Thr Ala Leu Thr Ser Asn Val Ser Asn Lys Arg Ser Lys Pro Asp
225                 230                 235                 240

Ile Lys Met Glu Pro Ser Ala Gly Arg Pro Met Asp Tyr Gln Val Ser
                245                 250                 255

-continued

Ile Thr Val Ile Glu Ala Arg Gln Leu Val Gly Leu Asn Met Asp Pro
            260                 265                 270

Val Val Cys Val Glu Val Gly Asp Lys Lys Tyr Thr Ser Met Lys
        275                 280                 285

Glu Ser Thr Asn Cys Pro Tyr Tyr Asn Glu Tyr Phe Val Phe Asp Phe
290                 295                 300

His Val Ser Pro Asp Val Met Phe Asp Lys Ile Ile Lys Ile Ser Val
305                 310                 315                 320

Ile His Ser Lys Asn Leu Leu Arg Ser Gly Thr Leu Val Gly Ser Phe
            325                 330                 335

Lys Met Asp Val Gly Thr Val Tyr Ser Gln Pro Glu His Gln Phe His
            340                 345                 350

His Lys Trp Ala Ile Leu Ser Asp Pro Asp Asp Ile Ser Ala Gly Leu
            355                 360                 365

Lys Gly Tyr Val Lys Cys Asp Val Ala Val Gly Lys Gly Asp Asn
        370                 375                 380

Ile Lys Thr Pro His Lys Ala Asn Glu Thr Asp Glu Asp Ile Glu
385                 390                 395                 400

Gly Asn Leu Leu Leu Pro Glu Gly Val Pro Pro Glu Arg Gln Trp Ala
            405                 410                 415

Arg Phe Tyr Val Lys Ile Tyr Arg Ala Glu Gly Leu Pro Arg Met Asn
            420                 425                 430

Thr Ser Leu Met Ala Asn Val Lys Lys Ala Phe Ile Gly Glu Asn Lys
            435                 440                 445

Asp Leu Val Asp Pro Tyr Val Gln Val Phe Phe Ala Gly Gln Lys Gly
        450                 455                 460

Lys Thr Ser Val Gln Lys Ser Ser Tyr Glu Pro Leu Trp Asn Glu Gln
465                 470                 475                 480

Val Val Phe Thr Asp Leu Phe Pro Pro Leu Cys Lys Arg Met Lys Val
            485                 490                 495

Gln Ile Arg Asp Ser Asp Lys Val Asn Asp Val Ala Ile Gly Thr His
            500                 505                 510

Phe Ile Asp Leu Arg Lys Ile Ser Asn Asp Gly Asp Lys Gly Phe Leu
            515                 520                 525

Pro Thr Leu Gly Pro Ala Trp Val Asn Met Tyr Gly Ser Thr Arg Asn
            530                 535                 540

Tyr Thr Leu Leu Asp Glu His Gln Asp Leu Asn Glu Gly Leu Gly Glu
545                 550                 555                 560

Gly Val Ser Phe Arg Ala Arg Leu Met Leu Gly Leu Ala Val Glu Ile
            565                 570                 575

Leu Asp Thr Ser Asn Pro Glu Leu Thr Ser Ser Thr Glu Val Gln Val
            580                 585                 590

Glu Gln Ala Thr Pro Val Ser Glu Ser Cys Thr Gly Arg Met Glu Glu
            595                 600                 605

Phe Phe Leu Phe Gly Ala Phe Leu Glu Ala Ser Met Ile Asp Arg Lys
610                 615                 620

Asn Gly Asp Lys Pro Ile Thr Phe Glu Val Thr Ile Gly Asn Tyr Gly
625                 630                 635                 640

Asn Glu Val Asp Gly Met Ser Arg Pro Leu Arg Pro Arg Pro Arg Lys
            645                 650                 655

Glu Pro Gly Asp Glu Glu Glu Val Asp Leu Ile Gln Asn Ser Ser Asp
            660                 665                 670

```
Asp Glu Gly Asp Glu Ala Gly Asp Leu Ala Ser Val Ser Ser Thr Pro
            675                 680                 685

Pro Met Arg Pro Gln Ile Thr Asp Arg Asn Tyr Phe His Leu Pro Tyr
690                 695                 700

Leu Glu Arg Lys Pro Cys Ile Tyr Ile Lys Ser Trp Trp Pro Asp Gln
705                 710                 715                 720

Arg Arg Arg Leu Tyr Asn Ala Asn Ile Met Asp His Ile Ala Asp Lys
                725                 730                 735

Leu Glu Glu Gly Leu Asn Asp Val Gln Glu Met Ile Lys Thr Glu Lys
            740                 745                 750

Ser Tyr Pro Glu Arg Arg Leu Arg Gly Val Leu Glu Glu Leu Ser Cys
        755                 760                 765

Gly Cys His Arg Phe Leu Ser Leu Ser Asp Lys Asp Gln Gly Arg Ser
770                 775                 780

Ser Arg Thr Arg Leu Asp Arg Glu Arg Leu Lys Ser Cys Met Arg Glu
785                 790                 795                 800

Leu Glu Ser Met Gly Gln Gln Ala Lys Ser Leu Arg Ala Gln Val Lys
                805                 810                 815

Arg His Thr Val Arg Asp Lys Leu Arg Ser Cys Gln Asn Phe Leu Gln
            820                 825                 830

Lys Leu Arg Phe Leu Ala Asp Glu Pro Gln His Ser Ile Pro Asp Val
        835                 840                 845

Phe Ile Trp Met Met Ser Asn Asn Lys Arg Ile Ala Tyr Ala Arg Val
    850                 855                 860

Pro Ser Lys Asp Leu Leu Phe Ser Ile Val Glu Glu Leu Gly Lys
865                 870                 875                 880

Asp Cys Ala Lys Val Lys Thr Leu Phe Leu Lys Leu Pro Gly Lys Arg
                885                 890                 895

Gly Phe Gly Ser Ala Gly Trp Thr Val Gln Ala Lys Leu Glu Leu Tyr
            900                 905                 910

Leu Trp Leu Gly Leu Ser Lys Gln Arg Lys Asp Phe Leu Cys Gly Leu
    915                 920                 925

Pro Cys Gly Phe Glu Glu Val Lys Ala Ala Gln Gly Leu Gly Leu His
930                 935                 940

Ser Phe Pro Pro Ile Ser Leu Val Tyr Thr Lys Lys Gln Ala Phe Gln
945                 950                 955                 960

Leu Arg Ala His Met Tyr Gln Ala Arg Ser Leu Phe Ala Ala Asp Ser
                965                 970                 975

Ser Gly Leu Ser Asp Pro Phe Ala Arg Val Phe Phe Ile Asn Gln Ser
            980                 985                 990

Gln Cys Thr Glu Val Leu Asn Glu Thr Leu Cys Pro Thr Trp Asp Gln
        995                 1000                1005

Met Leu Val Phe Asp Asn Leu Glu Leu Tyr Gly Glu Ala His Glu
    1010                1015                1020

Leu Arg Asp Asp Pro Pro Ile Ile Val Ile Glu Ile Tyr Asp Gln
    1025                1030                1035

Asp Ser Met Gly Lys Ala Asp Phe Met Gly Arg Thr Phe Ala Lys
    1040                1045                1050

Pro Leu Val Lys Met Ala Asp Glu Ala Tyr Cys Pro Pro Arg Phe
    1055                1060                1065

Pro Pro Gln Leu Glu Tyr Tyr Gln Ile Tyr Arg Gly Ser Ala Thr
    1070                1075                1080

Ala Gly Asp Leu Leu Ala Ala Phe Glu Leu Leu Gln Ile Gly Pro
```

-continued

```
                1085                1090                1095
Ser Gly Lys Ala Asp Leu Pro Pro Ile Asn Gly Pro Val Asp Met
            1100                1105                1110
Asp Arg Gly Pro Ile Met Pro Val Pro Val Gly Ile Arg Pro Val
            1115                1120                1125
Leu Ser Lys Tyr Arg Val Glu Val Leu Phe Trp Gly Leu Arg Asp
            1130                1135                1140
Leu Lys Arg Val Asn Leu Ala Gln Val Asp Arg Pro Arg Val Asp
            1145                1150                1155
Ile Glu Cys Ala Gly Lys Gly Val Gln Ser Ser Leu Ile His Asn
            1160                1165                1170
Tyr Lys Lys Asn Pro Asn Phe Asn Thr Leu Val Lys Trp Phe Glu
            1175                1180                1185
Val Asp Leu Pro Glu Asn Glu Leu Leu His Pro Pro Leu Asn Ile
            1190                1195                1200
Arg Val Val Asp Cys Arg Ala Phe Gly Arg Tyr Thr Leu Val Gly
            1205                1210                1215
Ser His Ala Val Ser Ser Leu Arg Arg Phe Ile Tyr Arg Pro Pro
            1220                1225                1230
Asp Arg Ser Ala Pro Asn Trp Asn Thr Thr Gly Glu Val Val Val
            1235                1240                1245
Ser Met Glu Pro Glu Glu Pro Val Lys Lys Leu Glu Thr Met Val
            1250                1255                1260
Lys Leu Asp Ala Thr Ser Asp Ala Val Val Lys Val Asp Val Ala
            1265                1270                1275
Glu Asp Glu Lys Glu Arg Lys Lys Lys Lys Lys Gly Pro Ser
            1280                1285                1290
Glu Glu Pro Glu Glu Glu Pro Asp Glu Ser Met Leu Asp Trp
            1295                1300                1305
Trp Ser Lys Tyr Phe Ala Ser Ile Asp Thr Met Lys Glu Gln Leu
            1310                1315                1320
Arg Gln His Glu Thr Ser Gly Thr Asp Leu Glu Glu Lys Glu Glu
            1325                1330                1335
Met Glu Ser Ala Glu Gly Leu Lys Gly Pro Met Lys Ser Lys Glu
            1340                1345                1350
Lys Ser Arg Ala Ala Lys Glu Glu Lys Lys Lys Asn Gln Ser
            1355                1360                1365
Pro Gly Pro Gly Gln Gly Ser Glu Ala Pro Glu Lys Lys Lys Ala
            1370                1375                1380
Lys Ile Asp Glu Leu Lys Val Tyr Pro Lys Glu Leu Glu Ser Glu
            1385                1390                1395
Phe Asp Ser Phe Glu Asp Trp Leu His Thr Phe Asn Leu Leu Arg
            1400                1405                1410
Gly Lys Thr Gly Asp Asp Glu Asp Gly Ser Thr Glu Glu Glu Arg
            1415                1420                1425
Ile Val Gly Arg Phe Lys Gly Ser Leu Cys Val Tyr Lys Val Pro
            1430                1435                1440
Leu Pro Glu Asp Val Ser Arg Glu Ala Gly Tyr Asp Pro Thr Tyr
            1445                1450                1455
Gly Met Phe Gln Gly Ile Pro Ser Asn Asp Pro Ile Asn Val Leu
            1460                1465                1470
Val Arg Ile Tyr Val Val Arg Ala Thr Asp Leu His Pro Ala Asp
            1475                1480                1485
```

```
Ile Asn Gly Lys Ala Asp Pro Tyr Ile Ala Ile Lys Leu Gly Lys
    1490                1495                1500

Thr Asp Ile Arg Asp Lys Glu Asn Tyr Ile Ser Lys Gln Leu Asn
    1505                1510                1515

Pro Val Phe Gly Lys Ser Phe Asp Ile Glu Ala Ser Phe Pro Met
    1520                1525                1530

Glu Ser Met Leu Thr Val Ala Val Tyr Asp Trp Asp Leu Val Gly
    1535                1540                1545

Thr Asp Asp Leu Ile Gly Glu Thr Lys Ile Asp Leu Glu Asn Arg
    1550                1555                1560

Phe Tyr Ser Lys His Arg Ala Thr Cys Gly Ile Ala Gln Thr Tyr
    1565                1570                1575

Ser Ile His Gly Tyr Asn Ile Trp Arg Asp Pro Met Lys Pro Ser
    1580                1585                1590

Gln Ile Leu Thr Arg Leu Cys Lys Glu Gly Lys Val Asp Gly Pro
    1595                1600                1605

His Phe Gly Pro His Gly Arg Val Arg Val Ala Asn Arg Val Phe
    1610                1615                1620

Thr Gly Pro Ser Glu Ile Glu Asp Glu Asn Gly Gln Arg Lys Pro
    1625                1630                1635

Thr Asp Glu His Val Ala Leu Ser Ala Leu Arg His Trp Glu Asp
    1640                1645                1650

Ile Pro Arg Val Gly Cys Arg Leu Val Pro Glu His Val Glu Thr
    1655                1660                1665

Arg Pro Leu Leu Asn Pro Asp Lys Pro Gly Ile Glu Gln Gly Arg
    1670                1675                1680

Leu Glu Leu Trp Val Asp Met Phe Pro Met Asp Met Pro Ala Pro
    1685                1690                1695

Gly Thr Pro Leu Asp Ile Ser Pro Arg Lys Pro Lys Lys Tyr Glu
    1700                1705                1710

Leu Arg Val Ile Val Trp Asn Thr Asp Glu Val Val Leu Glu Asp
    1715                1720                1725

Asp Asp Phe Phe Thr Gly Glu Lys Ser Ser Asp Ile Phe Val Arg
    1730                1735                1740

Gly Trp Leu Lys Gly Gln Gln Glu Asp Lys Gln Asp Thr Asp Val
    1745                1750                1755

His Tyr His Ser Leu Thr Gly Glu Gly Asn Phe Asn Trp Arg Tyr
    1760                1765                1770

Leu Phe Pro Phe Asp Tyr Leu Ala Ala Glu Glu Lys Ile Val Met
    1775                1780                1785

Ser Lys Lys Glu Ser Met Phe Ser Trp Asp Glu Thr Glu Tyr Lys
    1790                1795                1800

Ile Pro Ala Arg Leu Thr Leu Gln Ile Trp Asp Ala Asp His Phe
    1805                1810                1815

Ser Ala Asp Asp Phe Leu Gly Ala Ile Glu Leu Asp Leu Asn Arg
    1820                1825                1830

Phe Pro Arg Gly Ala Lys Thr Ala Lys Gln Cys Thr Met Glu Met
    1835                1840                1845

Ala Thr Gly Glu Val Asp Val Pro Leu Val Ser Ile Phe Lys Gln
    1850                1855                1860

Lys Arg Val Lys Gly Trp Trp Pro Leu Leu Ala Arg Asn Glu Asn
    1865                1870                1875
```

```
Asp Glu Phe Glu Leu Thr Gly Lys Val Glu Ala Glu Leu His Leu
    1880            1885                1890

Leu Thr Ala Glu Glu Ala Glu Lys Asn Pro Val Gly Leu Ala Arg
    1895            1900                1905

Asn Glu Pro Asp Pro Leu Glu Lys Pro Asn Arg Pro Asp Thr Ser
    1910            1915                1920

Phe Ile Trp Phe Leu Asn Pro Leu Lys Ser Ala Arg Tyr Phe Leu
    1925            1930                1935

Trp His Thr Tyr Arg Trp Leu Leu Lys Phe Leu Leu Leu Phe
    1940            1945                1950

Leu Leu Leu Leu Leu Phe Ala Leu Phe Leu Tyr Ser Leu Pro Gly
    1955            1960                1965

Tyr Leu Ala Lys Lys Ile Leu Gly Ala
    1970            1975

<210> SEQ ID NO 8
<211> LENGTH: 1992
<212> TYPE: PRT
<213> ORGANISM: Mus musculus

<400> SEQUENCE: 8

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Gly Val Ala Asp Phe Asp Glu Thr Phe
        35                  40                  45

Arg Trp Pro Val Ala Ser Ser Ile Asp Arg Asn Glu Val Leu Glu Ile
    50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Ser Lys Gly Arg Glu Lys Thr Lys
                165                 170                 175

Gly Gly Arg Asp Gly Glu His Lys Ala Gly Arg Ser Val Phe Ser Ala
            180                 185                 190

Met Lys Leu Gly Lys Thr Arg Ser His Lys Glu Glu Pro Gln Arg Gln
        195                 200                 205

Asp Glu Pro Ala Val Leu Glu Met Glu Asp Leu Asp His Leu Ala Ile
    210                 215                 220

Gln Leu Gly Asp Gly Leu Asp Pro Asp Ser Val Ser Leu Ala Ser Val
225                 230                 235                 240

Thr Ala Leu Thr Ser Asn Val Ser Asn Lys Arg Ser Lys Pro Asp Ile
                245                 250                 255

Lys Met Glu Pro Ser Ala Gly Arg Pro Met Asp Tyr Gln Val Ser Ile
            260                 265                 270
```

```
Thr Val Ile Glu Ala Arg Gln Leu Val Gly Leu Asn Met Asp Pro Val
    275                 280                 285
Val Cys Val Glu Val Gly Asp Asp Lys Lys Tyr Thr Ser Met Lys Glu
    290                 295                 300
Ser Thr Asn Cys Pro Tyr Tyr Asn Glu Tyr Phe Val Phe Asp Phe His
305                 310                 315                 320
Val Ser Pro Asp Val Met Phe Asp Lys Ile Ile Lys Ile Ser Val Ile
                325                 330                 335
His Ser Lys Asn Leu Leu Arg Ser Gly Thr Leu Val Gly Ser Phe Lys
                340                 345                 350
Met Asp Val Gly Thr Val Tyr Ser Gln Pro Glu His Gln Phe His His
                355                 360                 365
Lys Trp Ala Ile Leu Ser Asp Pro Asp Asp Ile Ser Ala Gly Leu Lys
    370                 375                 380
Gly Tyr Val Lys Cys Asp Val Ala Val Val Gly Lys Gly Asp Asn Ile
385                 390                 395                 400
Lys Thr Pro His Lys Ala Asn Glu Thr Asp Glu Asp Ile Glu Gly
                405                 410                 415
Asn Leu Leu Leu Pro Glu Gly Val Pro Pro Glu Arg Gln Trp Ala Arg
                420                 425                 430
Phe Tyr Val Lys Ile Tyr Arg Ala Glu Gly Leu Pro Arg Met Asn Thr
    435                 440                 445
Ser Leu Met Ala Asn Val Lys Lys Ala Phe Ile Gly Glu Asn Lys Asp
    450                 455                 460
Leu Val Asp Pro Tyr Val Gln Val Phe Phe Ala Gly Gln Lys Gly Lys
465                 470                 475                 480
Thr Ser Val Gln Lys Ser Ser Tyr Glu Pro Leu Trp Asn Glu Gln Val
                485                 490                 495
Val Phe Thr Asp Leu Phe Pro Pro Leu Cys Lys Arg Met Lys Val Gln
                500                 505                 510
Ile Arg Asp Ser Asp Lys Val Asn Asp Val Ala Ile Gly Thr His Phe
    515                 520                 525
Ile Asp Leu Arg Lys Ile Ser Asn Asp Gly Asp Lys Gly Phe Leu Pro
    530                 535                 540
Thr Leu Gly Pro Ala Trp Val Asn Met Tyr Gly Ser Thr Arg Asn Tyr
545                 550                 555                 560
Thr Leu Leu Asp Glu His Gln Asp Leu Asn Glu Gly Leu Gly Glu Gly
                565                 570                 575
Val Ser Phe Arg Ala Arg Leu Met Leu Gly Leu Ala Val Glu Ile Leu
                580                 585                 590
Asp Thr Ser Asn Pro Glu Leu Thr Ser Thr Glu Val Gln Val Glu
    595                 600                 605
Gln Ala Thr Pro Val Ser Glu Ser Cys Thr Gly Arg Met Glu Glu Phe
    610                 615                 620
Phe Leu Phe Gly Ala Phe Leu Glu Ala Ser Met Ile Asp Arg Lys Asn
625                 630                 635                 640
Gly Asp Lys Pro Ile Thr Phe Glu Val Thr Ile Gly Asn Tyr Gly Asn
                645                 650                 655
Glu Val Asp Gly Met Ser Arg Pro Leu Arg Pro Arg Pro Arg Lys Glu
                660                 665                 670
Pro Gly Asp Glu Glu Glu Val Asp Leu Ile Gln Asn Ser Ser Asp Asp
    675                 680                 685
```

```
Glu Gly Asp Glu Ala Gly Asp Leu Ala Ser Val Ser Ser Thr Pro Pro
    690             695                 700

Met Arg Pro Gln Ile Thr Asp Arg Asn Tyr Phe His Leu Pro Tyr Leu
705                 710                 715                 720

Glu Arg Lys Pro Cys Ile Tyr Ile Lys Ser Trp Trp Pro Asp Gln Arg
                725                 730                 735

Arg Arg Leu Tyr Asn Ala Asn Ile Met Asp His Ile Ala Asp Lys Leu
            740                 745                 750

Glu Glu Gly Leu Asn Asp Val Gln Glu Met Ile Lys Thr Glu Lys Ser
                755                 760                 765

Tyr Pro Glu Arg Arg Leu Arg Gly Val Leu Glu Glu Leu Ser Cys Gly
770                 775                 780

Cys His Arg Phe Leu Ser Leu Ser Asp Lys Asp Gln Gly Arg Ser Ser
785                 790                 795                 800

Arg Thr Arg Leu Asp Arg Glu Arg Leu Lys Ser Cys Met Arg Glu Leu
                805                 810                 815

Glu Ser Met Gly Gln Gln Ala Lys Ser Leu Arg Ala Gln Val Lys Arg
            820                 825                 830

His Thr Val Arg Asp Lys Leu Arg Ser Cys Gln Asn Phe Leu Gln Lys
            835                 840                 845

Leu Arg Phe Leu Ala Asp Glu Pro Gln His Ser Ile Pro Asp Val Phe
850                 855                 860

Ile Trp Met Met Ser Asn Asn Lys Arg Ile Ala Tyr Ala Arg Val Pro
865                 870                 875                 880

Ser Lys Asp Leu Leu Phe Ser Ile Val Glu Glu Glu Leu Gly Lys Asp
                885                 890                 895

Cys Ala Lys Val Lys Thr Leu Phe Leu Lys Leu Pro Gly Lys Arg Gly
                900                 905                 910

Phe Gly Ser Ala Gly Trp Thr Val Gln Ala Lys Leu Glu Leu Tyr Leu
            915                 920                 925

Trp Leu Gly Leu Ser Lys Gln Arg Lys Asp Phe Leu Cys Gly Leu Pro
930                 935                 940

Cys Gly Phe Glu Glu Val Lys Ala Ala Gln Gly Leu Gly Leu His Ser
945                 950                 955                 960

Phe Pro Pro Ile Ser Leu Val Tyr Thr Lys Lys Gln Ala Phe Gln Leu
                965                 970                 975

Arg Ala His Met Tyr Gln Ala Arg Ser Leu Phe Ala Ala Asp Ser Ser
            980                 985                 990

Gly Leu Ser Asp Pro Phe Ala Arg Val Phe Phe Ile Asn Gln Ser Gln
            995                 1000                1005

Cys Thr Glu Val Leu Asn Glu Thr Leu Cys Pro Thr Trp Asp Gln
    1010            1015                1020

Met Leu Val Phe Asp Asn Leu Glu Leu Tyr Gly Glu Ala His Glu
    1025            1030                1035

Leu Arg Asp Asp Pro Pro Ile Ile Val Ile Glu Ile Tyr Asp Gln
    1040            1045                1050

Asp Ser Met Gly Lys Ala Asp Phe Met Gly Arg Thr Phe Ala Lys
    1055            1060                1065

Pro Leu Val Lys Met Ala Asp Glu Ala Tyr Cys Pro Pro Arg Phe
    1070            1075                1080

Pro Pro Gln Leu Glu Tyr Tyr Gln Ile Tyr Arg Gly Ser Ala Thr
    1085            1090                1095

Ala Gly Asp Leu Leu Ala Ala Phe Glu Leu Leu Gln Ile Gly Pro
```

-continued

|   |   |   | 1100 |   |   |   | 1105 |   |   |   | 1110 |   |   |   |
|---|---|---|---|---|---|---|---|---|---|---|---|---|---|---|

Ser Gly Lys Ala Asp Leu Pro Pro Ile Asn Gly Pro Val Asp Met
    1115                1120                1125

Asp Arg Gly Pro Ile Met Pro Val Pro Val Gly Ile Arg Pro Val
    1130                1135                1140

Leu Ser Lys Tyr Arg Val Glu Val Leu Phe Trp Gly Leu Arg Asp
    1145                1150                1155

Leu Lys Arg Val Asn Leu Ala Gln Val Asp Arg Pro Arg Val Asp
    1160                1165                1170

Ile Glu Cys Ala Gly Lys Gly Val Gln Ser Ser Leu Ile His Asn
    1175                1180                1185

Tyr Lys Lys Asn Pro Asn Phe Asn Thr Leu Val Lys Trp Phe Glu
    1190                1195                1200

Val Asp Leu Pro Glu Asn Glu Leu Leu His Pro Pro Leu Asn Ile
    1205                1210                1215

Arg Val Val Asp Cys Arg Ala Phe Gly Arg Tyr Thr Leu Val Gly
    1220                1225                1230

Ser His Ala Val Ser Ser Leu Arg Arg Phe Ile Tyr Arg Pro Pro
    1235                1240                1245

Asp Arg Ser Ala Pro Asn Trp Asn Thr Thr Gly Glu Val Val Val
    1250                1255                1260

Ser Met Glu Pro Glu Glu Pro Val Lys Lys Leu Glu Thr Met Val
    1265                1270                1275

Lys Leu Asp Ala Thr Ser Asp Ala Val Val Lys Val Asp Val Ala
    1280                1285                1290

Glu Asp Glu Lys Glu Arg Lys Lys Lys Lys Lys Lys Gly Pro Ser
    1295                1300                1305

Glu Glu Pro Glu Glu Glu Pro Asp Glu Ser Met Leu Asp Trp
    1310                1315                1320

Trp Ser Lys Tyr Phe Ala Ser Ile Asp Thr Met Lys Glu Gln Leu
    1325                1330                1335

Arg Gln His Glu Thr Ser Gly Thr Asp Leu Glu Glu Lys Glu Glu
    1340                1345                1350

Met Glu Ser Ala Glu Gly Leu Lys Gly Pro Met Lys Ser Lys Glu
    1355                1360                1365

Lys Ser Arg Ala Ala Lys Glu Glu Lys Lys Lys Asn Gln Ser
    1370                1375                1380

Pro Gly Pro Gly Gln Gly Ser Glu Ala Pro Glu Lys Lys Lys Ala
    1385                1390                1395

Lys Ile Asp Glu Leu Lys Val Tyr Pro Lys Glu Leu Glu Ser Glu
    1400                1405                1410

Phe Asp Ser Phe Glu Asp Trp Leu His Thr Phe Asn Leu Leu Arg
    1415                1420                1425

Gly Lys Thr Gly Asp Asp Glu Asp Gly Ser Thr Glu Glu Glu Arg
    1430                1435                1440

Ile Val Gly Arg Phe Lys Gly Ser Leu Cys Val Tyr Lys Val Pro
    1445                1450                1455

Leu Pro Glu Asp Val Ser Arg Glu Ala Gly Tyr Asp Pro Thr Tyr
    1460                1465                1470

Gly Met Phe Gln Gly Ile Pro Ser Asn Asp Pro Ile Asn Val Leu
    1475                1480                1485

Val Arg Ile Tyr Val Val Arg Ala Thr Asp Leu His Pro Ala Asp
    1490                1495                1500

-continued

Ile Asn Gly Lys Ala Asp Pro Tyr Ile Ala Ile Lys Leu Gly Lys
1505                1510                1515

Thr Asp Ile Arg Asp Lys Glu Asn Tyr Ile Ser Lys Gln Leu Asn
1520                1525                1530

Pro Val Phe Gly Lys Ser Phe Asp Ile Glu Ala Ser Phe Pro Met
1535                1540                1545

Glu Ser Met Leu Thr Val Ala Val Tyr Asp Trp Asp Leu Val Gly
1550                1555                1560

Thr Asp Asp Leu Ile Gly Glu Thr Lys Ile Asp Leu Glu Asn Arg
1565                1570                1575

Phe Tyr Ser Lys His Arg Ala Thr Cys Gly Ile Ala Gln Thr Tyr
1580                1585                1590

Ser Ile His Gly Tyr Asn Ile Trp Arg Asp Pro Met Lys Pro Ser
1595                1600                1605

Gln Ile Leu Thr Arg Leu Cys Lys Glu Gly Lys Val Asp Gly Pro
1610                1615                1620

His Phe Gly Pro His Gly Arg Val Arg Val Ala Asn Arg Val Phe
1625                1630                1635

Thr Gly Pro Ser Glu Ile Glu Asp Glu Asn Gly Gln Arg Lys Pro
1640                1645                1650

Thr Asp Glu His Val Ala Leu Ser Ala Leu Arg His Trp Glu Asp
1655                1660                1665

Ile Pro Arg Val Gly Cys Arg Leu Val Pro Glu His Val Glu Thr
1670                1675                1680

Arg Pro Leu Leu Asn Pro Asp Lys Pro Gly Ile Glu Gln Gly Arg
1685                1690                1695

Leu Glu Leu Trp Val Asp Met Phe Pro Met Asp Met Pro Ala Pro
1700                1705                1710

Gly Thr Pro Leu Asp Ile Ser Pro Arg Lys Pro Lys Lys Tyr Glu
1715                1720                1725

Leu Arg Val Ile Val Trp Asn Thr Asp Glu Val Val Leu Glu Asp
1730                1735                1740

Asp Asp Phe Phe Thr Gly Glu Lys Ser Ser Asp Ile Phe Val Arg
1745                1750                1755

Gly Trp Leu Lys Gly Gln Gln Glu Asp Lys Gln Asp Thr Asp Val
1760                1765                1770

His Tyr His Ser Leu Thr Gly Glu Gly Asn Phe Asn Trp Arg Tyr
1775                1780                1785

Leu Phe Pro Phe Asp Tyr Leu Ala Ala Glu Glu Lys Ile Val Met
1790                1795                1800

Ser Lys Lys Glu Ser Met Phe Ser Trp Asp Glu Thr Glu Tyr Lys
1805                1810                1815

Ile Pro Ala Arg Leu Thr Leu Gln Ile Trp Asp Ala Asp His Phe
1820                1825                1830

Ser Ala Asp Asp Phe Leu Gly Ala Ile Glu Leu Asp Leu Asn Arg
1835                1840                1845

Phe Pro Arg Gly Ala Lys Thr Ala Lys Gln Cys Thr Met Glu Met
1850                1855                1860

Ala Thr Gly Glu Val Asp Val Pro Leu Val Ser Ile Phe Lys Gln
1865                1870                1875

Lys Arg Val Lys Gly Trp Trp Pro Leu Leu Ala Arg Asn Glu Asn
1880                1885                1890

```
Asp Glu Phe Glu Leu Thr Gly Lys Val Glu Ala Glu Leu His Leu
    1895                1900                1905

Leu Thr Ala Glu Glu Ala Glu Lys Asn Pro Val Gly Leu Ala Arg
    1910                1915                1920

Asn Glu Pro Asp Pro Leu Glu Lys Pro Asn Arg Pro Asp Thr Ala
    1925                1930                1935

Phe Val Trp Phe Leu Asn Pro Leu Lys Ser Ile Lys Tyr Leu Ile
    1940                1945                1950

Cys Thr Arg Tyr Lys Trp Leu Ile Ile Lys Ile Val Leu Ala Leu
    1955                1960                1965

Leu Gly Leu Leu Met Leu Ala Leu Phe Leu Tyr Ser Leu Pro Gly
    1970                1975                1980

Tyr Met Val Lys Lys Leu Leu Gly Ala
    1985                1990

<210> SEQ ID NO 9
<211> LENGTH: 1977
<212> TYPE: PRT
<213> ORGANISM: Mus musculus

<400> SEQUENCE: 9

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Gly Val Ala Asp Phe Asp Glu Thr Phe
        35                  40                  45

Arg Trp Pro Val Ala Ser Ser Ile Asp Arg Asn Glu Val Leu Glu Ile
    50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Arg Ala Gly Arg Ser Val Phe Ser
                165                 170                 175

Ala Met Lys Leu Gly Lys Thr Arg Ser His Lys Glu Glu Pro Gln Arg
            180                 185                 190

Gln Asp Glu Pro Ala Val Leu Glu Met Glu Asp Leu Asp His Leu Ala
        195                 200                 205

Ile Gln Leu Gly Asp Gly Leu Asp Pro Asp Ser Val Ser Leu Ala Ser
    210                 215                 220

Val Thr Ala Leu Thr Ser Asn Val Ser Asn Lys Arg Ser Lys Pro Asp
225                 230                 235                 240

Ile Lys Met Glu Pro Ser Ala Gly Arg Pro Met Asp Tyr Gln Val Ser
                245                 250                 255

Ile Thr Val Ile Glu Ala Arg Gln Leu Val Gly Leu Asn Met Asp Pro
            260                 265                 270
```

```
Val Val Cys Val Glu Val Gly Asp Asp Lys Lys Tyr Thr Ser Met Lys
            275                 280                 285

Glu Ser Thr Asn Cys Pro Tyr Tyr Asn Glu Tyr Phe Val Phe Asp Phe
        290                 295                 300

His Val Ser Pro Asp Val Met Phe Asp Lys Ile Ile Lys Ile Ser Val
305                 310                 315                 320

Ile His Ser Lys Asn Leu Leu Arg Ser Gly Thr Leu Val Gly Ser Phe
                325                 330                 335

Lys Met Asp Val Gly Thr Val Tyr Ser Gln Pro Glu His Gln Phe His
                340                 345                 350

His Lys Trp Ala Ile Leu Ser Asp Pro Asp Ile Ser Ala Gly Leu
                355                 360                 365

Lys Gly Tyr Val Lys Cys Asp Val Ala Val Val Gly Lys Gly Asp Asn
            370                 375                 380

Ile Lys Thr Pro His Lys Ala Asn Glu Thr Asp Glu Asp Ile Glu
385                 390                 395                 400

Gly Asn Leu Leu Leu Pro Glu Gly Val Pro Pro Glu Arg Gln Trp Ala
                    405                 410                 415

Arg Phe Tyr Val Lys Ile Tyr Arg Ala Glu Gly Leu Pro Arg Met Asn
                420                 425                 430

Thr Ser Leu Met Ala Asn Val Lys Lys Ala Phe Ile Gly Glu Asn Lys
                435                 440                 445

Asp Leu Val Asp Pro Tyr Val Gln Val Phe Phe Ala Gly Gln Lys Gly
        450                 455                 460

Lys Thr Ser Val Gln Lys Ser Ser Tyr Glu Pro Leu Trp Asn Glu Gln
465                 470                 475                 480

Val Val Phe Thr Asp Leu Phe Pro Pro Leu Cys Lys Arg Met Lys Val
                485                 490                 495

Gln Ile Arg Asp Ser Asp Lys Val Asn Asp Val Ala Ile Gly Thr His
            500                 505                 510

Phe Ile Asp Leu Arg Lys Ile Ser Asn Asp Gly Asp Lys Gly Phe Leu
        515                 520                 525

Pro Thr Leu Gly Pro Ala Trp Val Asn Met Tyr Gly Ser Thr Arg Asn
            530                 535                 540

Tyr Thr Leu Leu Asp Glu His Gln Asp Leu Asn Glu Gly Leu Gly Glu
545                 550                 555                 560

Gly Val Ser Phe Arg Ala Arg Leu Met Leu Gly Leu Ala Val Glu Ile
                565                 570                 575

Leu Asp Thr Ser Asn Pro Glu Leu Thr Ser Ser Thr Glu Val Gln Val
            580                 585                 590

Glu Gln Ala Thr Pro Val Ser Glu Ser Cys Thr Gly Arg Met Glu Glu
            595                 600                 605

Phe Phe Leu Phe Gly Ala Phe Leu Glu Ala Ser Met Ile Asp Arg Lys
        610                 615                 620

Asn Gly Asp Lys Pro Ile Thr Phe Glu Val Thr Ile Gly Asn Tyr Gly
625                 630                 635                 640

Asn Glu Val Asp Gly Met Ser Arg Pro Leu Arg Pro Arg Pro Arg Lys
                645                 650                 655

Glu Pro Gly Asp Glu Glu Val Asp Leu Ile Gln Asn Ser Ser Asp
            660                 665                 670

Asp Glu Gly Asp Glu Ala Gly Asp Leu Ala Ser Val Ser Ser Thr Pro
            675                 680                 685
```

```
Pro Met Arg Pro Gln Ile Thr Asp Arg Asn Tyr Phe His Leu Pro Tyr
690                 695                 700

Leu Glu Arg Lys Pro Cys Ile Tyr Ile Lys Ser Trp Trp Pro Asp Gln
705                 710                 715                 720

Arg Arg Arg Leu Tyr Asn Ala Asn Ile Met Asp His Ile Ala Asp Lys
            725                 730                 735

Leu Glu Glu Gly Leu Asn Asp Val Gln Glu Met Ile Lys Thr Glu Lys
            740                 745                 750

Ser Tyr Pro Glu Arg Arg Leu Arg Gly Val Leu Glu Leu Ser Cys
            755                 760                 765

Gly Cys His Arg Phe Leu Ser Leu Ser Asp Lys Asp Gln Gly Arg Ser
770                 775                 780

Ser Arg Thr Arg Leu Asp Arg Glu Arg Leu Lys Ser Cys Met Arg Glu
785                 790                 795                 800

Leu Glu Ser Met Gly Gln Gln Ala Lys Ser Leu Arg Ala Gln Val Lys
                805                 810                 815

Arg His Thr Val Arg Asp Lys Leu Arg Ser Cys Gln Asn Phe Leu Gln
            820                 825                 830

Lys Leu Arg Phe Leu Ala Asp Glu Pro Gln His Ser Ile Pro Asp Val
            835                 840                 845

Phe Ile Trp Met Met Ser Asn Asn Lys Arg Ile Ala Tyr Ala Arg Val
850                 855                 860

Pro Ser Lys Asp Leu Leu Phe Ser Ile Val Glu Glu Leu Gly Lys
865                 870                 875                 880

Asp Cys Ala Lys Val Lys Thr Leu Phe Leu Lys Leu Pro Gly Lys Arg
                885                 890                 895

Gly Phe Gly Ser Ala Gly Trp Thr Val Gln Ala Lys Leu Glu Leu Tyr
            900                 905                 910

Leu Trp Leu Gly Leu Ser Lys Gln Arg Lys Asp Phe Leu Cys Gly Leu
            915                 920                 925

Pro Cys Gly Phe Glu Glu Val Lys Ala Ala Gln Gly Leu Gly Leu His
930                 935                 940

Ser Phe Pro Pro Ile Ser Leu Val Tyr Thr Lys Lys Gln Ala Phe Gln
945                 950                 955                 960

Leu Arg Ala His Met Tyr Gln Ala Arg Ser Leu Phe Ala Ala Asp Ser
                965                 970                 975

Ser Gly Leu Ser Asp Pro Phe Ala Arg Val Phe Ile Asn Gln Ser
            980                 985                 990

Gln Cys Thr Glu Val Leu Asn Glu Thr Leu Cys Pro Thr Trp Asp Gln
            995                 1000                1005

Met Leu Val Phe Asp Asn Leu Glu Leu Tyr Gly Glu Ala His Glu
    1010                1015                1020

Leu Arg Asp Asp Pro Pro Ile Ile Val Ile Glu Ile Tyr Asp Gln
    1025                1030                1035

Asp Ser Met Gly Lys Ala Asp Phe Met Gly Arg Thr Phe Ala Lys
    1040                1045                1050

Pro Leu Val Lys Met Ala Asp Glu Ala Tyr Cys Pro Pro Arg Phe
    1055                1060                1065

Pro Pro Gln Leu Glu Tyr Tyr Gln Ile Tyr Arg Gly Ser Ala Thr
    1070                1075                1080

Ala Gly Asp Leu Leu Ala Ala Phe Glu Leu Leu Gln Ile Gly Pro
    1085                1090                1095

Ser Gly Lys Ala Asp Leu Pro Pro Ile Asn Gly Pro Val Asp Met
```

-continued

```
            1100                1105                1110

Asp Arg Gly Pro Ile Met Pro Val Pro Val Gly Ile Arg Pro Val
            1115                1120                1125

Leu Ser Lys Tyr Arg Val Glu Val Leu Phe Trp Gly Leu Arg Asp
            1130                1135                1140

Leu Lys Arg Val Asn Leu Ala Gln Val Asp Arg Pro Arg Val Asp
            1145                1150                1155

Ile Glu Cys Ala Gly Lys Gly Val Gln Ser Ser Leu Ile His Asn
            1160                1165                1170

Tyr Lys Lys Asn Pro Asn Phe Asn Thr Leu Val Lys Trp Phe Glu
            1175                1180                1185

Val Asp Leu Pro Glu Asn Glu Leu Leu His Pro Pro Leu Asn Ile
            1190                1195                1200

Arg Val Val Asp Cys Arg Ala Phe Gly Arg Tyr Thr Leu Val Gly
            1205                1210                1215

Ser His Ala Val Ser Ser Leu Arg Arg Phe Ile Tyr Arg Pro Pro
            1220                1225                1230

Asp Arg Ser Ala Pro Asn Trp Asn Thr Thr Gly Glu Val Val Val
            1235                1240                1245

Ser Met Glu Pro Glu Glu Pro Val Lys Lys Leu Glu Thr Met Val
            1250                1255                1260

Lys Leu Asp Ala Thr Ser Asp Ala Val Val Lys Val Asp Val Ala
            1265                1270                1275

Glu Asp Glu Lys Glu Arg Lys Lys Lys Lys Lys Gly Pro Ser
            1280                1285                1290

Glu Glu Pro Glu Glu Glu Pro Asp Glu Ser Met Leu Asp Trp
            1295                1300                1305

Trp Ser Lys Tyr Phe Ala Ser Ile Asp Thr Met Lys Glu Gln Leu
            1310                1315                1320

Arg Gln His Glu Thr Ser Gly Thr Asp Leu Glu Glu Lys Glu Glu
            1325                1330                1335

Met Glu Ser Ala Glu Gly Leu Lys Gly Pro Met Lys Ser Lys Glu
            1340                1345                1350

Lys Ser Arg Ala Ala Lys Glu Glu Lys Lys Lys Asn Gln Ser
            1355                1360                1365

Pro Gly Pro Gly Gln Gly Ser Glu Ala Pro Glu Lys Lys Lys Ala
            1370                1375                1380

Lys Ile Asp Glu Leu Lys Val Tyr Pro Lys Glu Leu Glu Ser Glu
            1385                1390                1395

Phe Asp Ser Phe Glu Asp Trp Leu His Thr Phe Asn Leu Leu Arg
            1400                1405                1410

Gly Lys Thr Gly Asp Asp Asp Gly Ser Thr Glu Glu Arg
            1415                1420                1425

Ile Val Gly Arg Phe Lys Gly Ser Leu Cys Val Tyr Lys Val Pro
            1430                1435                1440

Leu Pro Glu Asp Val Ser Arg Glu Ala Gly Tyr Asp Pro Thr Tyr
            1445                1450                1455

Gly Met Phe Gln Gly Ile Pro Ser Asn Asp Pro Ile Asn Val Leu
            1460                1465                1470

Val Arg Ile Tyr Val Val Arg Ala Thr Asp Leu His Pro Ala Asp
            1475                1480                1485

Ile Asn Gly Lys Ala Asp Pro Tyr Ile Ala Ile Lys Leu Gly Lys
            1490                1495                1500
```

```
Thr Asp Ile Arg Asp Lys Glu Asn Tyr Ile Ser Lys Gln Leu Asn
1505                1510                1515

Pro Val Phe Gly Lys Ser Phe Asp Ile Glu Ala Ser Phe Pro Met
1520                1525                1530

Glu Ser Met Leu Thr Val Ala Val Tyr Asp Trp Asp Leu Val Gly
1535                1540                1545

Thr Asp Asp Leu Ile Gly Glu Thr Lys Ile Asp Leu Glu Asn Arg
1550                1555                1560

Phe Tyr Ser Lys His Arg Ala Thr Cys Gly Ile Ala Gln Thr Tyr
1565                1570                1575

Ser Ile His Gly Tyr Asn Ile Trp Arg Asp Pro Met Lys Pro Ser
1580                1585                1590

Gln Ile Leu Thr Arg Leu Cys Lys Glu Gly Lys Val Asp Gly Pro
1595                1600                1605

His Phe Gly Pro His Gly Arg Val Arg Val Ala Asn Arg Val Phe
1610                1615                1620

Thr Gly Pro Ser Glu Ile Glu Asp Glu Asn Gly Gln Arg Lys Pro
1625                1630                1635

Thr Asp Glu His Val Ala Leu Ser Ala Leu Arg His Trp Glu Asp
1640                1645                1650

Ile Pro Arg Val Gly Cys Arg Leu Val Pro Glu His Val Glu Thr
1655                1660                1665

Arg Pro Leu Leu Asn Pro Asp Lys Pro Gly Ile Glu Gln Gly Arg
1670                1675                1680

Leu Glu Leu Trp Val Asp Met Phe Pro Met Asp Met Pro Ala Pro
1685                1690                1695

Gly Thr Pro Leu Asp Ile Ser Pro Arg Lys Pro Lys Lys Tyr Glu
1700                1705                1710

Leu Arg Val Ile Val Trp Asn Thr Asp Glu Val Val Leu Glu Asp
1715                1720                1725

Asp Asp Phe Phe Thr Gly Glu Lys Ser Ser Asp Ile Phe Val Arg
1730                1735                1740

Gly Trp Leu Lys Gly Gln Gln Glu Asp Lys Gln Asp Thr Asp Val
1745                1750                1755

His Tyr His Ser Leu Thr Gly Glu Gly Asn Phe Asn Trp Arg Tyr
1760                1765                1770

Leu Phe Pro Phe Asp Tyr Leu Ala Ala Glu Lys Ile Val Met
1775                1780                1785

Ser Lys Lys Glu Ser Met Phe Ser Trp Asp Glu Thr Glu Tyr Lys
1790                1795                1800

Ile Pro Ala Arg Leu Thr Leu Gln Ile Trp Asp Ala Asp His Phe
1805                1810                1815

Ser Ala Asp Asp Phe Leu Gly Ala Ile Glu Leu Asp Leu Asn Arg
1820                1825                1830

Phe Pro Arg Gly Ala Lys Thr Ala Lys Gln Cys Thr Met Glu Met
1835                1840                1845

Ala Thr Gly Glu Val Asp Val Pro Leu Val Ser Ile Phe Lys Gln
1850                1855                1860

Lys Arg Val Lys Gly Trp Trp Pro Leu Leu Ala Arg Asn Glu Asn
1865                1870                1875

Asp Glu Phe Glu Leu Thr Gly Lys Val Glu Ala Glu Leu His Leu
1880                1885                1890
```

| | | | | | | | | | | | |
|---|---|---|---|---|---|---|---|---|---|---|---|
| Leu | Thr | Ala | Glu | Glu | Ala | Glu | Lys | Asn | Pro | Val | Gly | Leu | Ala | Arg |
| | 1895 | | | | 1900 | | | | 1905 | | |

Leu Thr Ala Glu Glu Ala Glu Lys Asn Pro Val Gly Leu Ala Arg
        1895                1900                1905

Asn Glu Pro Asp Pro Leu Glu Lys Pro Asn Arg Pro Asp Thr Ala
    1910                1915                1920

Phe Val Trp Phe Leu Asn Pro Leu Lys Ser Ile Lys Tyr Leu Ile
    1925                1930                1935

Cys Thr Arg Tyr Lys Trp Leu Ile Ile Lys Ile Val Leu Ala Leu
    1940                1945                1950

Leu Gly Leu Leu Met Leu Ala Leu Phe Leu Tyr Ser Leu Pro Gly
    1955                1960                1965

Tyr Met Val Lys Lys Leu Leu Gly Ala
    1970                1975

<210> SEQ ID NO 10
<211> LENGTH: 7171
<212> TYPE: DNA
<213> ORGANISM: Homo sapiens

<400> SEQUENCE: 10

| | |
|---|---|
| atcggagggg ggtcgggagg aggaggagga ggcagcggca gagaagagag aggcgtgtga | 60 |
| gccgtgctcc accggctagc tccttcccgc tgctcctgcc tggcagtgcc aggcagccca | 120 |
| caccagcatg gccttgctca tccacctcaa gacagtctcg gagctgcggg gcaggggcga | 180 |
| ccggatcgcc aaagtgactt ccgagggca atccttctac tctcgggtcc tggagaactg | 240 |
| tgaggatgtg gctgactttg atgagacatt tcggtggccg gtggccagca gcatcgacag | 300 |
| aaatgagatg ctggagattc aggttttcaa ctacagcaaa gtcttcagca acaagctcat | 360 |
| cgggaccttc cgcatggtgc tgcagaaggt ggtagaggag agccatgtgg aggtgactga | 420 |
| cacgctgatt gatgacaaca atgctatcat caagaccagc ctgtgcgtgg aggtccggta | 480 |
| tcaggccact gacggcacag tgggctcctg gacgatggg gacttcctgg agatgagtc | 540 |
| tcttcaagag gaagagaagg acagccaaga cacggatgga ctgctcccag gctcccggcc | 600 |
| cagctcccgg cccccaggag agaagagctt ccggagagcc gggaggagcg tgttctccgc | 660 |
| catgaagctc ggcaaaaaacc ggtctcacaa ggaggagccc caaagaccag atgaaccggc | 720 |
| ggtgctggag atggaagacc ttgaccatct ggccattcgg ctaggagatg gactggatcc | 780 |
| cgactcggtg tctctagcct cagtcacagc tctcaccact aatgtctcca acaagcgatc | 840 |
| taagccagac attaagatgg agccaagtgc tgggcggccc atggattacc aggtcagcat | 900 |
| cacggtgatc gaggcccggc agctggtggg cttgaacatg gaccctgtgg tgtgcgtgga | 960 |
| ggtgggtgac gacaagaagt acacatccat gaaggagtcc actaactgcc cctattacaa | 1020 |
| cgagtacttc gtcttcgact tccatgtctc tccggatgtc atgtttgaca agatcatcaa | 1080 |
| gatttcggtg attcactcca gaacctgct gcgcagtggc accctggtgg ctccttcaa | 1140 |
| aatggacgtg ggaaccgtgt actcgcagcc agagcaccag ttccatcaca gtgggccat | 1200 |
| cctgtctgac cccgatgaca tctcctcggg gctgaagggc tacgtgaagt gtgacgttgc | 1260 |
| cgtggtgggc aaaggggaca acatcaagac gccccacaag gccaatgaga ccgacgaaga | 1320 |
| tgacattgag gggaacttgc tgctccccga ggggtgccc ccgaacgcc agtgggcccg | 1380 |
| gttctatgtg aaaatttacc gagcagaggg gctgccccgt atgaacacaa gcctcatggc | 1440 |
| caatgtaaag aaggctttca tcggtgaaaa caaggacctc gtggacccct acgtgcaagt | 1500 |
| cttctttgct ggccagaagg gcaagacttc agtgcagaag agcagctatg agcccctgtg | 1560 |
| gaatgagcag gtcgtcttta cagacctctt cccccccactc tgcaaacgca tgaaggtgca | 1620 |

-continued

```
gatccgagac tcggacaagg tcaacgacgt ggccatcggc acccacttca ttgacctgcg    1680
caagatttct aatgacggag acaaaggctt cctgcccaca ctgggcccag cctgggtgaa    1740
catgtacggc tccacacgta actacacgct gctggatgag catcaggacc tgaacgaggg    1800
cctgggggag ggtgtgtcct tccgggcccg gctcctgctg ggcctggctg tggagatcgt    1860
agacacctcc aaccctgagc tcaccagctc cacagaggtg caggtggagc aggccacgcc    1920
catctcggag agctgtgcag gtaaaatgga agaattcttt ctctttggag ccttcctgga    1980
ggcctcaatg atcgaccgga gaaacggaga caagcccatc acctttgagg tcaccatagg    2040
caactatggg aacgaagttg atggcctgtc ccggccccag cggcctcggc cccggaagga    2100
gccgggggat gaggaagaag tagacctgat tcagaacgca agtgatgacg aggccggtga    2160 tgccgggac ctggcctcag tctcctccac tccaccaatg cggccccagg tcaccgacag    2220
gaactacttc catctgccct acctggagcg aaagccctgc atctacatca gagctggtg    2280 gccgaccag cgccgccgcc tctacaatgc caacatcatg gaccacattg ccgacaagct    2340
ggaagaaggc ctgaacgaca tacaggagat gatcaaaacg gagaagtcct accctgagcg    2400
tcgcctgcgg ggcgtcctgg aggagctgag ctgtggctgc tgccgcttcc tctccctcgc    2460
tgacaaggac cagggccact catcccgcac caggcttgac cgggagcgcc tcaagtcctg    2520
catgagggag ctggaaaaca tggggcagca ggccaggatg ctgcgggccc aggtgaagcg    2580
gcacacggtg cgggacaagc tgaggctgtg ccagaacttc ctgcagaagc tgcgcttcct    2640
ggcggacgag ccccagcaca gcattcccga catcttcatc tggatgatga gcaacaacaa    2700
gcgtgtcgcc tatgcccgtg tgccctccaa ggacctgctc ttctccatcg tggaggagga    2760
gactggcaag gactgcgcca aggtcaagac gctcttcctt aagctgccag ggaagcgggg    2820
cttcggctcg gcaggctgga cagtgcaggc caaggtggag ctgtacctgt ggctgggcct    2880
cagcaaacag cgcaaggagt tcctgtgcgg cctgccctgt ggcttccagg aggtcaaggc    2940
agcccagggc ctgggcctgc atgccttccc accgtcagc ctggtctaca ccaagaagca    3000
ggcgttccag ctccgagcgc acatgtacca ggcccgcagc ctctttgccg ccgacagcag    3060
cggactctca gaccccttg cccgcgtctt cttcatcaat cagagtcagt gcacagaggt    3120
gctgaatgag accctgtgtc ccacctggga ccagatgctg gtgttcgaca acctggagct    3180
ctatggtgaa gctcatgagc tgagggacga tccgcccatc attgtcattg aaatctatga    3240
ccaggattcc atgggcaaag ctgacttcat gggccggacc ttcgccaaac ccctggtgaa    3300
gatggcagac gaggcgtact gcccacccg cttcccacct cagctcgagt actaccagat    3360
ctaccgtggc aacgccacag ctggagacct gctggcggcc ttcgagctgc tgcagattgg    3420
accagcaggg aaggctgacc tgcccccat caatggcccg gtgacgtgg accgaggtcc    3480 catcatgccc gtgcccatgg gcatccggcc cgtgctcagc aagtaccgag tggaggtgct    3540 gttctgggc ctacgggacc taaagcgggt gaacctggcc caggtggacc ggccacgggt    3600
ggacatcgag tgtgcaggga aggggtgca gtcgtccctg atccacaatt ataagaagaa    3660
ccccaacttc aacaccctcg tcaagtggtt tgaagtggac ctcccagaga acgagctgct    3720
gcacccgccc ttgaacatcc gtgtggtgga ctgccggca ttcggtcgct acacactggt    3780
gggctcccat gccgtcagct ccctgcgacg cttcatctac cggcccccag accgctcggc    3840
ccccagctgg aacaccacgg tcaggcttct ccggcgctgc cgtgtgctgt gcaatggggg    3900
ctcctcctct cactccacag gggaggttgt ggtgactatg gagccagagg tacccatcaa    3960
```

```
gaaactggag accatggtga agctggacgc gacttctgaa gctgttgtca aggtggatgt    4020
ggctgaggag gagaaggaga agaagaagaa gaagaagggc actgcggagg agccagagga    4080
ggaggagcca gacgagagca tgctggactg gtggtccaag tactttgcct ccattgacac    4140
catgaaggag caacttcgac aacaagagcc ctctggaatt gacttggagg agaaggagga    4200
agtggacaat accgagggcc tgaaggggtc aatgaagggc aaggagaagg caagggctgc    4260
caaagaggag aagaagaaga aaactcagag ctctggctct ggccagggt ccgaggcccc     4320
cgagaagaag aaacccaaga ttgatgagct taaggtatac cccaaagagc tggagtccga    4380
gtttgataac tttgaggact ggctgcacac tttcaacttg cttcggggca agaccgggga    4440
tgatgaggat ggctccaccg aggaggagcg cattgtggga cgcttcaagg gctccctctg    4500
cgtgtacaaa gtgccactcc cagaggacgt gtcccgggaa gccggctacg actccaccta    4560
cggcatgttc cagggcatcc cgagcaatga ccccatcaat gtgctggtcc gagtctatgt    4620
ggtccgggcc acggacctgc accctgctga catcaacggc aaagctgacc cctacatcgc    4680
catccggcta ggcaagactg acatccgcga caaggagaac tacatctcca agcagctcaa    4740
ccctgtctt gggaagtcct ttgacatcga ggcctccttc cccatggaat ccatgctgac     4800
ggtggctgtg tatgactggg acctggtggg cactgatgac ctcattgggg aaaccaagat    4860
cgacctggag aaccgcttct acagcaagca ccgcgccacc tgcggcatcg cccagaccta    4920
ctccacacat ggctacaata tctggcggga ccccatgaag cccagccaga tcctgacccg    4980
cctctgcaaa gacggcaaag tggacggccc ccactttggg ccccctggga gagtgaaggt    5040
ggccaaccgc gtcttcactg ggccctctga gattgaggac gagaacggtc agaggaagcc    5100
cacagacgag catgtggcgc tgttggccct gaggcactgg gaggacatcc ccgcgcagg     5160
ctgccgcctg gtgccagagc atgtggagac gaggccgctg ctcaacccccg acaagccggg    5220
catcgagcag ggccgcctgg agctgtgggt ggacatgttc cccatggaca tgccagcccc    5280
tgggacgcct ctggacatct cacctcggaa gcccaagaag tacgagctgc gggtcatcat    5340
ctggaacaca gatgaggtgg tcttggagga cgacgacttc ttcacagggg agaagtccag    5400
tgacatcttc gtgaggggt ggctgaaggg ccagcaggag gacaagcagg acacagacgt     5460
ccactaccac tccctcactg gcgagggcaa cttcaactgg cgctacctgt tcccctcga    5520
ctacctggcg gcgaggagga agatcgtcat ctccaagaag gagtccatgt tctcctggga    5580
cgagaccgag tacaagatcc ccgcgcggct caccctgcag atctgggatg cggaccactt    5640
ctccgctgac gacttcctgg gggccatcga gctggacctg aaccggttcc gcgggggcgc    5700
aaagacagcc aagcagtgca ccatggagat ggccaccggg gaggtggacg tgcccctcgt    5760
gtccatcttc aagcaaaagc gcgtcaaagg ctggtggccc ctcctggccc gcaatgagaa    5820
cgatgagttt gagctcacgg gcaaggtgga ggctgagctg catttactga cagcagagga    5880
ggcagagaag aacccagtgg gcctggcccg caatgaacct gaccccctag agaaacccaa    5940
ccggcccgac acgagcttca tctggttcct gaaccctctc aagtcggctc gctacttctt    6000
gtggcacacg tatcgctggc tgctcctcaa actgttgctg ctcctgctgc tgctcctcct    6060
cctcgccctt ttcctctact ctgtgcctgg ctacctggtc aagaaaatcc tcggggcctg    6120
agcccagtgg cctcctggcc ggcccgacac ggccttcgtc tggttcctca accctctcaa    6180
gtccatcaag tacctcatct gcacccggta caagtggctc atcatcaaga tcgtgctggc    6240
gctgttgggg ctgctcatgt tggggctctt cctctacagc ctccctggct acatggtcaa    6300
aaagctcctt ggggcatgaa ggccgccagc tcccgccagc cgctccccag ccctgccgca    6360
```

```
tttcctttca gtggcttgga ctctttccca tctccctgg ggagcctgag gagcccagcg    6420
tccactcttc atgccttggg ccgagcctgc ctcctgcttg cggggccgc ctgtcctcac    6480 tgccccaggc tgcggcttgc ccagtcccgc ccctctgacc cctgcctgtg ggctggggag    6540
ccttggatgg ggtggggacc tggaatgggt ctctcttgcc ccacctggct gaggcgccac    6600
ccttcttcag gcccaggctc cagaggaaga ctcctgaaac cctccccagg tcttccaagt    6660
acaggattga agctttagtg aaattaacca aggaccatgg gtcagtgccc agggcttaa    6720 aaagaatgaa cgagcaaaag gtatccccgc cgtgaccct gcagatagca ccggtctttg    6780
atccgcagca ggggccagac cctgcccaca agtcccagcg cggctgcttc tgccactgct    6840
gggctccact tggctcctct cacttcccag ggggtcgcct gtcctgcctg tgggtttcca    6900
tggcttccca gagctccctc tgccccagcc agcgcctcca gcccagctg aggagctgtg    6960 agaagcagca gagggactc cccatcccgg gcacccctg tcctcccacc cctgccccct    7020
tgcccttcca gccctttcag ctgcagctgg gagctggccc gtcaagtgct gcccctgcct    7080
gtgtctgggt ttctgttggc tgttttcttt tcttgagtg gtgatttttc tctaaataaa    7140
agaagtcaag cactgaaaaa aaaaaaaaa a                                    7171
```

<210> SEQ ID NO 11
<211> LENGTH: 4969
<212> TYPE: DNA
<213> ORGANISM: Homo sapiens

<400> SEQUENCE: 11

```
ccgtgagttc tgcccaggcc ctgtgagctc accagagcca cagactcaca gcccagaggt      60
ggcttcttcc ttcaggaact gaagaacccc catgaacacc aacatctcca ggttctgaga    120
acagaacctg ggaaattgat gacttcctca tgatgaccga tactcaggat ggccctagcg    180
agagctccca gatcatgagg aagaaggcct gaacgacata caggagatga tcaaaacgga    240
gaagtcctac cctgagcgtc gcctgcgggg cgtcctggag gagctgagct gtggctgctg    300
ccgcttcctc tccctcgctg acaaggacca gggccactca tcccgcacca ggcttgaccg    360
ggagcgcctc aagtcctgca tgagggagct ggaaaacatg gggcagcagg ccaggatgct    420
gcgggcccag gtgaagcggc acacggtgcg ggacaagctg aggctgtgcc agaacttcct    480
gcagaagctg cgcttcctgg cggacgagcc ccagcacagc attcccgaca tcttcatctg    540
gatgatgagc aacaacaagc gtgtcgccta tgcccgtgtg ccctccaagg acctgctctt    600
ctccatcgtg gaggaggaga ctggcaagga ctgcgccaag gtcaagacgc tcttccttaa    660
gctgccaggg aagcggggct tcggctcggc aggctggaca gtgcaggcca aggtggagct    720
gtacctgtgt ctgggcctca gcaaacagcg caaggagttc ctgtgcggcc tgccctgtgg    780
cttccaggag gtcaaggcag cccagggcct gggcctgcat gccttcccac ccgtcagcct    840
ggtctacacc aagaagcagg cgttccagct ccgagcgcac atgtaccagg cccgcagcct    900
ctttgccgcc gacagcagcg gactctcaga ccccttgcc cgcgtcttct tcatcaatca    960
gagtcagtgc acagaggtgc tgaatgagac cctgtgtccc acctgggacc agatgctggt    1020
gttcgacaac ctggagctct atggtgaagc tcatagctg agggacgatc cgcccatcat    1080
tgtcattgaa atctatgacc aggattccat gggcaaagct gacttcatgg gccggacctt    1140
cgccaaaccc ctggtgaaga tggcagacga ggcgtactgc ccaccccgct tcccacctca    1200
gctcgagtac taccagatct accgtggcaa cgccacagct ggagacctgc tggcggcctt    1260
```

-continued

```
cgagctgctg cagattggac cagcagggaa ggctgacctg cccccccatca atggcccggt    1320
ggacgtggac cgaggtccca tcatgcccgt gcccatgggc atccggcccg tgctcagcaa    1380
gtaccgagtg gaggtgctgt tctggggcct acgggaccta aagcgggtga acctggccca    1440
ggtggaccgg ccacgggtgg acatcgagtg tgcagggaag ggggtgcagt cgtccctgat    1500
ccacaattat aagaagaacc ccaacttcaa caccctcgtc aagtggtttg aagtggacct    1560
cccagagaac gagctgctgc acccgccctt gaacatccgt gtggtggact gccgggcctt    1620
cggtcgctac acactggtgg ctcccatgc cgtcagctcc ctgcgacgct tcatctaccg    1680
gcccccagac cgctcggccc ccagctgaaa caccacgggg gaggttgtgg tgactatgga    1740
gccagaggta cccatcaaga aactggagac catggtgaag ctggacgcga cttctgaagc    1800
tgttgtcaag gtggatgtgg ctgaggagga aaggagaag aagaagaaga gaaagggcac    1860
tgcggaggag ccagaggagg aggagccaga cgagagcatg ctggactggt ggtccaagta    1920
ctttgcctcc attgcacca tgaaggagca acttcgacaa caagagccct ctggaattga    1980
cttggaggag aaggaggaag tggacaatac cgagggcctg aaggggtcaa tgaagggcaa    2040
ggagaaggca agggctgcca agaggagaaa gaagaagaaa actcagagct ggctctgg    2100
ccaggggtcc gaggcccccg agaagaagaa acccaagatt gatgagctta aggtatcccc    2160
caaagagctg gagtccgagt ttgataactt tgaggactgg ctgcacactt tcaacttgct    2220
tcggggcaag accggggatg atgaggatgg ctccaccgag gaggagcgca ttgtgggacg    2280
cttcaagggc tccctctgcg tgtacaaagt gccactccca gaggacgtgt cccgggaagc    2340
cggctacgac tccacctacg gcatgttcca gggcatcccg agcaatgacc ccatcaatgt    2400
gctggtccga gtctatgtgg tccgggccac ggacctgcac cctgctgaca tcaacggcaa    2460
agctgacccc tacatcgcca tccggctagg caagactgac atccgcgaca aggagaacta    2520
catctccaag cagctcaacc ctgtctttgg gaagtccttt gacatcgagg cctccttccc    2580
catgaatccc atgctgacgg tggctgtgta tgactgggac ctggtgggca ctgatgacct    2640
cattggggaa accaagatcg acctggagaa ccgcttctac agcaagcacc gcgccacctg    2700
cggcatcgcc cagacctact ccacacatgg ctacaatatc tggcgggacc ccatgaagcc    2760
cagccagatc ctgacccgcc tctgcaaaga cggcaaagtg gacggccccc actttgggcc    2820
ccctgggaga gtgaaggtgg ccaaccgcgt cttcactggg ccctctgaga ttgaggacga    2880
gaacggtcag aggaagccca cagacgagca tgtggcgctg ttggccctga ggcactggga    2940
ggacatcccc cgcgcaggct gccgcctggt gccagagcat gtggagacga ggccgctgct    3000
caacccccgac aagccgggca tcgagcaggg ccgcctggag ctgtgggtgg acatgttccc    3060
catggacatg ccagccctg ggacgcctct ggacatctca cctcggaagc caagaagta    3120
cgagctgcgg gtcatcatct ggaacacaga tgaggtggtc ttggaggacg acgacttctt    3180
cacaggggag aagtccagtg acatcttcgt gaggggggtgg ctgaagggcc agcaggagga    3240
caagcaggac acagacgtcc actaccactc cctcactggc gagggcaact tcaactggcg    3300
ctacctgttc cccttcgact acctggcggc ggaggagaag atcgtcatct ccaagaagga    3360
gtccatgttc tcctgggacg agaccgagta caagatcccc gcgcggctca ccctgcagat    3420
ctgggatgcg gaccacttct ccgctgacga cttcctgggg gccatcgagc tggacctgaa    3480
ccggttcccg cggggcgcaa agacagccaa gcagtgcacc atggagatgg ccaccgggga    3540
ggtgacgtg cccctcgtgt ccatcttcaa gcaaaagcgc gtcaaaggct ggtggccct    3600
cctggcccgc aatgagaacg atgagtttga gctcacgggc aaggtggagg ctgagctgca    3660
```

-continued

```
tttactgaca gcagaggagg cagagaagaa cccagtgggc ctggcccgca atgaacctga    3720
cccctagag  aaacccaacc ggcccgacac gagcttcatc tggttcctga accctctcaa    3780
gtcggctcgc tacttcttgt ggcacacgta tcgctggctg ctcctcaaac tgttgctgct    3840
cctgctgctg ctcctcctcc tcgccctgtt cctctactct gtgcctggct acctggtcaa    3900
gaaaatcctc ggggcctgag cccagtggcc tcctggccgg cccgacacgg ccttcgtctg    3960
gttcctcaac cctctcaagt ccatcaagta cctcatctgc acccggtaca agtggctcat    4020
catcaagatc gtgctggcgc tgttggggct gctcatgttg gggctcttcc tctacagcct    4080
ccctggctac atggtcaaaa agctccttgg ggcatgaagg ccgccagctc ccgccagccg    4140
ctccccagcc ctgccgcatt tcctttcagt ggcttggact cttcccatc tccctgggg    4200
agcctgagga gccagcgtc cactcttcat gccttgggcc gagcctgcct cctgcttgcg    4260
ggggccgcct gtcctcactg ccccaggctg cggcttgccc agtcccgccc ctctgacccc    4320
tgcctgtggg ctggggagcc ttggatgggg tggggacctg gaatgggtct ctcttgcccc    4380
acctggctga ggcgccaccc ttcttcaggc ccaggctcca gaggaagact cctgaaaccc    4440
tccccaggtc ttccaagtac aggattgaag ctttagtgaa attaaccaag gaccatgggt    4500
cagtgcccag ggctttaaaa agaatgaacg agcaaaaggt atccccgccg tgaccctgc    4560
agatagcacc ggtctttgat ccgcagcagg ggccagaccc tgcccacaag tcccagcgcg    4620
gctgcttctg ccactgctgg gctccacttg gctcctctca cttcccaggg ggtcgcctgt    4680
cctgctgtg  ggtttccatg gcttcccaga gctccctctg ccccagccag cgcctccagg    4740
cccagctgag gagctgtgag aagcagcaga ggggactccc catcccgggc acccctgtc    4800
ctcccacccc tgcccccttg cccttccagc cctttcagct gcagctggga gctggcccgt    4860
caagtgctgc ccctgcctgt gtctgggttt ctgttggctg ttttctttt cttgagtggt    4920
gatttttctc taaataaaag aagtcaagca ctgaaaaaaa aaaaaaaaa               4969
```

<210> SEQ ID NO 12
<211> LENGTH: 4771
<212> TYPE: DNA
<213> ORGANISM: Homo sapiens

<400> SEQUENCE: 12

```
ccgtgagttc tgcccaggcc ctgtgagctc accagagcca cagactcaca gcccagaggt      60
ggcttcttcc ttcaggaact gaagaacccc catgaacacc aacatctcca ggttctgaga     120
acagaacctg ggaaattgat gacttcctca tgatgaccga tactcaggat ggccctagcg     180
agagctccca gatcatgagg aagaaggcct gaacgacata caggagatga tcaaaacgga     240
gaagtcctac cctgagcgtc gcctgcgggg cgtcctggag gagctgagct gtggctgctg     300
ccgcttcctc tccctcgctg acaaggacca gggccactca tcccgcacca ggcttgaccg     360
ggagcgcctc aagtcctgca tgagggagct ggaaaacatg gggcagcagg ccaggatgct     420
gcgggcccag gtgaagcggc acacggtgcg ggacaagctg aggctgtgcc agaacttcct     480
gcagaagctg cgcttcctgg cggacgagcc ccagcacagc attcccgaca tcttcatctg     540
gatgatgagc aacaacaagc gtgtcgccta tgccgtgtg cccctcaagg acctgctctct     600
ctccatcgtg gaggaggaga ctggcaagga ctgcgccaag gtcaagacgc tcttccttaa     660
gctgccaggg aagcggggct tcggctcggc aggctgaca gtgcaggcca aggtggagct     720
gtacctgtgg ctgggcctca gcaaacagcg caaggagttc ctgtgcggcc tgccctgtgg     780
```

```
cttccaggag gtcaaggcag cccagggcct gggcctgcat gccttcccac ccgtcagcct    840
ggtctacacc aagaagcagg cgttccagct ccgagcgcac atgtaccagg cccgcagcct    900
cttttgccgcc gacagcagcg gactctcaga cccctttgcc cgcgtcttct tcatcaatca   960
gagtcagtgc acagaggtgc tgaatgagac cctgtgtccc acctgggacc agatgctggt  1020
gttcgacaac ctggagctct atggtgaagc tcatgagctg agggacgatc cgcccatcat  1080
tgtcattgaa atctatgacc aggattccat gggcaaagct gacttcatgg gccgaccttt  1140
cgccaaaccc ctggtgaaga tggcagacga ggcgtactgc ccacccgct tcccacctca   1200
gctcgagtac taccagatct accgtggcaa cgccacagct ggagacctgc tggcggcctt  1260
cgagctgctg cagattggac cagcagggaa ggctgacctg cccccccatca atggcccggt  1320
ggacgtggac cgaggtccca tcatgcccgt gccatgggc atccggcccg tgctcagcaa   1380
gtaccgagtg gaggtgctgt tctggggcct acgggaccta aagcgggtga acctggccca  1440
ggtggaccgg ccacgggtgg acatcgagtg tgcaggaag ggggtgcagt cgtccctgat   1500
ccacaattat aagaagaacc ccaacttcaa caccctcgtc aagtggtttg aagtggacct  1560
cccagagaac gagctgctgc acccgcccctt gaacatccgt gtggtggact gccgggcctt  1620
cggtcgctac acactggtgg gctcccatgc cgtcagctcc ctgcgacgct tcatctaccg  1680
gcccccagac cgctcggccc ccagctggaa caccacgggg gaggttgtgg tgactatgga  1740
gccagaggta cccatcaaga aactggagac catggtgaag ctggacgcga cttctgaagc  1800
tgttgtcaag gtggatgtgg ctgaggagga gaaggagaag aagaagaaga agaagggcac  1860
tgcggaggag ccagaggagg aggagccaga cgagagcatg ctggactggt ggtccaagta  1920
ctttgcctcc attgacacca tgaaggagca acttcgacaa caagagccct ctggaattga  1980
cttggaggag aaggaggaag tggacaatac cgagggcctg aaggggtcaa tgaagggcaa  2040
ggagaaggca agggctgcca agaggagaa gaagaagaaa actcagagct ctggctctgg   2100
ccaggggtcc gaggcccccg agaagaagaa acccaagatt gatgagctta aggtataccc  2160
caaagagctg gagtccgagt ttgataactt tgaggactgg ctgcacactt tcaacttgct  2220
tcggggcaag accggggatg atgaggatgg ctccaccgag gaggagcgca ttgtgggacg  2280
cttcaagggc tccctctgcg tgtacaaagt gccactccca gaggacgtgt cccgggaagc  2340
cggctacgac tccacctacg gcatgttcca gggcatcccg agcaatgacc ccatcaatgt  2400
gctggtccga gtctatgtgg tccgggccac ggacctgcac cctgctgaca tcaacggcaa  2460
agctgacccc tacatcgcca tccggctagg caagactgac atccgcgaca aggagaacta  2520
catctccaag cagctcaacc ctgtctttgg gaagtccttt gacatcgagg cctccttccc  2580
catggaatcc atgctgacgg tggctgtgta tgactgggac ctggtgggca ctgatgacct  2640
cattggggaa accaagatcg acctggagaa ccgcttctac agcaagcacc gcgccacctg  2700
cggcatcgcc cagacctact ccacacatgg ctacaatatc tggcgggacc ccatgaagcc  2760
cagccagatc ctgacccgcc tctgcaaaga cggcaaagtg gacggccccc actttgggcc  2820
ccctgggaga gtgaaggtgg ccaaccgcgt cttcactggg ccctctgaga ttgaggacga  2880
gaacggtcag aggaagccca cagacgagca tgtggcgctg ttggccctga ggcactggga  2940
ggacatcccc cgcgcaggct gccgcctggt gccagagcat gtggagacga ggccgctgct  3000
caaccccgac aagccgggca tcgagcaggg ccgcctggag ctgtgggtgg acatgttccc  3060
catggacatg ccagccctg ggacgcctct ggacatctca cctcggaagc ccaagaagta   3120
cgagctgcgg gtcatcatct ggaacacaga tgaggtggtc ttggaggacg acgacttctt  3180
```

```
cacagggag    aagtccagtg   acatcttcgt   gaggggggtgg   ctgaagggcc   agcaggagga    3240
caagcaggac   acagacgtcc   actaccactc   cctcactggc   gagggcaact   tcaactggcg    3300
ctacctgttc   cccttcgact   acctggcggc   ggaggagaag   atcgtcatct   ccaagaagga    3360
gtccatgttc   tcctgggacg   agaccgagta   caagatcccc   gcgcggctca   ccctgcagat    3420
ctgggatgcg   gaccacttct   ccgctgacga   cttcctgggg   gccatcgagc   tggacctgaa    3480
ccggttcccg   cggggcgcaa   agacagccaa   gcagtgcacc   atggagatgg   ccaccgggga    3540
ggtggacgtg   cccctcgtgt   ccatcttcaa   gcaaaagcgc   gtcaaaggct   ggtggcccct    3600 cctgcccgc   aatgagaacg   atgagtttga   gctcacgggc   aaggtggagg   ctgagctgca    3660
tttactgaca   gcagaggagg   cagagaagaa   cccagtgggc   ctggcccgca   atgaacctga    3720 cccctagag   aaacccaacc   ggcccgacac   ggccttcgtc   tggttcctca   accctctcaa    3780
gtccatcaag   tacctcatct   gcacccggta   caagtggctc   atcatcaaga   tcgtgctggc    3840
gctgttgggg   ctgctcatgt   tggggctctt   cctctacagc   ctccctggct   acatggtcaa    3900
aaagctcctt   ggggcatgaa   ggccgccagc   tcccgccagc   cgctccccag   ccctgccgca    3960
tttcctttca   gtggcttgga   ctcttttccca   tctcccctgg   ggagcctgag   gagcccagcg    4020
tccactcttc   atgccttggg   ccgagcctgc   ctcctgcttg   cggggccgc   ctgtcctcac    4080 tgccccaggc   tgcggcttgc   ccagtcccgc   ccctctgacc   cctgcctgtg   ggctggggag    4140
ccttggatgg   ggtggggacc   tggaatgggt   ctctcttgcc   ccacctggct   gaggcgccac    4200
ccttcttcag   gcccaggctc   cagaggaaga   ctcctgaaac   cctccccagg   tcttccaagt    4260
acaggattga   agctttagtg   aaattaacca   aggaccatgg   gtcagtgccc   agggctttaa    4320
aaagaatgaa   cgagcaaaag   gtatccccgc   cgtgacccct   gcagatagca   ccggtctttg    4380
atccgcagca   ggggccagac   cctgcccaca   gtcccagcg   cggctgcttc   tgccactgct    4440
gggctccact   tggctcctct   cacttcccag   ggggtcgcct   gtcctgcctg   tgggtttcca    4500
tggcttccca   gagctccctc   tgccccagcc   agcgcctcca   ggcccagctg   aggagctgtg    4560
agaagcagca   gagggactc   cccatcccgg   gcacaccctg   tcctcccacc   cctgcccct    4620 tgcccttcca   gcccttcag   ctgcagctgg   gagctggccc   gtcaagtgct   gcccctgcct    4680
gtgtctgggt   ttctgttggc   tgttttttctt   ttcttgagtg   gtgattttc   tctaaataaa    4740 agaagtcaag   cactgaaaaa   aaaaaaaaa   a                                        4771
```

<210> SEQ ID NO 13
<211> LENGTH: 5123
<212> TYPE: DNA
<213> ORGANISM: Homo sapiens

<400> SEQUENCE: 13

```
ccgtgagttc   tgcccaggcc   ctgtgagctc   accagagcca   cagactcaca   gcccagaggt     60
ggcttcttcc   ttcaggaact   gaagaacccc   catgaacacc   aacatctcca   ggttctgaga    120
acagaacctg   ggaaattgat   gacttcctca   tgatgaccga   tactcaggat   ggccctagcg    180
agagctccca   gatcatgagg   tccctcactc   ccctgatcaa   cagggaggag   gcatttgggg    240
aggctgggga   ggcggggctg   tggcccagca   tcacccacac   tcctgattca   caggaagaag    300
gcctgaacga   catacaggag   atgatcaaaa   cggagaagtc   ctaccctgag   cgtcgcctgc    360
ggggcgtcct   ggaggagctg   agctgtggct   gctgccgctt   cctctccctc   gctgacaagg    420
accagggcca   ctcatcccgc   accaggcttg   accgggagcg   cctcaagtcc   tgcatgaggg    480
```

```
agctggaaaa catggggcag caggccagga tgctgcgggc ccaggtgaag cggcacacgg    540
tgcgggacaa gctgaggctg tgccagaact tcctgcagaa gctgcgcttc ctggcggacg    600
agccccagca cagcattccc gacatcttca tctggatgat gagcaacaac aagcgtgtcg    660
cctatgcccg tgtgccctcc aaggacctgc tcttctccat cgtggaggag gagactggca    720
aggactgcgc caaggtcaag acgctcttcc ttaagctgcc agggaagcgg ggcttcggct    780
cggcaggctg gacagtgcag gccaaggtgg agctgtacct gtggctgggc ctcagcaaac    840
agcgcaagga gttcctgtgc ggcctgccct gtggcttcca ggaggtcaag gcagcccagg    900
gcctgggcct gcatgccttc ccacccgtca gcctggtcta caccaagaag caggcgttcc    960
agctccgagc gcacatgtac caggcccgca gcctctttgc cgccgacagc agcggactct   1020
cagacccctt tgcccgcgtc ttcttcatca atcagagtca gtgcacagag gtgctgaatg   1080
agaccctgtg tcccacctgg gaccagatgc tggtgttcga caacctggag ctctatggtg   1140
aagctcatga gctgagggac gatccgccca tcattgtcat tgaaatctat gaccaggatt   1200
ccatgggcaa agctgacttc atgggccgga ccttcgccaa ccccctggtg aagatggcag   1260
acgaggcgta ctgcccaccc cgcttcccac ctcagctcga gtactaccag atctaccgtg   1320
gcaacgccac agctggagac ctgctggcgg ccttcgagct gctgcagatt ggaccagcag   1380
ggaaggctga cctgccccc atcaatgggcc cggtggacgt ggaccgaggt cccatcatgc   1440
ccgtgcccat gggcatccgg cccgtgctca gcaagtaccg agtggaggtg ctgttctggg   1500
gcctacggga cctaaagcgg gtgaacctgg cccaggtgga ccggccacgg gtggacatcg   1560
agtgtgcagg gaaggggggtg cagtcgtccc tgatccacaa ttataagaag aaccccaact   1620
tcaacaccct cgtcaagtgg tttgaagtgg acctcccaga gaacgagctg ctgcacccgc   1680
ccttgaacat ccgtgtggtg gactgccggg ccttcggtcg ctacacactg gtgggctccc   1740
atgccgtcag ctccctgcga cgcttcatct accggccccc agaccgctcg gcccccagct   1800
ggaacaccac ggtcaggctt ctccggcgct gccgtgtgct gtgcaatggg ggctcctcct   1860
ctcactccac aggggaggtt gtggtgacta tggagccaga ggtacccatc aagaaactgg   1920
agaccatggt gaagctggac gcgacttctg aagctgttgt caaggtggat gtggctgagg   1980
aggagaagga gaagaagaag aagaagaagg gcactgcgga ggagccagag gaggaggagc   2040
cagacgagag catgctggac tggtggtcca agtactttgc ctccattgac accatgaagg   2100
agcaacttcg acaacaagag ccctctggaa ttgacttgga ggagaaggag gaagtggaca   2160
ataccgaggg cctgaagggg tcaatgaagg gcaaggagaa ggcaagggct gccaaagagg   2220
agaagaagaa gaaaactcag agctctggct ctggccaggg gtccgaggcc cccgagaaga   2280
agaaacccaa gattgatgag cttaaggtat acccaaaga gctggagtcc gagtttgata   2340
actttgagga ctggctgcac actttcaact tgcttcgggg caagaccggg gatgatgagg   2400
atggctccac cgaggaggag cgcattgtgg acgcttcaa gggctccctc tgcgtgtaca   2460
aagtgccact cccagaggac gtgtcccggg aagccggcta cgactccacc tacggcatgt   2520
tccagggcat cccgagcaat gaccccatca atgtgctggt ccgagtctat gtggtccggg   2580
ccacggacct gcaccctgct gacatcaacg gcaaagctga cccctacatc gccatccggc   2640
taggcaagac tgacatccgc gacaaggaga actacatctc caagcagctc aaccctgtct   2700
ttgggaagtc ctttgacatc gaggcctcct tccccatgga atccatgctg acggtggctg   2760
tgtatgactg ggaccctggtg ggcactgatg acctcattgg ggaaaccaag atcgacctgg   2820
agaaccgctt ctacagcaag caccgcgcca cctgcggcat cgcccagacc tactccacac   2880
```

-continued

```
atggctacaa tatctggcgg gacccccatga agcccagcca gatcctgacc cgcctctgca    2940
aagacggcaa agtggacggc ccccactttg ggcccctgg gagagtgaag gtggccaacc    3000
gcgtcttcac tgggccctct gagattgagg acgagaacgg tcagaggaag cccacagacg    3060
agcatgtggc gctgttggcc ctgaggcact gggaggacat cccccgcgca ggctgccgcc    3120
tggtgccaga gcatgtggag acgaggccgc tgctcaaccc cgacaagccg ggcatcgagc    3180
agggccgcct ggagctgtgg gtggacatgt tccccatgga catgccagcc cctgggacgc    3240
ctctggacat ctcacctcgg aagcccaaga agtacgagct gcgggtcatc atctggaaca    3300
cagatgaggt ggtcttggag gacgacgact tcttcacagg ggagaagtcc agtgacatct    3360
tcgtgagggg gtggctgaag ggccagcagg aggacaagca ggacacagac gtccactacc    3420
actccctcac tggcgagggc aacttcaact ggcgctacct gttcccctcc gactacctgg    3480
cggcggagga aagatcgtc atctccaaga aggagtccat gttctcctgg gacgagaccg    3540
agtacaagat ccccgcgcgg ctcacccctgc agatctggga tgcggaccac ttctccgctg    3600
acgacttcct gggggccatc gagctggacc tgaaccggtt cccgcggggc gcaaagacag    3660
ccaagcagtg caccatggag atggccaccg gggaggtgga cgtgcccctc gtgtccatct    3720
tcaagcaaaa gcgcgtcaaa ggctggtggc ccctcctggc ccgcaatgag aacgatgagt    3780
ttgagctcac gggcaaggtg gaggctgagc tgcatttact gacagcagag gaggcagaga    3840
agaacccagt gggcctggcc cgcaatgaac ctgacccccct agagaaaccc aaccggcccg    3900
acacgagctt catctggttc ctgaaccctc tcaagtcggc tcgctacttc ttgtggcaca    3960
cgtatcgctg gctgctcctc aaactgttgc tgctcctgct gctgctcctc ctcctcgccc    4020
tgttcctcta ctctgtgcct ggctacctgg tcaagaaaat cctcgggggcc tgagcccagt    4080
ggcctcctgg ccggcccgac acggccttcg tctggttcct caaccctctc aagtccatca    4140
agtacctcat ctgcacccgg tacaagtggc tcatcatcaa gatcgtgctg gcgctgttgg    4200
ggctgctcat gttggggctc ttcctctaca gcctccctgg ctacatggtc aaaaagctcc    4260
ttggggcatg aaggccgcca gctcccgcca gccgctcccc agccctgccg catttccttt    4320
cagtggcttg gactctttcc catctcccct ggggagcctg aggagcccag cgtccactct    4380
tcatgccttg ggccgagcct gcctcctgct tgcggggggcc gcctgtcctc actgccccag    4440
gctgcggctt gcccagtccc gccccctctga ccccctgcctg tgggctgggg agccttggat    4500
ggggtgggga cctggaatgg gtctctcttg ccccacctgg ctgaggcgcc acccttcttc    4560
aggcccaggc tccagaggaa gactcctgaa accctcccca ggtcttccaa gtacaggatt    4620
gaagctttag tgaaattaac caaggaccat gggtcagtgc ccagggcttt aaaaagaatg    4680
aacgagcaaa aggtatcccc gccgtgaccc ctgcagatag caccggtctt tgatccgcag    4740
caggggccag accctgccca caagtcccag cgcggctgct tctgccactg ctgggctcca    4800
cttggctcct ctcacttccc aggggtcgc ctgtcctgcc tgtgggtttc catggcttcc    4860
cagagctccc tctgccccag ccagcgcctc caggcccagc tgaggagctg tgagaagcag    4920
cagaggggac tccccatccc gggcacaccc tgtcctccca cccctgcccc cttgcccttc    4980
cagcccttttc agctgcagct gggagctggc ccgtcaagtg ctgcccctgc ctgtgtctgg    5040
gtttctgttg gctgttttc ttttcttgag tggtgatttt tctctaaata aagaagtca    5100
agcactgaaa aaaaaaaaaa aaa                                             5123
```

<210> SEQ ID NO 14

<211> LENGTH: 6973
<212> TYPE: DNA
<213> ORGANISM: Homo sapiens

<400> SEQUENCE: 14

```
atcggagggg ggtcgggagg aggaggagga ggcagcggca gagaagagag aggcgtgtga      60
gccgtgctcc accggctagc tccttcccgc tgctcctgcc tggcagtgcc aggcagccca     120
caccagcatg gccttgctca tccacctcaa gacagtctcg gagctgcggg gcaggggcga     180
ccggatcgcc aaagtgactt tccgagggca atccttctac tctcgggtcc tggagaactg     240
tgaggatgtg gctgactttg atgagacatt tcggtggccg gtggccagca gcatcgacag     300
aaatgagatg ctggagattc aggttttcaa ctacagcaaa gtcttcagca caagctcat     360
cgggaccttc cgcatggtgc tgcagaaggt ggtagaggag agccatgtgg aggtgactga     420
cacgctgatt gatgacaaca atgctatcat caagaccagc ctgtgcgtgg aggtccggta     480
tcaggccact gacggcacag tgggctcctg ggacgatggg gacttcctgg agatgagtc     540
tcttcaagag gaagagaagg acagccaaga gacggatgga ctgctcccag gctcccggcc     600
cagctcccgg cccccaggag agaagagctt ccggagagcc gggaggagcg tgttctccgc     660
catgaagctc ggcaaaaacc ggtctcacaa ggaggagccc caaagaccag atgaaccggc     720
ggtgctggag atggaagacc ttgaccatct ggccattcgg ctaggagatg gactggatcc     780
cgactcggtg tctctagcct cagtcacagc tctcaccact aatgtctcca caagcgatc     840
taagccagac attaagatgg agccaagtgc tgggcggccc atggattacc aggtcagcat     900
cacggtgatc gaggcccggc agctggtggg cttgaacatg gaccctgtgg tgtgcgtgga     960
ggtgggtgac gacaagaagt acacatccat gaaggagtcc actaactgcc cctattacaa    1020
cgagtacttc gtcttcgact tccatgtctc tccggatgtc atgtttgaca agatcatcaa    1080
gatttcggtg attcactcca agaacctgct gcgcagtggc accctggtgg gctccttcaa    1140
aatggacgtg gaaccgtgt actcgcagcc agagcaccag ttccatcaca agtgggccat    1200
cctgtctgac cccgatgaca tctcctcggg gctgaagggc tacgtgaagt gtgacgttgc    1260
cgtggtgggc aaaggggaca acatcaagac gccccacaag gccaatgaga ccgacgaaga    1320
tgacattgag gggaacttgc tgctccccga ggggtgccc ccgaacgcc agtgggcccg     1380
gttctatgtg aaaatttacc gagcagaggg gctgccccgt atgaacacaa gcctcatggc    1440
caatgtaaag aaggctttca tcggtgaaaa caaggacctc gtggacccct acgtgcaagt    1500
cttctttgct ggccagaagg gcaagacttc agtgcagaag agcagctatg agccctgtg    1560
gaatgagcag gtcgtctta cagacctctt ccccccactc tgcaaacgca tgaaggtgca    1620
gatccgagac tcggacaagg tcaacgacgt ggccatcggc acccacttca ttgacctgcg    1680
caagatttct aatgacggag acaaaggctt cctgcccaca ctgggcccag cctgggtgaa    1740
catgtacggc tccacacgta actacacgct gctggatgag catcaggacc tgaacgaggg    1800
cctgggggag ggtgtgtcct tccgggcccg gctcctgctg ggcctggctg tggagatcgt    1860
agacacctcc aaccctgagc tcaccagctc cacagaggtg caggtggagc aggccacgcc    1920
catctcggag agctgtgcag gtaaaatgga agaattcttt ctctttggag ccttcctgga    1980
ggcctcaatg atcgaccgga gaaacggaga caagcccatc acctttgagg tcaccatagg    2040
caactatggg aacgaagttg atggcctgtc ccggccccag cggcctcggc cccggaagga    2100
gccggggat gaggaagaag tagacctgat tcagaacgca agtgatgacg aggccggtga    2160
tgccggggac ctggcctcag tctcctccac tccaccaatg cggccccagg tcaccgacag    2220
```

-continued

```
gaactacttc catctgccct acctggagcg aaagccctgc atctacatca agagctggtg    2280
gccggaccag cgccgccgcc tctacaatgc caacatcatg gacccacattg ccgacaagct    2340
ggaagaaggc ctgaacgaca tacaggagat gatcaaaacg gagaagtcct accctgagcg    2400
tcgcctgcgg ggcgtcctgg aggagctgag ctgtggctgc tgccgcttcc tctccctcgc    2460
tgacaaggac cagggccact catcccgcac caggcttgac cgggagcgcc tcaagtcctg    2520
catgagggag ctgaaaaaca tggggcagca ggccaggatg ctgcgggccc aggtgaagcg    2580
gcacacggtg cgggacaagc tgaggctgtg ccagaacttc ctgcagaagc tgcgcttcct    2640
ggcggacagg ccccagcaca gcattcccga catcttcatc tggatgatga gcaacaacaa    2700
gcgtgtcgcc tatgcccgtg tgccctccaa ggacctgctc ttctccatcg tggaggagga    2760
gactggcaag gactgcgcca aggtcaagac gctcttcctt aagctgccag ggaagcgggg    2820
cttcggctcg gcaggctgga cagtgcaggc caaggtggag ctgtacctgt ggctgggcct    2880
cagcaaacag cgcaaggagt tcctgtgcgg cctgccctgt ggcttccagg aggtcaaggc    2940
agcccagggc ctgggcctgc atgccttccc acccgtcagc ctggtctaca ccaagaagca    3000
ggcgttccag ctccgagcgc acatgtacca ggccccgcagc ctctttgccg ccgacagcag    3060
cggactctca gaccccttg cccgcgtctt cttcatcaat cagagtcagt gcacagaggt    3120
gctgaatgag accctgtgtc ccacctggga ccagatgctg gtgttcgaca acctggagct    3180
ctatggtgaa gctcatgagc tgagggacga tccgcccatc attgtcattg aaatctatga    3240
ccaggattcc atgggcaaag ctgacttcat gggccggacc ttcgccaaac ccctggtgaa    3300
gatggcagac gaggcgtact gcccaccccg cttcccacct cagctcgagt actaccagat    3360
ctaccgtggc aacgccacag ctggagacct gctggcggcc ttcgagctgc tgcagattgg    3420
accagcaggg aaggctgacc tgccccccat caatggcccg gtggacgtgg accgaggtcc    3480
catcatgccc gtgcccatgg gcatccggcc cgtgctcagc aagtaccgag tggaggtgct    3540
gttctggggc ctacgggacc taaagcgggt gaacctggcc caggtggacc ggccacgggt    3600
ggacatcgag tgtgcaggga aggggtgca gtcgtccctg atccacaatt ataagaagaa    3660
ccccaacttc aacaccctcg tcaagtggtt tgaagtggac ctcccagaga cgagctgct    3720
gcacccgccc ttgaacatcc gtgtggtgga ctgccgggcc ttcggtcgct acacactggt    3780
gggctcccat gccgtcagct ccctgcgacg cttcatctac cggcccccag accgctcggc    3840
ccccagctgg aacaccacgg tcaggcttct ccggcgctgc cgtgtgctgt gcaatggggg    3900
ctcctcctct cactccacag gggaggttgt ggtgactatg gagccagagg tacccatcaa    3960
gaaactggag accatggtga agctggacgc gacttctgaa gctgttgtca aggtggatgt    4020
ggctgaggag gagaaggaga agaagaagaa gaagaagggc actgcggagg agccagagga    4080
ggaggagcca gacgagagca tgctggactg gtggtccaag tactttgcct ccattgacac    4140
catgaaggag caacttcgac aacaagagcc ctctggaatt gacttggagg agaaggagga    4200
agtggacaat accgagggcc tgaaggggtc aatgaagggc aaggagaagg caagggctgc    4260
caaagaggag aagaagaaga aaactcagag ctctggctct ggccaggggt ccgaggcccc    4320
cgagaagaag aaacccaaga ttgatgagct taaggtatac cccaaagagc tggagtccga    4380
gtttgataac tttgaggact ggctgcacac tttcaacttg cttcggggca agaccgggga    4440
tgatgaggat ggctccaccg aggaggagcg cattgtggga cgcttcaagg gctccctctg    4500
cgtgtacaaa gtgccactcc cagaggacgt gtcccgggaa gccggctacg actccaccta    4560
```

-continued

```
cggcatgttc cagggcatcc cgagcaatga ccccatcaat gtgctggtcc gagtctatgt    4620
ggtccgggcc acggacctgc accctgctga catcaacggc aaagctgacc cctacatcgc    4680
catccggcta ggcaagactg acatccgcga caaggagaac tacatctcca agcagctcaa    4740
ccctgtcttt gggaagtcct ttgacatcga ggcctccttc cccatggaat ccatgctgac    4800
ggtggctgtg tatgactggg acctggtggg cactgatgac ctcattgggg aaaccaagat    4860
cgacctggag aaccgcttct acagcaagca ccgcgccacc tgcggcatcg cccagaccta    4920
ctccacacat ggctacaata tctggcggga ccccatgaag cccagccaga tcctgacccg    4980
cctctgcaaa gacggcaaag tggacggccc ccactttggg cccctgggag agtgaaggt     5040 ggccaaccgc gtcttcactg ggccctctga gattgaggac gagaacggtc agaggaagcc    5100
cacagacgag catgtggcgc tgttggccct gaggcactgg gaggacatcc cccgcgcagg    5160
ctgccgcctg gtgccagagc atgtggagac gaggccgctg ctcaacccc acaagccggg    5220 catcgagcag ggccgcctgg agctgtgggt ggacatgttc cccatggaca tgccagcccc    5280
tgggacgcct ctggacatct cacctcgaa gcccaagaag tacgagctgc gggtcatcat    5340
ctggaacaca gatgaggtgg tcttggagga cgacgacttc ttcacagggg agaagtccag    5400
tgacatcttc gtgaggggt ggctgaaggg ccagcaggag gacaagcagg acacagacgt    5460
ccactaccac tccctcactg gcgagggcaa cttcaactgg cgctacctgt tcccttcga    5520 ctacctggcg gcgaggaga agatcgtcat ctccaagaag gagtccatgt tctcctggga    5580
cgagaccgag tacaagatcc ccgcgcggct caccctgcag atctgggatg cggaccactt    5640
ctccgctgac gacttcctgg gggccatcga gctggacctg aaccggttcc cgcggggcgc    5700
aaagacagcc aagcagtgca ccatggagat ggccaccggg gaggtggacg tgcccctcgt    5760
gtccatcttc aagcaaaagc gcgtcaaagg ctggtggccc ctcctggccc gcaatgagaa    5820
cgatgagttt gagctcacgg gcaaggtgga ggctgagctg catttactga cagcagagga    5880
ggcagagaag aacccagtgg gcctggcccg caatgaacct gaccccctag agaaacccaa    5940
ccggcccgac acggccttcg tctggttcct caaccctctc aagtccatca gtacctcat     6000 ctgcacccgg tacaagtggc tcatcatcaa gatcgtgctg cgctgttgg ggctgctcat    6060 gttgggctc ttcctctaca gcctccctgg ctacatggtc aaaaagctcc ttggggcatg    6120
aaggccgcca gctcccgcca gccgctcccc agccctgccg catttccttt cagtggcttg    6180
gactctttcc catctcccct ggggagcctg aggagcccag cgtccactct tcatgccttg    6240
ggccgagcct gcctcctgct tgcggggcc gcctgtcctc actgcccag gctgcggctt    6300 gcccagtccc gcccctctga cccctgcctg tgggctgggg agccttggat ggggtgggga    6360
cctggaatgg gtctctcttg ccccacctgg ctgaggcgcc acccttcttc aggcccaggc    6420
tccagaggaa gactcctgaa accctcccca ggtcttccaa gtacaggatt gaagctttag    6480
tgaaattaac caaggaccat gggtcagtgc ccagggcttt aaaaagaatg aacgagcaaa    6540
aggtatcccc gccgtgaccc ctgcagatag caccggtctt tgatccgcag caggggccag    6600
accctgccca caagtcccag cgcggctgct tctgccactg ctgggctcca cttggctcct    6660
ctcacttccc aggggtcgc ctgtcctgcc tgtgggtttc catggcttcc cagagctccc    6720
tctgccccag ccagcgcctc caggcccagc tgaggagctg tgagaagcag cagaggggac    6780
tccccatccc gggcacaccc tgtcctccca ccctgcccc cttgcccttc agccctttc     6840 agctgcagct gggagctggc ccgtcaagtg ctgcccctgc ctgtgtctgg gtttctgttg    6900
gctgtttttc ttttcttgag tggtgatttt tctctaaata aaagaagtca agcactgaaa    6960
```
aaaaaaaaaa aaa 6973

<210> SEQ ID NO 15
<211> LENGTH: 7125
<212> TYPE: DNA
<213> ORGANISM: Mus musculus

<400> SEQUENCE: 15

| | | | | | |
|---|---|---|---|---|---|
| ttggttgcct | tggtctctgt | gggcagcagc | aggaggaggc | ggcagcagcc | agagaagagg | 60 |
| gaggcgtgtg | agccacactc | caccagcgag | cttcttcccg | ctgctctgga | actgcccagg | 120 |
| ctctccccac | cagcatggcc | ctgattgttc | acctcaagac | tgtctcagag | ctccgaggca | 180 |
| aaggtgaccg | gattgccaaa | gtcactttcc | gagggcagtc | tttctactcc | cgggtcctgg | 240 |
| agaactgcga | gggtgtggct | gactttgatg | agacgttccg | gtggccagtg | ccagcagca | 300 |
| tcgaccggaa | tgaagtgttg | gagattcaga | ttttcaacta | cagcaaagtc | ttcagcaaca | 360 |
| agctgatagg | gaccttctgc | atggtgctgc | agaaagtggt | ggaggagaat | cgggtagagg | 420 |
| tgaccgacac | gctgatggat | gacagcaatg | ctatcatcaa | gaccagcctg | agcatggagg | 480 |
| tccggtatca | ggccacagat | ggcactgtgg | gcccctggga | tgatgagac | ttcctgggag | 540 |
| atgaatccct | ccaggaggag | aaggacagcc | aggagacaga | tgggctgcta | cctggttccc | 600 |
| gacccagcac | ccggatatct | ggcgagaaga | gctttcgcag | agcgggaagg | agtgtgttct | 660 |
| cggccatgaa | actcggcaaa | actcggtccc | acaaagagga | gccccaaaga | caagatgagc | 720 |
| cagcagtgct | ggagatggag | gacctggacc | acctagccat | tcagctgggg | gatgggctgg | 780 |
| atcctgactc | cgtgtctcta | gcctcggtca | ccgctctcac | cagcaatgtc | tccaacaaac | 840 |
| ggtctaagcc | agatattaag | atggagccca | gtgctggaag | gcccatggat | taccaggtca | 900 |
| gcatcacagt | gattgaggct | cggcagctgg | tgggcttgaa | catggaccct | gtggtgtgtg | 960 |
| tggaggtggg | tgatgacaag | aaatacacgt | caatgaagga | gtccacaaac | tgcccttact | 1020 |
| acaacgagta | ctttgtcttc | gacttccatg | tctctcctga | tgtcatgttt | gacaagatca | 1080 |
| tcaagatctc | ggttatccat | tctaagaacc | tgcttcggag | cggcacctg | gtgggttcct | 1140 |
| tcaaaatgga | tgtggggact | gtgtattccc | agcctgaaca | ccagttccat | cacaaatggg | 1200 |
| ccatcctgtc | agaccccgat | gacatctctg | ctgggttgaa | gggttatgta | aagtgtgatg | 1260 |
| tcgctgtggt | gggcaaggga | gacaacatca | agacaccca | caaggccaac | gagacggatg | 1320 |
| aggacgacat | tgaagggaac | ttgctgctcc | ccgagggcgt | gccccccgaa | cggcagtggg | 1380 |
| cacggttcta | tgtgaaaatt | taccgagcag | agggactgcc | ccggatgaac | acaagcctca | 1440 |
| tggccaacgt | gaagaaggcg | ttcatcggtg | agaacaagga | cctcgtcgac | ccctatgtgc | 1500 |
| aagtcttctt | tgctggacaa | aagggcaaaa | catcagtgca | gaagagcagc | tatgagccgc | 1560 |
| tatggaatga | gcaggtcgtc | ttcacagact | tgttccccc | actctgcaaa | cgcatgaagg | 1620 |
| tgcagatccg | ggactctgac | aaggtcaatg | atgtggccat | cggcacccac | ttcatcgacc | 1680 |
| tgcgcaagat | ttccaacgat | ggagacaaag | gcttcctgcc | taccctcggt | ccagcctggg | 1740 |
| tgaacatgta | cggctccacg | cgcaactaca | cactgctgga | cgagcaccag | gacttgaatg | 1800 |
| aaggcctggg | ggagggtgtg | tccttccggg | cccgcctcat | gttgggacta | gctgtggaga | 1860 |
| tcctggacac | ctccaaccca | gagctcacca | gctccacgga | ggtgcaggtg | gagcaggcca | 1920 |
| cgcctgtctc | ggagagctgc | acagggagaa | tggaagaatt | ttttctatt | ggagccttct | 1980 |
| tggaagcctc | aatgattgac | cggaaaaatg | gggacaagcc | aattaccttt | gaggtgacca | 2040 |

```
taggaaacta cggcaatgaa gtcgatggta tgtcccggcc cctgaggcct cggcccggga    2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggct ggatcgagag cgtcttaagt    2520
cctgtatgag ggagttggag agcatgggac agcaggccaa gagcctgagg gctcaggtga    2580
agcggcacac tgttcgggac aagctgaggt catgccagaa cttctctgcag aagctacgct    2640 tcctggcgga tgagccccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca agaccctctt cctgaagctg ccagggaaga    2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctcttt gctgctgaca    3060
gcagtgggct ctctgatccc tttgcccgtg tcttcttcat caaccagagc caatgcactg    3120
aggttctaaa cgagacactg tgtcccacct gggaccagat gctggtattt gacaacctgg    3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactggc tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
gggtggacat cgagtgtgca ggaaagggg tacaatcctc cctgattcac aattataaga    3660
agaaccccaa cttcaacacg ctggtcaagt ggtttgaagt ggacctcccg gagaatgagc    3720
tcctgcaccc acccttgaac atccgagtgg tagattgccg ggccttttgga cgatacaccc    3780 tggtgggttc ccacgcagtc agctcactga ggcgcttcat ctaccgacct ccagaccgct    3840
cagcccccaa ctggaacacc acagtcaggc tgctccgggg ctgccacagg ctgcgcaatg    3900
ggggcccctc ttctcgcccc acaggggagg ttgtagtaag catggagcct gaggagccag    3960
ttaagaagct ggagaccatg gtgaaactgg atgcgacttc tgatgctgtg gtcaaggtgg    4020
atgtggctga agatgagaag gaaaggaaga agaagaaaaa gaaaggcccg tcagaggagc    4080
cagaggagga agagcccgat gagagcatgc tggattggtg gtccaagtac ttcgcctcca    4140
tcgacacaat gaaggagcaa cttcgacaac atgagacctc tggaactgac ttggaagaga    4200
aggaagagat ggaaagcgct gagggcctga agggaccaat gaagagcaag gagaagtcca    4260
gagctgcaaa ggaggagaaa aagaagaaaa accagagccc tggccctggc cagggatcgg    4320
aggctcctga gaagaagaaa gccaagatcg atgagcttaa ggtgtacccc aaggagctgg    4380
aatcggagtt tgacagcttt gaggactggc tgcacacctt caacctgttg aggggcaaga    4440
```

```
cgggagatga tgaggatggc tccacagagg aggagcgcat agtaggccga ttcaagggct    4500
ccctctgtgt gtacaaagtg ccactcccag aagatgtatc tcgagaagct ggctatgatc    4560
ccacctatgg aatgttccag ggcatcccaa gcaatgaccc catcaatgtg ctggtccgaa    4620
tctatgtggt ccgggccaca gacctgcacc cggccgacat caatggcaaa gctgacccct    4680
atattgccat caagttaggc aagaccgaca tccgagacaa ggagaactac atctccaagc    4740
agctcaaccc tgtgtttggg aagtcctttg acattgaggc ctccttcccc atggagtcca    4800
tgttgacagt ggccgtgtac gactgggatc tggtgggcac tgatgacctc atcggagaaa    4860
ccaagattga cctggaaaac cgcttctaca gcaagcatcg cgccacctgc ggcatcgcac    4920
agacctattc catacatggc tacaatatct ggagggaccc catgaagccc agccagatcc    4980
tgacacgcct ctgtaaagag ggcaaagtgg acggccccca ctttggtccc catgggagag    5040
tgagggttgc caaccgtgtc ttcacggggc cttcagaaat agaggatgag aatggtcaga    5100
ggaagcccac agatgagcac gtggcactgt ctgctctgag acactgggag gacatccccc    5160
gggtgggctg ccgccttgtg ccggaacacg tggagaccag gccgctgctc aaccctgaca    5220
agccaggcat tgagcagggc cgcctggagc tgtgggtgga catgttcccc atggacatgc    5280
cagcccctgg gacacctctg gatatatccc ccaggaaacc caagaagtac gagctgcggg    5340
tcatcgtgtg gaacacagac gaggtggtcc tggaagacga tgatttcttc acgggagaga    5400
agtccagtga cattttttgtg aggggtggc tgaagggcca gcaggaggac aaacaggaca    5460
cagatgtcca ctatcactcc ctcacggggg agggcaactt caactggaga tacctcttcc    5520
ccttcgacta cctagcggcc gaagagaaga tcgttatgtc caaaaaggag tctatgttct    5580
cctgggatga gacggagtac aagatccctg cgcggctcac cctgcagatc tgggacgctg    5640
accacttctc ggctgacgac ttcctggggg ctatcgagct ggacctgaac cggttcccga    5700
ggggcgctaa gacagccaag cagtgcacca tggagatggc caccggggag gtggacgtac    5760
ccctggtttc catctttaaa cagaaacgtg tcaaaggctg gtggcccctc ctggcccgca    5820
atgagaatga tgagtttgag ctcacaggca aagtggaggc ggagctacac ctactcacgg    5880
cagaggaggc agagaagaac cctgtgggcc tggctcgcaa tgaacctgat cccctagaaa    5940
aacccaatcg gccggacaca agcttcatct ggttcttgaa ccctctcaag tctgcccgct    6000
acttcctgtg gcatacctac cgctggctac tcctcaaatt cctgctgctc ttcctcctgc    6060
tgctgctctt cgccctgttt ctctactctc tgcctggcta cctggccaag aagatccttg    6120
gggcctgagc cctgcagtcg cctaggcctg ccggcctgac acggcattcg tctggttcct    6180
gaacccactc aaatctatca agtacctcat ctgcacccgg tacaagtggc tgatcatcaa    6240
gatcgtgctg cgcgctgctgg ggctgctcat gctggccctc ttcctttaca gcctcccagg    6300
ctacatggtc aagaagctcc taggggcctg aagtgtgccc cacccccagcc cgctccagca    6360 tccctccagg ggctgctgcg tattttgcct tccctcacct ggactctctc ccaactccct    6420
gaggagccct cccacgcctg ccagccttga gcaagacacc tgcttgctgg acttcatccc    6480 cacccccacac ccaaactgtt gcttgcctga tcttgtccca ggcctgcctg gggtttgggg    6540
cacagttggc ctcaaaaacc agataccctc ttgtctaaag taccaggttc ctctgcccaa    6600
ccccaagagt ggtagtggcc caaccctccc tgtgctttcc aaatcttgtc ttaaggcacc    6660
agtgaaatta accaagaaac gcggagcaat gcccaaggct ctgatgagta ggaacacgtg    6720
gaaagcacca ggaatgccag cagaggcgag gcggcacacc tctctgcaga gcatccaggc    6780
```

```
cgagcggcgg gcagcggcca gctgcttctg cgcatgctct cctcttggct ctgcttcttt      6840
ctcacagtca cagtcacttc acagcttagc cttgggcttc ccatcacttc cagggggtgcc     6900 tctgccttgg ccagtgtgtg tcagctagta cacaagctcc aagtgtgaat caggtgtact      6960
ggccgtcctg aagactgact gccctgtcct tcctgccgac agccacaccc gagtgtacac      7020
ttaaagcggt gcccttctgc ctctgtgggc ctgctggctg ctgttccttt cttgagtgtg      7080
attttttttt tctctccctc aataaaataa atcaaactct gagac                     7125

<210> SEQ ID NO 16
<211> LENGTH: 7065
<212> TYPE: DNA
<213> ORGANISM: Mus musculus

<400> SEQUENCE: 16
ttggttgcct tggtctctgt gggcagcagc aggaggaggc ggcagcagcc agagaagagg        60
gaggcgtgtg agccacactc caccagcgag cttcttcccg ctgctctgga actgcccagg      120
ctctccccac cagcatggcc ctgattgttc acctcaagac tgtctcagag ctccgaggca      180
aaggtgaccg gattgccaaa gtcactttcc gagggcagtc tttctactcc cgggtcctgg      240
agaactgcga gggtgtggct gactttgatg agacgttccg gtggccagtg ccagcagca       300 tcgaccggaa tgaagtgttg gagattcaga ttttcaacta cagcaaagtc ttcagcaaca      360
agctgatagg gaccttctgc atggtgctgc agaaagtggt ggaggagaat cgggtagagg      420
tgaccgacac gctgatggat gacagcaatg ctatcatcaa gaccagcctg agcatggagg      480
tccggtatca ggccacagat ggcactgtgg gcccctggga tgatggagac ttcctgggag      540
atgaatccct ccaggaggag aaggacagcc aggagacaga tgggctgcta cctggttccc      600
gacccagcac ccggatatct ggcgagaaga gctttcgcag agcgggaagg agtgtgttct      660
cggccatgaa actcggcaaa actcggtccc acaaagagga gccccaaaga caagatgagc      720
cagcagtgct ggagatggag gacctggacc acctagccat tcagctgggg gatgggctgg      780
atcctgactc cgtgtctcta gcctcggtca ccgctctcac cagcaatgtc tccaacaaac      840
ggtctaagcc agatattaag atggagccca gtgctggaag gcccatggat taccaggtca      900
gcatcacagt gattgaggct cggcagctgg tgggcttgaa catggaccct gtggtgtgtg      960
tggaggtggg tgatgacaag aaatacacgt caatgaagga gtccacaaac tgcccttact     1020
acaacgagta ctttgtcttc gacttccatg tctctcctga tgtcatgttt gacaagatca     1080
tcaagatctc ggttatccat tctaagaacc tgcttcggag cggcaccctg gtgggttcct     1140
tcaaaatgga tgtggggact gtgtattccc agcctgaaca ccagttccat cacaaatggg     1200
ccatcctgtc agaccccgat gacatctctg ctggggttgaa gggttatgta aagtgtgatg     1260
tcgctgtggt gggcaaggga gacaacatca agacacccca caggccaac gagacggatg       1320 aggacgacat tgaagggaac ttgctgctcc ccgagggcgt gccccccgaa cggcagtggg     1380
cacggttcta tgtgaaaatt taccgagcag agggactgcc ccggatgaac acaagcctca     1440
tggccaacgt gaagaaggcg ttcatcggtg agaacaagga cctcgtcgac ccctatgtgc     1500
aagtcttctt tgctggacaa aagggcaaaa catcagtgca aagagcagc tatgagccgc      1560 tatggaatga gcaggtcgtc ttcacagact tgttcccccc actctgcaaa cgcatgaagg     1620
tgcagatccg ggactctgac aaggtcaatg atgtggccat cggcaccac ttcatcgacc      1680 tgcgcaagat ttccaacgat ggagacaaag gcttcctgcc tacccttcggt ccagcctggg   1740 tgaacatgta cggctccacg cgcaactaca cactgctgga cgagcaccag gacttgaatg     1800
```

```
aaggcctggg ggagggtgtg tccttccggg cccgcctcat gttgggacta gctgtggaga    1860
tcctggacac ctccaaccca gagctcacca gctccacgga ggtgcaggtg gagcaggcca    1920
cgcctgtctc ggagagctgc acagggagaa tggaagaatt ttttctattt ggagccttct    1980
tggaagcctc aatgattgac cggaaaaatg gggacaagcc aattaccttt gaggtgacca    2040
taggaaacta cggcaatgaa gtcgatggta tgtcccggcc cctgaggcct cggccccgga    2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggct ggatcgagag cgtcttaagt    2520
cctgtatgag ggagttggag agcatgggac agcaggccaa gagcctgagg gctcaggtga    2580
agcggcacac tgttcgggac aagctgaggt catgccagaa cttttctgcag aagctacgct    2640 tcctggcgga tgagccccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca agaccctctt cctgaagctg ccagggaaga    2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctcttt gctgctgaca    3060
gcagtgggct ctctgatccc tttgccccgtg tcttcttcat caaccagagc caatgcactg    3120
aggttctaaa cgagacactg tgtcccacct gggaccagat gctggtattt gacaacctgg    3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactggc tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
gggtggacat cgagtgtgca ggaaaggggg tacaatcctc cctgattcac aattataaga    3660
agaaccccaa cttcaacacg ctggtcaagt ggtttgaagt ggacctcccg gagaatgagc    3720
tcctgcaccc acccttgaac atccgagtgg tagattgccg ggcctttgga cgatacaccc    3780
tggtgggttc ccacgcagtc agctcactga ggcgcttcat ctaccgacct ccagaccgct    3840
cagcccccaa ctgaacaccc acaggggagg ttgtagtaag catggagcct gaggagccag    3900
ttaagaagct ggagaccatg gtgaaactgg atgcgacttc tgatgctgtg gtcaaggtgg    3960
atgtggctga agatgagaag gaaaggaaga agaagaaaaa gaaaggcccg tcagaggagc    4020
cagaggagga gagcccgat gagagcatgc tggattggtg gtccaagtac ttcgcctcca    4080
tcgacacaat gaaggagcaa ctcgacaac atgagacctc tggaactgac ttggaagaga    4140
```

```
aggaagagat ggaaagcgct gagggcctga agggaccaat gaagagcaag gagaagtcca    4200
gagctgcaaa ggaggagaaa aagaagaaaa accagagccc tggccctggc cagggatcgg    4260
aggctcctga gaagaagaaa gccaagatcg atgagcttaa ggtgtacccc aaggagctgg    4320
aatcggagtt tgacagcttt gaggactggc tgcacacctt caacctgttg aggggcaaga    4380
cgggagatga tgaggatggc tccacagagg aggagcgcat agtaggccga ttcaagggct    4440
ccctctgtgt gtacaaagtg ccactcccag aagatgtatc tcgagaagct ggctatgatc    4500
ccacctatgg aatgttccag ggcatcccaa gcaatgaccc catcaatgtg ctggtccgaa    4560
tctatgtggt ccgggccaca gacctgcacc cggccgacat caatggcaaa gctgacccct    4620
atattgccat caagttaggc aagaccgaca tccgagacaa ggagaactac atctccaagc    4680
agctcaaccc tgtgtttggg aagtcctttg acattgaggc ctccttcccc atggagtcca    4740
tgttgacagt ggccgtgtac gactgggatc tggtgggcac tgatgacctc atcggagaaa    4800
ccaagattga cctggaaaac cgcttctaca gcaagcatcg cgccacctgc ggcatcgcac    4860
agacctattc catacatggc tacaatatct ggagggaccc catgaagccc agccagatcc    4920
tgacacgcct ctgtaaagag ggcaaagtgg acggccccca ctttggtccc catgggagag    4980
tgagggttgc caaccgtgtc ttcacggggc cttcagaaat agaggatgag aatggtcaga    5040
ggaagcccac agatgagcac gtggcactgt ctgctctgag acactgggag gacatccccc    5100
gggtgggctg ccgccttgtg ccggaacacg tggagaccag gccgctgctc aaccctgaca    5160
agccaggcat tgagcagggc cgcctggagc tgtgggtgga catgttcccc atggacatgc    5220
cagcccctgg gacacctctg gatatatccc ccaggaaacc caagaagtac gagctgcggg    5280
tcatcgtgtg gaacacagac gaggtggtcc tggaagacga tgatttcttc acgggagaga    5340
agtccagtga cattttttgtg aggggtggc tgaagggcca gcaggaggac aaacaggaca    5400
cagatgtcca ctatcactcc ctcacggggg agggcaactt caactggaga tacctcttcc    5460
ccttcgacta cctagcggcc gaagagaaga tcgttatgtc caaaaaggag tctatgttct    5520
cctgggatga gacggagtac aagatccctg cgcggctcac cctgcagatc tgggacgctg    5580
accacttctc ggctgacgac ttcctggggg ctatcgagct ggacctgaac cggttcccga    5640
ggggcgctaa gacagccaag cagtgcacca tggagatggc caccggggag gtggacgtac    5700
ccctggtttc catcttttaaa cagaaacgtg tcaaaggctg gtggcccctc ctggcccgca    5760
atgagaatga tgagtttgag ctcacaggca aagtggaggc ggagctacac ctactcacgg    5820
cagaggaggc agagaagaac cctgtgggcc tggctcgcaa tgaacctgat cccctagaaa    5880
aacccaatcg gccggacaca agcttcatct ggttcttgaa ccctctcaag tctgcccgct    5940
acttcctgtg gcatacctac cgctggctac tcctcaaatt cctgctgctc ttcctcctgc    6000
tgctgctctt cgccctgttt ctctactctc tgcctggcta cctggccaag aagatccttg    6060
gggcctgagc cctgcagtcg cctaggcctg ccggcctgac acggcattcg tctggttcct    6120
gaacccactc aaatctatca agtacctcat ctgcacccgg tacaagtggc tgatcatcaa    6180
gatcgtgctg gcgctgctgg ggctgctcat gctggccctc ttcctttaca gcctcccagg    6240
ctacatggtc aagaagctcc taggggcctg aagtgtgccc caccccagcc cgctccagca    6300
tccctccagg ggctgctgcg tattttgcct tccctcacct ggactctctc ccaactccct    6360
gaggagccct cccacgcctg ccagccttga gcaagacacc tgcttgctgg acttcatccc    6420 cacccccacac ccaaactgtt gcttgcctga tcttgtccca ggcctgcctg gggtttgggg    6480
cacagttggc ctccaaaacc agataccctc ttgtctaaag taccaggttc ctctgcccaa    6540
```

```
ccccaagagt ggtagtggcc caaccctccc tgtgctttcc aaatcttgtc ttaaggcacc    6600
agtgaaatta accaagaaac gcggagcaat gcccaaggct ctgatgagta ggaacacgtg    6660
gaaagcacca ggaatgccag cagaggcgag gcggcacacc tctctgcaga gcatccaggc    6720
cgagcggcgg gcagcggcca gctgcttctg cgcatgctct cctcttggct ctgcttcttt    6780
ctcacagtca cagtcacttc acagcttagc cttgggcttc ccatcacttc caggggtgcc    6840
tctgccttgg ccagtgtgtg tcagctagta cacaagctcc aagtgtgaat caggtgtact    6900
ggccgtcctg aagactgact gccctgtcct tcctgccgac agccacaccc gagtgtacac    6960
ttaaagcggt gccttctgc ctctgtgggc ctgctggctg ctgttccttt cttgagtgtg    7020
attttttttt tctctccctc aataaaataa atcaaactct gagac                   7065
```

<210> SEQ ID NO 17
<211> LENGTH: 6907
<212> TYPE: DNA
<213> ORGANISM: Mus musculus

<400> SEQUENCE: 17

```
ttggttgcct tggtctctgt gggcagcagc aggaggaggc ggcagcagcc agagaagagg      60
gaggcgtgtg agccacactc caccagcgag cttcttcccg ctgctctgga actgcccagg     120
ctctccccac cagcatggcc ctgattgttc acctcaagac tgtctcagag ctccgaggca     180
aaggtgaccg gattgccaaa gtcactttcc gagggcagtc tttctactcc cgggtcctgg     240
agaactgcga gggtgtggct gactttgatg agacgttccg gtggccagtg ccagcagca      300 tcgaccggaa tgaagtgttg gagattcaga ttttcaacta cagcaaagtc ttcagcaaca     360
agctgatagg gaccttctgc atggtgctgc agaaagtggt ggaggagaat cgggtagagg     420
tgaccgacac gctgatggat gacagcaatg ctatcatcaa gaccagcctg agcatggagg     480
tccggtatca ggccacagat ggcactgtgg gccctggga tgatggagac ttcctgggag     540
atgaatccct ccaggaggag aaggacagcc aggagacaga tgggctgcta cctggttccc     600
gacccagcac ccggatatct ggcgagaaga gctttcgcag caaaggcaga gagaagacca     660
agggaggcag agatggcgag cacaaagcgg gaaggagtgt gttctcggcc atgaaactcg     720
gcaaaactcg gtcccacaaa gaggagcccc aaagacaaga tgagccagca gtgctggaga     780
tggaggacct ggaccaccta gccattcagc tgggggatgg gctggatcct gactccgtgt     840
ctctagcctc ggtcaccgct ctcaccagca atgtctccaa caacggtct aagccagata     900 ttaagatgga gcccagtgct ggaaggccca tggattacca ggtcagcatc acagtgattg     960
aggctcggca gctggtgggc ttgaacatgg accctgtggt gtgtgtggag gtgggtgatg    1020
acaagaaata cacgtcaatg aaggagtcca caaactgccc ttactacaac gagtactttg    1080
tcttcgactt ccatgtctct cctgatgtca tgtttgacaa gatcatcaag atctcggtta    1140
tccattctaa gaacctgctt cggagcggca ccctggtggg ttccttcaaa atggatgtgg    1200
ggactgtgta ttcccagcct gaacaccagt tccatcacaa atgggccatc ctgtcagacc    1260
ccgatgacat ctctgctggg ttgaagggtt atgtaaagtg tgatgtcgct gtggtgggca    1320
agggagacaa catcaagaca ccccacaagg ccaacgagac ggatgaggac gacattgaag    1380
ggaacttgct gctccccgag ggcgtgcccc ccgaacggca gtgggcacgg ttctatgtga    1440
aaatttaccg agcagaggga ctgccccgga tgaacacaag cctcatggcc aacgtgaaga    1500
aggcgttcat cggtgagaac aaggacctcg tcgaccccta tgtgcaagtc ttctttgctg    1560
```

-continued

```
gacaaaaggg caaaacatca gtgcagaaga gcagctatga gccgctatgg aatgagcagg    1620
tcgtcttcac agacttgttc cccccactct gcaaacgcat gaaggtgcag atccgggact    1680
ctgacaaggt caatgatgtg gccatcggca cccacttcat cgacctgcgc aagatttcca    1740
acgatggaga caaaggcttc ctgcctaccc tcggtccagc ctgggtgaac atgtacggct    1800
ccacgcgcaa ctacacactg ctggacgagc accaggactt gaatgaaggc ctgggggagg    1860
gtgtgtcctt ccgggcccgc ctcatgttgg gactagctgt ggagatcctg acacctcca     1920 acccagagct caccagctcc acggaggtgc aggtggagca ggccacgcct gtctcggaga    1980
gctgcacagg gagaatggaa gaattttttc tatttggagc cttcttggaa gcctcaatga    2040
ttgaccggaa aaatggggac aagccaatta cctttgaggt gaccataggaa aactacggca   2100 atgaagtcga tggtatgtcc cggccctga ggcctcggcc ccggaaagag cctggggatg     2160
aagaagaggt agacctgatt cagaactcca gtgacgatga aggtgacgaa gccggggacc    2220
tggcctcggt gtcctccacc ccacctatgc ggccccagat cacggacagg aactatttcc    2280
acctgcccta cctggagcgc aagccctgca tctatatcaa gagctggtgg cctgaccaga    2340
ggcggcgcct ctacaatgcc aacatcatgg atcacattgc tgacaagctg aagaaggcc     2400 tgaatgatgt acaggagatg atcaaaacgg agaagtccta cccggagcgc cgcctgcggg    2460
gtgtgctaga ggaactcagc tgtggctgcc accgcttcct ctccctctcg gacaaggacc    2520
agggccgctc gtcccgcacc aggctggatc gagagcgtct taagtcctgt atgagggagt    2580
tggagagcat gggacagcag gccaagagcc tgagggctca ggtgaagcgg cacactgttc    2640
gggacaagct gaggtcatgc cagaactttc tgcagaagct acgcttcctg gcggatgagc    2700
cccagcacag cattcctgat gtgttcattt ggatgatgag caacaacaaa cgtatcgcct    2760
atgcccgcgt gccttccaaa gacctgctct ctccatcgt ggaggaggaa ctgggcaagg     2820
actgcgccaa agtcaagacc ctcttcctga agctgccagg gaagaggggc ttcggctcgg    2880
caggctggac agtacaggcc aagctggagc tctacctgtg gctgggcctc agcaagcagc    2940
gaaaggactt cctgtgtggt ctgccctgtg gcttcgagga ggtcaaggca gcccaaggcc    3000
tgggcctgca ttccttttccg cccatcagcc tagtctacac caagaagcaa gccttccagc    3060
tccgagcaca catgtatcag gcccgaagcc tctttgctgc tgacagcagt gggctctctg    3120 atcccttttgc ccgtgtcttc ttcatcaacc agagccaatg cactgaggtt ctaaacgaga    3180
cactgtgtcc cacctgggac cagatgctgg tatttgacaa cctggagctg tacggtgaag    3240
ctcacgagtt acgagatgat cccccccatca ttgtcattga aatctacgac caggacagca    3300
tgggcaaagc cgacttcatg ggccggacct tcgccaagcc cctggtgaag atggcagatg    3360
aagcatactg cccacctcgc ttcccgccgc agcttgagta ctaccagatc taccgaggca    3420
gtgccactgc cggagaccta ctggctgcct tcagctgct gcagattggg ccatcaggga    3480
aggctgacct gccacccatc aatgcccag tggacatgga cagagggccc atcatgcctg     3540
tgcccgtggg aatccggcca gtgctcagca agtaccgagt ggaggtgctg ttctggggcc    3600
tgagggacct aaagagggtg aacctggccc aggtggaccg accacgggtg gacatcgagt    3660
gtgcaggaaa gggggtacaa tcctcccctga ttcacaatta taagaagaac cccaacttca    3720
acacgctggt caagtggttt gaagtggacc tcccggagaa tgagctcctg cacccaccct    3780
tgaacatccg agtggtagat tgccgggcct ttgacgata cacccctggtg ggttcccacg    3840 cagtcagctc actgaggcgc ttcatctacc gacctccaga ccgctcagcc cccaactgga    3900
acaccacagg ggaggttgta gtaagcatgg agcctgagga gccagttaag aagctggaga    3960
```

```
ccatggtgaa actggatgcg acttctgatg ctgtggtcaa ggtggatgtg gctgaagatg    4020
agaaggaaag gaagaagaag aaaaagaaag gcccgtcaga ggagccagag gaggaagagc    4080
ccgatgagag catgctggat tggtggtcca agtacttcgc ctccatcgac acaatgaagg    4140
agcaacttcg acaacatgag acctctggaa ctgacttgga agagaaggaa gagatggaaa    4200
gcgctgaggg cctgaaggga ccaatgaaga gcaaggagaa gtccagagct gcaaaggagg    4260
agaaaaagaa gaaaaaccag agccctggcc ctggccaggg atcggaggct cctgagaaga    4320
agaaagccaa gatcgatgag cttaaggtgt accccaagga gctggaatcg agtttgaca    4380 gctttgagga ctggctgcac accttcaacc tgttgagggg caagacggga gatgatgagg    4440
atggctccac agaggaggag cgcatagtag gccgattcaa gggctccctc tgtgtgtaca    4500
aagtgccact cccagaagat gtatctcgag aagctggcta tgatcccacc tatgaatgt    4560 tccagggcat cccaagcaat gaccccatca atgtgctggt ccgaatctat gtggtccggg    4620
ccacagacct gcacccggcc gacatcaatg caaagctga ccctatatt gccatcaagt    4680 taggcaagac cgacatccga gacaaggaga actacatctc caagcagctc aaccctgtgt    4740
ttgggaagtc cttttgacatt gaggcctcct tccccatgga gtccatgttg acagtggccg    4800
tgtacgactg ggatctggtg ggcactgatg acctcatcgg agaaaccaag attgacctgg    4860
aaaaccgctt ctacagcaag catcgcgcca cctgcggcat cgcacagacc tattccatac    4920
atggctacaa tatctggagg gaccccatga agcccagcca gatcctgaca cgcctctgta    4980
aagagggcaa agtggacggc ccccactttg gtccccatgg gagagtgagg gttgccaacc    5040
gtgtcttcac ggggccttca gaaatagagg atgagaatgg tcagaggaag cccacagatg    5100
agcacgtggc actgtctgct ctgagacact gggaggacat ccccgggtg gctgccgcc     5160 ttgtgccgga acacgtggag accaggccgc tgctcaaccc tgacaagcca ggcattgagc    5220
agggccgcct ggagctgtgg gtggacatgt tccccatgga catgccagcc cctgggacac    5280
ctctggatat atcccccagg aaacccaaga agtacgagct gcgggtcatc gtgtggaaca    5340
cagacgaggt ggtcctggaa gacgatgatt tcttcacggg agagaagtcc agtgacattt    5400
ttgtgagggg gtggctgaag gccagcagg aggacaaaca ggacacagat gtccactatc    5460
actccctcac gggggagggc aacttcaact ggagatacct cttcccttc gactacctag    5520 cggccgaaga gaagatcgtt atgtccaaaa aggagtctat gttctcctgg gatgagacgg    5580
agtacaagat ccctgcgcgg ctcaccctgc agatctggga cgctgaccac ttctcggctg    5640
acgacttcct gggggctatc gagctggacc tgaaccggtt cccgagggc gctaagacag    5700 ccaagcagtg caccatggag atggccaccg gggaggtgga cgtacccctg gtttccatct    5760
ttaaacagaa acgtgtcaaa ggctggtggc ccctcctggc ccgcaatgag aatgatgagt    5820
ttgagctcac aggcaaagtg gaggcggagc tacacctact cacggcagag gaggcagaga    5880
agaaccctgt gggcctggct cgcaatgaac ctgatcccct agaaaaaccc aaccggcctg    5940
acacggcatt cgtctggttc ctgaacccac tcaaatctat caagtacctc atctgcaccc    6000
ggtacaagtg gctgatcatc aagatcgtgc tggcgctgct ggggctgctc atgctggccc    6060
tcttcccttt cagcctccca ggctacatgg tcaagaagct cctagggcc tgaagtgtgc    6120 cccacccag cccgctccag catccctcca ggggctgctg cgtattttgc cttccctcac    6180
ctggactctc tcccaactcc ctgaggagcc ctcccacgcc tgccagcctt gagcaagaca    6240
cctgcttgct ggacttcatc cccaccccac acccaaactg ttgcttgcct gatcttgtcc    6300
```

```
caggcctgcc tggggtttgg ggcacagttg gcctccaaaa ccagatacccc tcttgtctaa    6360 agtaccaggt tcctctgccc aaccccaaga gtggtagtgg cccaaccctc cctgtgcttt    6420
ccaaatcttg tcttaaggca ccagtgaaat taaccaagaa acgcggagca atgcccaagg    6480
ctctgatgag taggaacacg tggaaagcac caggaatgcc agcagaggcg aggcggcaca    6540
cctctctgca gagcatccag gccgagcggc gggcagcggc cagctgcttc tgcgcatgct    6600
ctcctcttgg ctctgcttct ttctcacagt cacagtcact tcacagctta gccttgggct    6660
tcccatcact tccaggggtg cctctgcctt ggccagtgtg tgtcagctag tacacaagct    6720
ccaagtgtga atcaggtgta ctggccgtcc tgaagactga ctgccctgtc cttcctgccg    6780
acagccacac ccgagtgtac acttaaagcg gtgcccttct gcctctgtgg gcctgctggc    6840
tgctgttcct ttcttgagtg tgattttttt tttctctccc tcaataaaat aaatcaaact    6900
ctgagac                                                              6907

<210> SEQ ID NO 18
<211> LENGTH: 6862
<212> TYPE: DNA
<213> ORGANISM: Mus musculus

<400> SEQUENCE: 18
ttggttgcct tggtctctgt gggcagcagc aggaggaggc ggcagcagcc agagaagagg      60
gaggcgtgtg agccacactc caccagcgag cttcttcccg ctgctctgga actgcccagg     120
ctctccccac cagcatggcc ctgattgttc acctcaagac tgtctcagag ctccgaggca     180
aaggtgaccg gattgccaaa gtcactttcc gagggcagtc tttctactcc cgggtcctgg     240
agaactgcga gggtgtggct gactttgatg agacgttccg gtggccagtg gccagcagca     300
tcgaccggaa tgaagtgttg gagattcaga ttttcaacta cagcaaagtc ttcagcaaca     360
agctgatagg gaccttctgc atggtgctgc agaaagtggt ggaggagaat cgggtagagg     420
tgaccgacac gctgatggat gacagcaatg ctatcatcaa gaccagcctg agcatggagg     480
tccggtatca ggccacagat ggcactgtgg gcccctggga tgatggagac ttcctgggag     540
atgaatccct ccaggaggag aaggacagcc aggagacaga tgggctgcta cctggttccc     600
gacccagcac ccggatatct ggcgagaaga gctttcgcag agcgggaagg agtgtgttct     660
cggccatgaa actcggcaaa actcggtccc acaaagagga gccccaaaga caagatgagc     720
cagcagtgct ggagatggag gacctggacc acctagccat tcagctgggg gatgggctgg     780
atcctgactc cgtgtctcta gcctcggtca ccgctctcac cagcaatgtc tccaacaaac     840
ggtctaagcc agatattaag atggagccca gtgctggaag gcccatggat taccaggtca     900
gcatcacagt gattgaggct cggcagctgg tgggcttgaa catggaccct gtggtgtgtg     960
tggaggtggg tgatgacaag aaatacacgt caatgaagga gtccacaaac tgcccttact    1020
acaacgagta ctttgtcttc gacttccatg tctctcctga tgtcatgttt gacaagatca    1080
tcaagatctc ggttatccat tctaagaacc tgcttcggag cggcacctg gtgggttcct    1140 tcaaaatgga tgtggggact gtgtattccc agcctgaaca ccagttccat cacaaatggg    1200
ccatcctgtc agacccgat gacatctctg ctgggttgaa gggttatgta agtgtgatg     1260 tcgctgtggt gggcaaggga gacaacatca agacacccca aaggccaac gagacggatg     1320 aggacgacat tgaagggaac ttgctgctcc ccgagggcgt gccccccgaa cggcagtggg    1380
cacggttcta tgtgaaaatt taccgagcag agggactgcc ccggatgaac acaagcctca    1440
tggccaacgt gaagaaggcg ttcatcggtg agaacaagga cctcgtcgac ccctatgtgc    1500
```

```
aagtcttctt tgctggacaa aagggcaaaa catcagtgca gaagagcagc tatgagccgc    1560
tatggaatga gcaggtcgtc ttcacagact tgttcccccc actctgcaaa cgcatgaagg    1620
tgcagatccg ggactctgac aaggtcaatg atgtggccat cggcacccac ttcatcgacc    1680
tgcgcaagat ttccaacgat ggagacaaag gcttcctgcc taccctcggt ccagcctggg    1740
tgaacatgta cggctccacg cgcaactaca cactgctgga cgagcaccag gacttgaatg    1800
aaggcctggg ggagggtgtg tccttccggg cccgcctcat gttgggacta gctgtggaga    1860
tcctggacac ctccaaccca gagctcacca gctccacgga ggtgcaggtg gagcaggcca    1920
cgcctgtctc ggagagctgc acaggggaaa tggaagaatt ttttctattt ggagccttct    1980
tggaagcctc aatgattgac cggaaaaatg gggacaagcc aattacccttt gaggtgacca    2040
taggaaacta cggcaatgaa gtcgatggta tgtcccggcc cctgaggcct cggccccgga    2100
aagagcctgg ggatgaagaa gaggtagacc tgattcagaa ctccagtgac gatgaaggtg    2160
acgaagccgg ggacctggcc tcggtgtcct ccaccccacc tatgcggccc cagatcacgg    2220
acaggaacta tttccacctg ccctacctgg agcgcaagcc ctgcatctat atcaagagct    2280
ggtggcctga ccagaggcgg cgcctctaca atgccaacat catggatcac attgctgaca    2340
agctggaaga aggcctgaat gatgtacagg agatgatcaa aacggagaag tcctacccgg    2400
agcgccgcct gcggggtgtg ctagaggaac tcagctgtgg ctgccaccgc ttcctctccc    2460
tctcggacaa ggaccagggc cgctcgtccc gcaccaggct ggatcgagag cgtcttaagt    2520
cctgtatgag ggagttggag agcatggac agcaggccaa gagcctgagg gctcaggtga    2580
agcggcacac tgttcgggac aagctgaggt catgccagaa ctttctgcag aagctacgct    2640
tcctggcgga tgagcccag cacagcattc ctgatgtgtt catttggatg atgagcaaca    2700
acaaacgtat cgcctatgcc cgcgtgcctt ccaaagacct gctcttctcc atcgtggagg    2760
aggaactggg caaggactgc gccaaagtca gaccctcctt cctgaagctg ccagggaaga    2820
ggggcttcgg ctcggcaggc tggacagtac aggccaagct ggagctctac ctgtggctgg    2880
gcctcagcaa gcagcgaaag gacttcctgt gtggtctgcc ctgtggcttc gaggaggtca    2940
aggcagccca aggcctgggc ctgcattcct ttccgcccat cagcctagtc tacaccaaga    3000
agcaagcctt ccagctccga gcacacatgt atcaggcccg aagcctcttt gctgctgaca    3060
gcagtgggct ctctgatccc tttgcccgtg tcttcttcat caaccagagc caatgcactg    3120
aggttctaaa cgagacactg tgtcccacct gggaccagat gctggtatt gacaacctgg    3180
agctgtacgg tgaagctcac gagttacgag atgatccccc catcattgtc attgaaatct    3240
acgaccagga cagcatgggc aaagccgact tcatgggccg gaccttcgcc aagcccctgg    3300
tgaagatggc agatgaagca tactgcccac ctcgcttccc gccgcagctt gagtactacc    3360
agatctaccg aggcagtgcc actgccggag acctactggc tgccttcgag ctgctgcaga    3420
ttgggccatc agggaaggct gacctgccac ccatcaatgg cccagtggac atggacagag    3480
ggcccatcat gcctgtgccc gtgggaatcc ggccagtgct cagcaagtac cgagtggagg    3540
tgctgttctg gggcctgagg gacctaaaga gggtgaacct ggcccaggtg gaccgaccac    3600
gggtggacat cgagtgtgca ggaaagggg tacaatcctc cctgattcac aattataaga    3660
agaaccccaa cttcaacacg ctggtcaagt ggtttgaagt ggacctcccg gagaatgagc    3720
tcctgcaccc acccttgaac atccgagtgg tagattgccg ggccttttgga cgatacaccc    3780
tggtgggttc ccacgcagtc agctcactga ggcgcttcat ctaccgacct ccagaccgct    3840
```

-continued

```
cagcccccaa ctggaacacc acaggggagg ttgtagtaag catggagcct gaggagccag    3900
ttaagaagct ggagaccatg gtgaaactgg atgcgacttc tgatgctgtg gtcaaggtgg    3960
atgtggctga agatgagaag gaaaggaaga agaagaaaaa gaaaggcccg tcagaggagc    4020
cagaggagga agagcccgat gagagcatgc tggattggtg gtccaagtac ttcgcctcca    4080
tcgacacaat gaaggagcaa cttcgacaac atgagacctc tggaactgac ttggaagaga    4140
aggaagagat ggaaagcgct gagggcctga agggaccaat gagagcaag gagaagtcca    4200
gagctgcaaa ggaggagaaa aagaagaaaa accagagccc tggccctggc cagggatcgg    4260
aggctcctga agaagaaaa gccaagatcg atgagcttaa ggtgtacccc aaggagctgg    4320
aatcggagtt tgacagcttt gaggactggc tgcacacctt caacctgttg aggggcaaga    4380
cgggagatga tgaggatggc tccacagagg aggagcgcat agtaggccga ttcaagggct    4440
ccctctgtgt gtacaaagtg ccactcccag aagatgtatc tcgagaagct ggctatgatc    4500
ccacctatgg aatgttccag ggcatcccaa gcaatgaccc catcaatgtg ctggtccgaa    4560
tctatgtggt ccgggccaca gacctgcacc cggccgacat caatggcaaa gctgacccct    4620
atattgccat caagttaggc aagaccgaca tccgagacaa ggagaactac atctccaagc    4680
agctcaaccc tgtgtttggg aagtcctttg acattgaggc ctccttcccc atggagtcca    4740
tgttgacagt ggccgtgtac gactgggatc tggtgggcac tgatgacctc atcggagaaa    4800
ccaagattga cctggaaaac cgcttctaca gcaagcatcg cgccacctgc ggcatcgcac    4860
agacctattc catacatggc tacaatatct ggagggaccc catgaagccc agccagatcc    4920
tgacacgcct ctgtaaagag ggcaaagtgg acggccccca ctttggtccc catgggagag    4980
tgagggttgc caaccgtgtc ttcacggggc cttcagaaat agaggatgag aatggtcaga    5040
ggaagcccac agatgagcac gtggcactgt ctgctctgag acactgggag gacatccccc    5100
gggtgggctg ccgccttgtg ccggaacacg tggagaccag gccgctgctc aaccctgaca    5160
agccaggcat tgagcagggc cgcctggagc tgtgggtgga catgttcccc atggacatgc    5220
cagcccctgg gacacctctg gatatatccc caggaaaacc caagaagtac gagctgcggg    5280
tcatcgtgtg gaacacagac gaggtggtcc tggaagacga tgatttcttc acggagagaa    5340
agtccagtga catttttgtg aggggggtgc tgaagggcca gcaggaggac aaacaggaca    5400
cagatgtcca ctatcactcc ctcacggggg agggcaactt caactggaga tacctcttcc    5460
ccttcgacta cctagcggcc gaagagaaga tcgttatgtc caaaaaggag tctatgttct    5520
cctgggatga gacggagtac aagatccctg cgcggctcac cctgcagatc tgggacgctg    5580
accacttctc ggctgacgac ttcctggggg ctatcgagct ggacctgaac cggttcccga    5640
ggggcgctaa gacagccaag cagtgcacca tggagatggc caccggggag gtggacgtac    5700
ccctggtttc catcttaaa cagaaacgtg tcaaaggctg gtggcccctc ctggcccgca    5760
atgagaatga tgagtttgag ctcacaggca agtggaggc ggagctacac ctactcacgg    5820
cagaggaggc agagaagaac cctgtgggcc tggctcgcaa tgaacctgat cccctagaaa    5880
aacccaaccg gcctgacacg gcattcgtct ggttcctgaa cccactcaaa tctatcaagt    5940
acctcatctg cacccggtac aagtggctga tcatcaagat cgtgctggcg ctgctggggc    6000
tgctcatgct ggccctcttc ctttacagcc tccaggcta catggtcaag aagctcctag    6060
gggcctgaag tgtgccccac ccagcccgc tccagcatcc ctccaggggc tgctgcgtat    6120
tttgccttcc ctcacctgga ctctctccca actccctgag gagccctccc acgcctgcca    6180
gccttgagca agacacctgc ttgctggact tcatccccac cccacaccca aactgttgct    6240
```

```
tgcctgatct tgtcccaggc ctgcctgggg tttggggcac agttggcctc caaaaccaga    6300
taccctcttg tctaaagtac caggttcctc tgcccaaccc caagagtggt agtggcccaa    6360
ccctccctgt gctttccaaa tcttgtctta aggcaccagt gaaattaacc aagaaacgcg    6420
gagcaatgcc caaggctctg atgagtagga cacgtggaa agcaccagga atgccagcag     6480
aggcgaggcg gcacacctct ctgcagagca tccaggccga gcggcgggca gcggccagct    6540
gcttctgcgc atgctctcct cttggctctg cttctttctc acagtcacag tcacttcaca    6600
gcttagcctt gggcttccca tcacttccag gggtgcctct gccttggcca gtgtgtgtca    6660
gctagtacac aagctccaag tgtgaatcag gtgtactggc cgtcctgaag actgactgcc    6720
ctgtccttcc tgccgacagc cacacccgag tgtacactta aagcggtgcc cttctgcctc    6780
tgtgggcctg ctggctgctg ttcctttctt gagtgtgatt ttttttttct ctccctcaat    6840
aaaataaatc aaactctgag ac                                             6862

<210> SEQ ID NO 19
<211> LENGTH: 77
<212> TYPE: DNA
<213> ORGANISM: Artificial Sequence
<220> FEATURE:
<223> OTHER INFORMATION: Synthetic Construct

<400> SEQUENCE: 19
gggattttgc cgatttcggc ctattggtta aaaatgagc tgatttaaca aaaatttaac     60
gcgaatttta acaaaat                                                   77

<210> SEQ ID NO 20
<211> LENGTH: 82
<212> TYPE: DNA
<213> ORGANISM: Artificial Sequence
<220> FEATURE:
<223> OTHER INFORMATION: Synthetic Construct

<400> SEQUENCE: 20
gtaagtatca aggttacaag acaggtttaa ggagaccaat agaaactggg cttgtcgaga    60
cagagaagac tcttgcgttt ct                                             82

<210> SEQ ID NO 21
<211> LENGTH: 51
<212> TYPE: DNA
<213> ORGANISM: Artificial Sequence
<220> FEATURE:
<223> OTHER INFORMATION: Synthetic Construct

<400> SEQUENCE: 21
gataggcacc tattggtctt actgacatcc actttgcctt tctctccaca g             51

<210> SEQ ID NO 22
<211> LENGTH: 48
<212> TYPE: DNA
<213> ORGANISM: Artificial Sequence
<220> FEATURE:
<223> OTHER INFORMATION: Synthetic Construct

<400> SEQUENCE: 22
gcctgcaaga actggttcag cagcctgagc cacttcgtga tccacctg                 48

<210> SEQ ID NO 23
<211> LENGTH: 548
<212> TYPE: DNA
```

<213> ORGANISM: Artificial Sequence
<220> FEATURE:
<223> OTHER INFORMATION: Synthetic Construct

<400> SEQUENCE: 23

| | |
|---|---|
| gatccaatca acctctggat tacaaaattt gtgaaagatt gactggtatt cttaactatg | 60 |
| ttgctcctttt tacgctatgt ggatacgctg ctttaatgcc tttgtatcat gctattgctt | 120 |
| cccgtatggc tttcattttc tcctccttgt ataaatcctg gttgctgtct ctttatgagg | 180 |
| agttgtggcc cgttgtcagg caacgtggcg tggtgtgcac tgtgtttgct gacgcaaccc | 240 |
| ccactggttg gggcattgcc accacctgtc agctcctttc cgggactttc gctttccccc | 300 |
| tccctattgc cacggcggaa ctcatcgccg cctgccttgc ccgctgctgg acaggggctc | 360 |
| ggctgttggg cactgacaat tccgtggtgt tgtcggggaa atcatcgtcc tttccttggc | 420 |
| tgctcgcctg tgttgccacc tggattctgc gcgggacgtc cttctgctac gtcccttcgg | 480 |
| ccctcaatcc agcggacctt ccttcccgcg gcctgctgcc ggctctgcgg cctcttccgc | 540 |
| gtcttcga | 548 |

<210> SEQ ID NO 24
<211> LENGTH: 454
<212> TYPE: DNA
<213> ORGANISM: Mus musculus

<400> SEQUENCE: 24

| | |
|---|---|
| ctgcagctca gcctactact tgctttccag gctgttccta gttcccatgt cagctgcttg | 60 |
| tgctttccag agacaaaaca ggaataatag atgtcattaa atatacattg gccccaggc | 120 |
| ggtcaatgtg gcagcctgag cctcctttcc atctctgtgg aggcagacat aggaccccca | 180 |
| acaaacagca tgcaggttgg gagccagcca caggacccag gtaaggggcc ctgggtcctt | 240 |
| aagcttctgc cactggctcc ggcattgcag agagaagaga aggggcggca gagctgaacc | 300 |
| ttagccttgc cttcctgggt acccttctga gcctcactgt cttctgtgag atgggcaaag | 360 |
| tgcgggtgtg actccttggc aacggtgtta caccagggca ggtaaagttg tagttatttg | 420 |
| tggggtacac caggactgtt aaaggtgtaa ctat | 454 |

<210> SEQ ID NO 25
<211> LENGTH: 1157
<212> TYPE: DNA
<213> ORGANISM: Mus musculus

<400> SEQUENCE: 25

| | |
|---|---|
| ggtctcaccc agcattttca cttctaataa gttcaaatgt gatacggcac ctttctaaaa | 60 |
| attagttttc agggaaatag ggttcaaaac tggtagtggt agggtccatt ctcacgaccc | 120 |
| ccaggcctgc taaccctgac caagctacct attacttacc ctcctctttc tcctcctcct | 180 |
| ctttctcctt ctcctgcttc ccctcttcct tctccctccc ttcctctccc tcctcccct | 240 |
| ccttggctgt gatcagatcc agagcctgaa tgagcctcct gaccccacac ccccactagc | 300 |
| atgggcctgc aagtgcccag aagtccctcc tgcctcctaa actgcccagc cgatccatta | 360 |
| gctcttcctt cttcccagtg aaagaagcag gcacagcctg tccctcccgt tctacagaaa | 420 |
| ggaagctaca gcacagggag ggccaaaggc cttcctggga ctagacagtt gatcaacagc | 480 |
| aggactggag agctgggctc catttttgtt ccttggtgcc ctgcccctcc ccatgacctg | 540 |
| cagagacatt cagcctgcca ggctttatga ggtgggagct gggctctccc tgatgtatta | 600 |
| ttcagctccc tggagttggc cagctcctgt tacactggcc acagccctgg gcatccgctt | 660 |

```
ctcacttcta gtttccctc caaggtaatg tggtgggtca tgatcattct atcctggctt    720
cagggacctg actccacttt ggggccattc gaggggtcta ggtagatga tgtcccctg     780 tggggattaa tgtcctgctc tgtaaaactg agctagctga gatccaggag ggcttggcca   840
gagacagcaa gttgttgcca tggtgacttt aaagccaggt tgctgcccca gcacaggcct   900
cccagtctac cctcactaga aaacaacacc caggcacttt ccaccacctc tcaaaggtga   960
aacccaaggc tggtctagag aatgaattat ggatcctcgc tgtccgtgcc acccagctag  1020
tcccagcggc tcagacactg aggagagact gtaggttcag ctacaagcaa aaagacctag  1080
ctggtctcca agcagtgtct ccaagtccct gaacctgtga cacctgcccc aggcatcatc  1140
aggcacagag ggccacc                                                 1157
```

<210> SEQ ID NO 26
<211> LENGTH: 76
<212> TYPE: DNA
<213> ORGANISM: Mus musculus

<400> SEQUENCE: 26

```
cccatgtcag ctgcttgtgc tttccagaga caaaacagga ataatagatg tcattaaata    60
tacattgggc cccagg                                                     76
```

<210> SEQ ID NO 27
<211> LENGTH: 95
<212> TYPE: DNA
<213> ORGANISM: Mus musculus

<400> SEQUENCE: 27

```
agcctgagcc tcctttccat ctctgtggag gcagacatag gaccccaac aaacagcatg    60 caggttggga gccagccaca ggacccaggt aaggg                               95
```

<210> SEQ ID NO 28
<211> LENGTH: 171
<212> TYPE: DNA
<213> ORGANISM: Artificial Sequence
<220> FEATURE:
<223> OTHER INFORMATION: Synthetic Construct

<400> SEQUENCE: 28

```
cccatgtcag ctgcttgtgc tttccagaga caaaacagga ataatagatg tcattaaata    60
tacattgggc cccaggagcc tgagcctcct ttccatctct gtggaggcag acataggacc  120
cccaacaaac agcatgcagg ttgggagcca gccacaggac ccaggtaagg g            171
```

<210> SEQ ID NO 29
<211> LENGTH: 171
<212> TYPE: DNA
<213> ORGANISM: Artificial Sequence
<220> FEATURE:
<223> OTHER INFORMATION: Synthetic Construct

<400> SEQUENCE: 29

```
agcctgagcc tcctttccat ctctgtggag gcagacatag gaccccaac aaacagcatg    60 caggttggga gccagccaca ggacccaggt aagggcccat gtcagctgct tgtgctttcc  120
agagacaaaa caggaataat agatgtcatt aaatatacat tgggccccag g            171
```

<210> SEQ ID NO 30
<211> LENGTH: 184
<212> TYPE: DNA

<213> ORGANISM: Mus musculus

<400> SEQUENCE: 30

```
cccatgtcag ctgcttgtgc tttccagaga caaaacagga ataatagatg tcattaaata      60
tacattgggc cccaggcggt caatgtggca gcctgagcct cctttccatc tctgtggagg     120
cagacatagg accccaaca aacagcatgc aggttgggag ccagccacag gacccaggta     180
aggg                                                                 184
```

<210> SEQ ID NO 31
<211> LENGTH: 82
<212> TYPE: DNA
<213> ORGANISM: Mus musculus

<400> SEQUENCE: 31

```
tgaggtggga gctgggctct ccctgatgta ttattcagct ccctggagtt ggccagctcc      60
tgttacactg gccacagccc tg                                              82
```

<210> SEQ ID NO 32
<211> LENGTH: 106
<212> TYPE: DNA
<213> ORGANISM: Mus musculus

<400> SEQUENCE: 32

```
cacaggcctc ccagtctacc ctcactagaa acaacaccc aggcactttc caccacctct      60
caaaggtgaa acccaaggct ggtctagaga atgaattatg gatcct                   106
```

<210> SEQ ID NO 33
<211> LENGTH: 188
<212> TYPE: DNA
<213> ORGANISM: Artificial Sequence
<220> FEATURE:
<223> OTHER INFORMATION: Synthetic Construct

<400> SEQUENCE: 33

```
tgaggtggga gctgggctct ccctgatgta ttattcagct ccctggagtt ggccagctcc      60
tgttacactg gccacagccc tgcacaggcc tcccagtcta ccctcactag aaaacaacac    120
ccaggcactt tccaccacct ctcaaaggtg aaacccaagg ctggtctaga gaatgaatta    180
tggatcct                                                            188
```

<210> SEQ ID NO 34
<211> LENGTH: 188
<212> TYPE: DNA
<213> ORGANISM: Artificial Sequence
<220> FEATURE:
<223> OTHER INFORMATION: Synthetic Construct

<400> SEQUENCE: 34

```
cacaggcctc ccagtctacc ctcactagaa acaacaccc aggcactttc caccacctct      60
caaaggtgaa acccaaggct ggtctagaga atgaattatg gatccttgag gtgggagctg    120
ggctctccct gatgtattat tcagctccct ggagttggcc agctcctgtt acactggcca    180
cagccctg                                                            188
```

<210> SEQ ID NO 35
<211> LENGTH: 430
<212> TYPE: DNA
<213> ORGANISM: Mus musculus

<400> SEQUENCE: 35

```
tgaggtggga gctgggctct ccctgatgta ttattcagct ccctggagtt ggccagctcc    60
tgttacactg gccacagccc tgggcatccg cttctcactt ctagtttccc ctccaaggta   120
atgtggtggg tcatgatcat tctatcctgg cttcagggac ctgactccac tttggggcca   180
ttcgaggggt ctagggtaga tgatgtcccc ctgtggggat taatgtcctg ctctgtaaaa   240
ctgagctagc tgagatccag gagggcttgg ccagagacag caagttgttg ccatggtgac   300
tttaaagcca ggttgctgcc ccagcacagg cctcccagtc taccctcact agaaaacaac   360
acccaggcac tttccaccac ctctcaaagg tgaaacccaa ggctggtcta gagaatgaat   420
tatggatcct                                                          430
```

<210> SEQ ID NO 36
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 36

```
ctgcagctca gcctactact tgctttccag gctgttccta gttcccatgt cagctgcttg    60
tgctttccag agacaaaaca ggaataatag atgtcattaa atatacattg gccccaggc    120 ggtcaatgtg gcagcctgag cctcctttcc atctctgtgg aggcagacat aggaccccca   180
acaaacagca tgcaggttgg gagccagcca caggacccag gtaaggggcc ctgggtcctt   240
aagcttctgc cactggctcc ggcattgcag agagaagaga aggggcggca gagctgaacc   300
ttagccttgc cttcctgggt acccttctga gcctcactgt cttctgtgag atgggcaaag   360
tgcgggtgtg actccttggc aacggtgtta caccagggca ggtaaagttg tagttatttg   420
tggggtacac caggactgtt aaaggtgtaa ctatggtctc acccagcatt tcacttcta   480 ataagttcaa atgtgatacg gcacctttct aaaaattagt tttcagggaa atagggttca   540
aaactggtag tggtagggtc cattctcacg accccaggc ctgctaaccc tgaccaagct   600
acctattact taccctcctc tttctcctcc tcctctttct ccttctcctg cttccctct   660 tccttctccc tcccttcctc tccctcctcc ccctccttgg ctgtgatcag atccagagcc   720
tgaatgagcc tcctgacccc acaccccac tagcatgggc ctgcaagtgc ccagaagtcc   780
ctcctgcctc ctaaactgcc cagccgatcc attagctctt ccttcttccc agtgaaagaa   840
gcaggcacag cctgtccctc ccgttctaca gaaaggaagc tacagcacag ggagggccaa   900
aggccttcct gggactagac agttgatcaa cagcaggact ggagagctgg gctccatttt   960
tgttccttgg tgccctgccc ctccccatga cctgcagaga cattcagcct gccaggcttt  1020
atgaggtggg agctgggctc tccctgatgt attattcagc tccctggagt tggccagctc  1080
ctgttacact ggccacagcc ctgggcatcc gcttctcact tctagtttcc cctccaaggt  1140
aatgtggtgg gtcatgatca ttctatcctg gcttcaggga cctgactcca ctttggggcc  1200
attcgagggg tctagggtag atgatgtccc cctgtgggga ttaatgtcct gctctgtaaa  1260
actgagctag ctgagatcca ggagggcttg gccagagaca gcaagttgtt gccatggtga  1320
ctttaaagcc aggttgctgc cccagcacag gcctcccagt ctaccctcac tagaaaacaa  1380
cacccaggca cttccacca cctctcaaag gtgaaaccca aggctggtct agagaatgaa  1440
ttatggatcc tcgctgtccg tgccaccag ctagtcccag cggctcagac actgaggaga  1500
gactgtaggt tcagctacaa gcaaaaagac ctagctggtc tccaagcagt gtctccaagt  1560
```

```
cctgaacct gtgacacctg ccccaggcat catcaggcac agagggccac c         1611
```

<210> SEQ ID NO 37
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 37

```
ggtctcaccc agcattttca cttctaataa gttcaaatgt gatacggcac ctttctaaaa   60
attagttttc agggaaatag ggttcaaaac tggtagtggt agggtccatt ctcacgaccc  120
ccaggcctgc taaccctgac caagctacct attacttacc ctcctctttc tcctcctcct  180
ctttctcctt ctcctgcttc ccctcttcct tctccctccc ttcctctccc tcctccccct  240
ccttggctgt gatcagatcc agagcctgaa tgagcctcct gaccccacac ccccactagc  300
atgggcctgc aagtgcccag aagtccctcc tgcctcctaa actgcccagc cgatccatta  360
gctcttcctt cttcccagtg aaagaagcag gcacagcctg tccctcccgt tctacagaaa  420
ggaagctaca gcacagggag ggccaaaggc cttcctggga ctagacagtt gatcaacagc  480
aggactggag agctgggctc cattttttgtt ccttggtgcc ctgcccctcc ccatgacctg  540
cagagacatt cagcctgcca ggctttatga ggtgggagct gggctctccc tgatgtatta  600
ttcagctccc tggagttggc cagctcctgt tacactggcc acagccctgg gcatccgctt  660
ctcacttcta gtttcccctc caaggtaatg tggtgggtca tgatcattct atcctggctt  720
cagggacctg actccacttt ggggccattc gaggggtcta gggtagatga tgtcccctg   780
tggggattaa tgtcctgctc tgtaaaactg agctagctga gatccaggag ggcttggcca  840
gagacagcaa gttgttgcca tggtgacttt aaagccaggt tgctgcccca gcacaggcct  900
cccagtctac cctcactaga aacaacacc caggcacttt ccaccacctc tcaaaggtga  960
aacccaaggc tggtctagag aatgaattat ggatcctcgc tgtccgtgcc acccagctag 1020
tcccagcggc tcagacactg aggagagact gtaggttcag ctacaagcaa aaagacctag 1080
ctggtctcca agcagtgtct ccaagtccct gaacctgtga cacctgcccc aggcatcatc 1140
aggcacagag ggccaccctg cagctcagcc tactacttgc tttccaggct gttcctagtt 1200
cccatgtcag ctgcttgtgc tttccagaga caaaacagga ataatagatg tcattaaata 1260
tacattgggc cccaggcggt caatgtggca gcctgagcct cctttccatc tctgtggagg 1320
cagacatagg acccccaaca aacagcatgc aggttgggag ccagccacag gacccaggta 1380
aggggccctg ggtccttaag cttctgccac tggctccggc attgcagaga aagagaagg  1440
ggcggcagag ctgaacctta gccttgcctt cctgggtacc cttctgagcc tcactgtctt 1500
ctgtgagatg ggcaaagtgc gggtgtgact ccttggcaac ggtgttacac cagggcaggt 1560
aaagttgtag ttatttgtgg ggtacaccag gactgttaaa ggtgtaacta t         1611
```

<210> SEQ ID NO 38
<211> LENGTH: 425
<212> TYPE: DNA
<213> ORGANISM: Artificial Sequence
<220> FEATURE:
<223> OTHER INFORMATION: Synthetic Construct

<400> SEQUENCE: 38

```
aatcaacctc tggattacaa aatttgtgaa agattgactg gtattcttaa ctatgttgct   60
cctttacgc tatgtggata cgctgcttta atgcctttgt atcatgctat tgcttcccgt   120
```

```
atggctttca ttttctcctc cttgtataaa tcctggttag ttcttgccac ggcggaactc    180
atcgccgcct gccttgcccg ctgctggaca ggggctcggc tgttgggcac tgacaattcc    240
gtggtgttta tttgtgaaat ttgtgatgct attgctttat tgtaaccat ctagctttat     300 ttgtgaaatt tgtgatgcta ttgctttatt tgtaaccatt ataagctgca ataaacaagt    360
taacaacaac aattgcattc attttatgtt tcaggttcag ggggagatgt gggaggtttt    420
ttaaa                                                                425
```

<210> SEQ ID NO 39
<211> LENGTH: 865
<212> TYPE: DNA
<213> ORGANISM: Homo sapiens

<400> SEQUENCE: 39

```
ccccgggtgc gcggcgtcgg tggtgccggc gggggcgcc aggtcgcagg cggtgtaggg    60
ctccaggcag gcggcgaagg ccatgacgtg cgctatgaag gtctgctcct gcacgccgtg   120
aaccaggtgc gcctgcgggc cgcgcgcgaa caccgccacg tcctcgcctg cgtgggtctc   180
ttcgtccagg ggcactgctg actgctgccg atactcgggg ctcccgctct cgctctcggt   240
aacatccggc cgggcgccgt ccttgagcac atagcctgga ccgtttccgt ataggaggac   300
cgtgtaggcc ttcctgtccc gggccttgcc agcggccagc ccgatgaagg agctccctcg   360 caggggtag cctccgaagg agaagacgtg ggagtggtcg gcagtgacga ggctcagcgt    420
gtcctcctcg ctggtgagct ggcccgcccct ctcaatggcg tcgtcgaaca tgatcgtctc   480
agtcagtgcc cggtaagccc tgctttcatg atgaccatgg tcgatgcgac caccctccac   540
gaagaggaag aagccgcggg ggtgtctgct cagcaggcgc agggcagcct ctgtcatctc   600
catcagggag gggtccagtg tggagtctcg gtggatctcg tatttcatgt ctccaggctc   660
aaagagaccc atgagatggg tcacagacgg gtccagggaa gcctgcatga gctcagtgcg   720
gttccacacg taccgggcac cctggcgttc gccgagccat tcctgcacca gattcttccc   780
gtccagcctg gtcccacctt ggctgtagtc atctgggtac tcagggtctg gggttcccat   840
gcgaaacatg tactttcggc ctcca                                         865
```

<210> SEQ ID NO 40
<211> LENGTH: 437
<212> TYPE: DNA
<213> ORGANISM: Homo sapiens

<400> SEQUENCE: 40

```
ccccgggtgc gcggcgtcgg tggtgccggc gggggcgcc aggtcgcagg cggtgtaggg    60
ctccaggcag gcggcgaagg ccatgacgtg cgctatgaag gtctgctcct gcacgccgtg   120
aaccaggtgc gcctgcgggc cgcgcgcgaa caccgccacg tcctcgcctg cgtgggtctc   180
ttcgtccagg ggcactgctg actgctgccg atactcgggg ctcccgctct cgctctcggt   240
aacatccggc cgggcgccgt ccttgagcac atagcctgga ccgtttccgt ataggaggac   300
cgtgtaggcc ttcctgtccc gggccttgcc agcggccagc ccgatgaagg agctccctcg   360 caggggtag cctccgaagg agaagacgtg ggagtggtcg gcagtgacga ggctcagcgt    420
gtcctcctcg ctggtga                                                  437
```

<210> SEQ ID NO 41
<211> LENGTH: 428
<212> TYPE: DNA

<213> ORGANISM: Homo sapiens

<400> SEQUENCE: 41

| | |
|---|---|
| gctggcccgc cctctcaatg gcgtcgtcga acatgatcgt ctcagtcagt gcccggtaag | 60 |
| ccctgctttc atgatgacca tggtcgatgc gaccaccctc cacgaagagg aagaagccgc | 120 |
| gggggtgtct gctcagcagg cgcagggcag cctctgtcat ctccatcagg gaggggtcca | 180 |
| gtgtggagtc tcggtggatc tcgtatttca tgtctccagg ctcaaagaga cccatgagat | 240 |
| gggtcacaga cgggtccagg gaagcctgca tgagctcagt gcggttccac acgtaccggg | 300 |
| caccctggcg ttcgccgagc cattcctgca ccagattctt cccgtccagc ctggtcccac | 360 |
| cttggctgta gtcatctggg tactcagggt ctggggttcc catgcgaaac atgtactttc | 420 |
| ggcctcca | 428 |

<210> SEQ ID NO 42
<211> LENGTH: 287
<212> TYPE: DNA
<213> ORGANISM: Homo sapiens

<400> SEQUENCE: 42

| | |
|---|---|
| ccccgggtgc gcggcgtcgg tggtgccggc gggggcgcc aggtcgcagg cggtgtaggg | 60 |
| ctccaggcag gcggcgaagg ccatgacgtg cgctatgaag gtctgctcct gcacgccgtg | 120 |
| aaccaggtgc gcctgcgggc cgcgcgcgaa caccgccacg tcctcgcctg cgtgggtctc | 180 |
| ttcgtccagg ggcactgctg actgctgccg atactcgggg ctcccgctct cgctctcggt | 240 |
| aacatccggc cgggcgccgt ccttgagcac atagcctgga ccgttttc | 287 |

<210> SEQ ID NO 43
<211> LENGTH: 290
<212> TYPE: DNA
<213> ORGANISM: Homo sapiens

<400> SEQUENCE: 43

| | |
|---|---|
| cgtataggag gaccgtgtag gccttcctgt cccgggcctt gccagcggcc agcccgatga | 60 |
| aggagctccc tcgcaggggg tagcctccga aggagaagac gtgggagtgg tcggcagtga | 120 |
| cgaggctcag cgtgtcctcc tcgctggtga gctggcccgc cctctcaatg gcgtcgtcga | 180 |
| acatgatcgt ctcagtcagt gcccggtaag ccctgctttc atgatgacca tggtcgatgc | 240 |
| gaccaccctc cacgaagagg aagaagccgc gggggtgtct gctcagcagg | 290 |

<210> SEQ ID NO 44
<211> LENGTH: 288
<212> TYPE: DNA
<213> ORGANISM: Homo sapiens

<400> SEQUENCE: 44

| | |
|---|---|
| cgcagggcag cctctgtcat ctccatcagg gaggggtcca gtgtggagtc tcggtggatc | 60 |
| tcgtatttca tgtctccagg ctcaaagaga cccatgagat gggtcacaga cgggtccagg | 120 |
| gaagcctgca tgagctcagt gcggttccac acgtaccggg caccctggcg ttcgccgagc | 180 |
| cattcctgca ccagattctt cccgtccagc ctggtcccac cttggctgta gtcatctggg | 240 |
| tactcagggt ctggggttcc catgcgaaac atgtactttc ggcctcca | 288 |

COMPOSITIONS AND METHODS FOR TREATING SENSORINEURAL HEARING LOSS USING OTOFERLIN DUAL VECTOR SYSTEMS

FIELD OF THE INVENTION

Described herein are compositions and methods for the treatment of sensorineural hearing loss and auditory neuropathy, particularly forms of the disease that are associated with mutations in otoferlin (OTOF), by way of OTOF gene therapy. The disclosure provides dual vector systems that include a first nucleic acid vector that contains a polynucleotide encoding an N-terminal portion of an OTOF protein and a second nucleic acid vector that contains a polynucleotide encoding a C-terminal portion of an OTOF protein. These vectors can be used to increase the expression of or provide wild-type OTOF to a subject, such as a human subject suffering from sensorineural hearing loss.

BACKGROUND

Sensorineural hearing loss is a type of hearing loss caused by defects in the cells of the inner ear or the neural pathways that project from the inner ear to the brain. Although sensorineural hearing loss is often acquired, and can be caused by noise, infections, head trauma, ototoxic drugs, or aging, there are also congenital forms of sensorineural hearing loss associated with autosomal recessive mutations. One such form of autosomal recessive sensorineural hearing loss is associated with mutation of the otoferlin (OTOF) gene, which is implicated in prelingual nonsyndromic hearing loss. In recent years, efforts to treat hearing loss have increasingly focused on gene therapy as a possible solution; however, OTOF is too large to allow for treatment using standard gene therapy approaches. There is a need for new therapeutics to treat OTOF-related sensorineural hearing loss.

SUMMARY OF THE INVENTION

The present invention provides compositions and methods for treating sensorineural hearing loss or auditory neuropathy in a subject, such as a human subject. The compositions and methods of the disclosure pertain to dual vector systems for the delivery of a polynucleotide encoding an otoferlin (OTOF) protein to a subject having or at risk of developing sensorineural hearing loss or auditory neuropathy (e.g., a subject with a mutation in OTOF). For example, using the compositions and methods described herein, a first nucleic acid vector and a second nucleic acid vector that each encode a portion of a functional OTOF protein may be delivered to a subject by way of viral gene therapy. The compositions and methods described herein may also be used to increase expression of a WT OTOF protein in a cochlear hair cell (e.g., an inner hair cell).

In a first aspect, the invention provides a composition comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a myosin 15 (Myo15) promoter, a vesicular glutamate transporter 3 (VGLUT3) promoter, and a fibroblast growth factor 8 (FGF8) promoter operably linked to a first coding polynucleotide that encodes an N-terminal portion of an otoferlin (OTOF) protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a composition comprising: a first nucleic acid vector containing a promoter selected from the group consisting of a CAG promoter, a cytomegalovirus (CMV) promoter, a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In another aspect, the invention provides a dual vector system comprising: a first nucleic acid vector containing a promoter selected from the group consisting of a CAG promoter, a cytomegalovirus (CMV) promoter, a Myo15 promoter, a Myosin 7A (Myo7A) promoter, a Myosin 6 (Myo6) promoter, a POU Class 4 Homeobox 3 (POU4F3) promoter, an OTOF promoter, an FGF8 promoter, and a VGLUT3 promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein; and a second nucleic acid vector containing a second coding polynucleotide that encodes a C-terminal portion of an OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein; and a second nucleic acid vector containing a second coding polynucleotide that encodes a C-terminal portion of a human OTOF protein and a polyadenylation (poly(A)) sequence positioned at the 3' end of the second coding polynucleotide; wherein the first coding polynucleotide partially overlaps with the second coding polynucleotide, wherein neither the first nor second nucleic acid vector encodes a full-length OTOF protein, and, when introduced into a mammalian cell, the two first and second nucleic acid vectors undergo homologous recombination to form a recombined nucleic acid that encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein comprises or consists of the sequence of SEQ ID NO: 1.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, each of the first and second coding polynucleotides encode about half of the OTOF protein sequence.

In some embodiments of any of the foregoing aspects, wherein the first coding polynucleotide overlaps with the second coding polynucleotide by at least 1 kilobase (kb).

In some embodiments of any of the foregoing aspects, the region of overlap between the first and second coding polynucleotides is centered at an OTOF exon boundary. In some embodiments of any of the foregoing aspects, the first coding polynucleotide encodes an N-terminal portion of the OTOF protein containing the OTOF N-terminus to 500 kb 3' of the exon boundary at the center of the overlap region; and the second coding polynucleotide encodes a C-terminal portion of the OTOF protein containing 500 kb 5' of the exon boundary at the center of the overlap region to the OTOF C-terminus.

In some embodiments of any of the foregoing aspects, the exon boundary at the center of the overlap region is not within a portion of the first coding polynucleotide or second coding polynucleotide that encodes a C2 domain.

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of the sequence of SEQ ID NO: 36).

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide contains exons 1-21 of a polynucleotide encoding the OTOF protein and 500 kb 3' of the exon 21/22 boundary; and the second coding polynucleotide contains 500 kb 5' of the exon 21/22 boundary and exons 22-48 of a polynucleotide encoding the OTOF protein. In some embodiments of any of the foregoing aspects, the first nucleic acid vector and the second nucleic acid vector do not contain OTOF untranslated regions (UTRs).

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a Myo15 promoter that is 1 kb or shorter.

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide contains exons 1-24 of a polynucleotide encoding the OTOF protein and 500 kb 3' of the exon 24/25 boundary; and the second coding polynucleotide contains 500 kb 5' of the exon 24/25 boundary and exons 25-48 of a polynucleotide encoding the OTOF protein. In some embodiments of any of the foregoing aspects, the first and second nucleic acid vectors include OTOF UTRs (e.g., full-length 3' and 5' UTRs).

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide contains exons 1-28 of a polynucleotide encoding the OTOF protein and 500 kb 3' of the exon 28/29 boundary; and the second coding polynucleotide contains 500 kb 5' of the exon 28/29 boundary and exons 29-48 of a polynucleotide encoding the OTOF protein. In some embodiments of any of the foregoing aspects, the second nucleic acid vector contains a full-length OTOF 3' UTR.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a Myo15 promoter, a VGLUT3 promoter, and an FGF8 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are adeno-associated virus (AAV) vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, and a splice donor signal sequence positioned at the 3' end of the first coding polynucleotide; and a second nucleic acid vector containing a splice acceptor signal sequence, a second coding polynucleotide that encodes a C-terminal portion of an OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, and a splice donor signal sequence positioned at the 3' end of the first coding polynucleotide; and a second nucleic acid vector containing a splice acceptor signal sequence, a second coding polynucleotide that encodes a C-terminal portion of a human OTOF protein positioned at the 3' end of the splice acceptor signal sequence, and a poly(A) sequence at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, and wherein neither the first nor second nucleic acid vector encodes a full-length OTOF protein.

In some embodiments of any of the foregoing aspects, the first and second nucleic acid vectors are AAV vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter selected from the group consisting of a CAG promoter, a CMV promoter, a Myo15 promoter, a Myo7A promoter, a Myo6 promoter, a POU4F3 promoter, an OTOF promoter, an FGF8 promoter, and a VGLUT3 promoter operably linked to a first coding polynucleotide that encodes an N-terminal portion of an OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of an OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a composition comprising: a first nucleic acid vector containing a promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In another aspect, the invention provides a dual vector system comprising: a first nucleic acid vector containing a promoter operably linked to a first coding polynucleotide that encodes an N-terminal portion of a human OTOF protein, a splice donor signal sequence positioned at the 3' end of the first coding polynucleotide, and a recombinogenic region positioned 3' of the splice donor signal sequence; and a second nucleic acid vector containing a second recombinogenic region, a splice acceptor signal sequence positioned 3' of the second recombinogenic region, a second coding polynucleotide that encodes a C-terminal portion of a human OTOF protein positioned at the 3' end of the splice acceptor signal sequence, and a poly(A) sequence positioned at the 3' end of the second coding polynucleotide; wherein the first coding polynucleotide and the second coding polynucleotide do not overlap, wherein neither the first nor second nucleic acid vector encodes a full-length OTOF protein, and wherein the first and second nucleic acid vectors are AAV vectors having a serotype selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S.

In some embodiments of any of the foregoing aspects, the first and second coding polynucleotides that encode the OTOF protein (e.g., the human OTOF protein) do not contain introns.

In some embodiments of any of the foregoing aspects, the OTOF protein is a mammalian OTOF protein.

In some embodiments of any of the foregoing aspects, the OTOF protein is a murine OTOF protein. In some embodiments of any of the foregoing aspects, the murine OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 6, SEQ ID NO: 7, SEQ ID NO: 8, or SEQ ID NO: 9. In some embodiments of any of the foregoing aspects, the murine OTOF protein comprises or consists of the sequence of SEQ ID NO: 6.

In some embodiments of any of the foregoing aspects, the OTOF protein is a human OTOF protein. In some embodiments of any of the foregoing aspects, the human OTOF protein has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the human OTOF protein comprises or consists of the sequence of SEQ ID NO: 1.

In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments, of any of the foregoing aspects, the first and second recombinogenic regions are the same. In some embodiments, of any of the foregoing aspects, the recombinogenic region is an AP gene fragment or an F1 phage AK gene. In some embodiments of any of the foregoing aspects, the recombinogenic region is an F1 phage AK gene. In some embodiments of any of the foregoing aspects, the F1 phage AK gene comprises or consists of the sequence of SEQ ID NO: 19. In some embodiments of any of the foregoing aspects, the recombinogenic region is an AP gene fragment. In some embodiments of any of the foregoing aspects, the AP gene fragment comprises or consists of the sequence of any one of SEQ ID NOs 39-44.

In some embodiments of any of the foregoing aspects, the first nucleic acid vector further includes a degradation signal sequence positioned 3' of the recombinogenic region; and the second nucleic acid vector further includes a degradation signal sequence positioned between the recombinogenic region and the splice acceptor signal sequence. In some embodiments of any of the foregoing aspects, the degradation signal sequence comprises or consists of the sequence of SEQ ID NO: 22.

In some embodiments of any of the foregoing aspects, each of the first and second coding polynucleotides encode about half of the OTOF protein sequence.

In some embodiments of any of the foregoing aspects, the division between the first and second coding polynucleotides is at an OTOF exon boundary.

In some embodiments of any of the foregoing aspects, the OTOF exon boundary is not within a portion of the first coding polynucleotide or second coding polynucleotide that encodes a C2 domain.

In some embodiments of any of the foregoing aspects, the promoter is a short promoter (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). In some embodiments, the short promoter is a CAG promoter. In some embodiments, the short promoter is a CMV promoter. In some embodiments, the short promoter is a Myo15 promoter that is 1 kb or shorter.

In some embodiments of any of the foregoing aspects, the exon boundary is selected such that the first coding polynucleotide encodes the entire C2D domain and the second coding polynucleotide encodes the entire C2E domain. In some embodiments of any of the foregoing aspects, the first coding polynucleotide encodes exons 1-26 of a polynucleotide encoding the OTOF protein and the second coding polynucleotide encodes exons 27-48 of a polynucleotide encoding the OTOF protein. In some embodiments of any of the foregoing aspects, the first coding polynucleotide encodes exons 1-28 of a polynucleotide encoding the OTOF protein and the second coding polynucleotide encodes exons 29-48 of a polynucleotide encoding the OTOF protein. In some embodiments of any of the foregoing aspects, the first and second nucleic acid vectors contain OTOF UTRs (e.g., full-length 3' and 5' UTRs).

In some embodiments of any of the foregoing aspects, the promoter is a Myo15 promoter.

In some embodiments of any of the foregoing aspects, the promoter is a long promoter (e.g., a promoter that is longer than 1 kb, e.g., 1.1 kb, 1.25 kb, 1.5 kb, 1.75 kb, 2 kb, 2.5 kb, 3 kb or longer). In some embodiments, the long promoter is a Myo15 promoter that is longer than 1 kb (e.g., a Myo15 promoter comprising or consisting of the sequence of SEQ ID NO: 36).

In some embodiments of any of the foregoing aspects, the OTOF exon boundary is not within a portion of the first coding polynucleotide or second coding polynucleotide that encodes a C2 domain.

In some embodiments of any of the foregoing aspects, the exon boundary is selected such that the first coding polynucleotide encodes the entire C2C domain and the second coding polynucleotide encodes the entire C2D domain. In some embodiments of any of the foregoing aspects, the first coding polynucleotide encodes exons 1-19 of a polynucleotide encoding the OTOF protein and the second coding polynucleotide encodes exons 20-48 of a polynucleotide encoding the OTOF protein. In some embodiments of any of the foregoing aspects, the first coding polynucleotide encodes exons 1-20 of a polynucleotide encoding the OTOF protein and the second coding polynucleotide encodes exons 21-48 of a polynucleotide encoding the OTOF protein. In some embodiments of any of the foregoing aspects, the first nucleic acid vector and the second nucleic acid vector do not contain OTOF UTRs.

In some embodiments of any of the foregoing aspects, the exon boundary is within a portion of the first coding polynucleotide and the second coding polynucleotide that encodes the C2D domain. In some embodiments of any of the foregoing aspects, the first coding polynucleotide encodes exons 1-25 of a polynucleotide encoding the OTOF protein and the second coding polynucleotide encodes exons 26-48 of a polynucleotide encoding the OTOF protein. In some embodiments of any of the foregoing aspects, the first coding polynucleotide encodes exons 1-24 of a polynucleotide encoding the OTOF protein and the second coding polynucleotide encodes exons 25-48 of a polynucleotide encoding the OTOF protein. In some embodiments of any of the foregoing aspects, the second nucleic acid vector contains a full-length OTOF 3' UTR.

In some embodiments of any of the foregoing aspects, the splice donor sequence comprises or consists of the sequence of SEQ ID NO: 20.

In some embodiments of any of the foregoing aspects, the splice acceptor sequence comprises or consists of the sequence of SEQ ID NO: 21.

In some embodiments, the first and second nucleic acid vectors contain inverted terminal repeats (ITRs). In some embodiments of any of the foregoing aspects, the ITRs are AAV2 ITRs.

In some embodiments of any of the foregoing aspects, the poly(A) sequence is a bovine growth hormone (bGH) poly(A) signal sequence.

In some embodiments of any of the foregoing aspects, the second nucleic acid vector contains a Woodchuck Hepatitis Virus Posttranscriptional Regulatory Element (WPRE). In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 38.

In some embodiments of any of the foregoing aspects, the composition contains a pharmaceutically acceptable excipient.

In another aspect, the invention provides a kit containing a composition of the invention.

In another aspect, the invention provides a method of increasing OTOF expression in a subject in need thereof by administering to the subject a therapeutically effective amount of a composition of the invention.

In another aspect, the invention provides a method of treating a subject having or at risk of developing sensorineural hearing loss by administering to the subject a therapeutically effective amount of a composition of the invention.

In another aspect, the invention provides a method of treating a subject having or at risk of developing auditory neuropathy by administering to the subject a therapeutically effective amount of a composition of the invention.

In another aspect, the invention provides a method of increasing OTOF expression in a subject in need thereof by administering to the subject a therapeutically effective amount of a pair of nucleic acid vectors listed in Table 4.

In another aspect, the invention provides a method of treating a subject having or at risk of developing sensorineural hearing loss by administering to the subject a therapeutically effective amount of a pair of nucleic acid vectors listed in Table 4.

In another aspect, the invention provides a method of treating a subject having or at risk of developing auditory neuropathy by administering to the subject a therapeutically effective amount of a pair of nucleic acid vectors listed in Table 4.

In some embodiments of any of the foregoing aspects, the subject has a mutation in OTOF.

In some embodiments of any of the foregoing aspects, the subject has been identified as having a mutation in OTOF.

In some embodiments of any of the foregoing aspects, the method further includes the step of identifying the subject as having a mutation in OTOF prior to administering the composition or the pair of nucleic acid vectors.

In some embodiments of any of the foregoing aspects, the method further includes the step of evaluating the hearing of the subject prior to administering the composition or the pair of nucleic acid vectors.

In some embodiments of any of the foregoing aspects, the composition or the pair of nucleic acid vectors is administered locally to the ear. In some embodiments of any of the foregoing aspects, the nucleic acid vectors are administered concurrently. In some embodiments of any of the foregoing aspects, the nucleic acid vectors are administered sequentially.

In some embodiments of any of the foregoing aspects, the method increases OTOF expression in a cochlear hair cell. In some embodiments of any of the foregoing aspects, the cochlear hair cell is an inner hair cell.

In some embodiments of any of the foregoing aspects, the subject is a mammal. In some embodiments of any of the foregoing aspects, the subject is a human.

In some embodiments of any of the foregoing aspects, the method further includes the step of evaluating the hearing of the subject after administering the composition or the pair of nucleic acid vectors. In some embodiments of any of the foregoing aspects, the method further includes the step of evaluating OTOF expression after administering the composition or the pair of nucleic acid vectors.

In some embodiments of any of the foregoing aspects, the composition or the pair of nucleic acid vectors increases OTOF expression in a cell (e.g., a cochlear hair cell), improves hearing (e.g., as assessed by standard tests, such as audiometry, auditory brainstem response (ABR), electrochocleography (ECOG), and otoacoustic emissions), prevents or reduces hearing loss, delays the development of hearing loss, slows the progression of hearing loss, improves speech discrimination, or improves hair cell function.

In some embodiments of any of the foregoing aspects, the composition or the pair of nucleic acid vectors is administered in an amount sufficient to increase OTOF expression in a cochlear hair cell, prevent or reduce hearing loss, delay the development of hearing loss, slow the progression of hearing loss, improve hearing (e.g., as assessed by standard tests, such as audiometry, ABR, ECOG, and otoacoustic emissions), improve speech discrimination, or improve hair cell function.

In another aspect, the invention provides a method of increasing OTOF expression in a cell by introducing a composition of the invention into the cell.

In another aspect, the invention provides a method of increasing OTOF expression in a cell by introducing a pair of nucleic acid vectors listed in Table 4 into the cell.

In some embodiments of any of the foregoing aspects, the cell is a cochlear hair cell. In some embodiments of any of the foregoing aspects, the cell is an inner hair cell.

In some embodiments of any of the foregoing aspects, the cell is a mammalian cell. In some embodiments of any of the foregoing aspects, the cell is a human cell.

In some embodiments of any of the foregoing aspects, the OTOF protein encoded by the pair of nucleic acid vectors has at least 85% sequence identity (e.g., 85%, 86%, 87%, 88%, 89%, 90%, 91%, 92%, 93%, 94%, 95%, 96%, 97%, 98%, 99%, or 100% identity) to the sequence of SEQ ID NO: 1, SEQ ID NO: 2, SEQ ID NO:3, SEQ ID NO: 4, or SEQ ID NO: 5. In some embodiments of any of the foregoing aspects, the OTOF protein encoded by the pair of nucleic acid vectors comprises or consists of the sequence of SEQ ID NO: 1.

In some embodiments of any of the foregoing aspects, the nucleic acid vectors are AAV vectors. In some embodiments of any of the foregoing aspects, the serotype of the AAV vectors is selected from the group consisting of AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, or 7m8. In some embodiments of any of the foregoing aspects, the serotype of the AAV vectors is AAV1. In some embodiments of any of the foregoing aspects, the serotype of the AAV vectors is AAV9. In some embodiments of any of the foregoing aspects, the serotype of the AAV vectors is AAV6. In some embodiments of any of the foregoing aspects, the serotype of the AAV vectors is Anc80. In some embodiments of any of the foregoing aspects, the serotype of the AAV vectors is Anc80L65. In some embodiments of any of the foregoing aspects, the serotype of the AAV vectors is DJ/9. In some embodiments of any of the foregoing aspects, the serotype of the AAV vectors is 7m8. In some embodiments of any of the foregoing aspects, the serotype of the AAV vectors is AAV2. In some embodiments of any of the foregoing aspects, the serotype of the AAV vectors is PHP.B. In some embodiments of any of the foregoing aspects, the serotype of the AAV vectors is AAV8. In some embodiments of any of the foregoing aspects, the first and second nucleic acid vectors have the same serotype (e.g., both the first and second nucleic acid vector are AAV vectors having an AAV1 serotype or an AAV9 serotype). In some embodiments of any of the foregoing aspects, the first and second nucleic acid vectors have different serotypes (e.g., the first nucleic acid vector is an AAV having an AAV1 serotype, and the second nucleic acid vector is an AAV having an AAV9 serotype).

In some embodiments of any of the foregoing aspects, the vectors contain AAV2 ITRs.

In some embodiments of any of the foregoing aspects, the second nucleic acid vector in the pair of nucleic acid vectors contains a WPRE. In some embodiments of any of the foregoing aspects, the WPRE comprises or consists of the sequence of SEQ ID NO: 23. In some embodiments of any of the foregoing aspects, the WPRE comprises or consists of the sequence of SEQ ID NO: 38.

In some embodiments of any of the foregoing aspects, the nucleic acid vectors are overlapping dual vectors.

In some embodiments of any of the foregoing aspects, the nucleic acid vectors are trans-splicing dual vectors.

In some embodiments of any of the foregoing aspects, the nucleic acid vectors are dual hybrid vectors.

In some embodiments of any of the foregoing aspects, the recombinogenic region in the dual hybrid vectors is an AP gene fragment or an F1 phage AK gene. In some embodiments of any of the foregoing aspects, the F1 phage AK gene comprises or consists of the sequence of SEQ ID NO: 19. In some embodiments of any of the foregoing aspects, the AP gene fragment comprises or consists of the sequence of any one of SEQ ID NOs 39-44. In some embodiments of any of the foregoing aspects, the first nucleic acid vector in the pair of nucleic acid vectors further contains a degradation signal sequence positioned 3' of the recombinogenic region; and the second nucleic acid vector in the pair of nucleic acid vectors further contains a degradation signal sequence positioned between the recombinogenic region and the splice acceptor sequence. In some embodiments of any of the foregoing aspects, the degradation signal sequence comprises or consists of the sequence of SEQ ID NO: 22.

In some embodiments of any of the foregoing aspects, the splice donor sequence in the first nucleic acid vector comprises or consists of the sequence of SEQ ID NO: 20.

In some embodiments of any of the foregoing aspects, the splice acceptor sequence in the second nucleic acid vector comprises or consists of the sequence of SEQ ID NO: 21.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, operably linked to a second region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 24. In some embodiments, the second region comprises or consists of the sequence of SEQ ID NO: 25.

In some embodiments of any of the foregoing aspects, the Myo15 promoter comprises or consists of the sequence of SEQ ID NO: 36.

In some embodiments of any of the foregoing aspects, the Myo15 promoter comprises or consists of a first region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32, operably linked to a second region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region. In some embodiments, the first region comprises or consists of the sequence of SEQ ID NO: 25. In some embodiments, the second region comprises or consists of the sequence of SEQ ID NO: 24.

In some embodiments of any of the foregoing aspects, the Myo15 promoter comprises or consists of the sequence of SEQ ID NO: 37.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 24 or a functional portion or derivative thereof including the sequence of SEQ ID NO: 26 and/or SEQ ID NO: 27. In some embodiments, the region comprises or consists of the sequence of SEQ ID NO: 24.

In some embodiments of any of the foregoing aspects, the Myo15 promoter comprises or consists of a region having at least 85% sequence identity (e.g., 85%, 90%, 95%, 96%, 97%, 98%, 99%, or more, sequence identity) to SEQ ID NO: 25 or a functional portion or derivative thereof including the sequence of SEQ ID NO: 31 and/or SEQ ID NO: 32. In some embodiments, the region comprises or consists of the sequence of SEQ ID NO: 25.

In some embodiments of any of the foregoing aspects, the functional portion of SEQ ID NO: 24 contains the sequence of SEQ ID NO: 26. In some embodiments of any of the foregoing aspects, the functional portion of SEQ ID NO: 24 contains the sequence of SEQ ID NO: 27. In some embodiments of any of the foregoing aspects, the functional portion of SEQ ID NO: 24 contains the sequence of SEQ ID NO: 26 and the sequence of SEQ ID NO: 27. In some embodiments of any of the foregoing aspects, the functional portion of SEQ ID NO: 24 contains the sequence of SEQ ID NO: 28. In some embodiments of any of the foregoing aspects, the functional portion of SEQ ID NO: 24 contains the sequence of SEQ ID NO: 29. In some embodiments of any of the foregoing aspects, the functional portion of SEQ ID NO: 24 contains the sequence of SEQ ID NO: 30.

In some embodiments of any of the foregoing aspects, the functional portion of SEQ ID NO: 25 contains the sequence of SEQ ID NO: 31. In some embodiments of any of the foregoing aspects, the functional portion of SEQ ID NO: 25 contains the sequence of SEQ ID NO: 32. In some embodiments of any of the foregoing aspects, the functional portion of SEQ ID NO: 25 contains the sequence of SEQ ID NO: 31 and the sequence of SEQ ID NO: 32. In some embodiments of any of the foregoing aspects, the functional portion of SEQ ID NO: 25 contains the sequence of SEQ ID NO: 33. In some embodiments of any of the foregoing aspects, the functional portion of SEQ ID NO: 25 contains the sequence of SEQ ID NO: 34. In some embodiments of any of the foregoing aspects, the functional portion of SEQ ID NO: 25 contains the sequence of SEQ ID NO: 35.

In some embodiments of any of the foregoing aspects, the Myo15 promoter induces transgene expression when operably linked to a transgene and introduced into a hair cell.

DEFINITIONS

As used herein, the term "about" refers to a value that is within 10% above or below the value being described.

As used herein, "administration" refers to providing or giving a subject a therapeutic agent (e.g., a composition containing a first nucleic acid vector containing a polynucleotide that encodes an N-terminal portion of an otoferlin protein and a second nucleic acid vector containing a polynucleotide that encodes a C-terminal portion of an otoferlin protein), by any effective route. Exemplary routes of administration are described herein below.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the term "cochlear hair cell" refers to group of specialized cells in the inner ear that are involved in sensing sound. There are two types of cochlear hair cells: inner hair cells and outer hair cells. Damage to cochlear hair cells and genetic mutations that disrupt cochlear hair cell function are implicated in hearing loss and deafness.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |

TABLE 1-continued

Representative physicochemical properties of naturally-occurring amino acids

| Amino Acid | 3 Letter Code | 1 Letter Code | Side-chain Polarity | Electrostatic character at physiological pH (7.4) | Steric Volume† |
|---|---|---|---|---|---|
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

†based on volume in $A^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the term "degradation signal sequence" refers to a sequence (e.g., a nucleotide sequence that can be translated into an amino acid sequence) that mediates the degradation of a polypeptide in which it is contained. Degradation signal sequences can be included in the nucleic acid vectors of the invention to reduce or prevent the expression of portions of otoferlin proteins that have not undergone recombination and/or splicing. An exemplary degradation signal sequence for use in the invention is GCCTGCAAGAACTGGTTCAGCAGCCTGAGCCACT-TCGTGATCCACCTG (SEQ ID NO: 22).

As used herein, the terms "effective amount," "therapeutically effective amount," and a "sufficient amount" of a composition, vector construct, or viral vector described herein refer to a quantity sufficient to, when administered to the subject in need thereof, including a mammal, for example a human, effect beneficial or desired results, including clinical results, and, as such, an "effective amount" or synonym thereto depends upon the context in which it is being applied. For example, in the context of treating sensorineural hearing loss, it is an amount of the composition, vector construct, or viral vector sufficient to achieve a treatment response as compared to the response obtained without administration of the composition, vector construct, or viral vector. The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, or viral vector of the present disclosure is an amount which results in a beneficial or desired result in a subject as compared to a control. Note that when a combination of active ingredients is administered, the effective amount of the combination may or may not include amounts of each ingredient that would have been effective if administered individually. As defined herein, a therapeutically effective amount of a composition, vector construct, viral vector or cell of the present disclosure may be readily determined by one of ordinary skill by routine methods known in the art. Dosage regime may be adjusted to provide the optimum therapeutic response.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human cochlear hair cell).

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell, e.g., a human cochlear hair cell). Exogenous materials include those that are provided from an external source to an organism or to cultured matter extracted there from.

As used herein, the term "hair cell-specific expression" refers to production of an RNA transcript or polypeptide primarily within hair cells (e.g., cochlear hair cells) as compared to other cell types of the inner ear (e.g., spiral ganglion neurons, glia, or other inner ear cell types). Hair cell-specific expression of a transgene can be confirmed by comparing transgene expression (e.g., RNA or protein expression) between various cell types of the inner ear (e.g., hair cells vs. non-hair cells) using any standard technique (e.g., quantitative RT PCR, immunohistochemistry, Western Blot analysis, or measurement of the fluorescence of a reporter (e.g., GFP) operably linked to a promoter). A hair cell-specific promoter induces expression (e.g., RNA or protein expression) of a transgene to which it is operably linked that is at least 50% greater (e.g., 50%, 75%, 100%, 125%, 150%, 175%, 200% greater or more) in hair cells (e.g., cochlear hair cells) compared to at least 3 (e.g., 3, 4, 5, 6, 7, 8, 9, 10, or more) of the following inner ear cell types: Border cells, inner phalangeal cells, inner pillar cells, outer pillar cells, first row Deiter cells, second row Deiter cells, third row Deiter cells, Hensen's cells, Claudius cells, inner sulcus cells, outer sulcus cells, spiral prominence cells, root cells, interdental cells, basal cells of the stria vascularis, intermediate cells of the stria vascularis, marginal cells of the stria vascularis, spiral ganglion neurons, Schwann cells.

As used herein, the terms "increasing" and "decreasing" refer to modulating resulting in, respectively, greater or lesser amounts, of function, expression, or activity of a metric relative to a reference. For example, subsequent to administration of a composition in a method described herein, the amount of a marker of a metric (e.g., OTOF expression) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "intron" refers to a region within the coding region of a gene, the nucleotide sequence of which is not translated into the amino acid sequence of the corresponding protein. The term intron also refers to the corresponding region of the RNA transcribed from a gene. Introns are transcribed into pre-mRNA, but are removed during processing, and are not included in the mature mRNA.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, administration to the inner ear, and administration to a mucous membrane of the subject, wherein the administration is intended to have a local and not a systemic effect.

As used herein, the term "operably linked" refers to a first molecule that can be joined to a second molecule, wherein the molecules are so arranged that the first molecule affects the function of the second molecule. The term "operably linked" includes the juxtaposition of two or more components (e.g., a promoter and another sequence element) such that both components function normally and allow for the possibility that at least one of the components can mediate a function that is exerted upon at least one of the other components. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the terms "otoferlin" and "OTOF" refer to the gene associated with nonsyndromic recessive deafness DNFB9. The terms "otoferlin" and "OTOF" also refer to variants of wild-type OTOF protein and nucleic acids encoding the same, such as variant proteins having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the amino acid sequence of a wild-type OTOF protein (e.g., SEQ ID NO: 1) or polynucleotides having at least 85% sequence identity (e.g., 85%, 86%, 87%, 88%, 89%, 90%, 91%, 92%, 93%, 94%, 95%, 96%, 97%, 98%, 99%, or 99.9% identity, or more) to the nucleic acid sequence of a wild-type OTOF gene, provided that the OTOF analog encoded retains the therapeutic function of wild-type OTOF. As used herein, OTOF may refer to the protein localized to inner hair cells or to the gene encoding this protein, depending upon the context, as will be appreciated by one of skill in the art.

As used herein, the term "plasmid" refers to a to an extrachromosomal circular double stranded DNA molecule into which additional DNA segments may be ligated. A plasmid is a type of vector, a nucleic acid molecule capable of transporting another nucleic acid to which it has been linked. Certain plasmids are capable of autonomous replication in a host cell into which they are introduced (e.g., bacterial plasmids having a bacterial origin of replication and episomal mammalian plasmids). Other vectors (e.g., non-episomal mammalian vectors) can be integrated into the genome of a host cell upon introduction into the host cell, and thereby are replicated along with the host genome. Certain plasmids are capable of directing the expression of genes to which they are operably linked.

As used herein, the terms "nucleic acid" and "polynucleotide," used interchangeably herein, refer to a polymeric form of nucleosides in any length. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules containing nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

As used herein, the terms "complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

As used herein, the term "promoter" refers to a recognition site on DNA that is bound by an RNA polymerase. The polymerase drives transcription of the transgene. Exemplary promoters suitable for use with the compositions and methods described herein include constitutive promoters (e.g., the CAG promoter and cytomegalovirus (CMV) promoter), cochlear hair cell-specific promoters (e.g., the Myosin 15 (Myo15) promoter, the Myosin 7A (Myo7A) promoter, the Myosin 6 (Myo6) promoter, the POU Class 4 Homeobox 3 (POU4F3) promoter), and inner hair cell-specific promoters (e.g., the Fibroblast growth factor 8 (FGF8) promoter, the vesicular glutamate transporter 3 (VGLUT3) promoter, and the OTOF promoter).

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full-length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

$$100 \text{ multiplied by (the fraction } X/Y)$$

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "derivative" as used herein refers to a nucleic acid, peptide, or protein or a variant or analog thereof comprising one or more mutations and/or chemical modifications as compared to a corresponding full-length wild-type nucleic acid, peptide, or protein. Non-limiting examples of chemical modifications involving nucleic acids include, for example, modifications to the base moiety, sugar moiety, phosphate moiety, phosphate-sugar backbone, or a combination thereof.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio. Preferably, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "recombinogenic region" refers to a region of homology that mediates recombination between two different sequences.

As used herein, the term "regulatory sequence" includes promoters, enhancers and other expression control elements (e.g., polyadenylation signals) that control the transcription or translation of the polynucleotides that encode OTOF. Such regulatory sequences are described, for example, in Goeddel, Gene Expression Technology: Methods in Enzymology 185 (Academic Press, San Diego, Calif., 1990); incorporated herein by reference.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection, Nucleofection, squeeze-poration, sonoporation, optical transfection, Magnetofection, impalefection and the like.

As used herein, the terms "subject" and "patient" refer to an animal (e.g., a mammal, such as a human), veterinary animals (e.g., cats, dogs, cows, horses, sheep, pigs, etc.) and experimental animal models of diseases (e.g., mice, rats). A subject to be treated according to the methods described herein may be one who has been diagnosed with hearing loss (e.g., hearing loss associated with a mutation in OTOF), or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the terms "transduction" and "transduce" refer to a method of introducing a vector construct or a part thereof into a cell. Wherein the vector construct is contained in a viral vector such as for example an AAV vector, transduction refers to viral infection of the cell and subsequent transfer and integration of the vector construct or part thereof into the cell genome.

As used herein, "treatment" and "treating" of a state, disorder or condition can include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO94/11026; incorporated herein by reference as it pertains to vectors suitable for the expression of a gene of interest. Expression vectors suitable for use with the compositions and methods described herein contain a polynucleotide sequence as well as, e.g., additional sequence elements used for the expression of proteins and/or the integration of these polynucleotide sequences into the genome of a mammalian cell. Certain vectors that can be used for the expression of OTOF as described herein include vectors that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "wild-type" refers to a genotype with the highest frequency for a particular gene in a given organism.

Figure 1A:
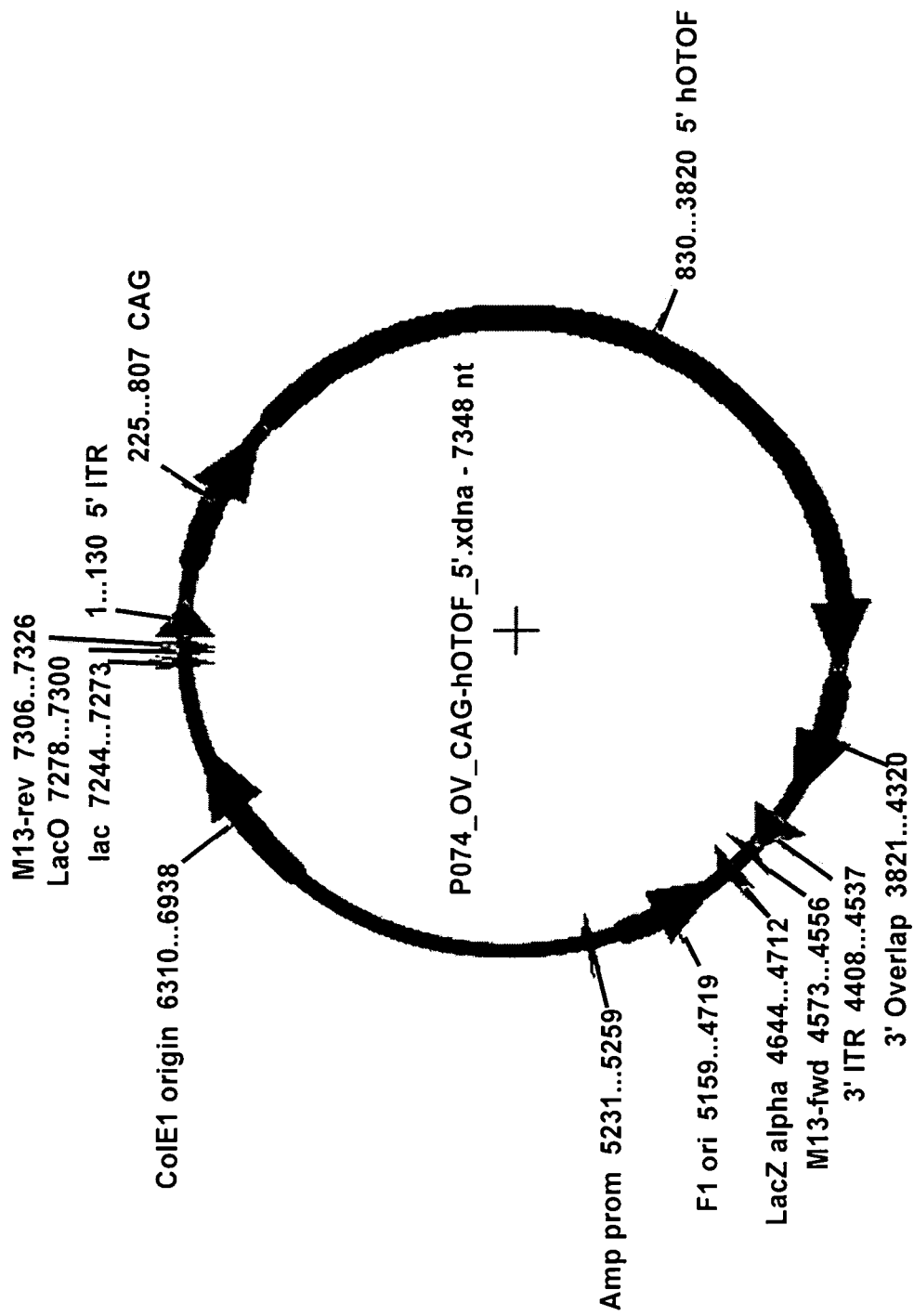
FIGS. 1A and 1B are maps of the 5' and 3' vectors in an overlapping dual vector system. The 5' vector contains AAV2 ITRs, and a CAG promoter operably linked to exons 1-24 of a polynucleotide encoding the human OTOF protein of SEQ ID NO: 1 and the 500 kb immediately 3' of the exon 24/25 boundary (FIG. 1A). The 3' vector contains AAV2 ITRs, the 500 kb immediately 5' of the exon 24/25 boundary and exons 25-48 of a polynucleotide encoding the human OTOF protein of SEQ ID NO: 1, and a WPRE sequence (SEQ ID NO: 23) (FIG. 1B).
Figure 1B:
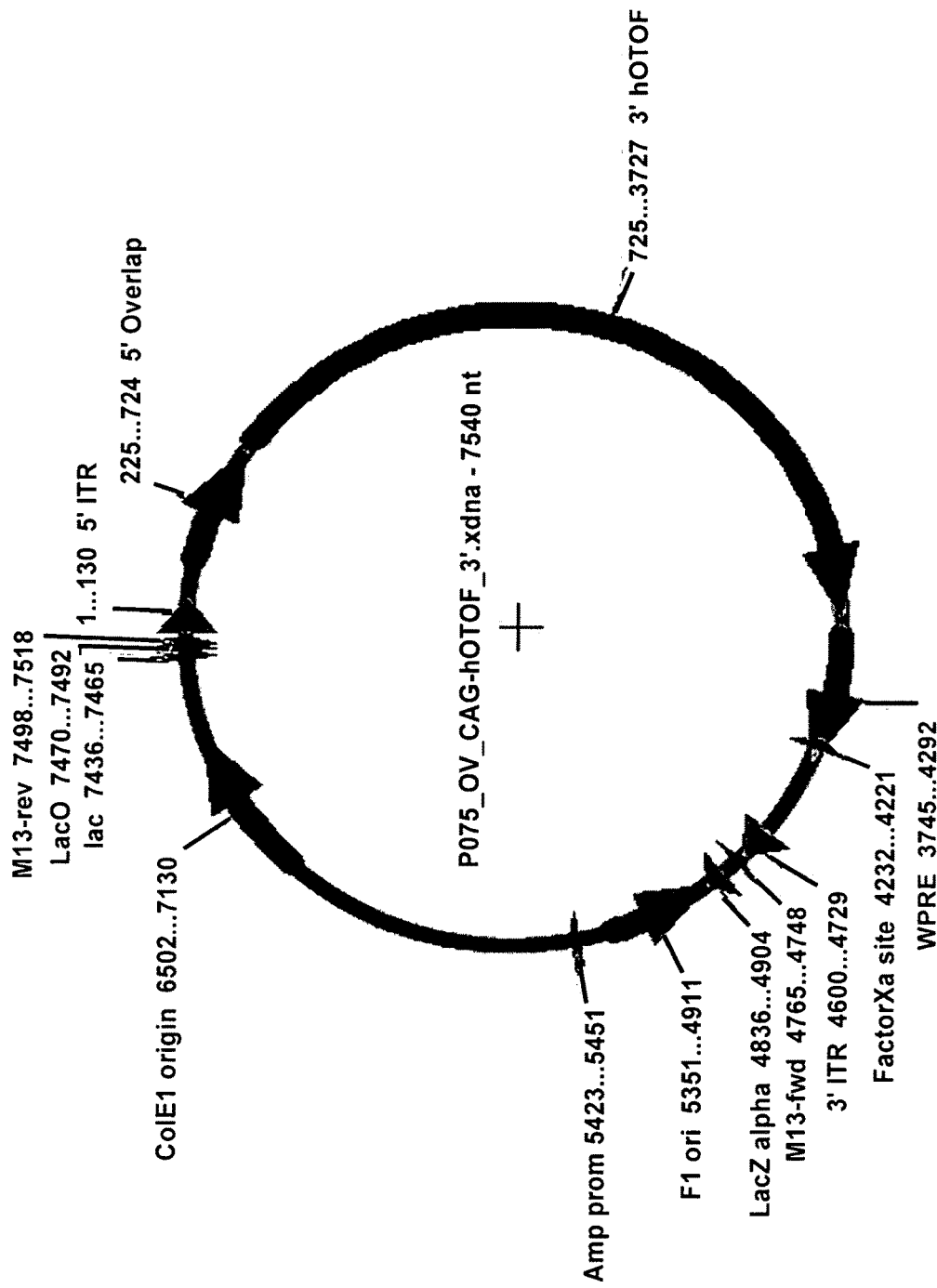
Figure 2A:
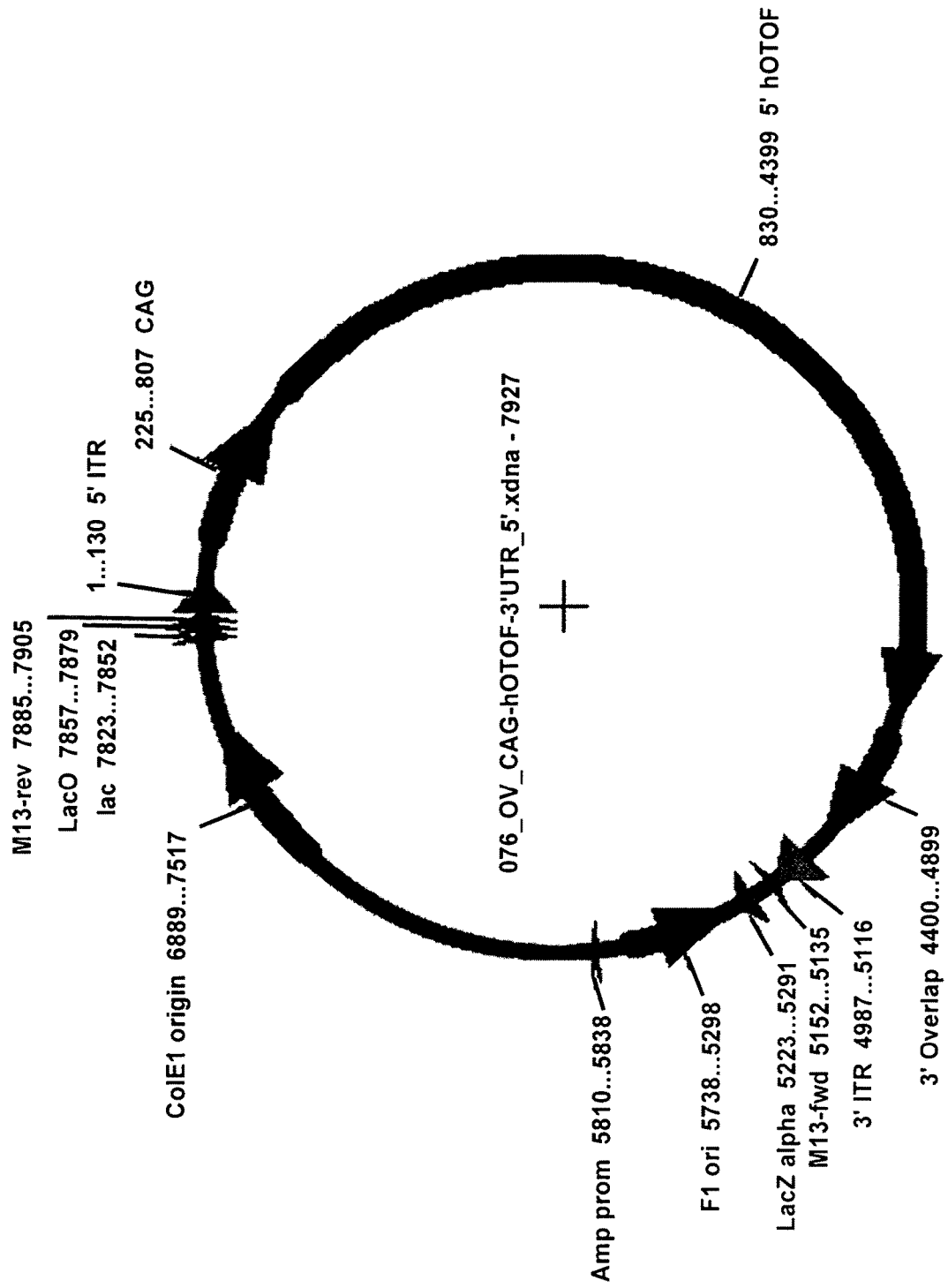
FIGS. 2A and 2B are maps of the 5' and 3' vectors in an overlapping dual vector system. The 5' vector contains AAV2 ITRs, and a CAG promoter operably linked to exons 1-28 of a polynucleotide encoding the human OTOF protein of SEQ ID NO: 1 and the 500 kb immediately 3' of the exon 28/29 boundary (FIG. 2A). The 3' vector contains AAV2 ITRs, the 500 kb immediately 5' of the exon 28/29 boundary and exons 29-48 of a polynucleotide encoding the human OTOF protein of SEQ ID NO: 1, the full-length human OTOF 3' UTR, and a WPRE sequence (SEQ ID NO: 23) (FIG. 2B).
Figure 2B:
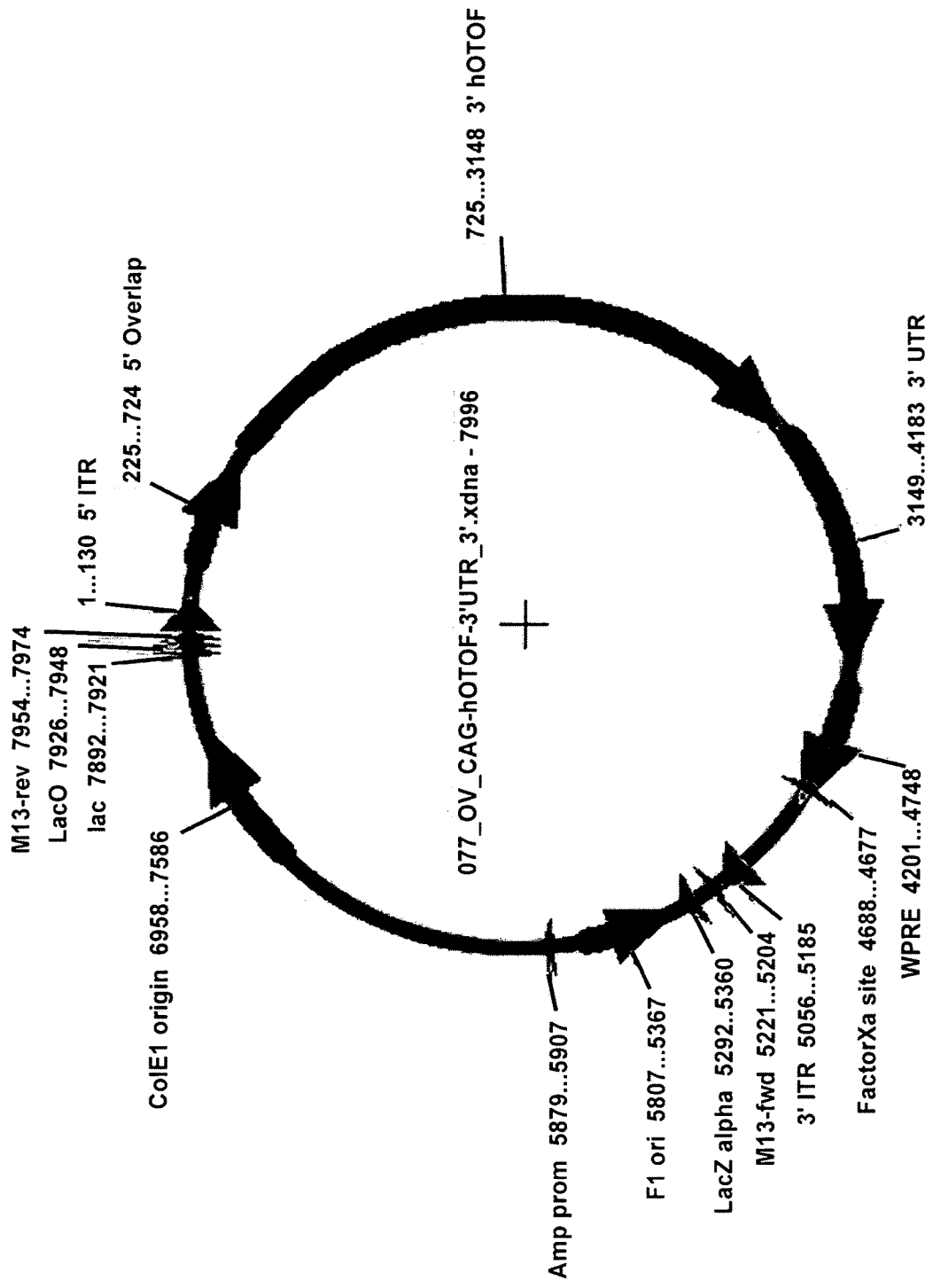
Figure 3A:
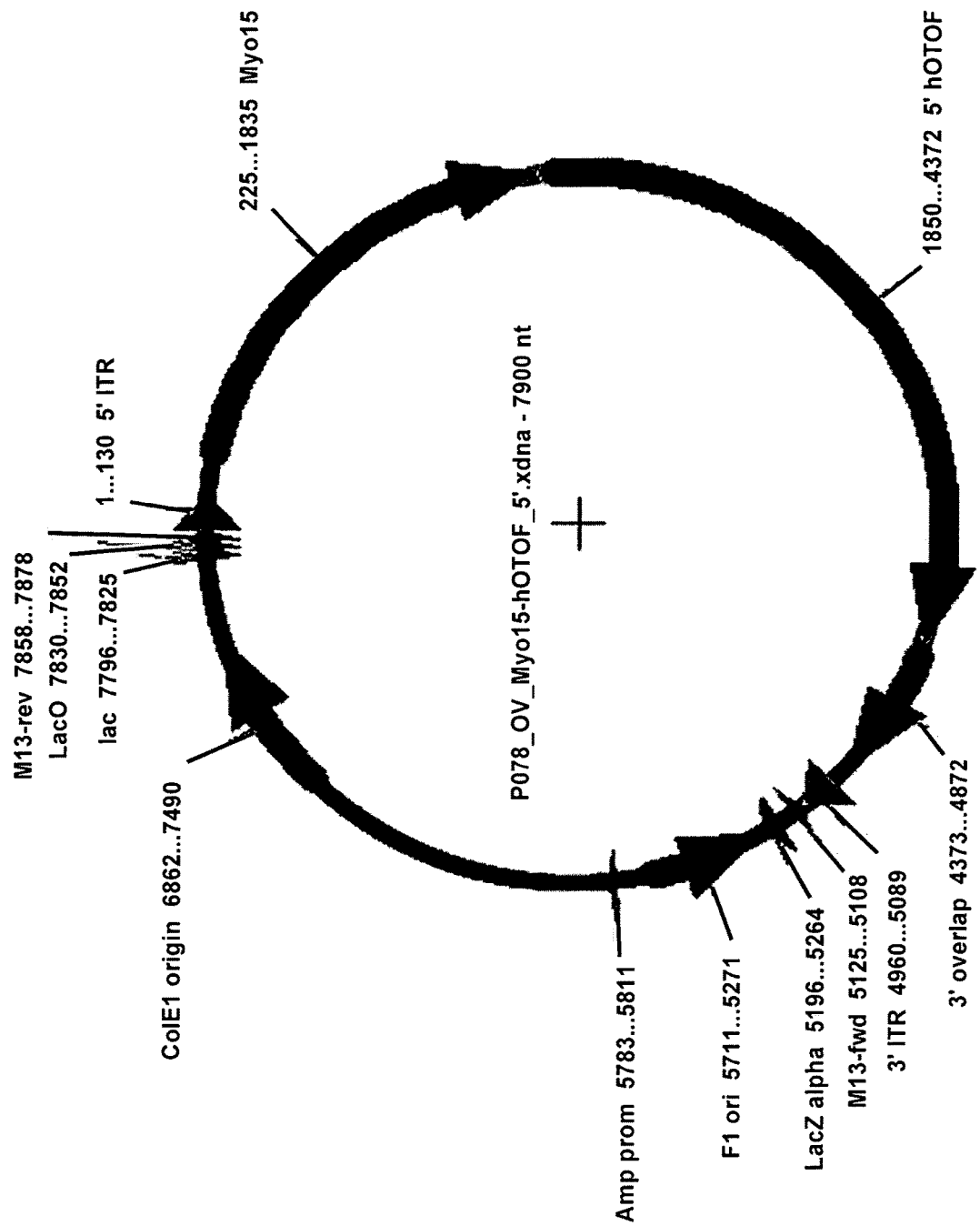
FIGS. 3A and 3B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary (FIG. 3A). The 3' vector contains AAV2 ITRs, the 500 kb immediately 5' of the exon 21/22 boundary and exons 22-48 of a polynucleotide encoding the human OTOF protein of SEQ ID NO: 1, and a WPRE sequence (SEQ ID NO: 23) (FIG. 3B).
Figure 3B:
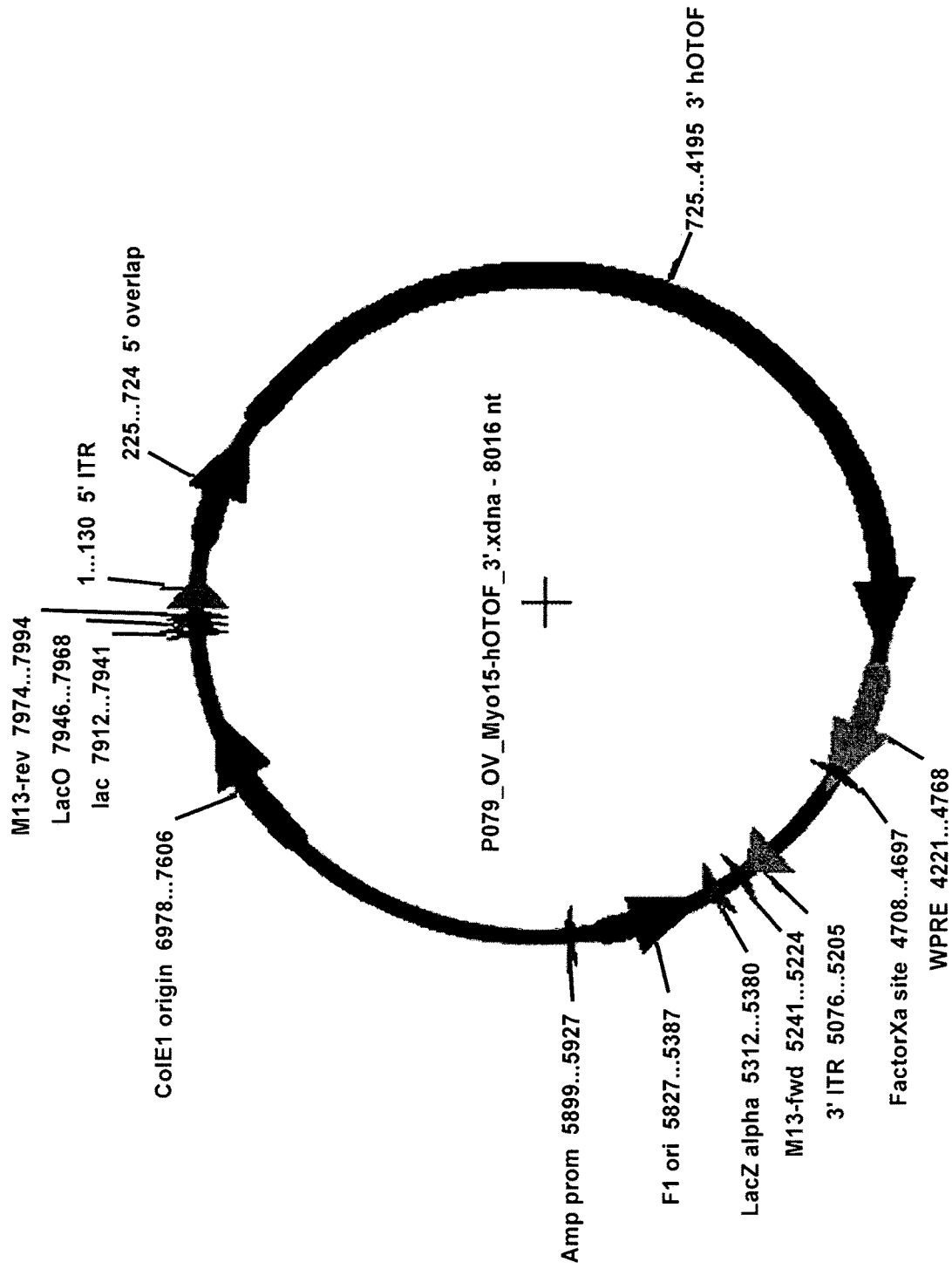
Figure 4A:
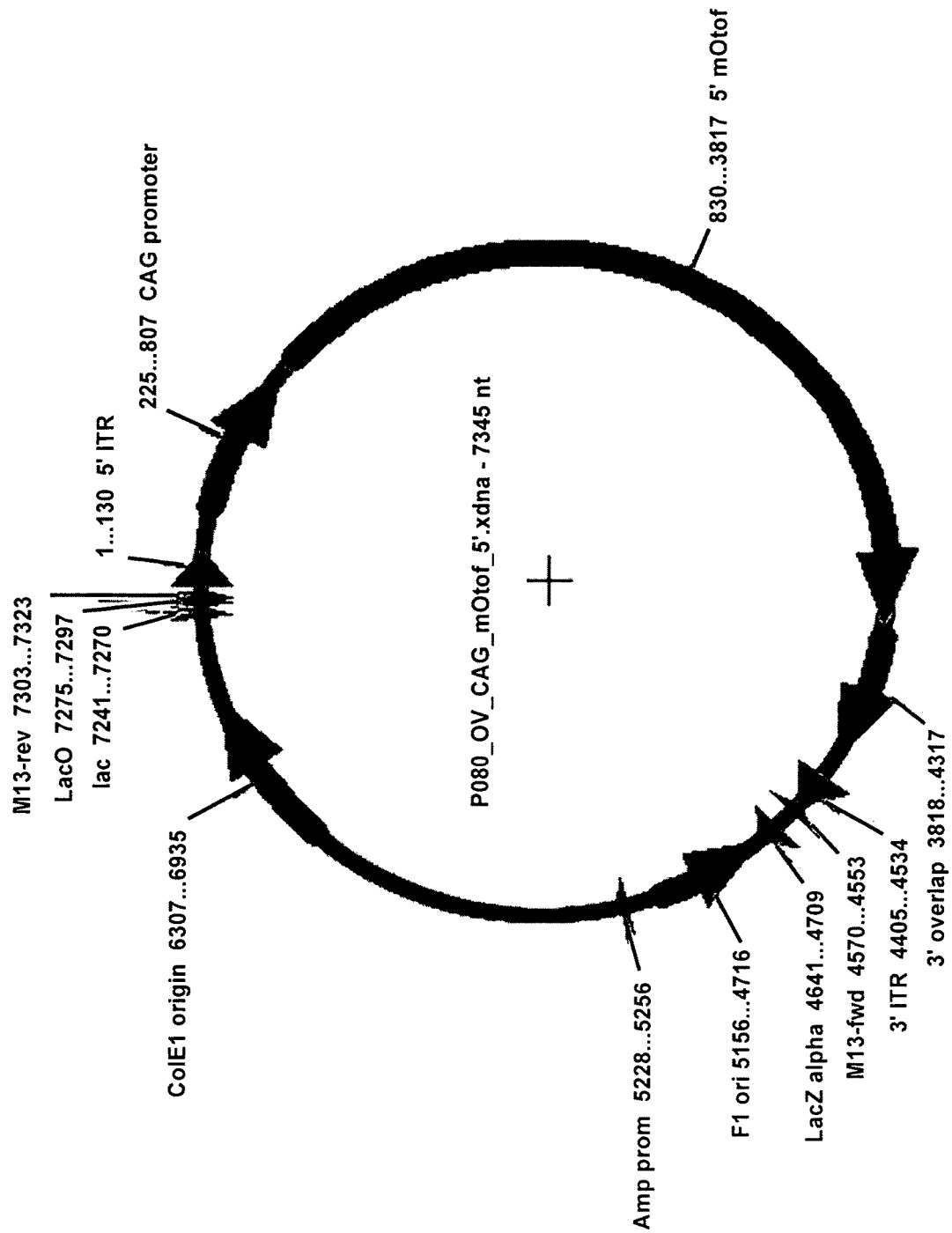
FIGS. 4A and 4B are maps of the 5' and 3' vectors in an overlapping dual vector system. The 5' vector contains AAV2 ITRs, and a CAG promoter operably linked to exons 1-24 of a polynucleotide encoding the mouse OTOF protein of SEQ ID NO: 6 and the 500 kb immediately 3' of the exon 24/25 boundary (FIG. 4A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 4B).
Figure 4B:
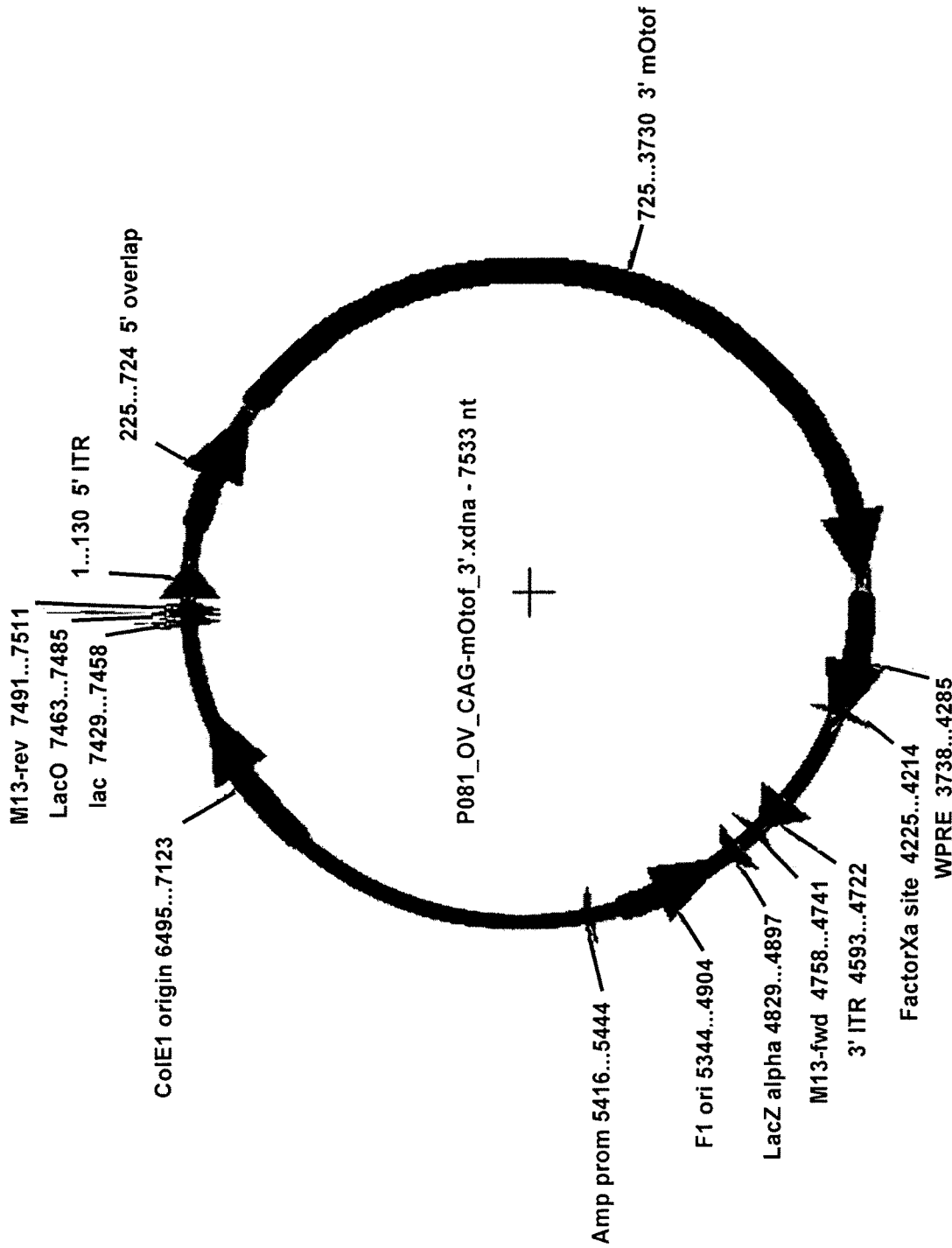
Figure 5A:
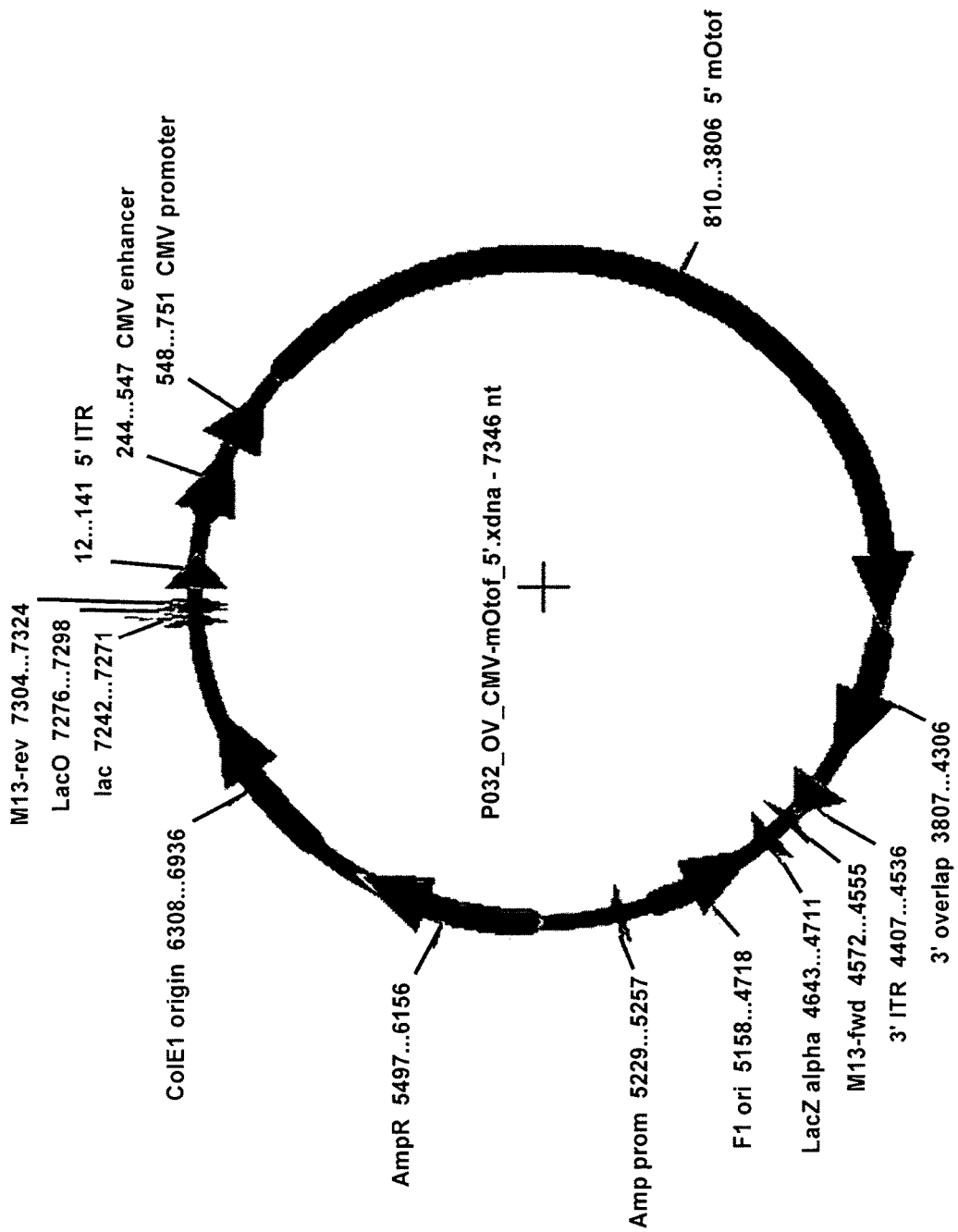
FIGS. 5A and 5B are maps of the 5' and 3' vectors in an overlapping dual vector system. The 5' vector contains AAV2 ITRs, a CMV enhancer, and a CMV promoter operably linked to exons 1-24 of a polynucleotide encoding the mouse OTOF protein of SEQ ID NO: 6 and the 500 kb immediately 3' of the exon 24/25 boundary (FIG. 5A). The 3' vector contains AAV2 ITRs, the 500 kb immediately 5' of the exon 24/25 boundary and exons 25-48 of a polynucleotide encoding the mouse OTOF protein of SEQ ID NO: 6, and a WPRE sequence (SEQ ID NO: 23) (FIG. 5B).
Figure 5B:
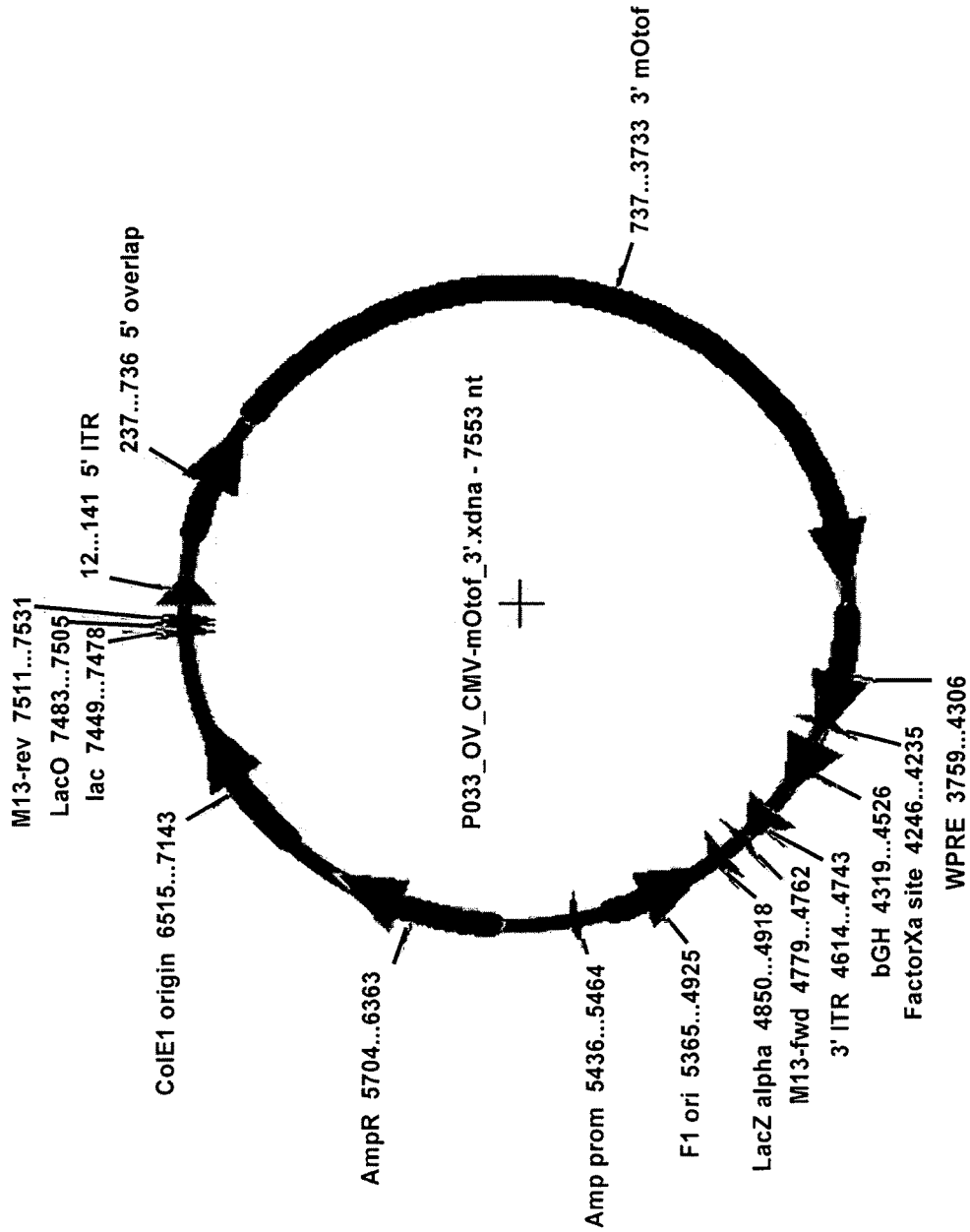
Figure 6A:
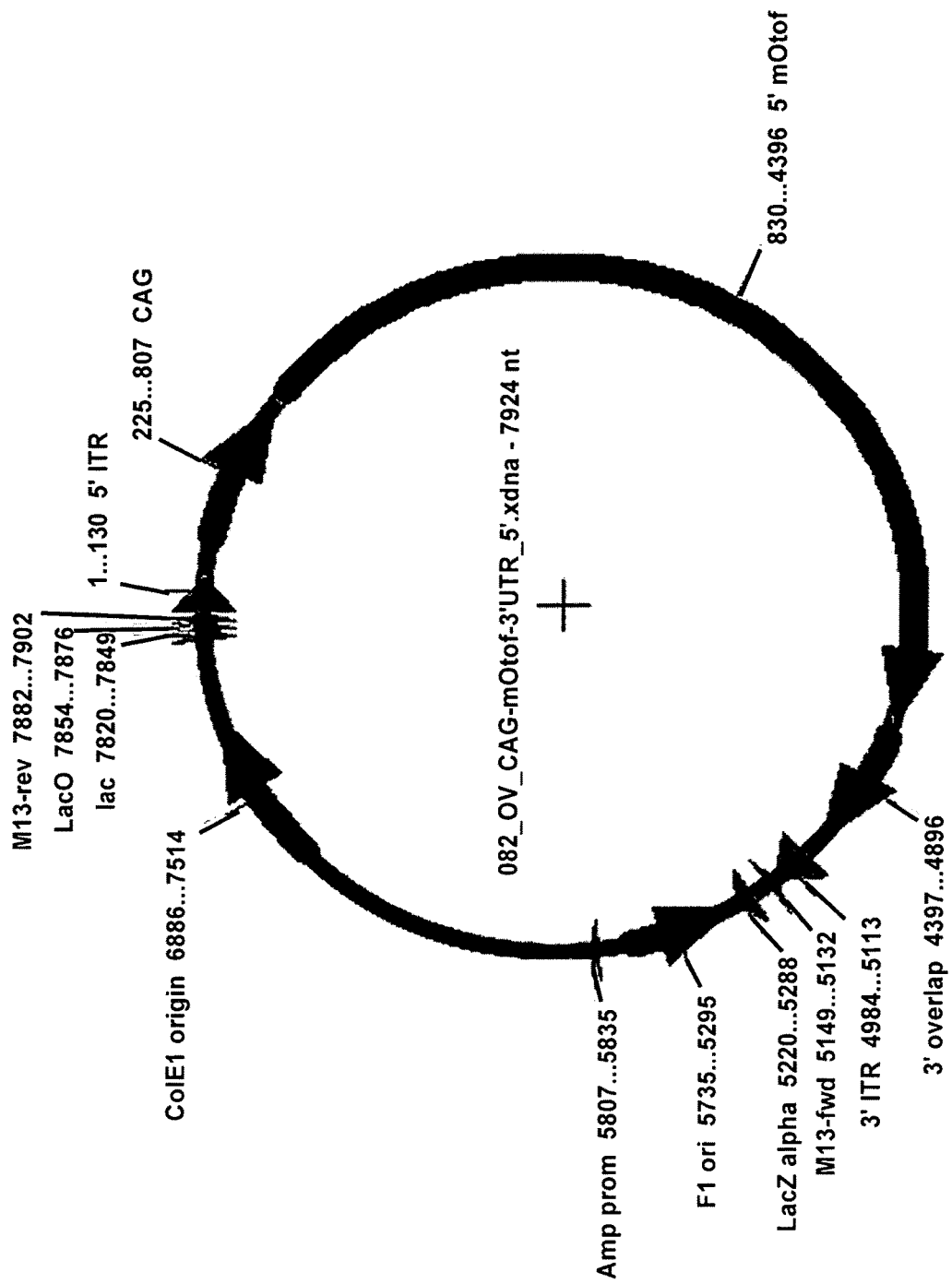
FIGS. 6A and 6B are maps of the 5' and 3' vectors in an overlapping dual vector system. The 5' vector contains AAV2 ITRs, and a CAG promoter operably linked to exons 1-28 of a polynucleotide encoding the mouse OTOF protein of SEQ ID NO: 6 and the 500 kb immediately 3' of the exon 28/29 boundary (FIG. 6A). The 3' vector contains AAV2 ITRs, the 500 kb immediately 5' of the exon 28/29 boundary and exons 29-48 of a polynucleotide encoding the mouse OTOF protein of SEQ ID NO: 6, the full-length mouse OTOF 3' UTR, and a WPRE sequence (SEQ ID NO: 23) (FIG. 6B).
Figure 6B:
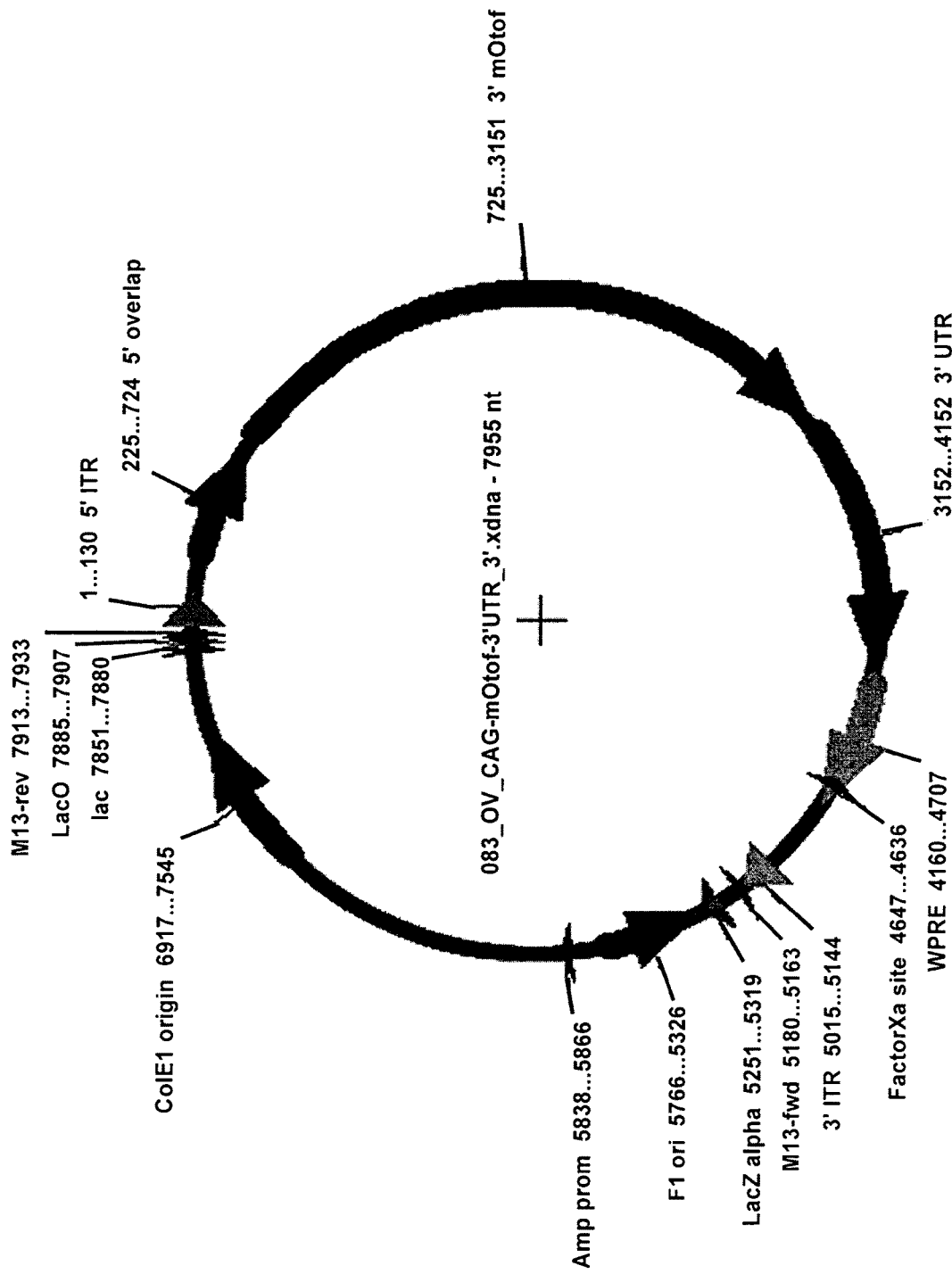
Figure 7A:
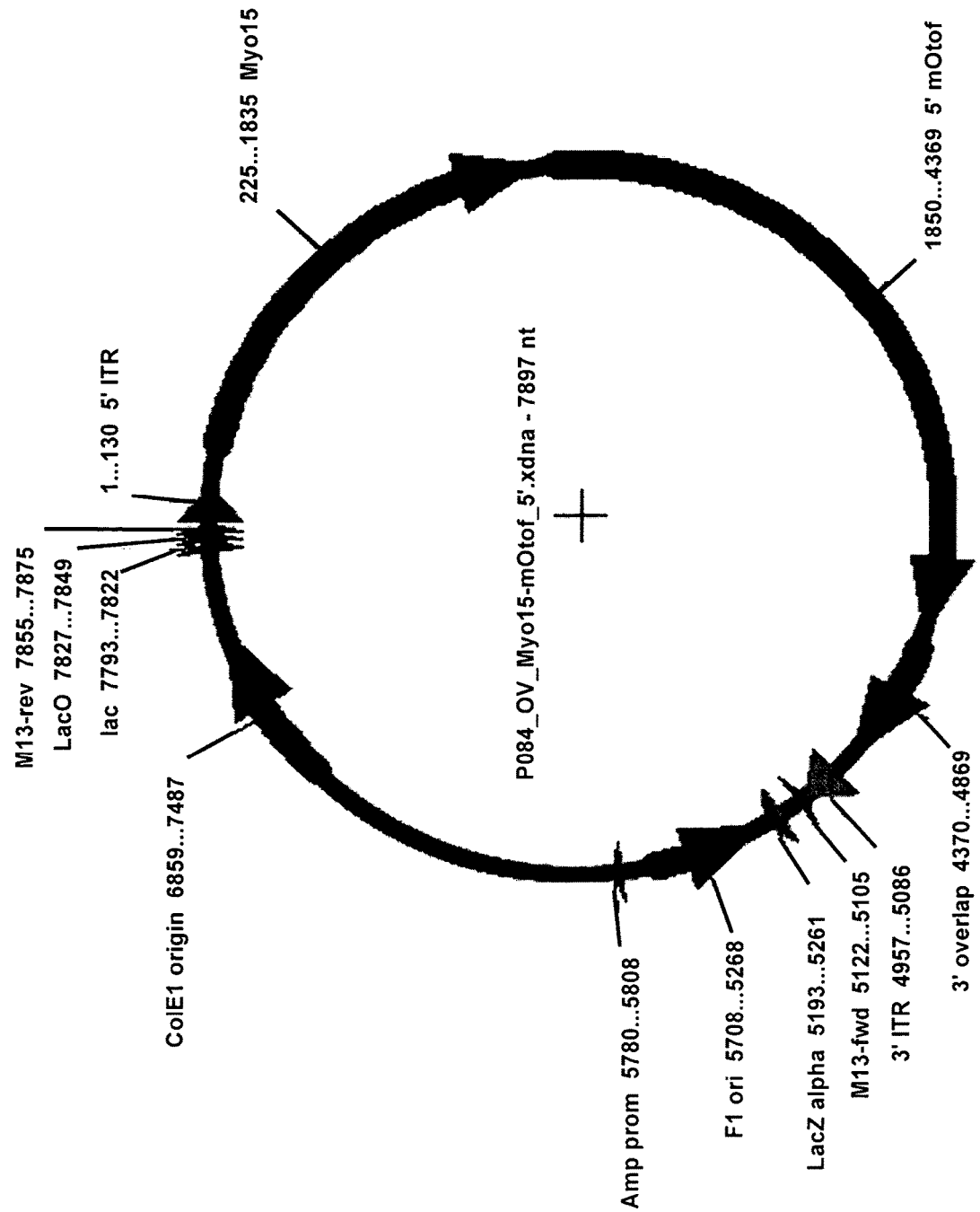
FIGS. 7A and 7B are maps of the 5' and 3' vectors in an overlapping dual vector system. The 5' vector contains AAV2 ITRs, and a Myo15 promoter (SEQ ID NO: 36) operably linked to exons 1-21 of a polynucleotide encoding the mouse OTOF protein of SEQ ID NO: 6 and the 500 kb immediately 3' of the exon 21/22 boundary (FIG. 7A). The 3' vector contains AAV2 ITRs, the 500 kb immediately 5' of the exon 21/22 boundary and exons 22-48 of a polynucleotide encoding the mouse OTOF protein of SEQ ID NO: 6, and a WPRE sequence (SEQ ID NO: 23) (FIG. 7B).
Figure 7B:
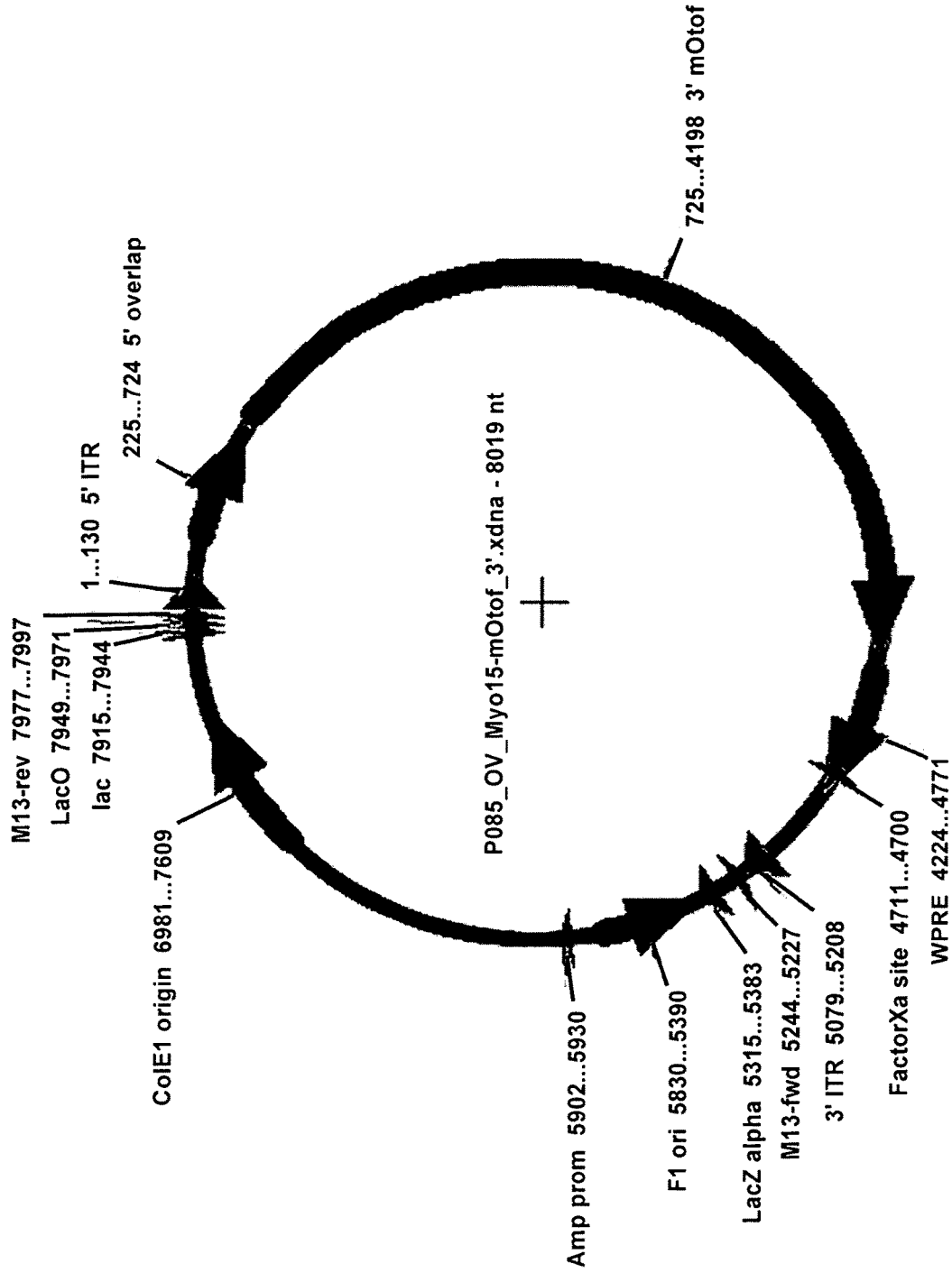
Figure 8A:
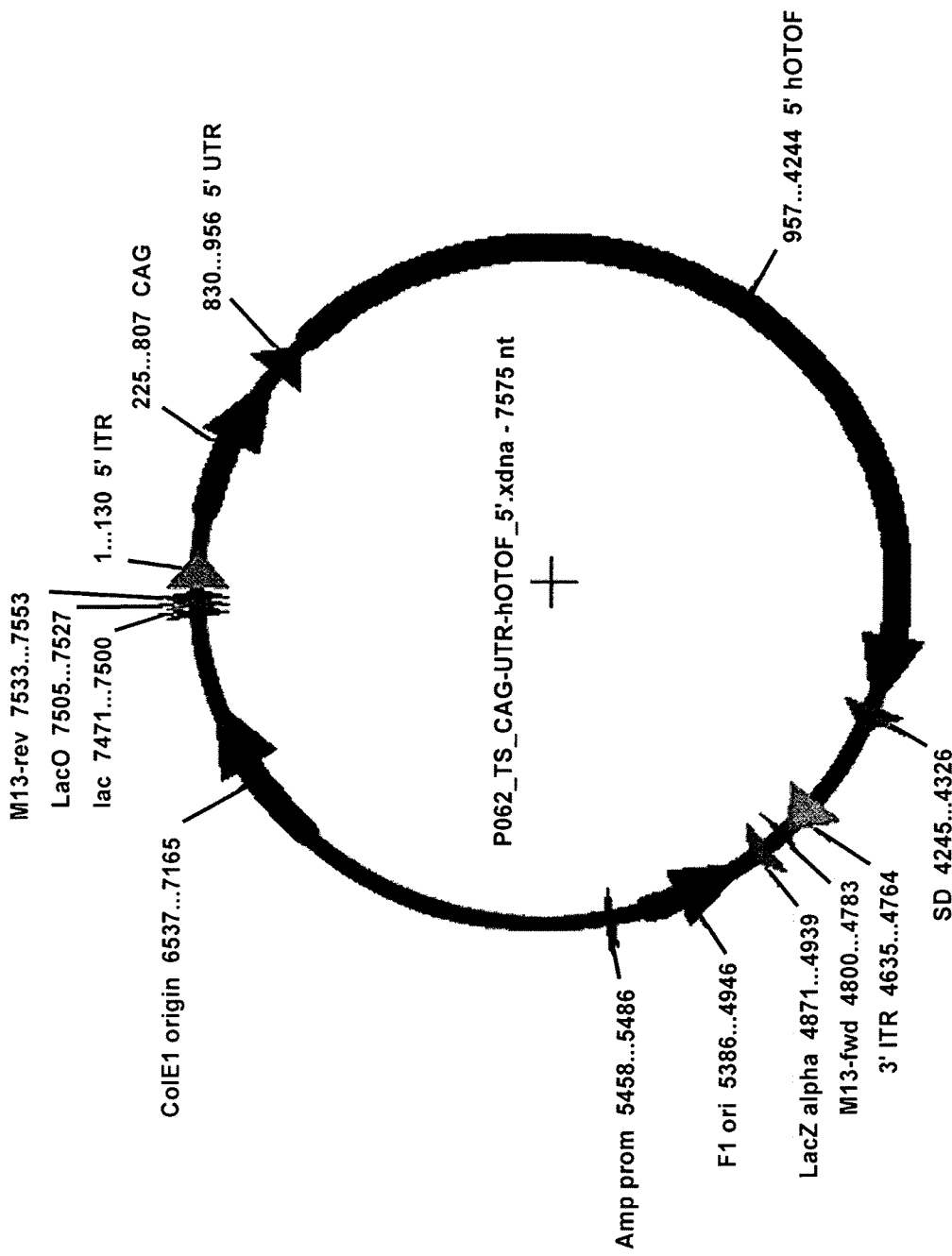
FIGS. 8A and 8B are maps of the 5' and 3' vectors in a trans-splicing dual vector system. The 5' vector contains AAV2 ITRs, a CAG promoter operably linked to the full-length human OTOF 5' UTR and exons 1-26 of a polynucleotide encoding the human OTOF protein of SEQ ID NO: 1, and a splice donor sequence (SD) (FIG. 8A). The 3' vector contains AAV2 ITRs, a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 8B).
Figure 8B:
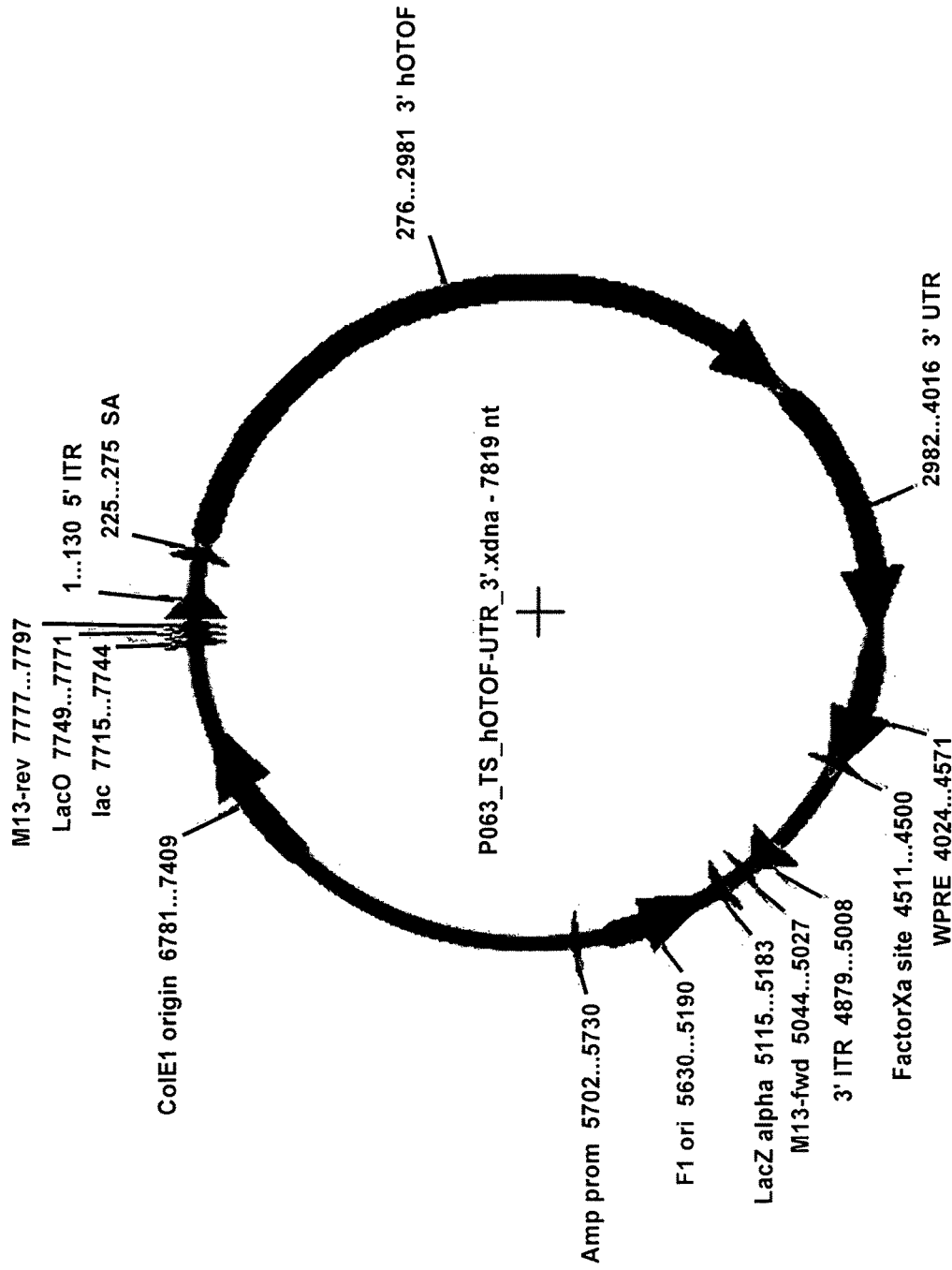
Figure 9A:
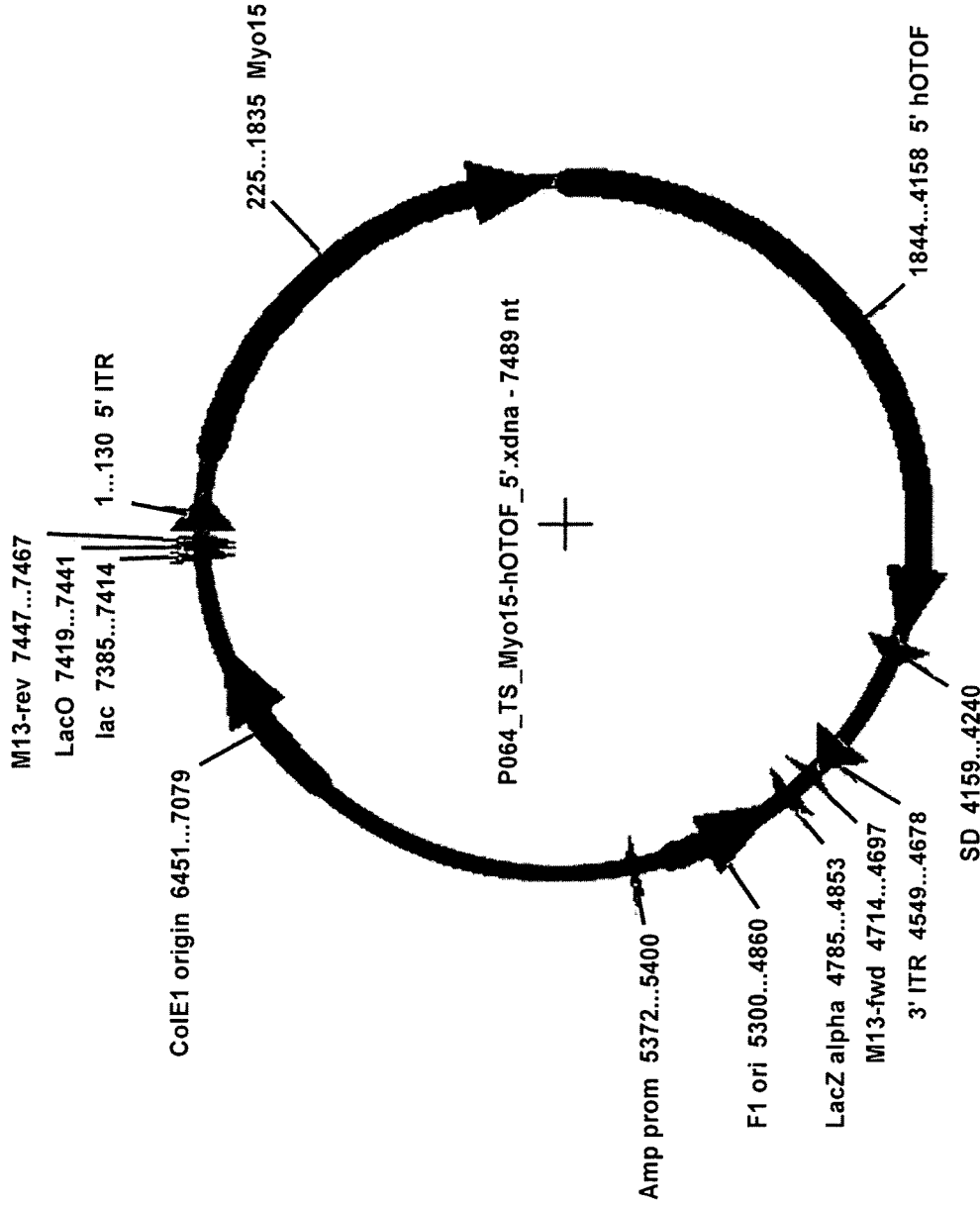
FIGS. 9A and 9B are maps of the 5' and 3' vectors in a trans-splicing dual vector system. The 5' vector contains AAV2 ITRs, a Myo15 promoter (SEQ ID NO: 36) operably linked to exons 1-19 of a polynucleotide encoding the human OTOF protein of SEQ ID NO: 1, and a splice donor sequence (SD) (FIG. 9A). The 3' vector contains AAV2 ITRs, a splice acceptor sequence (SA), exons 20-48 of a polynucleotide encoding the human OTOF protein of SEQ ID NO: 1, and a WPRE sequence (SEQ ID NO: 23) (FIG. 9B).
Figure 9B:
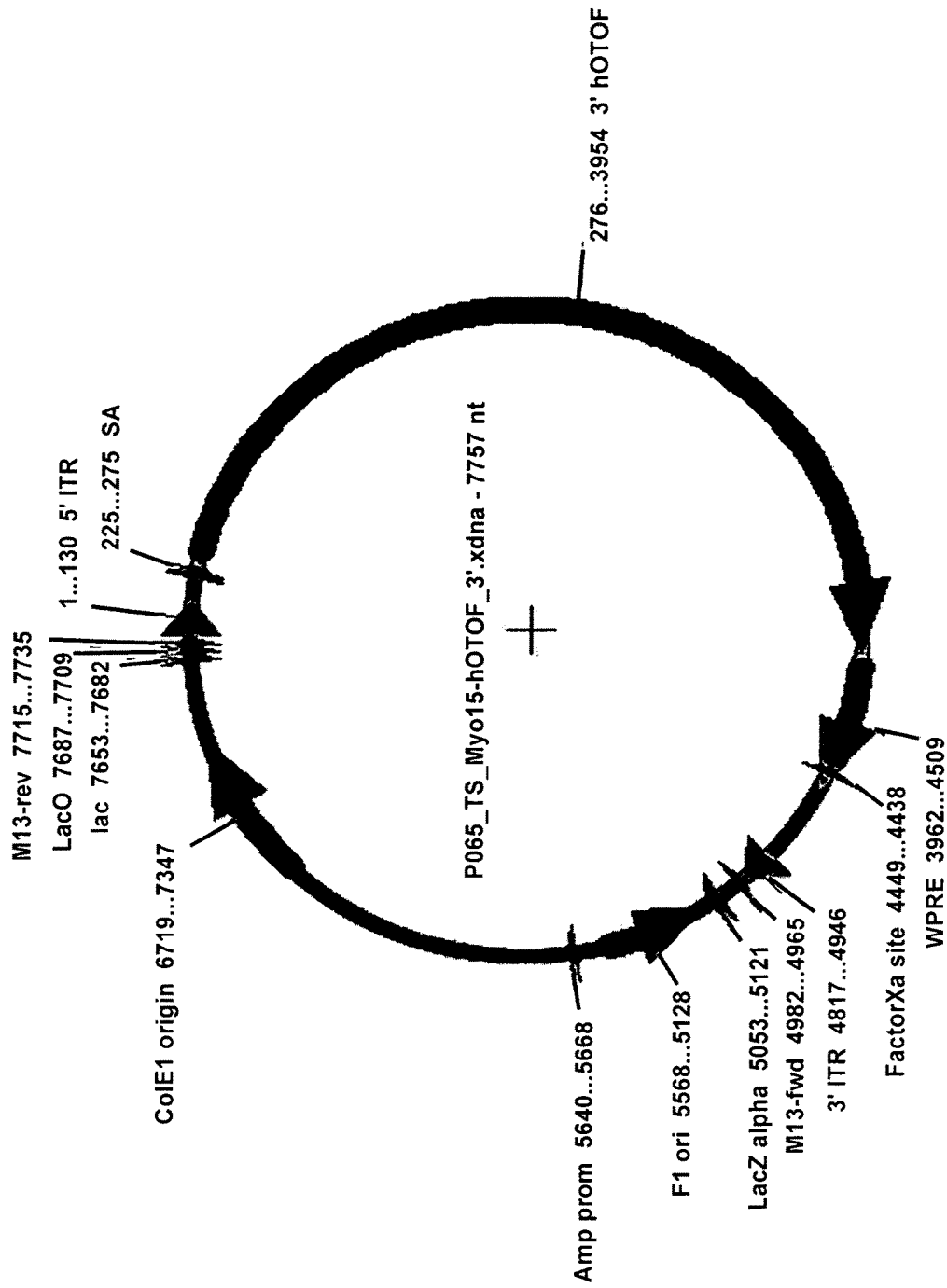
Figure 10A:
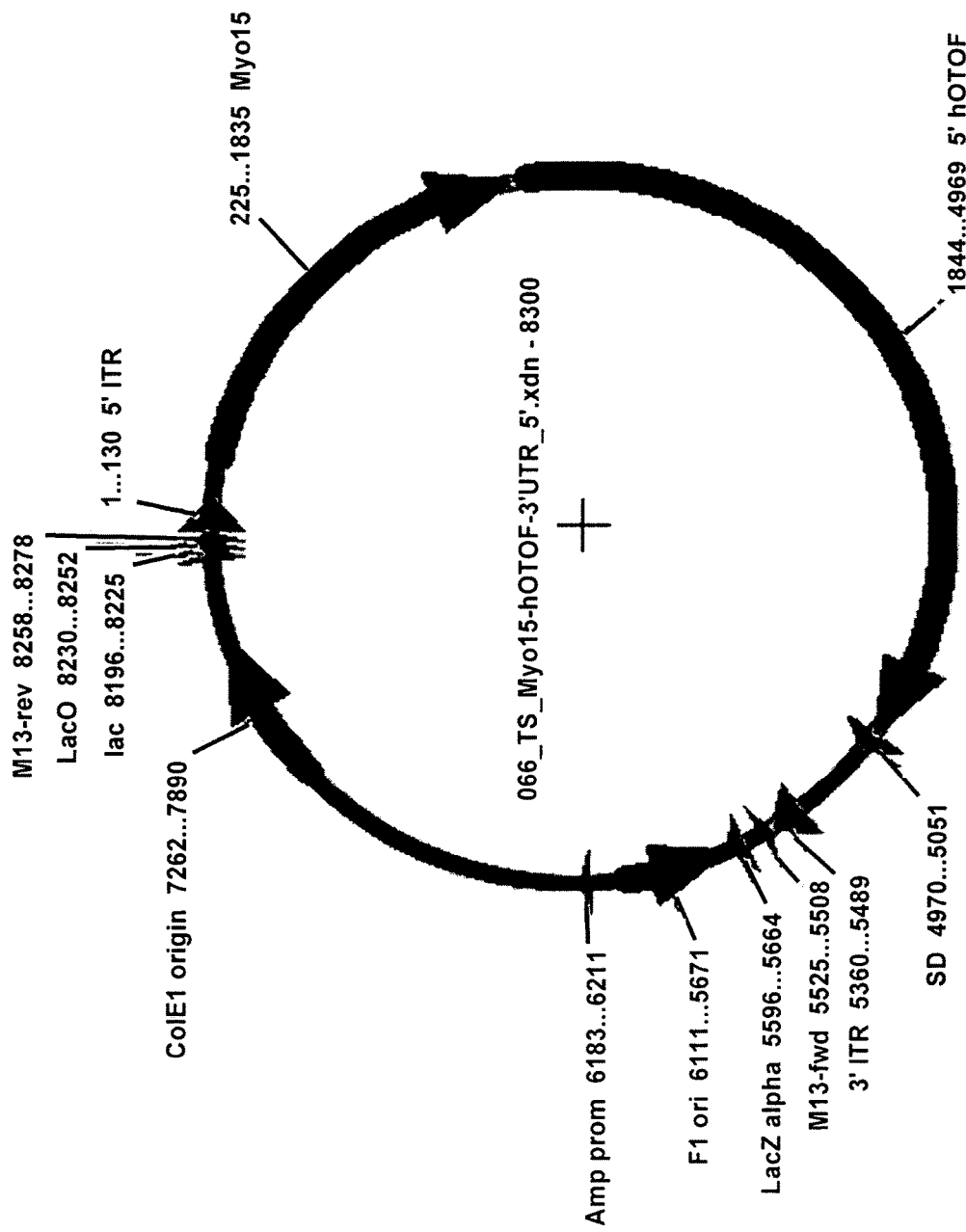
FIGS. 10A and 10B are maps of the 5' and 3' vectors in a trans-splicing dual vector system. The 5' vector contains AAV2 ITRs, a Myo15 promoter (SEQ ID NO: 36) operably linked to exons 1-25 of a polynucleotide encoding the human OTOF protein of SEQ ID NO: 1, and a splice donor sequence (SD) (FIG. 10A). The 3' vector contains AAV2
Figure 10B:
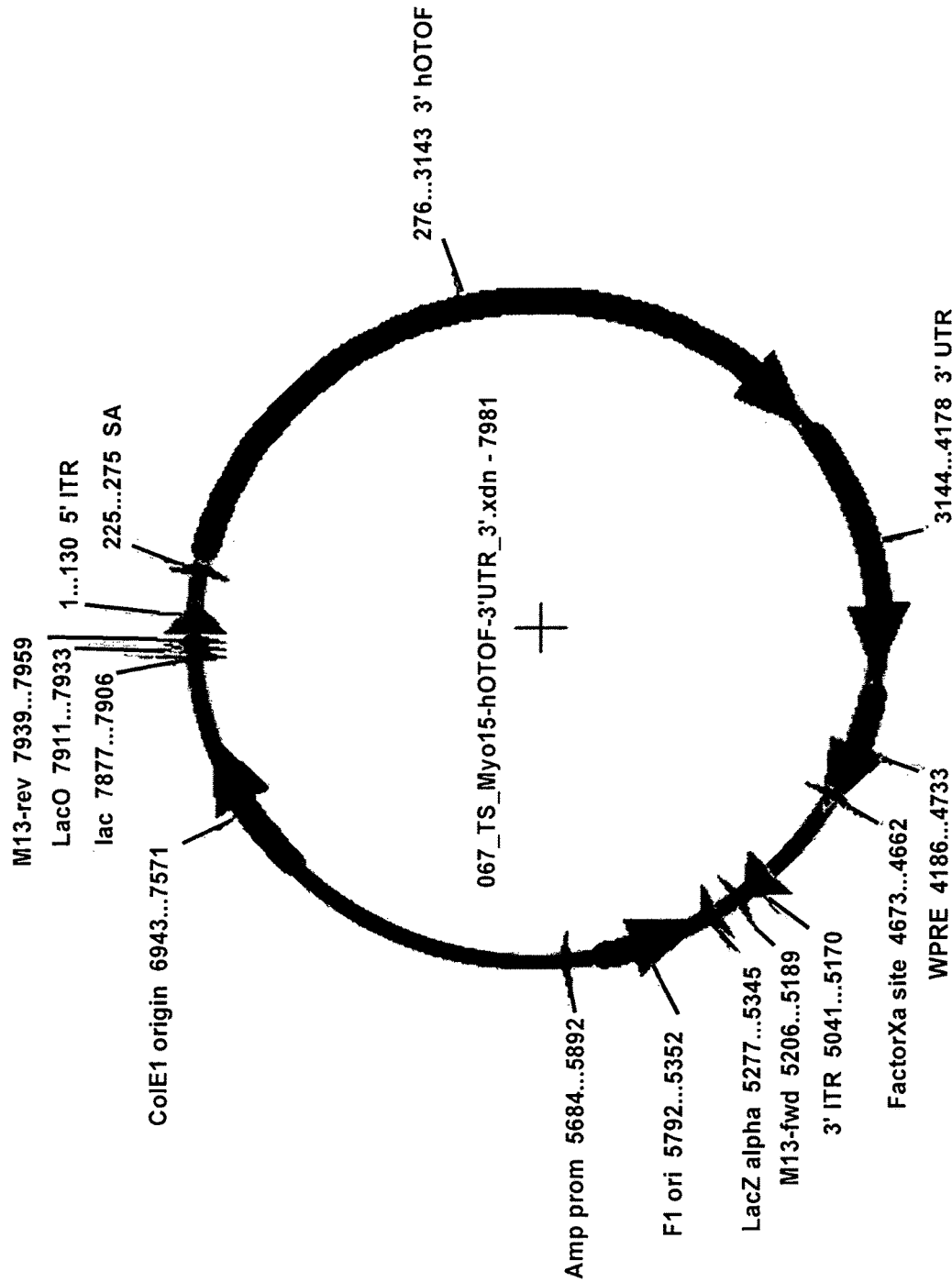

ITRs, a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 10B).

Figure 11A:
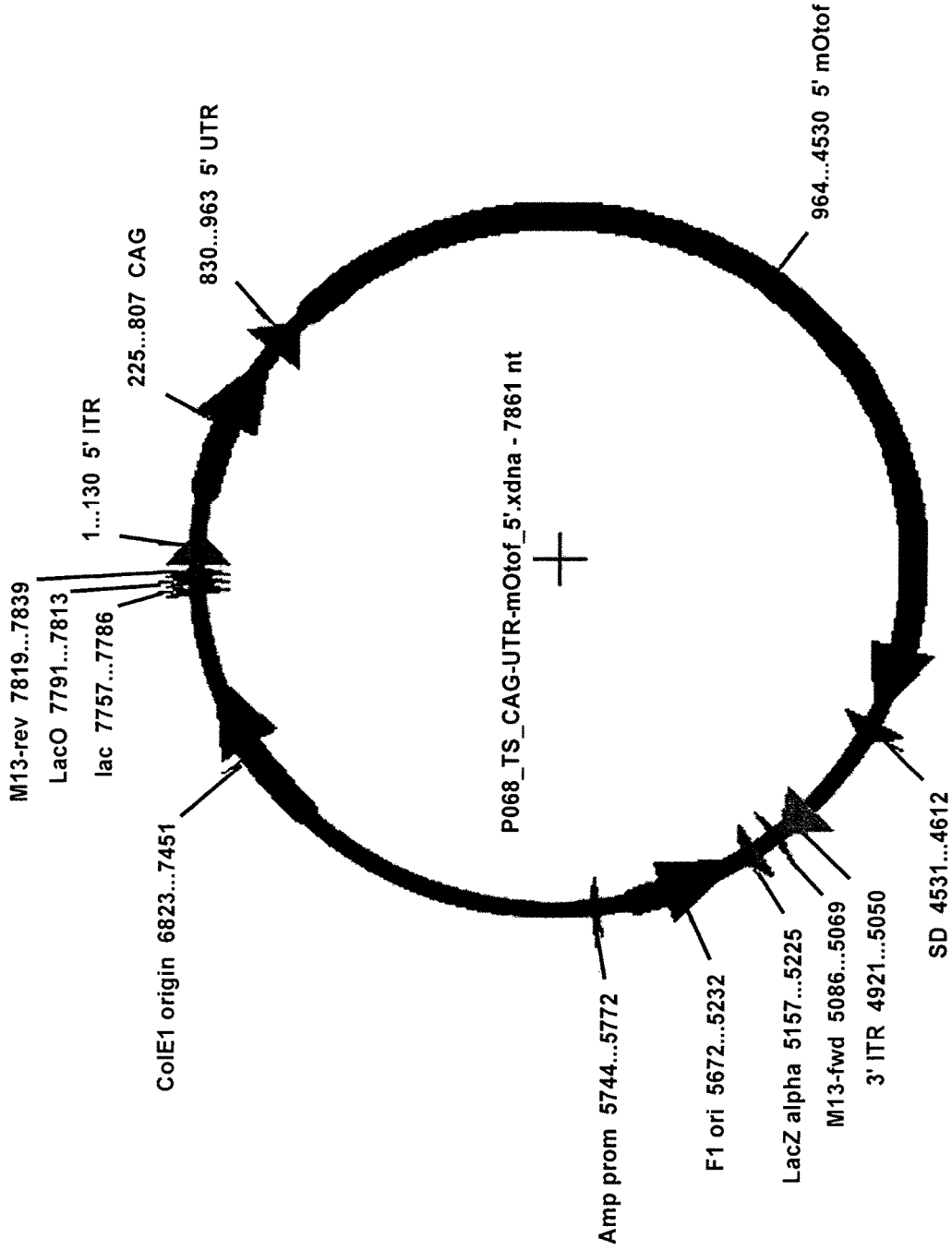
Figure 11B:
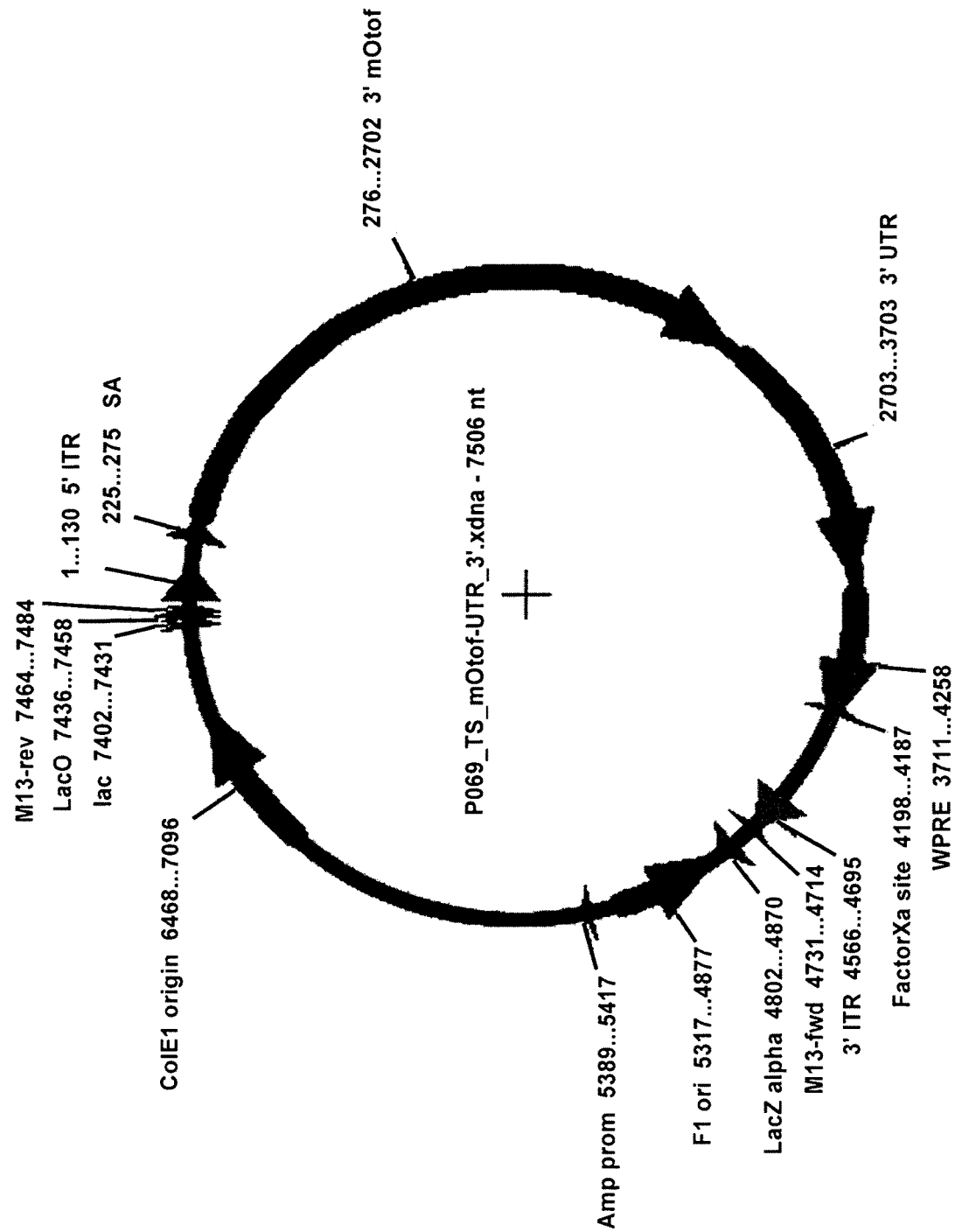

FIGS. 11A and 11B are maps of the 5' and 3' vectors in a trans-splicing dual vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, and a splice donor sequence (SD) (FIG. 11A). The 3' vector contains AAV2 ITRs, a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 11B).

Figure 12A:
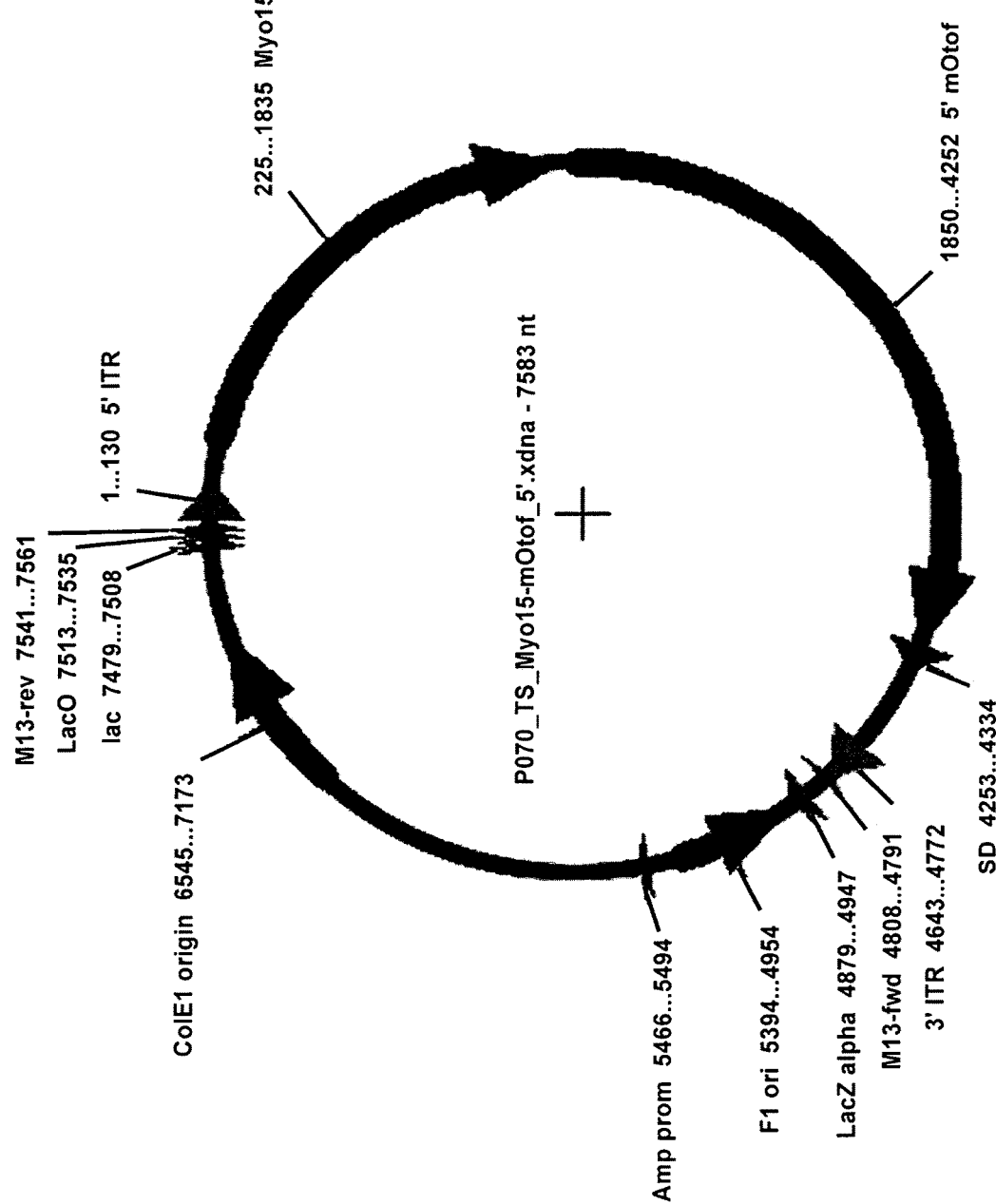
Figure 12B:
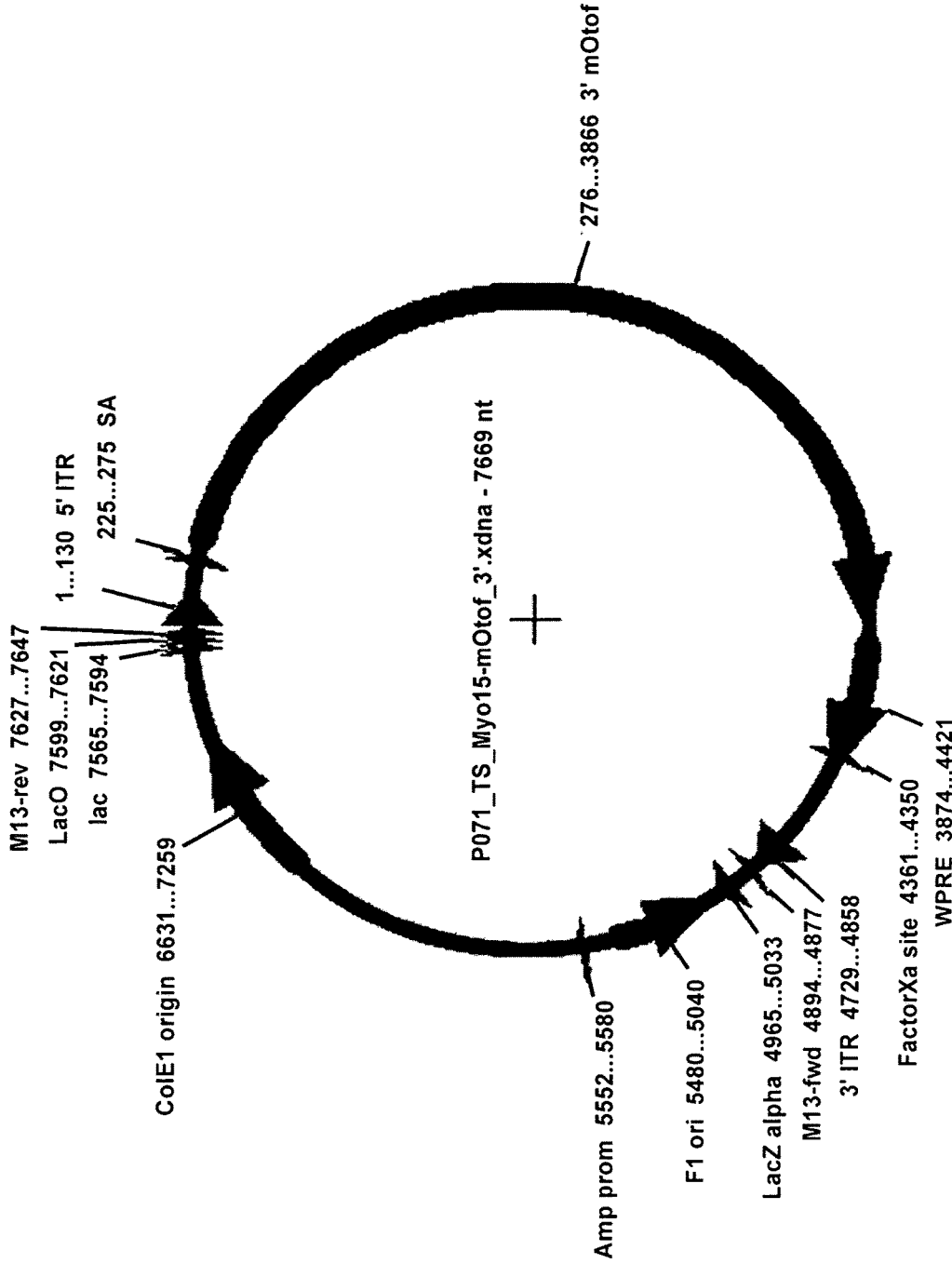

FIGS. 12A and 12B are maps of the 5' and 3' vectors in a trans-splicing dual vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, and a splice donor sequence (SD) (FIG. 12A). The 3' vector contains AAV2 ITRs, a splice acceptor sequence (SA), exons 21-48 of a polynucleotide encoding the mouse OTOF protein of SEQ ID NO: 6, and a WPRE sequence (SEQ ID NO: 23) (FIG. 12B).

Figure 13A:
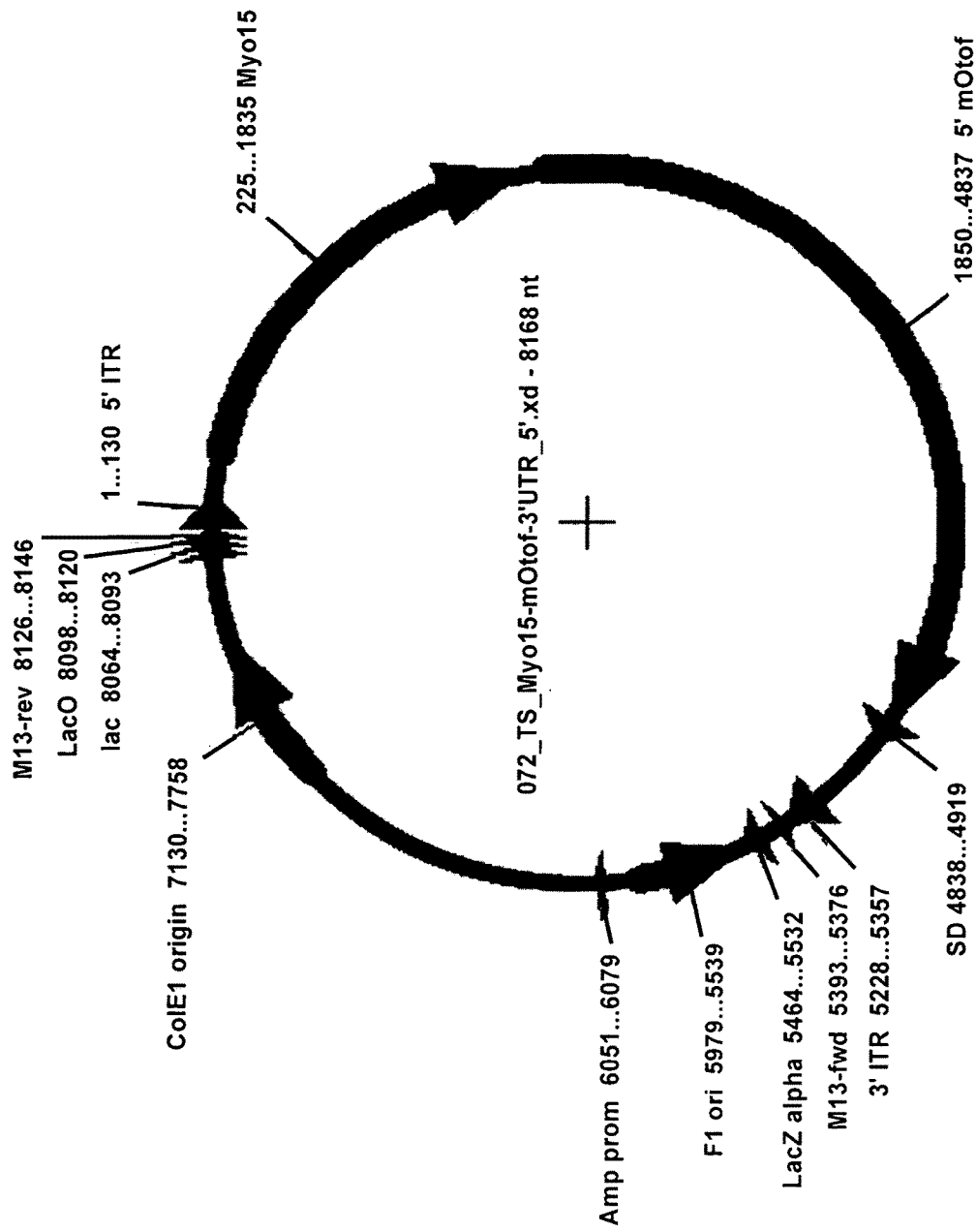
Figure 13B:
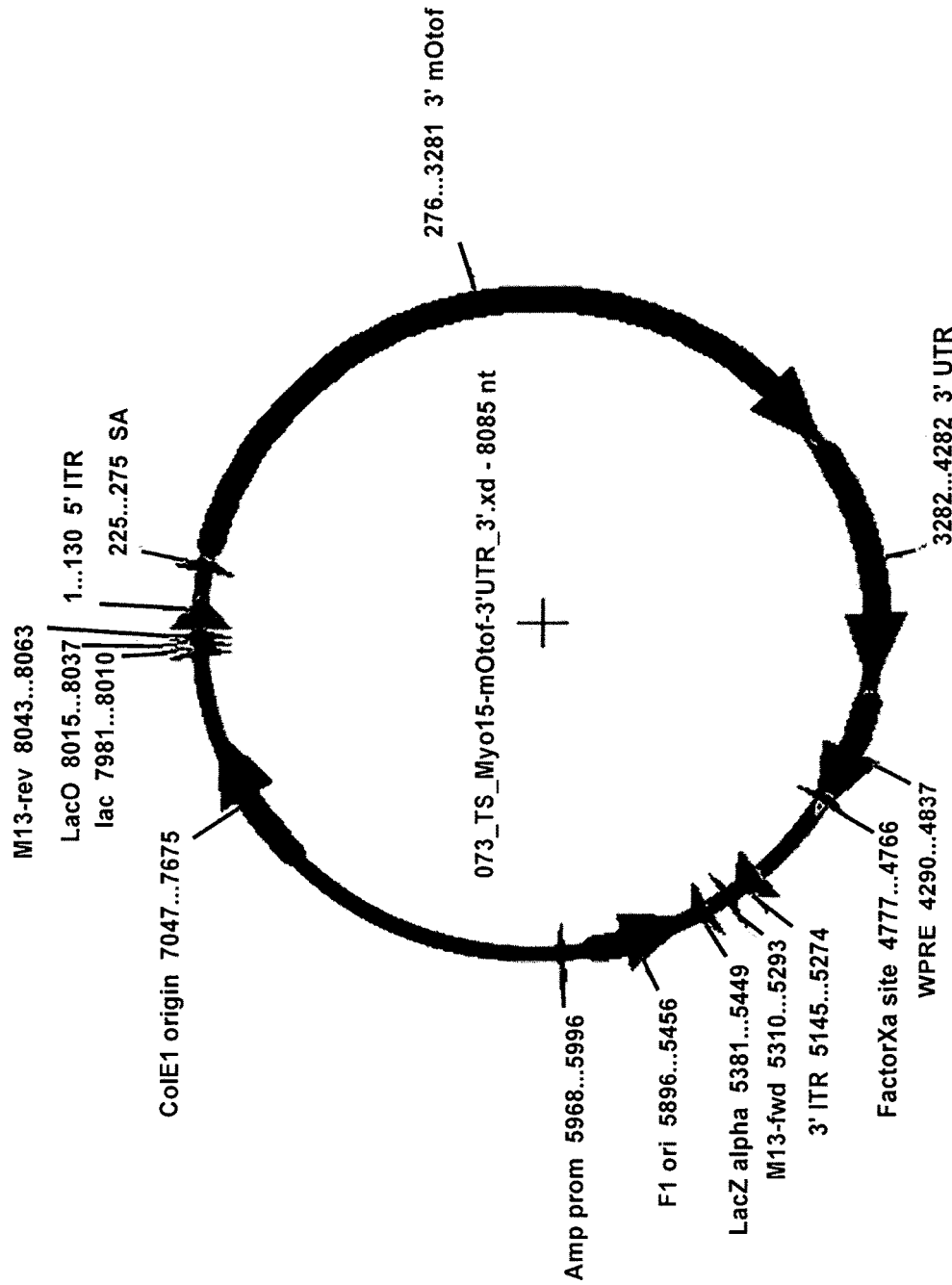

FIGS. 13A and 13B are maps of the 5' and 3' vectors in a trans-splicing dual vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, and a splice donor sequence (SD) (FIG. 13A). The 3' vector contains AAV2 ITRs, a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 13B).

Figure 14A:
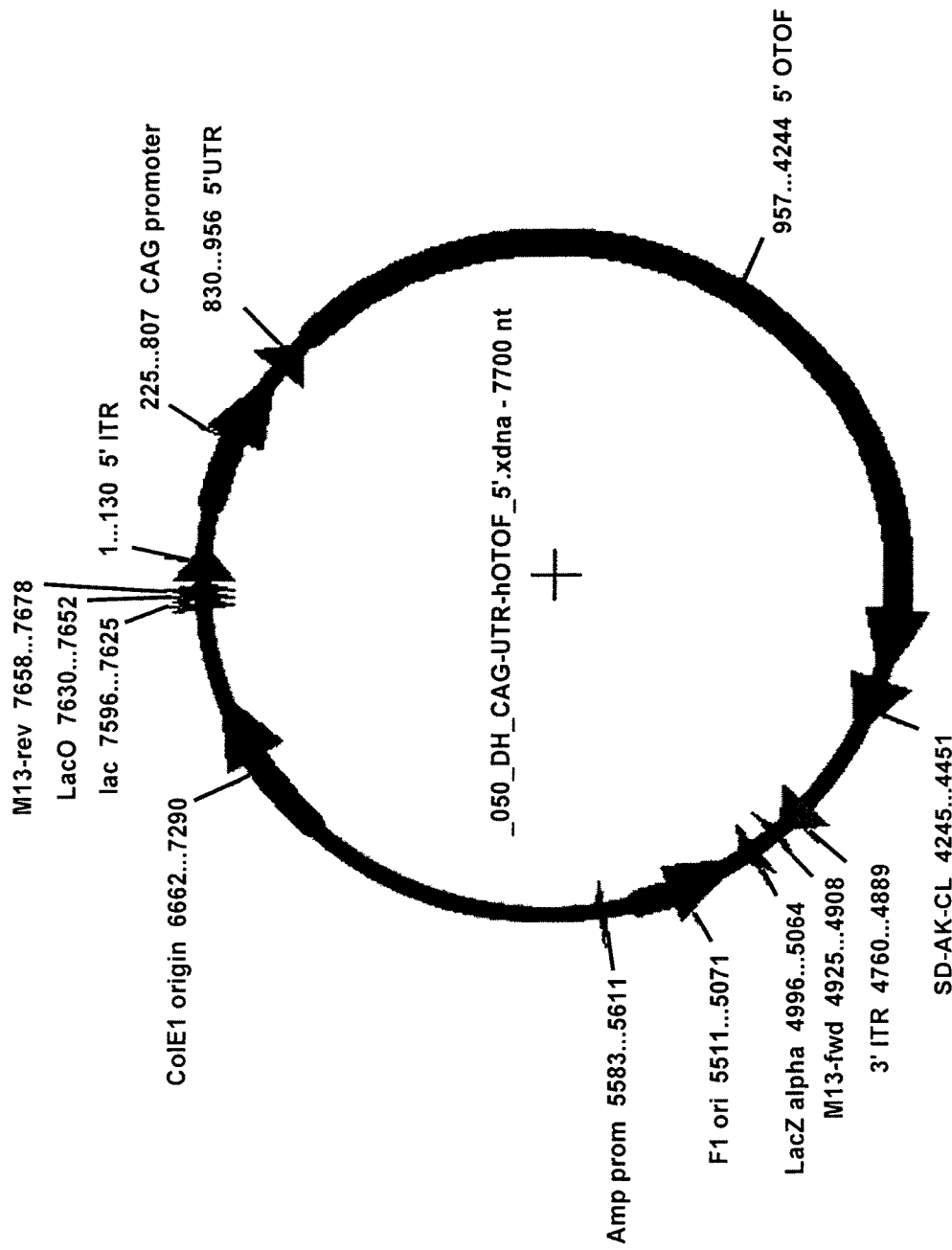
Figure 14B:
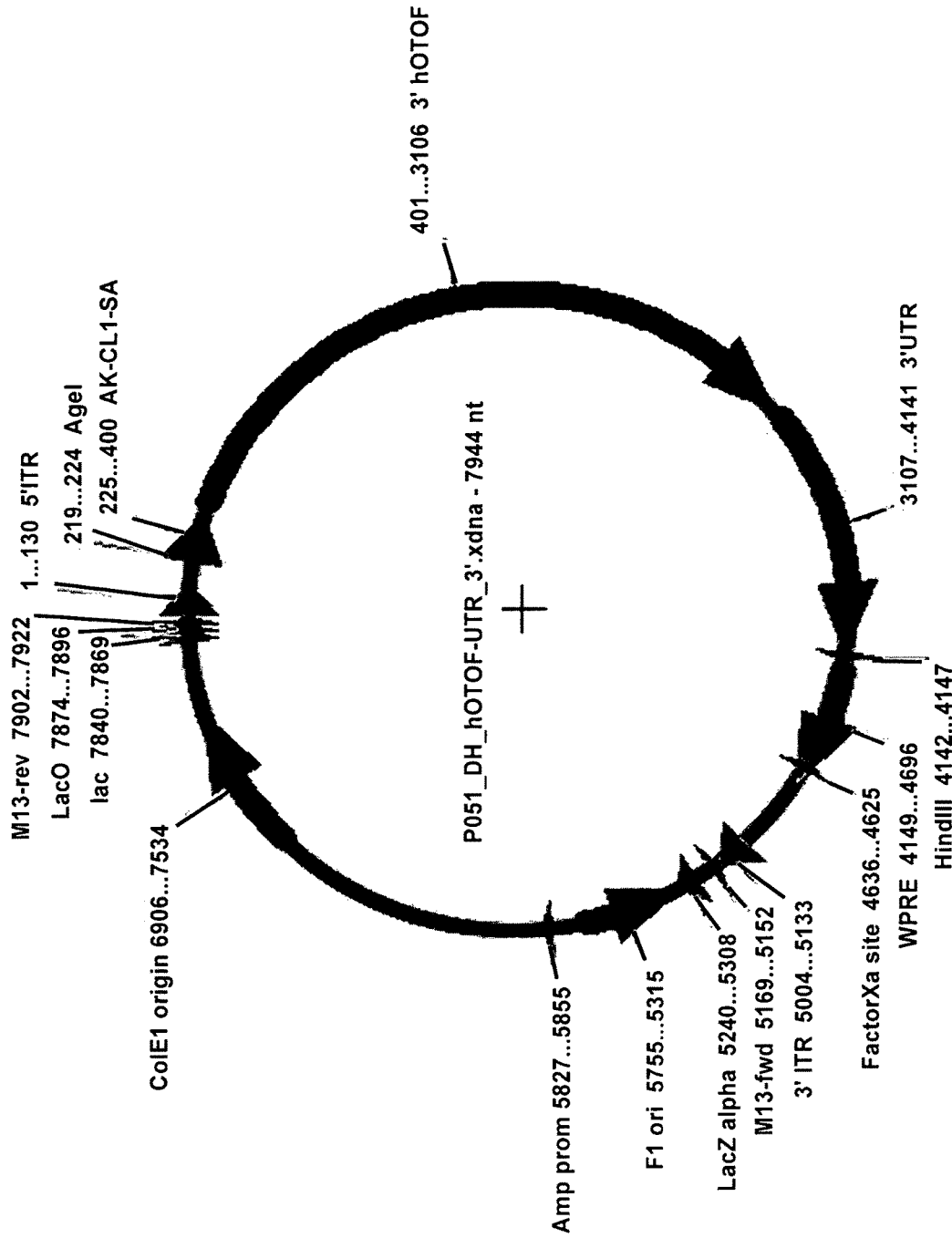

FIGS. 14A and 14B are maps of the 5' and 3' vectors in a dual hybrid vector system. The 5' vector contains AAV2 ITRs, a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1) (FIG. 14A). The 3' vector contains AAV2 ITRs, a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23) (FIG. 14B).

Figure 15A:
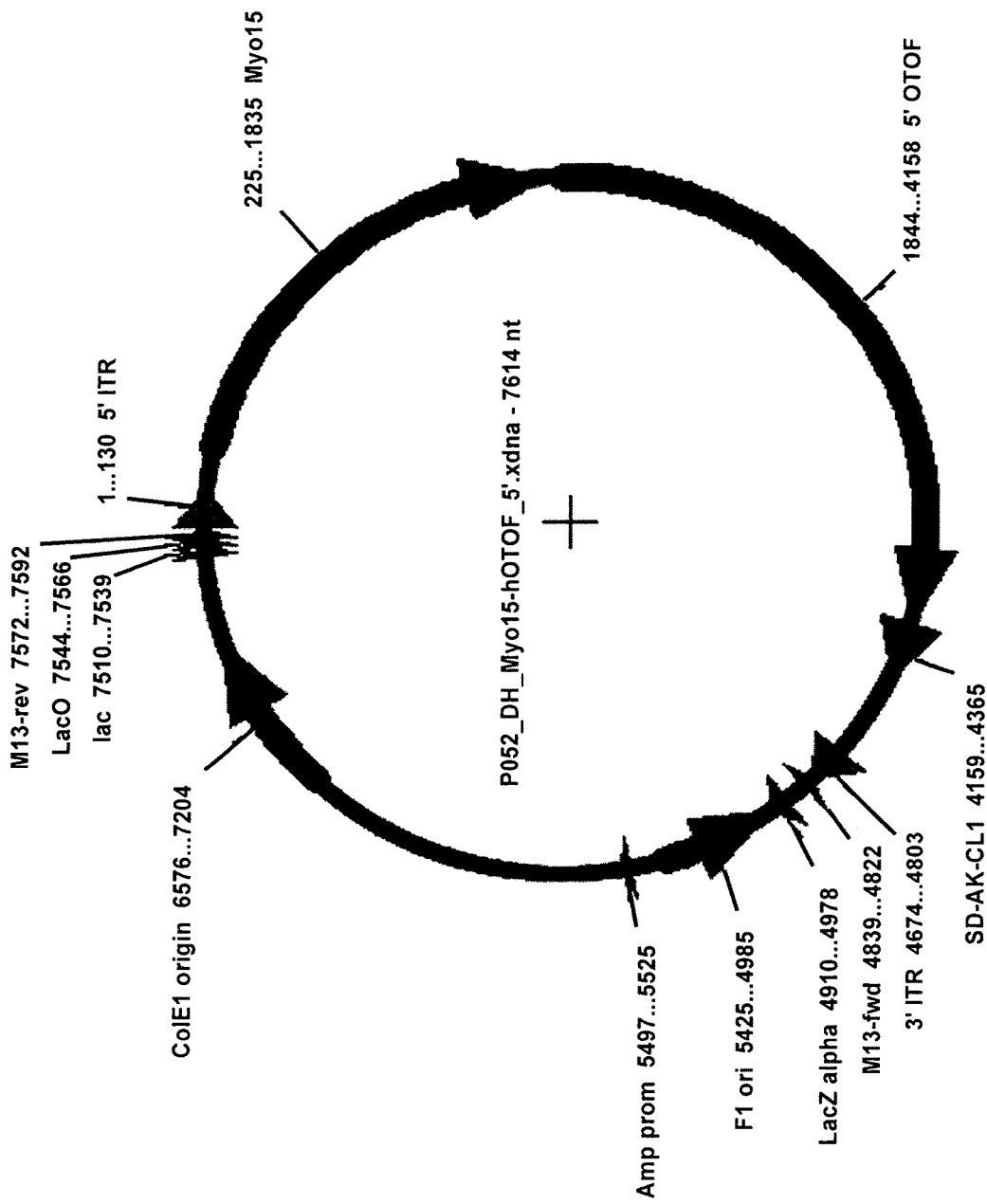
Figure 15B:
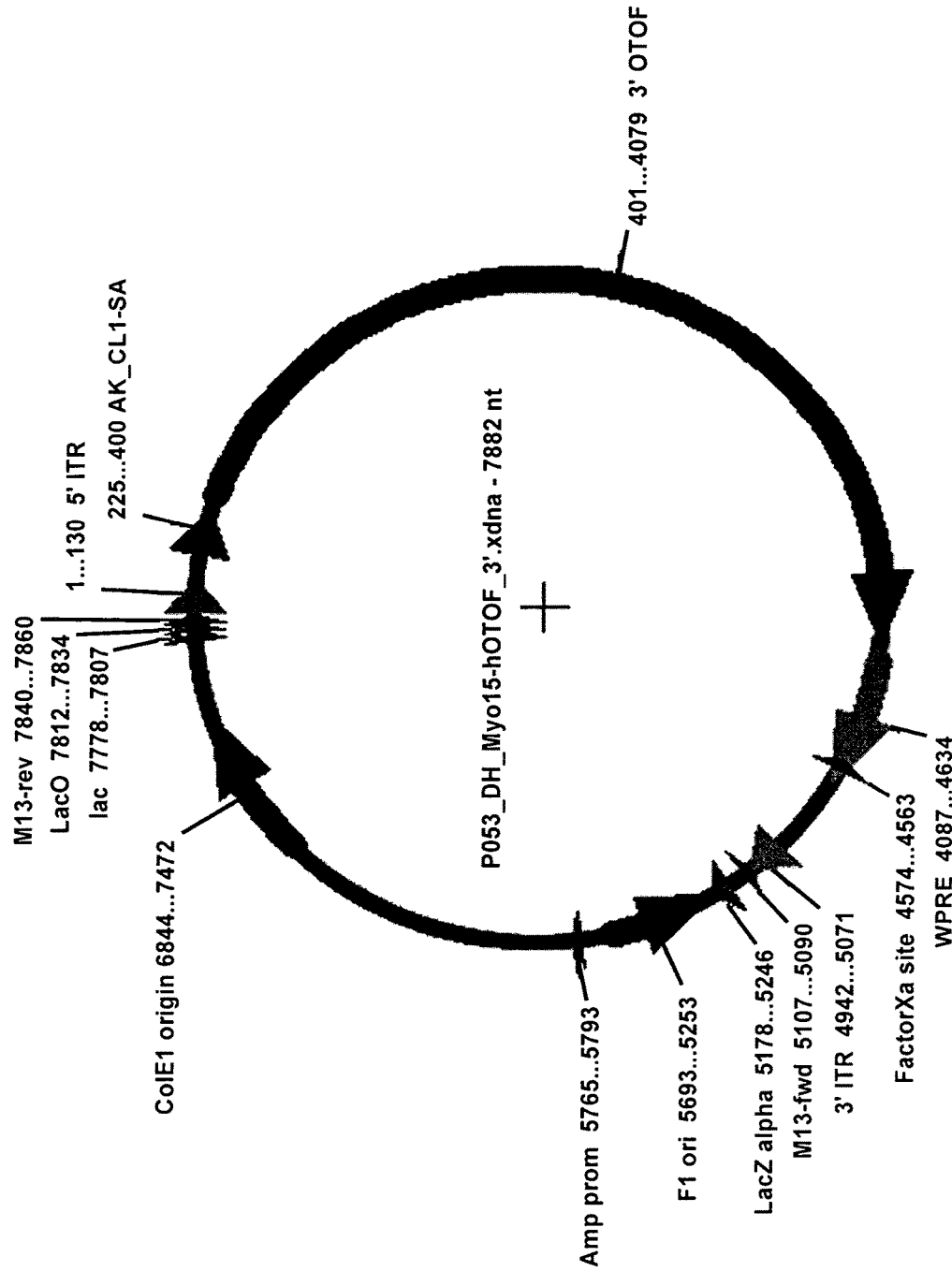

FIGS. 15A and 15B are maps of the 5' and 3' vectors in a dual hybrid vector system. The 5' vector contains AAV2 ITRs, a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1) (FIG. 15A). The 3' vector contains AAV2 ITRs, a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23) (FIG. 15B).

Figure 16A:
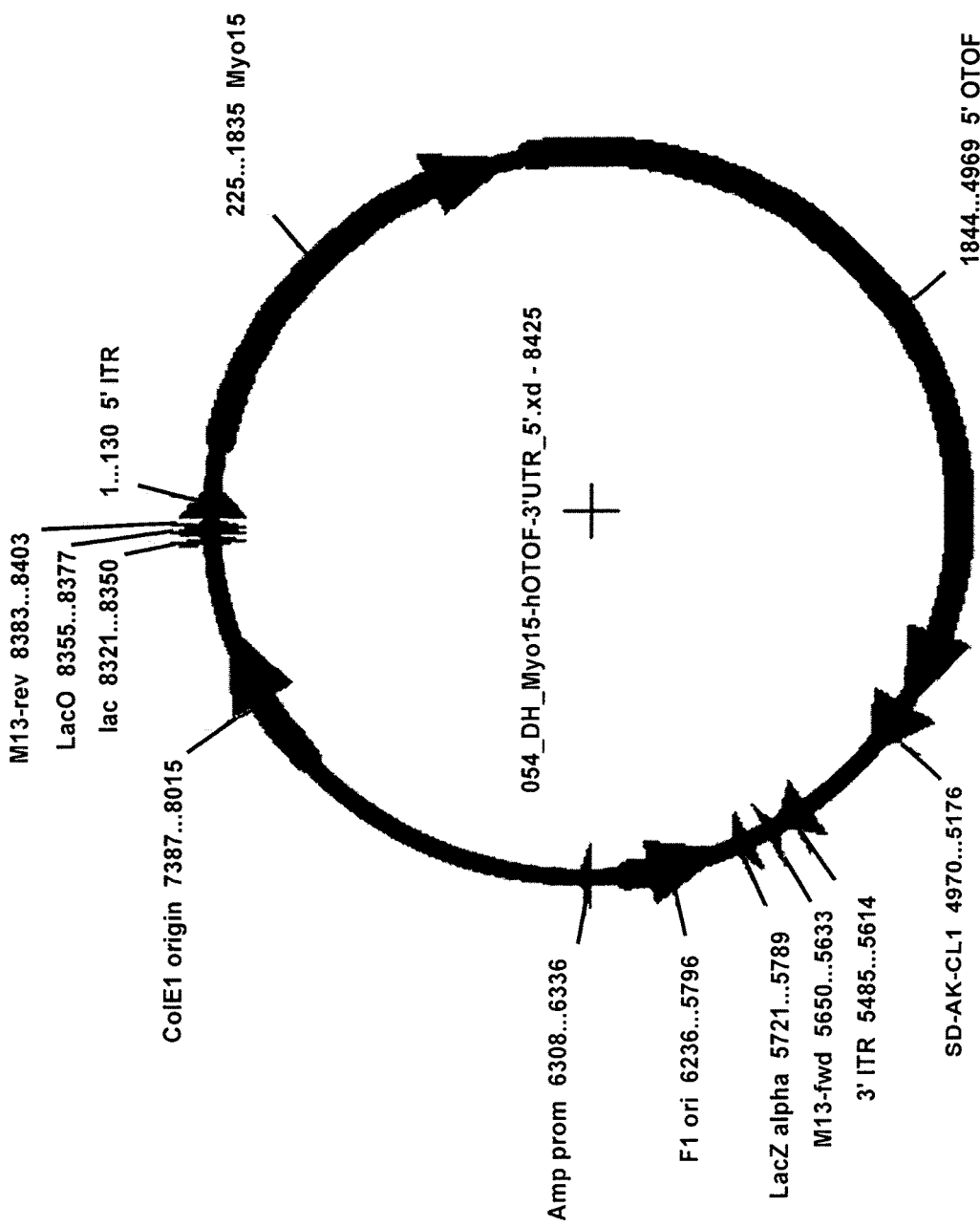
Figure 16B:
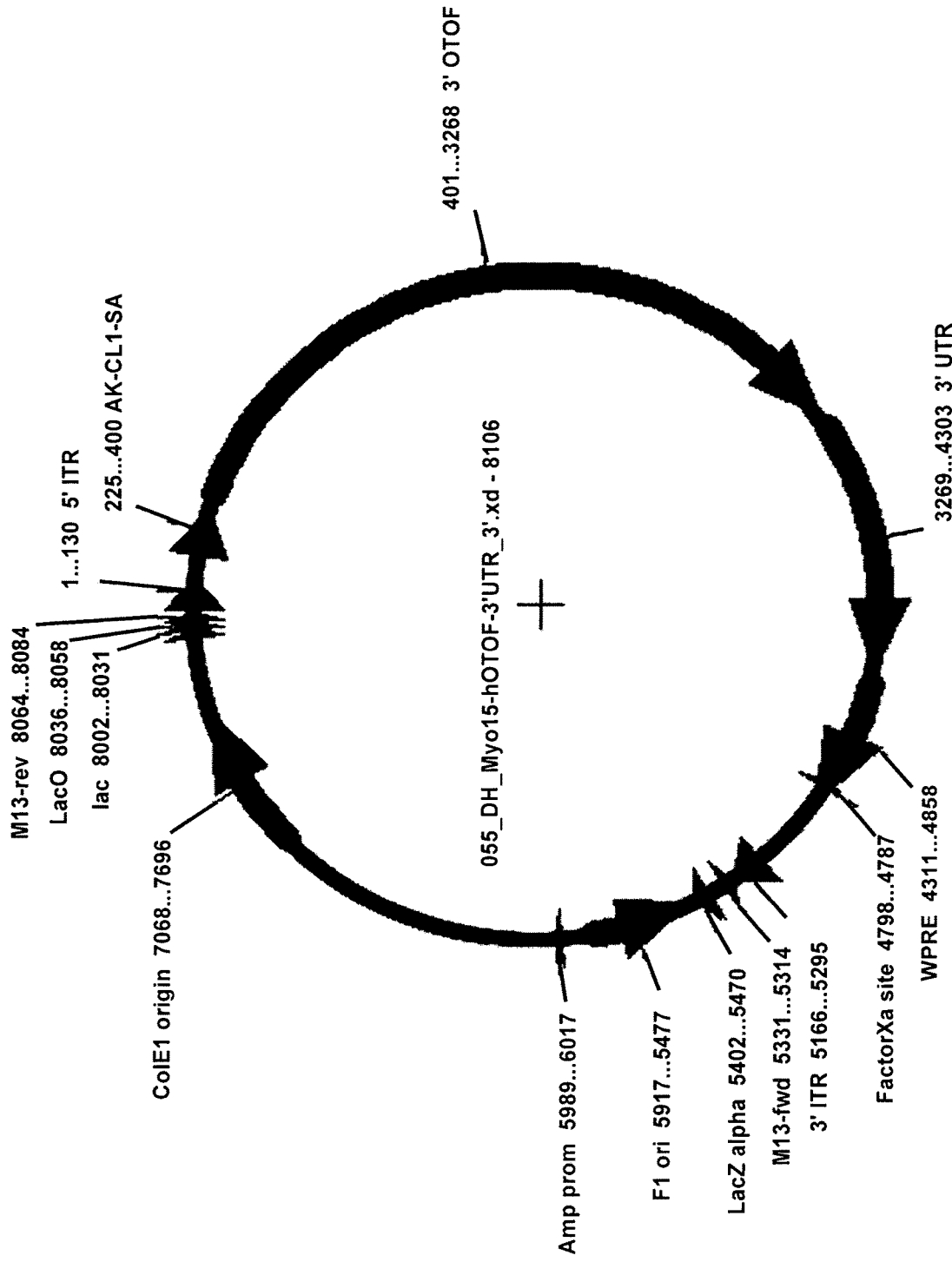

FIGS. 16A and 16B are maps of the 5' and 3' vectors in a dual hybrid vector system. The 5' vector contains AAV2 ITRs, a Myo15 promoter (SEQ ID NO: 36) operably linked to exons 1-25 of a polynucleotide encoding the human OTOF protein of SEQ ID NO: 1, a splice donor sequence (SD), a recombinogenic region (AK), and a degradation signal sequence (CL1) (FIG. 16A). The 3' vector contains AAV2 ITRs, a recombinogenic region (AK), a degradation signal sequence (CL1), a splice acceptor sequence (SA), exons 26-48 of a polynucleotide encoding the human OTOF protein of SEQ ID NO: 1, the full-length human OTOF 3' UTR, and a WPRE sequence (SEQ ID NO: 23) (FIG. 16B).

Figure 17A:
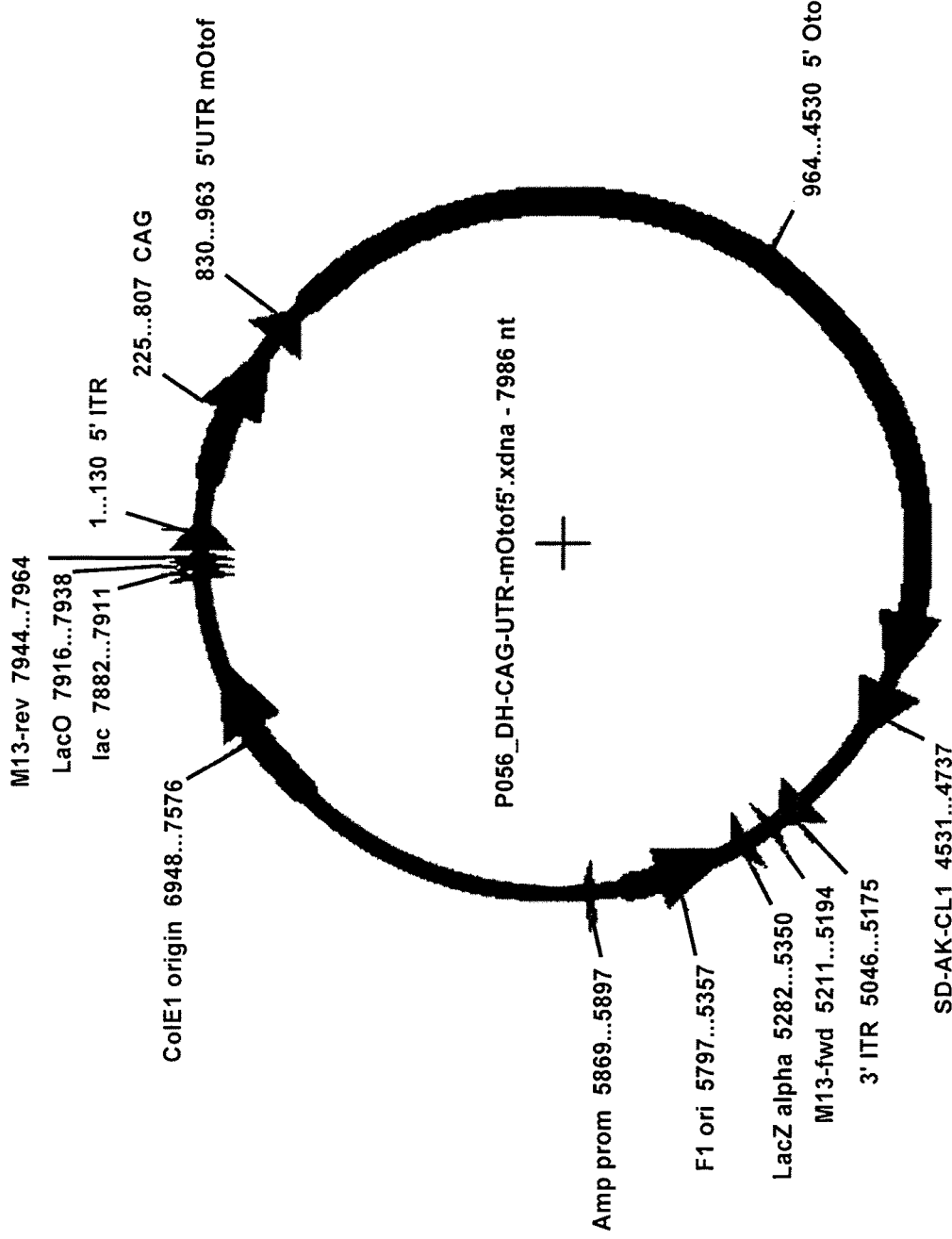
Figure 17B:
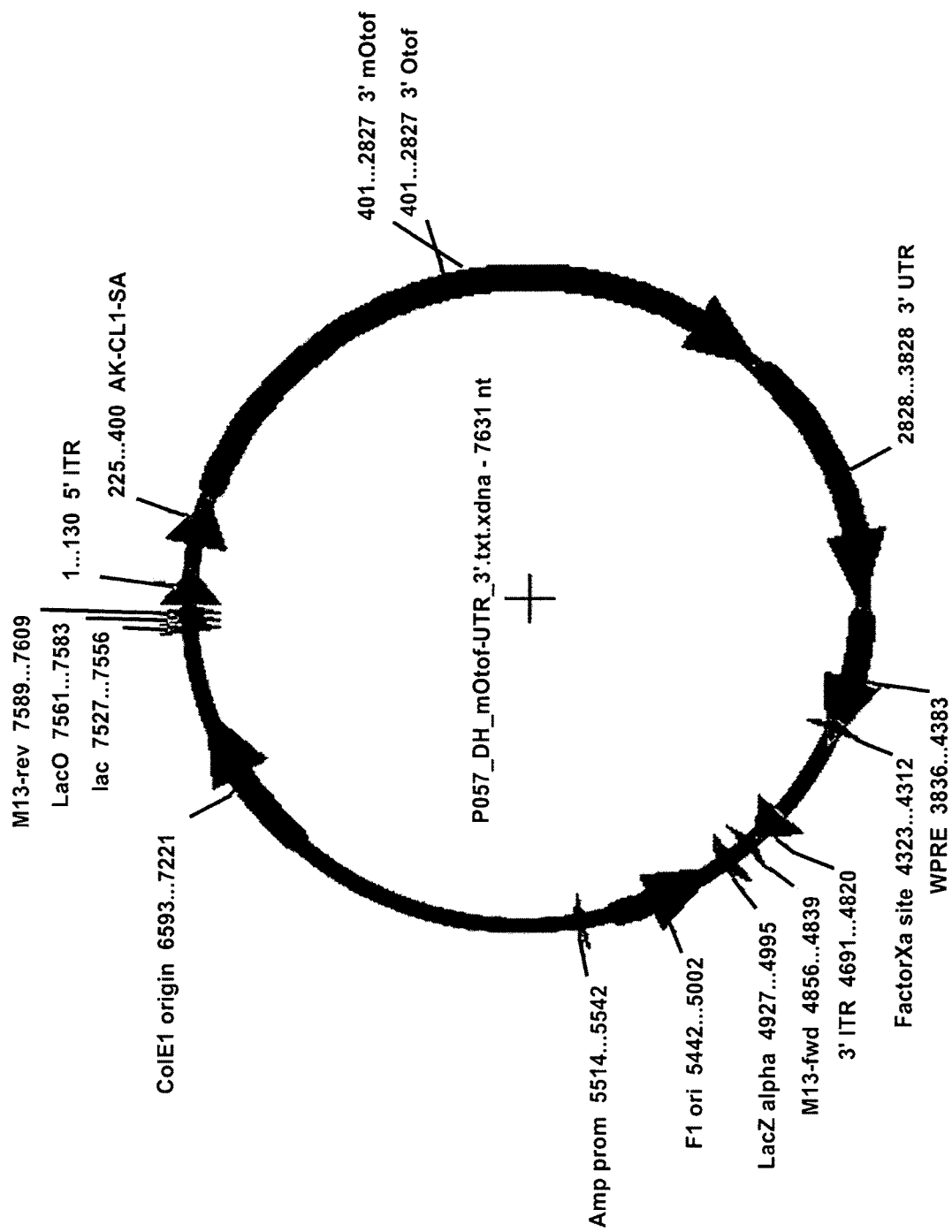

FIGS. 17A and 17B are maps of the 5' and 3' vectors in a dual hybrid vector system. The 5' vector contains AAV2 ITRs, a CAG promoter operably linked to the full-length mouse OTOF 5' UTR and exons 1-28 of a polynucleotide encoding the mouse OTOF protein of SEQ ID NO: 6, a splice donor sequence (SD), a recombinogenic region (AK), and a degradation signal sequence (CL1) (FIG. 17A). The 3' vector contains AAV2 ITRs, a recombinogenic region (AK), a degradation signal sequence (CL1), a splice acceptor sequence (SA), exons 29-48 of a polynucleotide encoding the mouse OTOF protein of SEQ ID NO: 6, the full-length mouse OTOF 3' UTR, and a WPRE sequence (SEQ ID NO: 23) (FIG. 17B).

Figure 18A:
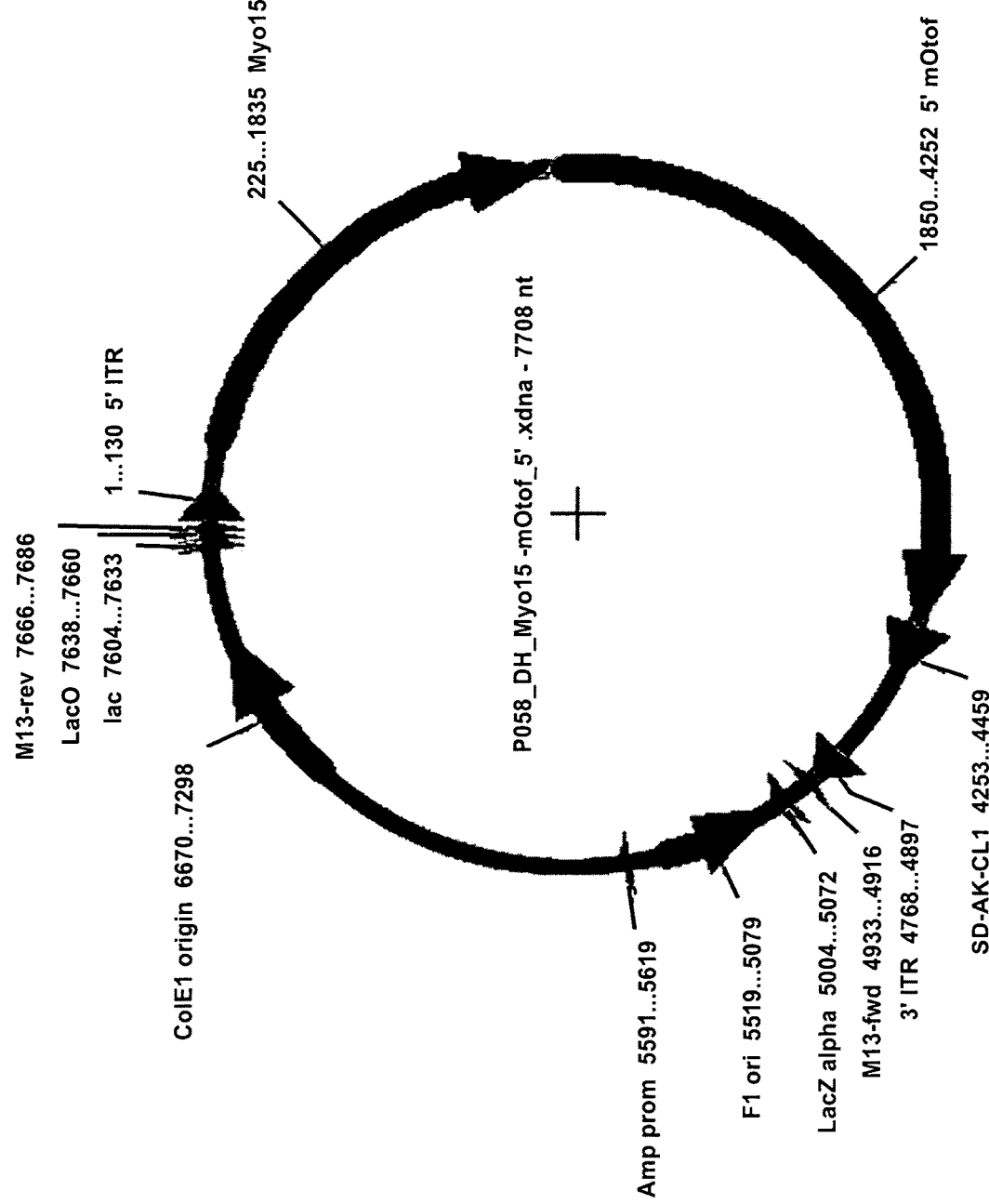
Figure 18B:
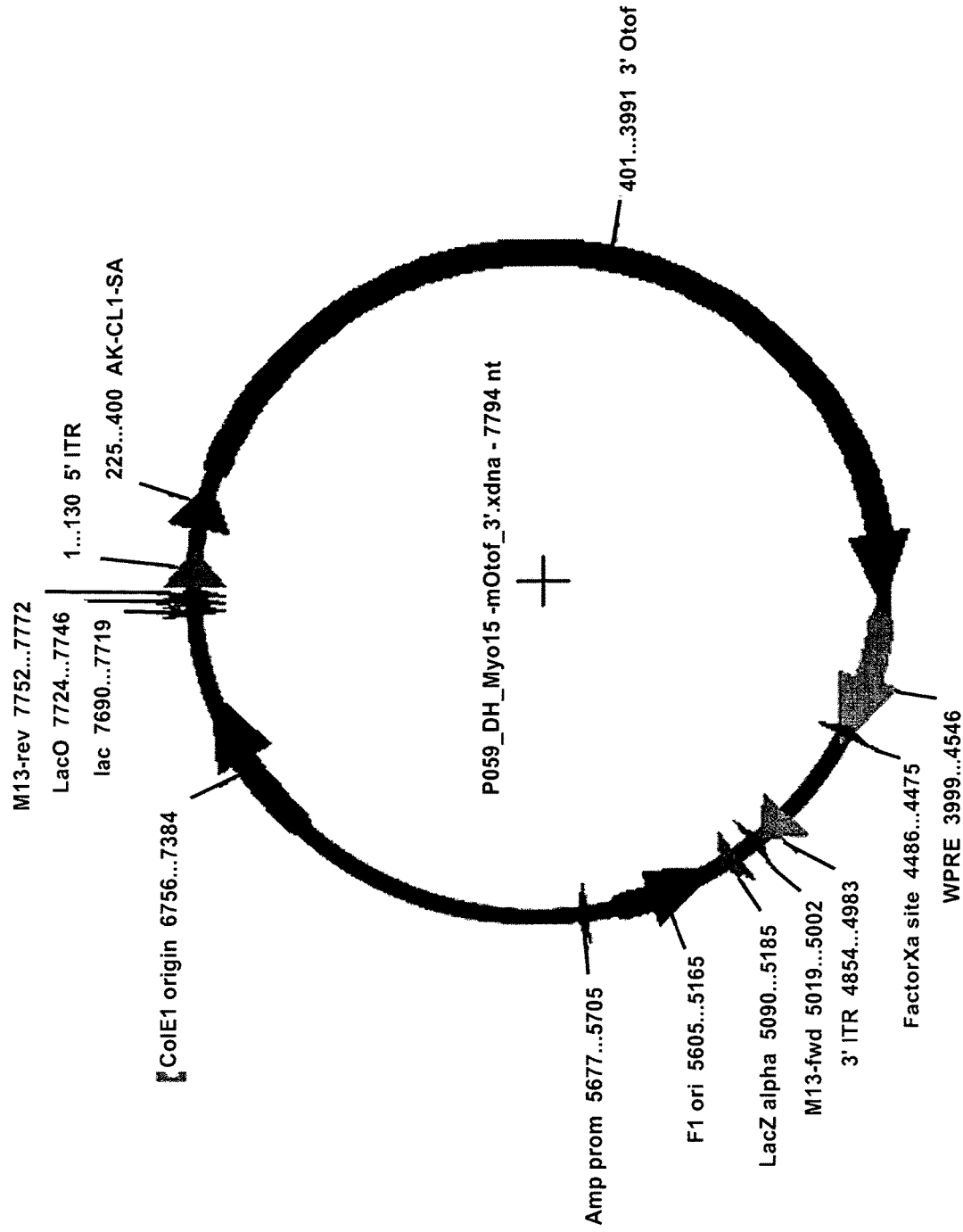

FIGS. 18A and 18B are maps of the 5' and 3' vectors in a dual hybrid vector system. The 5' vector contains AAV2 ITRs, a Myo15 promoter (SEQ ID NO: 36) operably linked to exons 1-20 of a polynucleotide encoding the mouse OTOF protein of SEQ ID NO: 6, a splice donor sequence (SD), a recombinogenic region (AK), and a degradation signal sequence (CL1) (FIG. 18A). The 3' vector contains AAV2 ITRs, a recombinogenic region (AK), a degradation signal sequence (CL1), a splice acceptor sequence (SA), exons 21-48 of a polynucleotide encoding the mouse OTOF protein of SEQ ID NO: 6, and aWPRE sequence (SEQ ID NO: 23) (FIG. 18B).

Figure 19A:
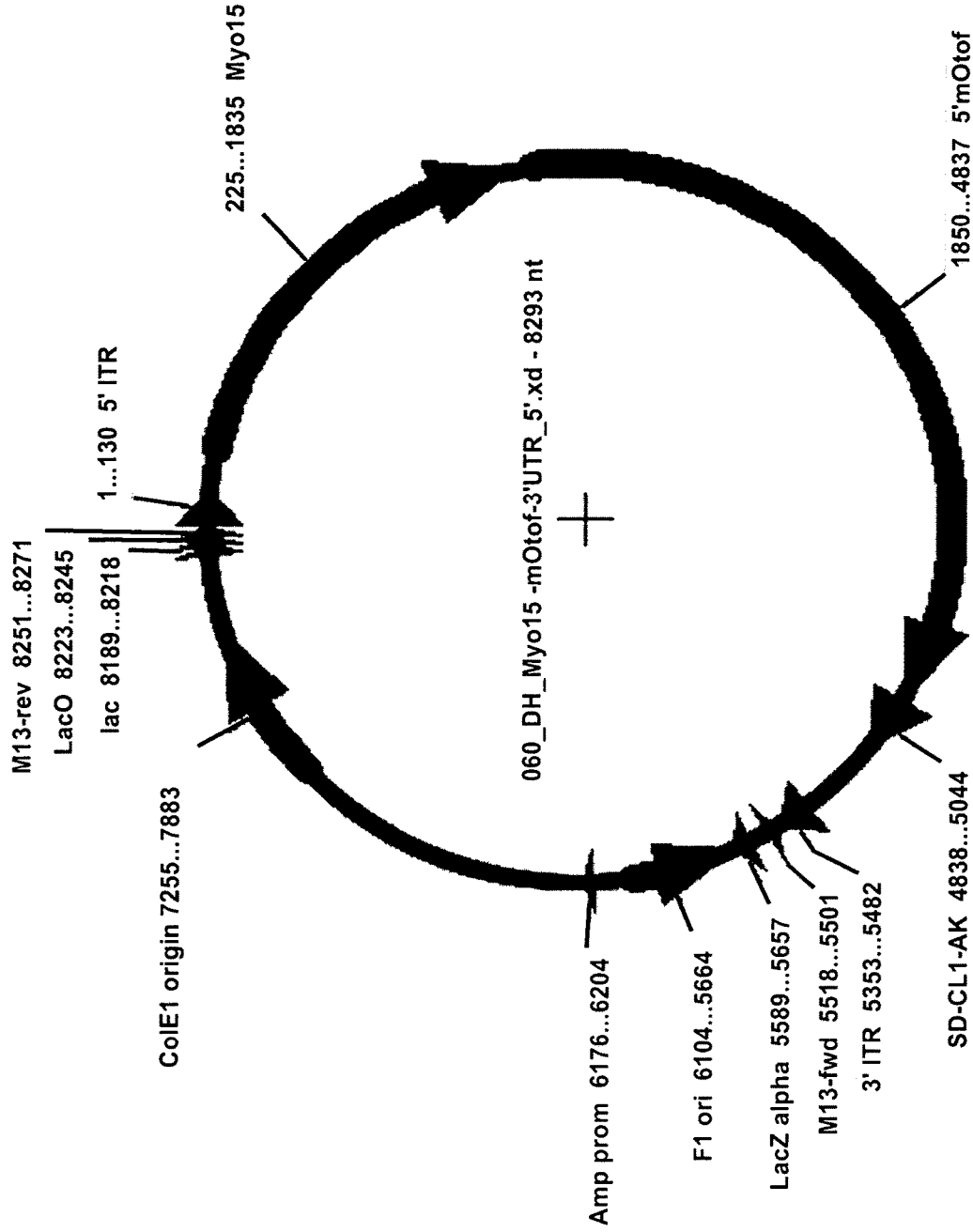
Figure 19B:
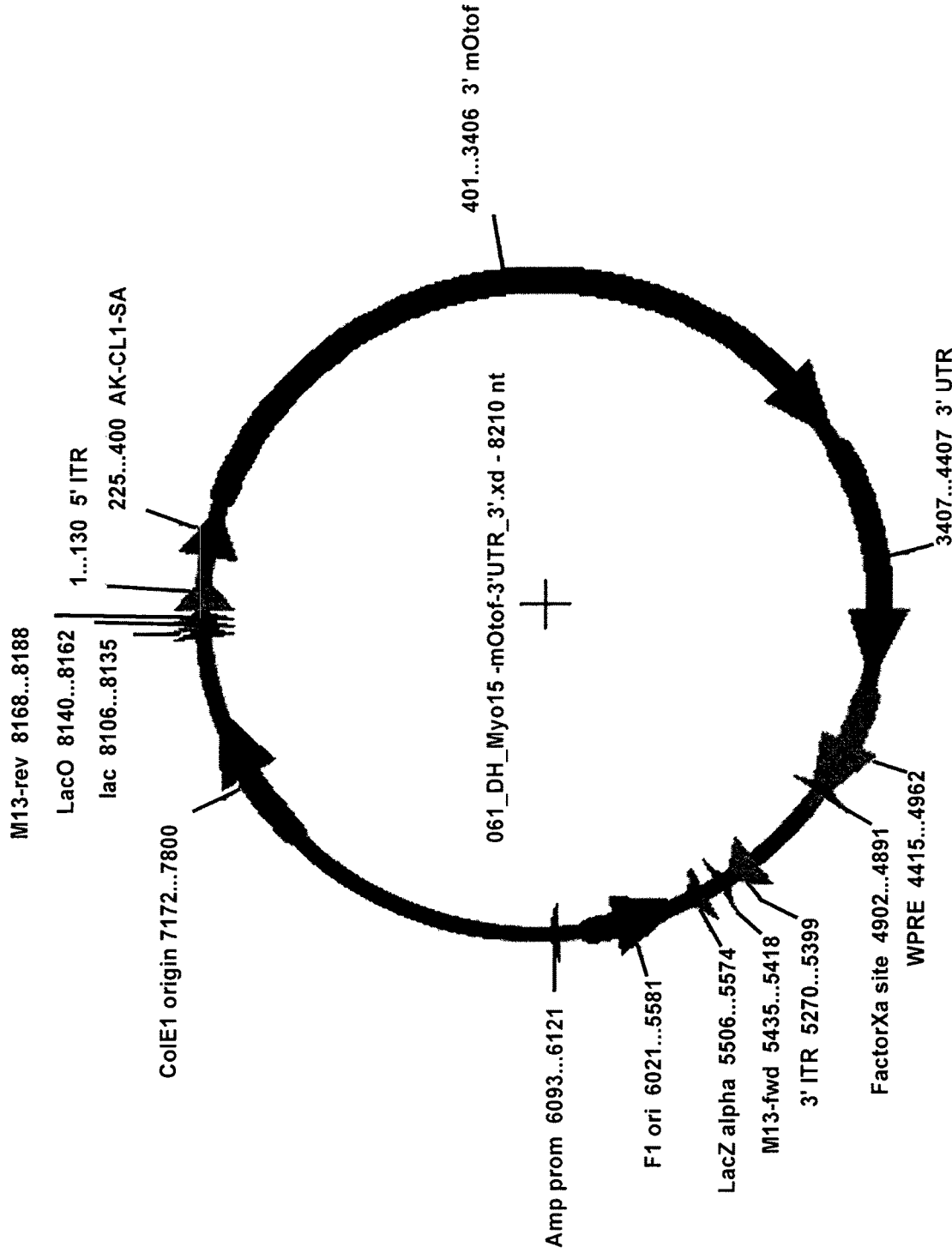

FIGS. 19A and 19B are maps of the 5' and 3' vectors in a dual hybrid vector system. The 5' vector contains AAV2 ITRs, a Myo15 promoter (SEQ ID NO: 36) operably linked to exons 1-24 of a polynucleotide encoding the mouse OTOF protein of SEQ ID NO: 6, a splice donor sequence (SD), a recombinogenic region (AK), and a degradation signal sequence (CL1) (FIG. 19A). The 3' vector contains AAV2 ITRs, a recombinogenic region (AK), a degradation signal sequence (CL1), a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23) (FIG. 19B).

FIGS. 20A and 20B are images demonstrating that polynucleotides encoded by dual hybrid vectors (FIG. 20A) and overlapping vectors (FIG. 20B) undergo recombination in cell culture (top). Beneath each image is a schematic depicting the type of recombination that occurs in each dual vector system (bottom). Inner ear-derived House Ear Institute-Organ of Corti 1 (HEI-OC1) cells were transfected with plasmids containing either the 5' half of OTOF alone, the 3' half of OTOF alone, or both the 5' and 3' halves together. For the dual hybrid vector experiment, the 5' vector contained a Myo15 promoter (SEQ ID NO: 36) operably linked to exons 1-19 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 20-48 of a polynucleotide encoding the human OTOF protein of SEQ ID NO: 1, and a WPRE sequence (SEQ ID NO: 23). For the overlapping dual vector experiment, the 5' vector contained a Myo15 promoter (SEQ ID NO: 36) operably linked to exons 1-21 of a polynucleotide encoding the human OTOF protein of SEQ ID NO: 1 and the 500 kb immediately 3' of the exon 21/22 boundary; and the 3' vector contained the 500 kb immediately 5' of the exon 21/22 boundary and exons 22-48 of a polynucleotide encoding the human OTOF protein of SEQ ID NO: 1, and a WPRE sequence (SEQ ID NO: 23). Full-length otoferlin was transfected as a positive control and untransfected cells were used a negative control. Genomic DNA was extracted from cells using a standard column from a gDNA isolation kit. PCR primers were designed to anneal outside of the region of splice sites or overlap and PCR was performed using standard molecular biology techniques. Amplicons were visualized using gel electrophoresis. The white box in the gel image indicates the lane in which 5' and 3' halves were transfected together and where a roughly 1 kb amplicon is seen, indicating recombination.

FIGS. 21A-21C are images demonstrating that polynucleotides encoded by dual hybrid vectors (FIG. 21A), trans-splicing vectors (FIG. 21B), and overlapping vectors (FIG. 21C) undergo recombination in cell culture and produce OTOF protein (top). Beneath each image is a schematic depicting the type of recombination that occurs in each dual vector system (bottom). Inner ear derived HEI-OC1 cells were transfected with plasmids containing either the 5' half of otoferlin alone, the 3' half of otoferlin alone, or both 5' and 3' halves together. For the dual hybrid vector experiment, the 5' vector contained a CAG promoter operably linked to the full-length human OTOF 5' UTR and exons 1-26 of a polynucleotide encoding the human OTOF protein of SEQ ID NO: 1, a splice donor sequence (SD), a recombinogenic region (AK), and a degradation signal sequence (CL1); and the 3' vector contained a recombinogenic region (AK), a degradation signal sequence (CL1), a splice acceptor sequence (SA), exons 27-48 of a polynucleotide encoding the human OTOF protein of SEQ ID NO: 1, the full-length human OTOF 3' UTR, and a WPRE sequence (SEQ ID NO: 23). For the trans-splicing dual vector experiment, the 5' vector contained a Myo15 promoter (SEQ ID NO: 36) operably linked to exons 1-24 of a polynucleotide encoding the mouse OTOF protein of SEQ ID NO: 6, and a splice donor sequence (SD); and the 3' vector contained a splice acceptor sequence (SA), exons 25-48 of a polynucleotide encoding the mouse OTOF protein of SEQ ID NO: 6, the full-length mouse OTOF 3' UTR, and a WPRE sequence (SEQ ID NO: 23). For the overlapping dual vector experiment, the 5' vector contained a CMV promoter operably linked to exons 1-24 of a polynucleotide encoding the mouse OTOF protein of SEQ ID NO: 6 and the 500 kb immediately 3' of the exon 24/25 boundary; and the 3' vector contained the 500 kb immediately 5' of the exon 24/25 boundary and exons 25-48 of a polynucleotide encoding the mouse OTOF protein of SEQ ID NO: 6, and a WPRE sequence (SEQ ID NO: 23). Cells were fixed in 4% PFA 48 hours post transfection and processed for immunohistochemistry. An antibody specific to OTOF protein labels some cells in the 5' alone transfected cells, no cells in the 3' alone transfected cells, and more cells than both previous conditions combined in the 5'+3' transfected cells.

DETAILED DESCRIPTION

Described herein are compositions and methods for the treatment of sensorineural hearing loss or auditory neuropathy in a subject (such as a mammalian subject, for instance, a human) by administering a first nucleic acid vector containing a promoter and a polynucleotide encoding an N-terminal portion of an otoferlin (OTOF) protein (e.g., a wild-type (WT) OTOF protein) and a second nucleic acid vector containing a polynucleotide encoding a C-terminal portion of an OTOF protein and a polyadenylation (poly(A)) sequence. When introduced into a mammalian cell, such as a cochlear hair cell, the polynucleotides encoded by the two nucleic acid vectors can combine to form a nucleic acid molecule that encodes the full-length OTOF protein. The compositions and methods described herein can, therefore, be used to induce or increase expression of WT OTOF in cochlear hair cells of a subject who has an OTOF deficiency (e.g., low OTOF expression or an OTOF mutation that impairs OTOF expression or function).

Otoferlin

OTOF is a 230 kDa membrane protein that contains at least six C2 domains implicated in calcium, phospholipid, and protein binding. It is encoded by a gene that contains 48 exons, and the full-length protein is made up of 1,997 amino acids. OTOF is located at ribbon synapses in inner hair cells, where it is believed to function as a calcium sensor in synaptic vesicle fusion, triggering the fusion of neurotransmitter-containing vesicles with the plasma membrane. It has also been implicated in vesicle replenishment and clathrin-mediated endocytosis, and has been shown to interact with Myosin VI, Rab8b, SNARE proteins, calcium channel Cav1.3, Ergic2, and AP-2. The mechanism by which OTOF mediates exocytosis and the physiological significance of its interactions with its binding partners remain to be determined.

OTOF-Associated Hearing Loss

OTOF was first identified by a study investigating the genetics of a non-syndromic form of deafness, autosomal recessive deafness-9 (DFNB9). Mutations in OTOF have since been found to cause sensorineural hearing loss in patients throughout the world, with many patients carrying OTOF mutations having auditory neuropathy, a disorder in which the inner ear detects sound, but is unable to properly transmit sound from the ear to the brain. These patients have an abnormal auditory brainstem response (ABR) and impaired speech discrimination with initially normal otoacoustic emissions. Patients carrying homozygous or compound heterozygous mutations often develop hearing loss in early childhood, and the severity of hearing impairment has been found to vary with the location and type of mutation in OTOF.

The compositions and methods described herein can be used to treat sensorineural hearing loss or auditory neuropathy by administering a first nucleic acid vector containing a polynucleotide encoding an N-terminal portion of an OTOF protein and a second nucleic acid vector containing a polynucleotide encoding a C-terminal portion of an OTOF protein. The full-length OTOF coding sequence is too large to include in the type of vector that is commonly used for gene therapy (e.g., an adeno-associated virus (AAV) vector, which is thought to have a packaging limit of 5 kb). The compositions and methods described herein overcome this problem by dividing the OTOF coding sequence between two different nucleic acid vectors that can recombine in a cell to reconstitute the full-length OTOF sequence. These compositions and methods can be used to treat subjects having one or more mutations in the OTOF gene, e.g., an OTOF mutation that reduces OTOF expression, reduces OTOF function, or is associated with hearing loss. When the first and second nucleic acid vectors are administered in a composition, the polynucleotides encoding the N-terminal and C-terminal portions of OTOF can combine within a cell (e.g., a human cell, e.g., a cochlear hair cell) to form a single nucleic acid molecule that contains the full-length OTOF coding sequence (e.g., through homologous recombination and/or splicing).

The nucleic acid vectors used in the compositions and methods described herein include nucleic acid sequences that encode wild-type OTOF, or a variant thereof, such as a nucleic acid sequences that, when combined, encode a protein having at least 85% sequence identity (e.g., 85%, 90%, 95%, 96%, 97%, 98%, 99%, or more, sequence identity) to the amino acid sequence of wild-type human or mouse OTOF. The polynucleotides used in the nucleic acid vectors described herein encode an N-terminal portion and a C-terminal portion of an OTOF amino acid sequence in Table 2 below (e.g., two portions that, when combined, encode a full-length OTOF amino acid sequence listed in Table 2, e.g., SEQ ID NO: 1).

According to the methods described herein, a subject can be administered a composition containing a first nucleic acid vector and a second nucleic acid vector that encode an N-terminal and C-terminal portion, respectively, of a nucleic acid sequence encoding the amino acid sequence of SEQ ID NO: 1, or a nucleic acid sequence encoding an amino acid sequence having at least 85% sequence identity (e.g., 85%, 90%, 95%, 96%, 97%, 98%, 99%, or more, sequence identity) to the amino acid sequence of SEQ ID NO: 1, or a nucleic acid sequence encoding an amino acid sequence that contains one or more conservative amino acid substitutions relative to SEQ ID NO: 1 (e.g., 1, 2, 3, 4, 5, 6, 7, 8, 9, or 10 or more conservative amino acid substitutions), provided that the OTOF analog encoded retains the therapeutic function of wild-type OTOF (e.g., the ability to regulate exocytosis at ribbon synapses).

TABLE 2

OTOF Sequences

| SEQ ID NO. | Sequence Name | Sequence |
|---|---|---|
| 1 | OTOF-201 protein (NP_919224.1), human otoferlin isoform a, 1997 aa | MALLIHLKTVSELRGRGDRIAKVTFRGQSFYSRVLENCEDVADFDE TFRWPVASSIDRNEMLEIQVFNYSKVFSNKLIGTFRMVLQKVVEES HVEVTDTLIDDNNAIIKTSLCVEVRYQATDGTVGSWDDGDFLGDES LQEEEKDSQETDGLLPGSRPSSRPPGEKSFRRAGRSVFSAMKLGK NRSHKEEPQRPDEPAVLEMEDLDHLAIRLGDGLDPDSVSLASVTAL TTNVSNKRSKPDIKMEPSAGRPMDYQVSITVIEARQLVGLNMDPVV CVEVGDDKKYTSMKESTNCPYYNEYFVFDPHVSPDVMFDKIIKISVI HSKNLLRSGTLVGSFKMDVGTVYSQPEHQFHHKWAILSDPDDISS GLKGYVKCDVAVVGKGDNIKTPHKANETDEDDIEGNLLLPEGVPPE RQWARFYVKIYRAEGLPRMNTSLMANVKKAFIGENKDLVDPYVQV FFAGQKGKTSVQKSSYEPLWNEQVVFTDLFPPLCKRMKVQIRDSD KVNDVAIGTHFIDLRKISNDGDKGFLPTLGPAWVNMYGSTRNYTLL DEHQDLNEGLGEGVSFRARLLLGLAVEIVDTSNPELTSSTEVQVEQ ATPISESCAGKMEEFFLFGAFLEASMIDRRNGDKPITFEVTIGNYGN EVDGLSRPQRPRPRKEPGDEEEVDLIQNASDDEAGDAGDLASVSS TPPMRPQVTDRNYFHLPYLERKPCIYIKSWWPDQRRRLYNANIMD HIADKLEEGLNDIQEMIKTEKSYPERRLRGVLEELSCGCCRFLSLAD KDQGHSSRTRLDRERLKSCMRELENMGQQARMLRAQVKRHTVRD KLRLCONFLQKLRFLADEPQHSIPDIFIWMMSNNKRVAYARVPSKD LLFSIVEEETGKDCAKVKTLFLKLPGKRGFGSAGWTVQAKVELYLW LGLSKQRKEFLCGLPCGFQEVKAAQGLGLHAFPPVSLVYTKKQAF QLRAHMYQARSLFAADSSGLSDPFARVFFINQSQCTEVLNETLCPT WDQMLVFDNLELYGEAHELRDDPPIIVIEIYDQDSMGKADFMGRTF AKPLVKMADEAYCPPRFPPQLEYYQIYRGNATAGDLLAAFELLQIG PAGKADLPPINGPVDVDRGPIMPVPMGIRPVLSKYRVEVLFWGLRD LKRVNLAQVDRPRVDIECAGKGVQSSLIHNYKKNPNFNTLVKWFEV DLPENELLHPPLNIRVVDCRAFGRYTLVGSHAVSSLRRFIYRPPDRS APSWNTTVRLLRRCRVLCNGGSSSHSTGEVVVTMEPEVPIKKLET MVKLDATSEAVVKVDVAEEEKEKKKKKKGTAEEPEEEEPDESMLD WWSKYFASIDTMKEQLRQQEPSGIDLEEKEEVDNTEGLKGSMKGK EKARAAKEEKKKKTQSSGSGQGSEAPEKKKPKIDELKVYPKELESE FDNFEDWLHTFNLLRGKTGDDEDGSTEEERIVGRFKGSLCVYKVPL PEDVSREAGYDSTYGMFQGIPSNDPINVLVRVYVVRATDLHPADIN GKADPYIAIRLGKTDIRDKENYISKQLNPVFGKSFDIEASFPMESMLT VAVYDWDLVGTDDLIGETKIDLENRFYSKHRATCGIAQTYSTHGYNI WRDPMKPSQILTRLCKDGKVDGPHFGPPGRVKVANRVFTGPSEIE DENGQRKPTDEHVALLALRHWEDIPRAGCRLVPEHVETRPLLNPD KPGIEQGRLELWVDMFPMDMPAPGTPLDISPRKPKKYELRVIIWNT DEVVLEDDDFFTGEKSSDIFVRGWLKGQQEDKQDTDVHYHSLTGE GNFNWRYLFPFDYLAAEEKIVISKKESMFSWDETEYKIPARLTLQIW DADHFSADDFLGAIELDLNRFPRGAKTAKQCTMEMATGEVDVPLV SIFKQKRVKGWWPLLARNENDEFELTGKVEAELHLLTAEEAEKNPV GLARNEPDPLEKPNRPDTSFIWFLNPLKSARYFLWHTYRWLLLKLL LLLLLLLLLALFLYSVPGYLVKKILGA |
| 2 | OTOF-202 protein (NP_004793.2), human otoferlin isoform b, 1230 aa | MIKTEKSYPERRLRGVLEELSCGCCRFLSLADKDQGHSSRTRLDRE RLKSCMRELENMGQQARMLRAQVKRHTVRDKLRLCQNFLQKLRF LADEPQHSIPDIFIWMMSNNKRVAYARVPSKDLLFSIVEEETGKDCA KVKTLFLKLPGKRGFGSAGWTVQAKVELYLWLGLSKQRKEFLCGL PCGFQEVKAAQGLGLHAFPPVSLVYTKKQAFQLRAHMYQARSLFA ADSSGLSDPFARVFFINQSQCTEVLNETLCPTWDQMLVFDNLELYG EAHELRDDPPIIVIEIYDQDSMGKADFMGRTFAKPLVKMADEAYCPP RFPPQLEYYQIYRGNATAGDLLAAFELLQIGPAGKADLPPINGPVDV DRGPIMPVPMGIRPVLSKYRVEVLFWGLRDLKRVNLAQVDRPRVDI ECAGKGVQSSLIHNYKKNPNFNTLVKWFEVDLPENELLHPPLNIRV VDCRAFGRYTLVGSHAVSSLRRFIYRPPDRSAPSWNTTGEVVVTM EPEVPIKKLETMVKLDATSEAVVKVDVAEEEKEKKKKKKGTAEEPE EEEPDESMLDWWSKYFASIDTMKEQLRQQEPSGIDLEEKEEVDNT |

TABLE 2-continued

OTOF Sequences

| SEQ ID NO. | Sequence Name | Sequence |
|---|---|---|
| | | EGLKGSMKGKEKARAAKEEKKKKTQSSGSGQGSEAPEKKKPKIDE<br>LKVYPKELESEFDNFEDWLHTFNLLRGKTGDDEDGSTEEERIVGRF<br>KGSLCVYKVPLPEDVSREAGYDSTYGMFQGIPSNDPINVLVRVYVV<br>RATDLHPADINGKADPYIAIRLGKTDIRDKENYISKQLNPVFGKSFDI<br>EASFPMESMLTVAVYDWDLVGTDDLIGETKIDLENRFYSKHRATCG<br>IAQTYSTHGYNIWRDPMKPSQILTRLCKDGKVDGPHFGPPGRVKVA<br>NRVFTGPSEIEDENGQRKPTDEHVALLALRHWEDIPRAGCRLVPEH<br>VETRPLLNPDKPGIEQGRLELWVDMFPMDMPAPGTPLDISPRKPKK<br>YELRVIIWNTDEVVLEDDDFFTGEKSSDIFVRGWLKGQQEDKQDTD<br>VHYHSLTGEGNFNWRYLFPPDYLAAEEKIVISKKESMFSWDETEYKI<br>PARLTLQIWDADHFSADDFLGAIELDLNRFPRGAKTAKQCTMEMAT<br>GEVDVPLVSIFKQKRVKGWWPLLARNENDEFELTGKVEAELHLLTA<br>EEAEKNPVGLARNEPDPLEKPNRPDTSFIWFLNPLKSARYFLWHTY<br>RWLLLKLLLLLLLLLLALFLYSVPGYLVKKILGA |
| 3 | OTOF-203 protein (NP_919304.1), human otoferlin isoform d, 1230 aa | MIKTEKSYPERRLRGVLEELSCGCCRFLSLADKDQGHSSRTRLDRE<br>RLKSCMRELENMGQQARMLRAQVKRHTVRDKLRLCQNFLQKLRF<br>LADEPQHSIPDIFIWMMSNNKRVAYARVPSKDLLFSIVEEETGKDCA<br>KVKTLFLKLPGKRGFGSAGWTVQAKVELYLWLGLSKQRKEFLCGL<br>PCGFQEVKAAQGLGLHAFPPVSLVYTKKQAFQLRAHMYQARSLFA<br>ADSSGLSDPFARVFFINQSQCTEVLNETLCPTWDQMLVFDNLELYG<br>EAHELRDDPPIIVIEIYDQDSMGKADFMGRTFAKPLVKMADEAYCPP<br>RFPPQLEYYQIYRGNATAGDLLAAFELLQIGPAGKADLPPINGPVDV<br>DRGPIMPVPMGIRPVLSKYRVEVLFWGLRDLKRVNLAQVDRPRVDI<br>ECAGKGVQSSLIHNYKKNPNFNTLVKWFEVDLPENELLHPPLNIRV<br>VDCRAFGRYTLVGSHAVSSLRRFIYRPPDRSAPSWNTTGEVVVTM<br>EPEVPIKKLETMVKLDATSEAVVKVDVAEEEKEKKKKKKGTAEEPE<br>EEEPDESMLDWWSKYFASIDTMKEQLRQQEPSGIDLEEKEEVDNT<br>EGLKGSMKGKEKARAAKEEKKKKTQSSGSGQGSEAPEKKKPKIDE<br>LKVYPKELESEFDNFEDWLHTFNLLRGKTGDDEDGSTEEERIVGRF<br>KGSLCVYKVPLPEDVSREAGYDSTYGMFQGIPSNDPINVLVRVYVV<br>RATDLHPADINGKADPYIAIRLGKTDIRDKENYISKQLNPVFGKSFDI<br>EASFPMESMLTVAVYDWDLVGTDDLIGETKIDLENRFYSKHRATCG<br>IAQTYSTHGYNIWRDPMKPSQILTRLCKDGKVDGPHFGPPGRVKVA<br>NRVFTGPSEIEDENGQRKPTDEHVALLALRHWEDIPRAGCRLVPEH<br>VETRPLLNPDKPGIEQGRLELWVDMFPMDMPAPGTPLDISPRKPKK<br>YELRVIIWNTDEVVLEDDDFFTGEKSSDIFVRGWLKGQQEDKQDTD<br>VHYHSLTGEGNFNWRYLFPPDYLAAEEKIVISKKESMFSWDETEYKI<br>PARLTLQIWDADHFSADDFLGAIELDLNRFPRGAKTAKQCTMEMAT<br>GEVDVPLVSIFKQKRVKGWWPLLARNENDEFELTGKVEAELHLLTA<br>EEAEKNPVGLARNEPDPLEKPNRPDTAFVWFLNPLKSIKYLICTRYK<br>WLIIKIVLALLGLLMLGLFLYSLPGYMVKKLLGA |
| 4 | OTOF-208 protein (NP_919303.1), human otoferlin isoform c, 1307 aa | MMTDTQDGPSESSQIMRSLTPLINREEAFGEAGEAGLWPSITHTPD<br>SQEEGLNDIQEMIKTEKSYPERRLRGVLEELSCGCCRFLSLADKDQ<br>GHSSRTRLDRERLKSCMRELENMGQQARMLRAQVKRHTVRDKLR<br>LCQNFLQKLRFLADEPQHSIPDIFIWMMSNNKRVAYARVPSKDLLFS<br>IVEEETGKDCAKVKTLFLKLPGKRGFGSAGWTVQAKVELYLWLGLS<br>KQRKEFLCGLPCGFQEVKAAQGLGLHAFPPVSLVYTKKQAFQLRA<br>HMYQARSLFAADSSGLSDPFARVFFINQSQCTEVLNETLCPTWDQ<br>MLVFDNLELYGEAHELRDDPPIIVIEIYDQDSMGKADFMGRTFAKPL<br>VKMADEAYCPPRFPPQLEYYQIYRGNATAGDLLAAFELLQIGPAGK<br>ADLPPINGPVDVDRGPIMPVPMGIRPVLSKYRVEVLFWGLRDLKRV<br>NLAQVDRPRVDIECAGKGVQSSLIHNYKKNPNFNTLVKWFEVDLPE<br>NELLHPPLNIRVVDCRAFGRYTLVGSHAVSSLRRFIYRPPDRSAPS<br>WNTTVRLLRRCRVLCNGGSSSHSTGEVVVTMEPEVPIKKLETMVK<br>LDATSEAVVKVDVAEEEKEKKKKKKGTAEEPEEEEPDESMLDWWS<br>KYFASIDTMKEQLRQQEPSGIDLEEKEEVDNTEGLKGSMKGKEKAR<br>AAKEEKKKKTQSSGSGQGSEAPEKKKPKIDELKVYPKELESEFDNF<br>EDWLHTFNLLRGKTGDDEDGSTEEERIVGRFKGSLCVYKVPLPED<br>VSREAGYDSTYGMFQGIPSNDPINVLVRVYVVRATDLHPADINGKA<br>DPYIAIRLGKTDIRDKENYISKQLNPVFGKSFDIEASFPMESMLTVAV<br>YDWDLVGTDDLIGETKIDLENRFYSKHRATCGIAQTYSTHGYNIWR<br>DPMKPSQILTRLCKDGKVDGPHFGPPGRVKVANRVFTGPSEIEDE<br>NGQRKPTDEHVALLALRHWEDIPRAGCRLVPEHVETRPLLNPDKP<br>GIEQGRLELWVDMFPMDMPAPGTPLDISPRKPKKYELRVIIWNTDE<br>VVLEDDDFFTGEKSSDIFVRGWLKGQQEDKQDTDVHYHSLTGEGN<br>FNWRYLFPPDYLAAEEKIVISKKESMFSWDETEYKIPARLTLQIWDA<br>DHFSADDFLGAIELDLNRFPRGAKTAKQCTMEMATGEVDVPLVSIF<br>KQKRVKGWWPLLARNENDEFELTGKVEAELHLLTAEEAEKNPVGL<br>ARNEPDPLEKPNRPDTSFIWFLNPLKSARYFLWHTYRWLLLKLLLLL<br>LLLLLLALFLYSVPGYLVKKILGA |

TABLE 2-continued

OTOF Sequences

| SEQ ID NO. | Sequence Name | Sequence |
|---|---|---|
| 5 | OTOF-205 protein (NP_001274418.1), human otoferlin isoform e, 1997 aa | MALLIHLKTVSELRGRGDRIAKVTFRGQSFYSRVLENCEDVADFDE TFRWPVASSIDRNEMLEIQVFNYSKVFSNKLIGTFRMVLQKVVEES HVEVTDTLIDDNNAIIKTSLCVEVRYQATDGTVGSWDDGDFLGDES LQEEEKDSQETDGLLPGSRPSSRPPGEKSFRRAGRSVFSAMKLGK NRSHKEEPQRPDEPAVLEMEDLDHLAIRLGDGLDPDSVSLASVTAL TTNVSNKRSKPDIKMEPSAGRPMDYQVSITVIEARQLVGLNMDPVV CVEVGDDKKYTSMKESTNCPYYNEYFVFDFHVSPDVMFDKIIKISVI HSKNLLRSGTLVGSFKMDVGTVYSQPEHQFHHKWAILSDPDDISS GLKGYVKCDVAVVGKGDNIKTPHKANETDEDDIEGNLLLPEGVPPE RQWARFYVKIYRAEGLPRMNTSLMANVKKAFIGENKDLVDPYVQV FFAGQKGKTSVQKSSYEPLWNEQVVFTDLFPPLCKRMKVQIRDSD KVNDVAIGTHFIDLRKISNDGDKGFLPTLGPAWVNMYGSTRNYTLL DEHQDLNEGLGEGVSFRARLLLGLAVEIVDTSNPELTSSTEVQVEQ ATPISESCAGKMEEFFLFGAFLEASMIDRRNGDKPITFEVTIGNYGN EVDGLSRPQRPRPRKEPGDEEEVDLIQNASDDEAGDAGDLASVSS TPPMRPQVTDRNYFHLPYLERKPCIYIKSWWPDQRRRLYNANIMD HIADKLEEGLNDIQEMIKTEKSYPERRLRGVLEELSCGCCRFLSLAD KDQGHSSRTRLDRERLKSCMRELENMGQQARMLRAQVKRHTVRD KLRLCQNFLQKLRFLADEPQHSIPDIFIWMMSNNKRVAYARVPSKD LLFSIVEEETGKDCAKVKTLFLKLPGKRGFGSAGWTVQAKVELYLW LGLSKQRKEFLCGLPCGFQEVKAAQGLGLHAFPPVSLVYTKKQAF QLRAHMYQARSLFAADSSGLSDPFARVFFINQSQCTEVLNETLCPT WDQMLVFDNLELYGEAHELRDDPPIIVIEIYDQDSMGKADFMGRTF AKPLVKMADEAYCPPRFPPQLEYYQIYRGNATAGDLLAAFELLQIG PAGKADLPPINGPVDVDRGPIMPVPMGIRPVLSKYRVEVLFWGLRD LKRVNLAQVDRPRVDIECAGKGVQSSLIHNYKKNPNFNTLVKWFEV DLPENELLHPPLNIRVVDCRAFGRYTLVGSHAVSSLRRFIYRPPDRS APSWNTTVRLLRRCRVLCNGGSSSHSTGEVVVTMEPEVPIKKLET MVKLDATSEAVVKVDVAEEEKEKKKKKKGTAEEPEEEEPDESMLD WWSKYFASIDTMKEQLRQQEPSGIDLEEKEEVDNTEGLKGSMKGK EKARAAKEEKKKKTQSSGSGQGSEAPEKKKPKIDELKVYPKELESE FDNFEDWLHTFNLLRGKTGDDEDGSTEEERIVGRFKGSLCVYKVPL PEDVSREAGYDSTYGMFQGIPSNDPINVLVRVYVVRATDLHPADIN GKADPYIAIRLGKTDIRDKENYISKQLNPVFGKSFDIEASFPMESMLT VAVYDWDLVGTDDLIGETKIDLENRFYSKHRATCGIAQTYSTHGYNI WRDPMKPSQILTRLCKDGKVDGPHFGPPGRVKVANRVFTGPSEIE DENGQRKPTDEHVALLALRHWEDIPRAGCRLVPEHVETRPLLNPD KPGIEQGRLELWVDMFPMDMPAPGTPLDISPRKPKKYELRVIIWNT DEVVLEDDDFFTGEKSSDIFVRGWLKGQQEDKQDTDVHYHSLTGE GNFNWRYLFPFDYLAAEEKIVISKKESMFSWDETEYKIPARLTLQIW DADHFSADDFLGAIELDLNRFPRGAKTAKQCTMEMATGEVDVPLV SIFKQKRVKGWWPLLARNENDEFELTGKVEAELHLLTAEEAEKNPV GLARNEPDPLEKPNRPDTAFVWFLNPLKSIKYLICTRYKWLIIKIVLAL LGLLMLGLFLYSLPGYMVKKLLGA |
| 6 | mOTOF-201_1 protein (NP_114081.2), mouse otoferlin isoform 2, 1997 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEEKDSQETDGLLPGSRPSTRISGEKSFRRAGRSVFSAMKLGKTR SHKEEPQRQDEPAVLEMEDLDHLAIQLGDGLDPDSVSLASVTALTS NVSNKRSKPDIKMEPSAGRPMDYQVSITVIEARQLVGLNMDPVVCV EVGDDKKYTSMKESTNCPYYNEYFVFDFHVSPDVMFDKIIKISVIHS KNLLRSGTLVGSFKMDVGTVYSQPEHQFHHKWAILSDPDDISAGLK GYVKCDVAVVGKGDNIKTPHKANETDEDDIEGNLLLPEGVPPERQ WARFYVKIYRAEGLPRMNTSLMANVKKAFIGENKDLVDPYVQVFFA GQKGKTSVQKSSYEPLWNEQVVFTDLFPPLCKRMKVQIRDSDKVN DVAIGTHFIDLRKISNDGDKGFLPTLGPAWVNMYGSTRNYTLLDEH QDLNEGLGEGVSFRARLMLGLAVEILDTSNPELTSSTEVQVEQATP VSESCTGRMEEFFLFGAFLEASMIDRKNGDKPITFEVTIGNYGNEV DGMSRPLRPRPRKEPGDEEEVDLIQNSSDDEGDEAGDLASVSSTP PMRPQITDRNYFHLPYLERKPCIYIKSWWPDQRRRLYNANIMDHIA DKLEEGLNDVQEMIKTEKSYPERRLRGVLEELSCGCHRFLSLSDKD QGRSSRTRLDRERLKSCMRELESMGQQAKSLRAQVKRHTVRDKL RSCQNFLQKLRFLADEPQHSIPDVFIWMMSNNKRIAYARVPSKDLL FSIVEEELGKDCAKVKTLFLKLPGKRGFGSAGWTVQAKLELYLWLG LSKQRKDFLCGLPCGFEEVKAAQGLGLHSFPPISLVYTKKQAFQLR AHMYQARSLFAADSSGLSDPFARVFFINQSQCTEVLNETLCPTWD QMLVFDNLELYGEAHELRDDPPIIVIEIYDQDSMGKADFMGRTFAKP LVKMADEAYCPPRFPPQLEYYQIYRGSATAGDLLAAFELLQIGPSG KADLPPINGPVDMDRGPIMPVPVGIRPVLSKYRVEVLFWGLRDLKR VNLAQVDRPRVDIECAGKGVQSSLIHNYKKNPNFNTLVKWFEVDLP ENELLHPPLNIRVVDCRAFGRYTLVGSHAVSSLRRFIYRPPDRSAP NWNTTVRLLRGCHRLRNGGPSSRPTGEVVVSMEPEEPVKKLETM VKLDATSDAVVKVDVAEDEKERKKKKKGPSEEPEEEEPDESMLD WWSKYFASIDTMKEQLRQHETSGTDLEEKEEMESAEGLKGPMKS |

TABLE 2-continued

OTOF Sequences

| SEQ ID NO. | Sequence Name | Sequence |
|---|---|---|
| | | KEKSRAAKEEKKKKNQSPGPGQGSEAPEKKKAKIDELKVYPKELES
EFDSFEDWLHTFNLLRGKTGDDEDGSTEEERIVGRFKGSLCVYKV
PLPEDVSREAGYDPTYGMFQGIPSNDPINVLVRIYVVRATDLHPADI
NGKADPYIAIKLGKTDIRDKENYISKQLNPVFGKSFDIEASFPMESML
TVAVYDWDLVGTDDLIGETKIDLENRFYSKHRATCGIAQTYSIHGYN
IWRDPMKPSQILTRLCKEGKVDGPHFGPHGRVRVANRVFTGPSEIE
DENGQRKPTDEHVALSALRHWEDIPRVGCRLVPEHVETRPLLNPD
KPGIEQGRLELWVDMFPMDMPAPGTPLDISPRKPKKYELRVIVWNT
DEVVLEDDDFFTGEKSSDIFVRGWLKGQQEDKQDTDVHYHSLTGE
GNFNWRYLFPFDYLAAEEKIVMSKKESMFSWDETEYKIPARLTLQI
WDADHFSADDFLGAIELDLNRFPRGAKTAKQCTMEMATGEVDVPL
VSIFKQKRVKGWWPLLARNENDEFELTGKVEAELHLLTAEEAEKNP
VGLARNEPDPLEKPNRPDTSFIWFLNPLKSARYFLWHTYRWLLLKF
LLLFLLLLLFALFLYSLPGYLAKKILGA |
| 7 | mOTOF-201_2 protein (NP_001273350.1), mouse otoferlin isoform 3, 1977 aa | MALIVHLKTVSELRGKGDRIAKVTFRGQSFYSRVLENCEGVADFDE
TFRWPVASSIDRNEVLEIQIFNYSKVFSNKLIGTFCMVLQKVVEENR
VEVTDTLMDDSNAIIKTSLSMEVRYQATDGTVGPWDDGDFLGDESL
QEEKDSQETDGLLPGSRPSTRISGEKSFRRAGRSVFSAMKLGKTR
SHKEEPQRQDEPAVLEMEDLDHLAIQLGDGLDPDSVSLASVTALTS
NVSNKRSKPDIKMEPSAGRPMDYQVSITVIEARQLVGLNMDPVVCV
EVGDDKKYTSMKESTNCPYYNEYFVFDFHVSPDVMFDKIIKISVIHS
KNLLRSGTLVGSFKMDVGTVYSQPEHQFHHKWAILSDPDDISAGLK
GYVKCDVAVVGKGDNIKTPHKANETEDDIEGNLLLPEGVPPERQ
WARFYVKIYRAEGLPRMNTSLMANVKKAFIGENKDLVDPYVQVFFA
GQKGKTSVQKSSYEPLWNEQVVFTDLFPPLCKRMKVQIRDSDKVN
DVAIGTHFIDLRKISNDGDKGFLPTLGPAWVNMYGSTRNYTLLDEH
QDLNEGLGEGVSFRARLMLGLAVEILDTSNPELTSSTEVQVEQATP
VSESCTGRMEEFFLFGAFLEASMIDRKNGDKPITFEVTIGNYGNEV
DGMSRPLRPRPRKEPGDEEEVDLIQNSSDDEGDEAGDLASVSSTP
PMRPQITDRNYFHLPYLERKPCIYIKSWWPDQRRRLYNANIMDHIA
DKLEEGLNDVQEMIKTEKSYPERRLRGVLEELSCGCHRFLSLSDKD
QGRSSRTRLDRERLKSCMRELESMGQQAKSLRAQVKRHTVRDKL
RSCQNFLQKLRFLADEPQHSIPDVFIWMMSNNKRIAYARVPSKDLL
FSIVEEELGKDCAKVKTLFLKLPGKRGFGSAGWTVQAKLELYLWLG
LSKQRKDFLCGLPCGFEEVKAAQGLGLHSFPPISLVYTKKQAFQLR
AHMYQARSLFAADSSGLSDPFARVFFINQASQCTEVLNETLCPTWD
QMLVFDNLELYGEAHELRDDPPIIVIEIYDQDSMGKADFMGRTFAKP
LVKMADEAYCPPRFPPQLEYYQIYRGSATAGDLLAAFELLQIGPSG
KADLPPINGPVDMDRGPIMPVPVGIRPVLSKYRVEVLFWGLRDLKR
VNLAQVDRPRVDIECAGKGVQSSLIHNYKKNPNFNTLVKWFEVDLP
ENELLHPPLNIRVVDCRAFGRYTLVGSHAVSSLRRFIYRPPDRSAP
NWNTTGEVVVSMEPEEPVKKLETMVKLDATSDAVVKVDVAEDEKE
RKKKKKGPSEEPEEEEPDESMLDWWSKYFASIDTMKEQLRQHET
SGTDLEEKEEMESAEGLKGPMKSKEKSRAAKEEKKKKNQSPGPG
QGSEAPEKKKAKIDELKVYPKELESEFDSFEDWLHTFNLLRGKTGD
DEDGSTEEERIVGRFKGSLCVYKVPLPEDVSREAGYDPTYGMFQGI
PSNDPINVLVRIYVVRATDLHPADINGKADPYIAIKLGKTDIRDKENYI
SKQLNPVFGKSFDIEASFPMESMLTVAVYDWDLVGTDDLIGETKIDL
ENRFYSKHRATCGIAQTYSIHGYNIWRDPMKPSQILTRLCKEGKVD
GPHFGPHGRVRVANRVFTGPSEIEDENGQRKPTDEHVALSALRHW
EDIPRVGCRLVPEHVETRPLLNPDKPGIEQGRLELWVDMFPMDMP
APGTPLDISPRKPKKYELRVIVWNTDEVVLEDDDFFTGEKSSDIFVR
GWLKGQQEDKQDTDVHYHSLTGEGNFNWRYLFPFDYLAAEEKIV
MSKKESMFSWDETEYKIPARLTLQIWDADHFSADDFLGAIELDLNR
FPRGAKTAKQCTMEMATGEVDVPLVSIFKQKRVKGWWPLLARNEN
DEFELTGKVEAELHLLTAEEAEKNPVGLARNEPDPLEKPNRPDTSFI
WFLNPLKSARYFLWHTYRWLLLKFLLLFLLLLLFALFLYSLPGYLAKK
ILGA |
| 8 | mOTOF-202_1 protein (NP_001093865.1), mouse otoferlin isoform 1, 1992 aa | MALIVHLKTVSELRGKGDRIAKVTFRGQSFYSRVLENCEGVADFDE
TFRWPVASSIDRNEVLEIQIFNYSKVFSNKLIGTFCMVLQKVVEENR
VEVTDTLMDDSNAIIKTSLSMEVRYQATDGTVGPWDDGDFLGDESL
QEEKDSQETDGLLPGSRPSTRISGEKSFRSKGREKTKGGRDGEHK
AGRSVFSAMKLGKTRSHKEEPQRQDEPAVLEMEDLDHLAIQLGDG
LDPDSVSLASVTALTSNVSNKRSKPDIKMEPSAGRPMDYQVSITVIE
ARQLVGLNMDPVVCVEVGDDKKYTSMKESTNCPYYNEYFVFDFHV
SPDVMFDKIIKISVIHSKNLLRSGTLVGSFKMDVGTVYSQPEHQFHH
KWAILSDPDDISAGLKGYVKCDVAVVGKGDNIKTPHKANETEDDIE
GNLLLPEGVPPERQWARFYVKIYRAEGLPRMNTSLMANVKKAFIGE
NKDLVDPYVQVFFAGQKGKTSVQKSSYEPLWNEQVVFTDLFPPLC
KRMKVQIRDSDKVNDVAIGTHFIDLRKISNDGDKGFLPTLGPAWVN
MYGSTRNYTLLDEHQDLNEGLGEGVSFRARLMLGLAVEILDTSNPE
LTSSTEVQVEQATPVSESCTGRMEEFFLFGAFLEASMIDRKNGDKP
ITFEVTIGNYGNEVDGMSRPLRPRPRKEPGDEEEVDLIQNSSDDEG |

TABLE 2-continued

OTOF Sequences

| SEQ ID NO. | Sequence Name | Sequence |
|---|---|---|
| | | DEAGDLASVSSTPPMRPQITDRNYFHLPYLERKPCIYIKSWWPDQR RRLYNANIMDHIADKLEEGLNDVQEMIKTEKSYPERRLRGVLEELSC GCHRFLSLSDKDQGRSSRTRLDRERLKSCMRELESMGQQAKSLR AQVKRHTVRDKLRSCQNFLQKLRFLADEPQHSIPDVFIWMMSNNK RIAYARVPSKDLLFSIVEEELGKDCAKVKTLFLKLPGKRGFGSAGWT VQAKLELYLWLGLSKQRKDFLCGLPCGFEEVKAAQGLGLHSFPPIS LVYTKKQAFQLRAHMYQARSLFAADSSGLSDPFARVFFINQSQCTE VLNETLCPTWDQMLVFDNLELYGEAHELRDDPPIIVIEIYDQDSMGK ADFMGRTFAKPLVKMADEAYCPPRFPPQLEYYQIYRGSATAGDLLA AFELLQIGPSGKADLPPINGPVDMDRGPIMPVPVGIRPVLSKYRVEV LFWGLRDLKRVNLAQVDRPRVDIECAGKGVQSSLIHNYKKNPNFNT LVKWFEVDLPENELLHPPLNIRVVDCRAFGRYTLVGSHAVSSLRRFI YRPPDRSAPNWNTTGEVVVSMEPEEPVKKLETMVKLDATSDAVVK VDVAEDEKERKKKKKKGPSEEPEEEEPDESMLDWWSKYFASIDTM KEQLRQHETSGTDLEEKEEMESAEGLKGPMKSKEKSRAAKEEKKK KNQSPGPGQGSEAPEKKKAKIDELKVYPKELESEFDSFEDWLHTF NLLRGKTGDDEDGSTEEERIVGRFKGSLCVYKVPLPEDVSREAGY DPTYGMFQGIPSNDPINVLVRIYVVRATDLHPADINGKADPYIAIKLG KTDIRDKENYISKQLNPVFGKSFDIEASFPMESMLTVAVYDWDLVG TDDLIGETKIDLENRFYSKHRATCGIAQTYSIFIGYNIWRDPMKPSQIL TRLCKEGKVDGPHFGPHGRVRVANRVFTGPSEIEDENGQRKPTDE HVALSALRHWEDIPRVGCRLVPEHVETRPLLNPDKPGIEQGRLELW VDMFPMDMPAPGTPLDISPRKPKKYELRVIVWNTDEVVLEDDDFFT GEKSSDIFVRGWLKGQQEDKQDTDVHYHSLTGEGNFNWRYLFPF DYLAAEEKIVMSKKESMFSWDETEYKIPARLTLQIWDADHFSADDF LGAIELDLNRFPRGAKTAKQCTMEMATGEVDVPLVSIFKQKRVKGW WPLLARNENDEFELTGKVEAELHLLTAEEAKNPVGLARNEPDPLE KPNRPDTAFVWFLNPLKSIKYLICTRYKWLIIKIVLALLGLLMLALFLY SLPGYMVKKLLGA |
| 9 | mOTOF-202_2 protein (NP_001300696.1), mouse otoferlin isoform 4, 1977 aa | MALIVHLKTVSELRGKGDRIAKVTFRGQSFYSRVLENCEGVADFDE TFRWPVASSIDRNEVLEIQIFNYSKVFSNKLIGTFCMVLQKVVEENR VEVTDTLMDDSNAIIKTSLSMEVRYQATDGTVGPWDDGDFLGDESL QEEKDSQETDGLLPGSRPSTRISGEKSFRRAGRSVFSAMKLGKTR SHKEEPQRQDEPAVLEMEDLDHLAIQLGDGLDPDSVSLASVTALTS NVSNKRSKPDIKMEPSAGRPMDYQVSITVIEARQLVGLNMDPVVCV EVGDDKKYTSMKESTNCPYYNEYFVFDPHVSPDVMFDKIIKISVIHS KNLLRSGTLVGSFKMDVGTVYSQPEHQFHHKWAILSDPDDISAGLK GYVKCDVAVVGKGDNIKTPHKANETDEDDIEGNLLLPEGVPPERQ WARFYVKIYRAEGLPRMNTSLMANVKKAFIGENKDLVDPYVQVFFA GQKGKTSVQKSSYEPLWNEQVVFTDLFPPLCKRMKVQIRDSDKVN DVAIGTHFIDLRKISNDGDKGFLPTLGPAWVNMYGSTRNYTLLDEH QDLNEGLGEGVSFRARLMLGLAVEILDTSNPELTSSTEVQVEQATP VSESCTGRMEEFFLFGAFLEASMIDRKNGDKPITFEVTIGNYGNEV DGMSRPLRPRPRKEPGDEEEVDLIQNSSDDEGDEAGDLASVSSTP PMRPQITDRNYFHLPYLERKPCIYIKSWWPDQRRRLYNANIMDHIA DKLEEGLNDVQEMIKTEKSYPERRLRGVLEELSCGCHRFLSLSDKD QGRSSRTRLDRERLKSCMRELESMGQQAKSLRAQVKRHTVRDKL RSCQNFLQKLRFLADEPQHSIPDVFIWMMSNNKRIAYARVPSKDLL FSIVEEELGKDCAKVKTLFLKLPGKRGFGSAGWTVQAKLELYLWLG LSKQRKDFLCGLPCGFEEVKAAQGLGLHSFPPISLVYTKKQAFQLR AHMYQARSLFAADSSGLSDPFARVFFINQSQCTEVLNETLCPTWD QMLVFDNLELYGEAHELRDDPPIIVIEIYDQDSMGKADFMGRTFAKP LVKMADEAYCPPRFPPQLEYYQIYRGSATAGDLLAAFELLQIGPSG KADLPPINGPVDMDRGPIMPVPVGIRPVLSKYRVEVLFWGLRDLKR VNLAQVDRPRVDIECAGKGVQSSLIHNYKKNPNFNTLVKWFEVDLP ENELLHPPLNIRVVDCRAFGRYTLVGSHAVSSLRRFIYRPPDRSAP NWNTTGEVVVSMEPEEPVKKLETMVKLDATSDAVVKVDVAEDEKE RKKKKKGPSEEPEEEEPDESMLDWWSKYFASIDTMKEQLRQHET SGTDLEEKEEMESAEGLKGPMKSKEKSRAAKEEKKKKNQSPGPG QGSEAPEKKKAKIDELKVYPKELESEFDSFEDWLHTFNLLRGKTGD DEDGSTEEERIVGRFKGSLCVYKVPLPEDVSREAGYDPTYGMFQGI PSNDPINVLVRIYVVRATDLHPADINGKADPYIAIKLGKTDIRDKENYI SKQLNPVFGKSFDIEASFPMESMLTVAVYDWDLVGTDDLIGETKIDL ENRFYSKHRATCGIAQTYSIHGYNIWRDPMKPSQILTRLCKEGKVD GPHFGPHGRVRVANRVFTGPSEIEDENGQRKPTDEHVALSALRHW EDIPRVGCRLVPEHVETRPLLNPDKPGIEQGRLELWVDMFPMDMP APGTPLDISPRKPKKYELRVIVWNTDEVVLEDDDFFTGEKSSDIFVR GWLKGQQEDKQDTDVHYHSLTGEGNFNWRYLFPFDYLAAEEKIV MSKKESMFSWDETEYKIPARLTLQIWDADHFSADDFLGAIELDLNR FPRGAKTAKQCTMEMATGEVDVPLVSIFKQKRVKGWWPLLARNEN DEFELTGKVEAELHLLTAEEAEKNPVGLARNEPDPLEKPNRPDTAF VWFLNPLKSIKYLICTRYKWLIIKIVLALLGLLMLALFLYSLPGYMVKK LLGA |

TABLE 2-continued

OTOF Sequences

| SEQ ID NO. | Sequence Name | Sequence |
|---|---|---|
| 10 | OTOF-201 transcript (NM_194248.1), human otoferlin transcript variant 1, 7156 bp, encodes the protein of SEQ ID NO: 1 | ATCGGAGGGGGTCGGGAGGAGGAGGAGGAGGCAGCGGCAG<br>AGAAGAGAGAGGCGTGTGAGCCGTGCTCCACCGGCTAGCTCCT<br>TCCCGCTGCTCCTGCCTGGCAGTGCCAGGCAGCCCACACCAGC<br>ATGGCCTTGCTCATCCACCTCAAGACAGTCTCGGAGCTGCGGG<br>GCAGGGGCGACCGGATCGCCAAAGTGACTTTCCGAGGGCAATC<br>CTTCTACTCTCGGGTCCTGGAGAACTGTGAGGATGTGGCTGACT<br>TTGATGAGACATTTCGGTGGCCGGTGGCCAGCAGCATCGACAG<br>AAATGAGATGCTGGAGATTCAGGTTTTCAACTACAGCAAAGTCTT<br>CAGCAACAAGCTCATCGGGACCTTCCGCATGGTGCTGCAGAAG<br>GTGGTAGAGGAGAGCCATGTGGAGGTGACTGACACGCTGATTG<br>ATGACAACAATGCTATCATCAAGACCAGCCTGTGCGTGGAGGTC<br>CGGTATCAGGCCACTGACGGCACAGTGGGCTCCTGGGACGATG<br>GGGACTTCCTGGGAGATGAGTCTCTTCAAGAGGAAGAGAAGGA<br>CAGCCAAGAGACGGATGGACTGCTCCCAGGCTCCCGGCCCAGC<br>TCCCGGCCCCCAGGAGAGAAGAGCTTCCGGAGAGCCGGGAGG<br>AGCGTGTTCTCCGCCATGAAGCTCGGCAAAAACCGGTCTCACAA<br>GGAGGAGCCCCAAAGACCAGATGAACCGGCGGTGCTGGAGAT<br>GGAAGACCTTGACCATCTGGCCATTCGGCTAGGAGATGGACTG<br>GATCCCGACTCGGTGTCTCTAGCCTCAGTCACAGCTCTCACCAC<br>TAATGTCTCCAACAAGCGATCTAAGCCAGACATTAAGATGGAGC<br>CAAGTGCTGGGCGGCCCATGGATTACCAGGTCAGCATCACGGT<br>GATCGAGGCCCGGCAGCTGGTGGGCTTGAACATGGACCCTGTG<br>GTGTGCGTGGAGGTGGGTGACGACAAGAAGTACACATCCATGA<br>AGGAGTCCACTAACTGCCCCTATTACAACGAGTACTTCGTCTTC<br>GACTTCCATGTCTCTCCGGATGTCATGTTTGACAAGATCATCAAG<br>ATTTCGGTGATTCACTCCAAGAACCTGCTGCGCAGTGGCACCCT<br>GGTGGGCTCCTTCAAAATGGACGTGGGAACCGTGTACTCGCAG<br>CCAGAGCACCAGTTCCATCACAAGTGGGCCATCCTGTCTGACCC<br>CGATGACATCTCCTCGGGGCTGAAGGGCTACGTGAAGTGTGAC<br>GTTGCCGTGGTGGGCAAAGGGGACAACATCAAGACGCCCCACA<br>AGGCCAATGAGACCGACGAAGATGACATTGAGGGGAACTTGCT<br>GCTCCCCGAGGGGGTGCCCCCCGAACGCCAGTGGGCCCGGTT<br>CTATGTGAAAATTTACCGAGCAGAGGGGCTGCCCCGTATGAACA<br>CAAGCCTCATGGCCAATGTAAAGAAGGCTTTCATCGGTGAAAAC<br>AAGGACCTCGTGGACCCCTACGTGCAAGTCTTCTTTGCTGGCCA<br>GAAGGGCAAGACTTCAGTGCAGAAGAGCAGCTATGAGCCCCTG<br>TGGAATGAGCAGGTCGTCTTTACAGACCTCTTCCCCCCACTCTG<br>CAAACGCATGAAGGTGCAGATCCGAGACTCGGACAAGGTCAAC<br>GACGTGGCCATCGGCACCCACTTCATTGACCTGCGCAAGATTTC<br>TAATGACGGAGACAAAGGCTTCCTGCCCACACTGGGCCCAGCC<br>TGGGTGAACATGTACGGCTCCACACGTAACTACACGCTGCTGGA<br>TGAGCATCAGGACCTGAACGAGGGCCTGGGGGAGGGTGTGTC<br>CTTCCGGGCCCGGCTCCTGCTGGGCCTGGCTGTGGAGATCGTA<br>GACACCTCCAACCCTGAGCTCACCAGCTCCACAGAGGTGCAGG<br>TGGAGCAGGCCACGCCCATCTCGGAGAGCTGTGCAGGTAAAAT<br>GGAAGAATTCTTTCTCTTTGGAGCCTTCCTGGAGGCCTCAATGA<br>TCGACCGGAGAAACGGAGACAAGCCCATCACCTTTGAGGTCAC<br>CATAGGCAACTATGGGAACGAAGTTGATGGCCTGTCCCGGCCC<br>CAGCGGCCTCGGCCCCGGAAGGAGCCGGGGGATGAGGAAGAA<br>GTAGACCTGATTCAGAACGCAAGTGATGACGAGGCCGGTGATG<br>CCGGGGACCTGGCCTCAGTCTCCTCCACTCCACCAATGCGGCC<br>CCAGGTCACCGACAGGAACTACTTCCATCTGCCCTACCTGGAGC<br>GAAAGCCCTGCATCTACATCAAGAGCTGGTGGCCGGACCAGCG<br>CCGCCGCCTCTACAATGCCAACATCATGGACCACATTGCCGACA<br>AGCTGGAAGAAGGCCTGAACGACATACAGGAGATGATCAAAAC<br>GGAGAAGTCCTACCCTGAGCGTCGCCTGCGGGGCGTCCTGGA<br>GGAGCTGAGCTGTGGCTGCTGCCGCTTCCTCTCCCTCGCTGAC<br>AAGGACCAGGGCCACTCATCCCGCACCAGGCTTGACCGGGAGC<br>GCCTCAAGTCCTGCATGAGGGAGCTGGAAAACATGGGGCAGCA<br>GGCCAGGATGCTGCGGGCCCAGGTGAAGCGGCACACGGTGCG<br>GGACAAGCTGAGGCTGTGCCAGAACTTCCTGCAGAAGCTGCGC<br>TTCCTGGCCGACGAGCCCCAGCACAGCATTCCCGACATCTTCAT<br>CTGGATGATGAGCAACAACAAGCGTGTCGCCTATGCCCGTGTG<br>CCCTCCAAGGACCTGCTCTTCTCCATCGTGGAGGAGGAGACTG<br>GCAAGGACTGCGCCAAGGTCAAGACGCTCTTCCTTAAGCTGCC<br>AGGGAAGCGGGGCTTCGGCTCGGCAGGCTGGACAGTGCAGGC<br>CAAGGTGGAGCTGTACCTGTGGCTGGGCCTCAGCAAACAGCGC<br>AAGGAGTTCCTGTGCGGCCTGCCCTGTGGCTTCCAGGAGGTCA<br>AGGCAGCCCAGGGCCTGGGCCTGCATGCCTTCCCACCCGTCAG<br>CCTGGTCTACACCAAGAAGCAGGCGTTCCAGCTCCGAGCGCAC<br>ATGTACCAGGCCCGCAGCCTCTTTGCCGCCGACAGCAGCGGAC<br>TCTCAGACCCCTTTGCCCGCGTCTTCTTCATCAATCAGAGTCAG<br>TGCACAGAGGTGCTGAATGAGACCCTGTGTCCCACCTGGGACC<br>AGATGCTGGTGTTCGACAACCTGGAGCTCTATGGTGAAGCTCAT<br>GAGCTGAGGGACGATCCGCCCATCATTGTCATTGAAATCTATGA |

TABLE 2-continued

OTOF Sequences

| SEQ ID NO. | Sequence Name | Sequence |
|---|---|---|
| | | CCAGGATTCCATGGGCAAAGCTGACTTCATGGGCCGGACCTTC<br>GCCAAACCCCTGGTGAAGATGGCAGACGAGGCGTACTGCCCAC<br>CCCGCTTCCCACCTCAGCTCGAGTACTACCAGATCTACCGTGGC<br>AACGCCACAGCTGGAGACCTGCTGGCGGCCTTCGAGCTGCTGC<br>AGATTGGACCAGCAGGGAAGGCTGACCTGCCCCCCATCAATGG<br>CCCGGTGGACGTGGACCGAGGTCCCATCATGCCCGTGCCCATG<br>GGCATCCGGCCCGTGCTCAGCAAGTACCGAGTGGAGGTGCTGT<br>TCTGGGGCCTACGGGACCTAAAGCGGGTGAACCTGGCCCAGGT<br>GGACCGGCCACGGGTGGACATCGAGTGTGCAGGGAAGGGGGT<br>GCAGTCGTCCCTGATCCACAATTATAAGAAGAACCCCAACTTCA<br>ACACCCTCGTCAAGTGGTTTGAAGTGGACCTCCCAGAGAACGA<br>GCTGCTGCACCCGCCCTTGAACATCCGTGTGGTGGACTGCCGG<br>GCCTTCGGTCGCTACACACTGGTGGGCTCCCATGCCGTCAGCT<br>CCCTGCGACGCTTCATCTACCGGCCCCAGACCGCTCGGCCCC<br>CAGCTGGAACACCACGGTCAGGCTTCTCCGGCGCTGCCGTGTG<br>CTGTGCAATGGGGGCTCCTCCTCTCACTCCACAGGGGAGGTTG<br>TGGTGACTATGGAGCCAGAGGTACCCATCAAGAAACTGGAGAC<br>CATGGTGAAGCTGGACGCGACTTCTGAAGCTGTTGTCAAGGTG<br>GATGTGGCTGAGGAGGAGAAGGAGAAGAAGAAGAAGAAGAAGG<br>GCACTGCGGAGGAGCCAGAGGAGGAGGAGCCAGACGAGAGCA<br>TGCTGGACTGGTGGTCCAAGTACTTTGCCTCCATTGACACCATG<br>AAGGAGCAACTTCGACAACAAGAGCCCTCTGGAATTGACTTGGA<br>GGAGAAGGAGGAAGTGGACAATACCGAGGGCCTGAAGGGGTC<br>AATGAAGGGCAAGGAGAAGGCAAGGGCTGCCAAAGAGGAGAAG<br>AAGAAGAAAACTCAGAGCTCTGGCTCTGGCCAGGGGTCCGAGG<br>CCCCCGAGAAGAAGAAACCCAAGATTGATGAGCTTAAGGTATAC<br>CCCAAAGAGCTGGAGTCCGAGTTTGATAACTTTGAGGACTGGCT<br>GCACACTTTCAACTTGCTTCGGGGCAAGACCGGGGATGATGAG<br>GATGGCTCCACCGAGGAGGAGCGCATTGTGGGACGCTTCAAGG<br>GCTCCCTCTGCGTGTACAAAGTGCCACTCCCAGAGGACGTGTC<br>CCGGGAAGCCGGCTACGACTCCACCTACGGCATGTTCCAGGGC<br>ATCCCGAGCAATGACCCCATCAATGTGCTGGTCCGAGTCTATGT<br>GGTCCGGGCCACGGACCTGCACCCTGCTGACATCAACGGCAAA<br>GCTGACCCCTACATCGCCATCCGGCTAGGCAAGACTGACATCC<br>GCGACAAGGAGAACTACATCTCCAAGCAGCTCAACCCTGTCTTT<br>GGGAAGTCCTTTGACATCGAGGCCTCCTTCCCCATGGAATCCAT<br>GCTGACGGTGGCTGTGTATGACTGGGACCTGGTGGGCACTGAT<br>GACCTCATTGGGGAAACCAAGATCGACCTGGAGAACCGCTTCTA<br>CAGCAAGCACCGCGCCACCTGCGGCATCGCCCAGACCTACTCC<br>ACACATGGCTACAATATCTGGCGGGACCCCATGAAGCCCAGCC<br>AGATCCTGACCCGCCTCTGCAAAGACGGCAAAGTGGACGGCCC<br>CCACTTTGGGCCCCCTGGGAGAGTGAAGGTGGCCAACCGCGTC<br>TTCACTGGGCCCTCTGAGATTGAGGACGAGAACGGTCAGAGGA<br>AGCCCACAGACGAGCATGTGGCGCTGTTGGCCCTGAGGCACTG<br>GGAGGACATCCCCCGCGCAGGCTGCCGCCTGGTGCCAGAGCA<br>TGTGGAGACGAGGCCGCTGCTCAACCCCGACAAGCCGGGCATC<br>GAGCAGGGCCGCCTGGAGCTGTGGGTGGACATGTTCCCCATGG<br>ACATGCCAGCCCCTGGGACGCCTCTGGACATCTCACCTCGGAA<br>GCCCAAGAAGTACGAGCTGCGGGTCATCATCTGGAACACAGAT<br>GAGGTGGTCTTGGAGGACGACGACTTCTTCACAGGGGAGAAGT<br>CCAGTGACATCTTCGTGAGGGGGTGGCTGAAGGGCCAGCAGGA<br>GGACAAGCAGGACACAGACGTCCACTACCACTCCCTCACTGGC<br>GAGGGCAACTTCAACTGGCGCTACCTGTTCCCCTTCGACTACCT<br>GGCGGCGGAGGAGAAGATCGTCATCTCCAAGAAGGAGTCCATG<br>TTCTCCTGGGACGAGACCGAGTACAAGATCCCCGCGCGGCTCA<br>CCCTGCAGATCTGGGATGCGGACCACTTCTCCGCTGACGACTT<br>CCTGGGGGCCATCGAGCTGGACCTGAACCGGTTCCCGCGGGG<br>CGCAAAGACAGCCAAGCAGTGCACCATGGAGATGGCCACCGGG<br>GAGGTGGACGTGCCCCTCGTGTCCATCTTCAAGCAAAAGCGCG<br>TCAAAGGCTGGTGGCCCCTCCTGGCCCGCAATGAGAACGATGA<br>GTTTGAGCTCACGGGCAAGGTGGAGGCTGAGCTGCATTTACTG<br>ACAGCAGAGGAGGCAGAGAAGAACCCAGTGGGCCTGGCCCGC<br>AATGAACCTGACCCCCTAGAGAAACCCAACCGGCCCGACACGA<br>GCTTCATCTGGTTCCTGAACCCTCTCAAGTCGGCTCGCTACTTC<br>TTGTGGCACACGTATCGCTGGCTGCTCCTCAAACTGTTGCTGCT<br>CCTGCTGCTGCTCCTCCTCCTCGCCCTGTTCCTCTACTCTGTGC<br>CTGGCTACCTGGTCAAGAAAATCCTCGGGGCTGAGCCCAGTG<br>GCCTCCTGGCCGGCCCGACACGGCCTTCGTCTGGTTCCTCAAC<br>CCTCTCAAGTCCATCAAGTACCTCATCTGCACCCGGTACAAGTG<br>GCTCATCATCAAGATCGTGCTGGCGTGTTGGGGCTGCTCATGT<br>TGGGGCTCTTCCTCTACAGCCTCCCTGGCTACATGGTCAAAAAG<br>CTCCTTGGGGCATGAAGGCCGCCAGCTCCCGCCAGCCGCTCCC<br>CAGCCCTGCCGCATTTCCTTTCAGTGGCTTGGACTCTTTCCCAT<br>CTCCCCTGGGGAGCCTGAGGAGCCCAGCGTCCACTCTTCATGC<br>CTTGGGCCGAGCCTGCCTCCTGCTTGCGGGGGCCGCCTGTCCT |

TABLE 2-continued

OTOF Sequences

| SEQ ID NO. | Sequence Name | Sequence |
|---|---|---|
| | | CACTGCCCCAGGCTGCGGCTTGCCCAGTCCCGCCCCTCTGACC<br>CCTGCCTGTGGGCTGGGGAGCCTTGGATGGGGTGGGGACCTG<br>GAATGGGTCTCTCTTGCCCCACCTGGCTGAGGCGCCACCCTTC<br>TTCAGGCCCAGGCTCCAGAGGAAGACTCCTGAAACCCTCCCCA<br>GGTCTTCCAAGTACAGGATTGAAGCTTTAGTGAAATTAACCAAG<br>GACCATGGGTCAGTGCCCAGGGCTTTAAAAAGAATGAACGAGC<br>AAAAGGTATCCCCGCCGTGACCCCTGCAGATAGCACCGGTCTTT<br>GATCCGCAGCAGGGGCCAGACCCTGCCCACAAGTCCCAGCGC<br>GGCTGCTTCTGCCACTGCTGGGCTCCACTTGGCTCCTCTCACTT<br>CCCAGGGGGTCGCCTGTCCTGCCTGTGGGTTTCCATGGCTTCC<br>CAGAGCTCCCTCTGCCCCAGCCAGCGCCTCCAGGCCCAGCTGA<br>GGAGCTGTGAGAAGCAGCAGAGGGGACTCCCCATCCGGGCA<br>CACCCTGTCCTCCCACCCCTGCCCCCTTGCCCTTCCAGCCCTTT<br>CAGCTGCAGCTGGGAGCTGGCCCGTCAAGTGCTGCCCCTGCCT<br>GTGTCTGGGTTTCTGTTGGCTGTTTTTCTTTTCTTGAGTGGTGAT<br>TTTTCTCTAAATAAAAGAAGTCAAGCACTGAAAAAAAAAAAAAAA<br>A |
| 11 | OTOF-202 transcript (NM_004802.3), human otoferlin transcript variant 2, 4954 bp, encodes the protein of SEQ ID NO: 2 | CCGTGAGTTCTGCCCAGGCCCTGTGAGCTCACCAGAGCCACAG<br>ACTCACAGCCCAGAGGTGGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGAAGAAGGCCTGAACGACA<br>TACAGGAGATGATCAAAACGGAGAAGTCCTACCCTGAGCGTCG<br>CCTGCGGGGCGTCCTGGAGGAGCTGAGCTGTGGCTGCTGCCG<br>CTTCCTCTCCCTCGCTGACAAGGACCAGGGCCACTCATCCCGC<br>ACCAGGCTTGACCGGGAGCGCCTCAAGTCCTGCATGAGGGAGC<br>TGGAAAACATGGGGCAGCAGGCCAGGATGCTGCGGGCCCAGG<br>TGAAGCGGCACACGGTGCGGGACAAGCTGAGGCTGTGCCAGAA<br>CTTCCTGCAGAAGCTGCGCTTCCTGGCGGACGAGCCCCAGCAC<br>AGCATTCCCGACATCTTCATCTGGATGATGAGCAACAACAAGCG<br>TGTCGCCTATGCCCGTGTGCCCTCCAAGGACCTGCTCTTCTCCA<br>TCGTGGAGGAGGAGACTGGCAAGGACTGCGCCAAGGTCAAGAC<br>GCTCTTCCTTAAGCTGCCAGGGAAGCGGGGCTTCGGCTCGGCA<br>GGCTGGACAGTGCAGGCCAAGGTGGAGCTGTACCTGTGGCTGG<br>GCCTCAGCAAACAGCGCAAGGAGTTCCTGTGCGGCCTGCCCTG<br>TGGCTTCCAGGAGGTCAAGGCAGCCCAGGGCCTGGGCCTGCAT<br>GCCTTCCCACCCGTCAGCCTGGTCTACACCAAGAAGCAGGCGT<br>TCCAGCTCCGAGCGCACATGTACCAGGCCCGCAGCCTCTTTGC<br>CGCCGACAGCAGCGGACTCTCAGACCCCTTTGCCCGCGTCTTC<br>TTCATCAATCAGAGTCAGTGCACAGAGGTGCTGAATGAGACCCT<br>GTGTCCCACCTGGGACCAGATGCTGGTGTTCGACAACCTGGAG<br>CTCTATGGTGAAGCTCATGAGCTGAGGGACGATCCGCCCATCAT<br>TGTCATTGAAATCTATGACCAGGATTCCATGGGCAAAGCTGACT<br>TCATGGGCCGGACCTTCGCCAAACCCCTGGTGAAGATGGCAGA<br>CGAGGCGTACTGCCCACCCCGCTTCCCACCTCAGCTCGAGTAC<br>TACCAGATCTACCGTGGCAACGCCACAGCTGGAGACCTGCTGG<br>CGGCCTTCGAGCTGCTGCAGATTGGACCAGCAGGGAAGGCTGA<br>CCTGCCCCCCATCAATGGCCCGGTGGACGTGGACCGAGGTCCC<br>ATCATGCCCGTGCCCATGGGCATCCGGCCCGTGCTCAGCAAGT<br>ACCGAGTGGAGGTGCTGTTCTGGGGCCTACGGGACCTAAAGCG<br>GGTGAACCTGGCCCAGGTGGACCGGCCACGGGTGGACATCGA<br>GTGTGCAGGGAAGGGGTGCAGTCGTCCCTGATCCACACAATTAT<br>AAGAAGAACCCCAACTTCAACACCCTCGTCAAGTGGTTTGAAGT<br>GGACCTCCCAGAGAACGAGCTGCTGCACCCGCCCTTGAACATC<br>CGTGTGGTGGACTGCCGGGCCTTCGGTCGCTACACACTGGTGG<br>GCTCCCATGCCGTCAGCTCCCTGCGACGCTTCATCTACCGGCC<br>CCCAGACCGCTCGGCCCCCAGCTGGAACACCACGGGGGAGGT<br>TGTGGTGACTATGGAGCCAGAGGTACCCATCAAGAAACTGGAG<br>ACCATGGTGAAGCTGGACGCGACTTCTGAAGCTGTTGTCAAGGT<br>GGATGTGGCTGAGGAGGAGAAGGAGAAGAAGAAGAAGAAGAAG<br>GGCACTGCGGAGGAGCCAGAGGAGGAGGAGCCAGACGAGAGC<br>ATGCTGGACTGGTGGTCCAAGTACTTTGCCTCCATTGACACCAT<br>GAAGGAGCAACTTCGACAACAAGAGCCCTCTGGAATTGACTTGG<br>AGGAGAAGGAGGAAGTGGACAATACCGAGGGCCTGAAGGGGT<br>CAATGAAGGGCAAGGAGAAGGCAAGGGCTGCCAAAGAGGAGAA<br>GAAGAAGAAAACTCAGAGCTCTGGCTCTGGCCAGGGGTCCGAG<br>GCCCCCGAGAAGAAGAAACCCAAGATTGATGAGCTTAAGGTATA<br>CCCCAAAGAGCTGGAGTCCGAGTTTGATAACTTTGAGGACTGGC<br>TGCACACTTTCAACTTGCTTCGGGGCAAGACCGGGGATGATGA<br>GGATGGCTCCACCGAGGAGGAGCGCATTGTGGGACGCTTCAAG<br>GGCTCCCTCTGCGTGTACAAAGTGCCACTCCCAGAGGACGTGT<br>CCCGGGAAGCCGGCTACGACTCCACCTACGGCATGTTCCAGGG<br>CATCCCGAGCAATGACCCCATCAATGTGCTGGTCCGAGTCTATG<br>TGGTCCGGGCCACGGACCTGCACCCTGCTGACATCAACGGCAA |

TABLE 2-continued

OTOF Sequences

| SEQ ID NO. | Sequence Name | Sequence |
|---|---|---|
| | | AGCTGACCCCTACATCGCCATCCGGCTAGGCAAGACTGACATC<br>CGCGACAAGGAGAACTACATCTCCAAGCAGCTCAACCCTGTCTT<br>TGGGAAGTCCTTTGACATCGAGGCCTCCTTCCCCATGGAATCCA<br>TGCTGACGGTGGCTGTGTATGACTGGGACCTGGTGGGCACTGA<br>TGACCTCATTGGGGAAACCAAGATCGACCTGGAGAACCGCTTCT<br>ACAGCAAGCACCGCGCCACCTGCGGCATCGCCCAGACCTACTC<br>CACACATGGCTACAATATCTGGCGGGACCCCATGAAGCCCAGC<br>CAGATCCTGACCCGCCTCTGCAAAGACGGCAAAGTGGACGGCC<br>CCCACTTTGGGCCCCCTGGGAGAGTGAAGGTGGCCAACCGCGT<br>CTTCACTGGGCCCTCTGAGATTGAGGACGAGAACGGTCAGAGG<br>AAGCCCACAGACGAGCATGTGGCGCTGTTGGCCCTGAGGCACT<br>GGGAGGACATCCCCCGCGCAGGCTGCCGCCTGGTGCCAGAGC<br>ATGTGGAGACGAGGCCGCTGCTCAACCCCGACAAGCCGGGCAT<br>CGAGCAGGGCCGCCTGGAGCTGTGGGTGGACATGTTCCCCATG<br>GACATGCCAGCCCCTGGGACGCCTCTGGACATCTCACCTCGGA<br>AGCCCAAGAAGTACGAGCTGCGGGTCATCATCTGGAACACAGA<br>TGAGGTGGTCTTGGAGGACGACGACTTCTTCACAGGGGAGAAG<br>TCCAGTGACATCTTCGTGAGGGGGTGGCTGAAGGGCCAGCAGG<br>AGGACAAGCAGGACACAGACGTCCACTACCACTCCCTCACTGG<br>CGAGGGCAACTTCAACTGGCGCTACCTGTTCCCCTTCGACTACC<br>TGGCGGCGGAGGAGAAGATCGTCATCTCCAAGAAGGAGTCCAT<br>GTTCTCCTGGGACGAGACCGAGTACAAGATCCCCGCGCGGCTC<br>ACCCTGCAGATCTGGGATGCGGACCACTTCTCCGCTGACGACTT<br>CCTGGGGGCCATCGAGCTGGACCTGAACCGGTTCCCGCGGGG<br>CGCAAAGACAGCCAAGCAGTGCACCATGGAGATGGCCACCGGG<br>GAGGTGGACGTGCCCCTCGTGTCCATCTTCAAGCAAAAGCGCG<br>TCAAAGGCTGGTGGCCCCTCCTGGCCCGCAATGAGAACGATGA<br>GTTTGAGCTCACGGGCAAGGTGGAGGCTGAGCTGCATTTACTG<br>ACAGCAGAGGAGGCAGAGAAGAACCCAGTGGGCCTGGCCCGC<br>AATGAACCTGACCCCCTAGAGAAACCCAACCGGCCCGACACGA<br>GCTTCATCTGGTTCCTGAACCCTCTCAAGTCGGCTCGCTACTTC<br>TTGTGGCACACGTATCGCTGGCTGCTCCTCAAACTGTTGCTGCT<br>CCTGCTGCTGCTCCTCCTCCTCGCCCTGTTCCTCTACTCTGTGC<br>CTGGCTACCTGGTCAAGAAAATCCTCGGGGCCTGAGCCCAGTG<br>GCCTCCTGGCCGGCCCGACACGGCCTTCGTCTGGTTCCTCAAC<br>CCTCTCAAGTCCATCAAGTACCTCATCTGCACCCGGTACAAGTG<br>GCTCATCATCAAGATCGTGCTGGCGCTGTTGGGGCTGCTCATGT<br>TGGGGCTCTTCCTCTACAGCCTCCCTGGCTACATGGTCAAAAAG<br>CTCCTTGGGGCATGAAGGCCGCCAGCTCCCGCCAGCCGCTCCC<br>CAGCCCTGCCGCATTTCCTTTCAGTGGCTTGGACTCTTTCCCAT<br>CTCCCCTGGGGAGCCTGAGGAGCCCAGCGTCCACTCTTCATGC<br>CTTGGGCCGAGCCTGCCTCCTGCTTGCGGGGGCCGCCTGTCCT<br>CACTGCCCCAGGCTGCGGCTTGCCCAGTCCCGCCCCTCTGACC<br>CCTGCCTGTGGGCTGGGGAGCCTTGGATGGGGTGGGGACCTG<br>GAATGGGTCTCTCTTGCCCCACCTGGCTGAGGCGCCACCCTTC<br>TTCAGGCCCAGGCTCCAGAGGAAGACTCCTGAAACCCTCCCCA<br>GGTCTTCCAAGTACAGGATTGAAGCTTTAGTGAAATTAACCAAG<br>GACCATGGGTCAGTGCCCAGGGCTTTAAAAAGAATGAACGAGC<br>AAAAGGTATCCCCGCCGTGACCCCTGCAGATAGCACCGGTCTTT<br>GATCCGCAGCAGGGGCCAGACCCTGCCCACAAGTCCCAGCGC<br>GGCTGCTTCTGCCACTGCTGGGCTCCACTTGGCTCCTCTCACTT<br>CCCAGGGGGTCGCCTGTCCTGCCTGTGGGTTTCCATGGCTTCC<br>CAGAGCTCCCTCTGCCCCAGCCAGCGCCTCCAGGCCCAGCTGA<br>GGAGCTGTGAGAAGCAGCAGAGGGGACTCCCCATCCCGGGCA<br>CACCCTGTCCTCCCACCCCTGCCCCCTTGCCCTTCCAGCCCTTT<br>CAGCTGCAGCTGGGAGCTGGCCCGTCAAGTGCTGCCCCTGCCT<br>GTGTCTGGGTTTCTGTTGGCTGTTTTTCTTTTCTTGAGTGGTGAT<br>TTTTCTCTAAATAAAAGAAGTCAAGCACTGAAAAAAAAAAAAAAA<br>A |
| 12 | OTOF-203 transcript (NM_194323.2), human otoferlin transcript variant 4, 4756 bp, encodes the protein of SEQ ID NO: 3 | CCGTGAGTTCTGCCCAGGCCCTGTGAGCTCACCAGAGCCACAG<br>ACTCACAGCCCAGAGGTGCTTCTTCCTTCAGGAACTGAAGAAC<br>CCCCATGAACACCAACATCTCCAGGTTCTGAGAACAGAACCTGG<br>GAAATTGATGACTTCCTCATGATGACCGATACTCAGGATGGCCC<br>TAGCGAGAGCTCCCAGATCATGAGGAAGAAGGCCTGAACGACA<br>TACAGGAGATGATCAAAACGGAGAAGTCCTACCCTGAGCGTCG<br>CCTGCGGGGCGTCCTGGAGGAGCTGAGCTGTGGCTGCTGCCG<br>CTTCCTCTCCCTCGCTGACAAGGACCAGGGCCACTCATCCCGC<br>ACCAGGCTTGACCGGGAGCGCCTCAAGTCCTGCATGAGGGAGC<br>TGGAAAACATGGGGCAGCAGGCCAGGATGCTGCGGGCCCAGG<br>TGAAGCGGCACACGGTGCGGGACAAGCTGAGGCTGTGCCAGAA<br>CTTCCTGCAGAAGCTGCGCTTCCTGGCGGACGAGCCCCAGCAC<br>AGCATTCCCGACATCTTCATCTGGATGATGAGCAACAACAAGCG<br>TGTCGCCTATGCCCGTGTGCCCTCCAAGGACCTGCTCTTCTCCA<br>TCGTGGAGGAGGAGACTGGCAAGGACTGCGCCAAGGTCAAGAC |

TABLE 2-continued

OTOF Sequences

| SEQ ID NO. | Sequence Name | Sequence |
|---|---|---|
| | | GCTCTTCCTTAAGCTGCCAGGGAAGCGGGGCTTCGGCTCGGCA
GGCTGGACAGTGCAGGCCAAGGTGGAGCTGTACCTGTGGCTGG
GCCTCAGCAAACAGCGCAAGGAGTTCCTGTGCGGCCTGCCCTG
TGGCTTCCAGGAGGTCAAGGCAGCCCAGGGCCTGGGCCTGCAT
GCCTTCCCACCCGTCAGCCTGGTCTACACCAAGAAGCAGGCGT
TCCAGCTCCGAGCGCACATGTACCAGGCCCGCAGCCTCTTTGC
CGCCGACAGCAGCGGACTCTCAGACCCCTTTGCCCGCGTCTTC
TTCATCAATCAGAGTCAGTGCACAGAGGTGCTGAATGAGACCCT
GTGTCCCACCTGGGACCAGATGCTGGTGTTCGACAACCTGGAG
CTCTATGGTGAAGCTCATGAGCTGAGGGACGATCCGCCCATCAT
TGTCATTGAAATCTATGACCAGGATTCCATGGGCAAAGCTGACT
TCATGGGCCGGACCTTCGCCAAACCCCTGGTGAAGATGGCAGA
CGAGGCGTACTGCCCACCCCGCTTCCCACCTCAGCTCGAGTAC
TACCAGATCTACCGTGGCAACGCCACAGCTGGAGACCTGCTGG
CGGCCTTCGAGCTGCTGCAGATTGGACCAGCAGGGAAGGCTGA
CCTGCCCCCCATCAATGGCCCGGTGGACGTGGACCGAGGTCCC
ATCATGCCCGTGCCCATGGGCATCCGGCCCGTGCTCAGCAAGT
ACCGAGTGGAGGTGCTGTTCTGGGGCCTACGGGACCTAAAGCG
GGTGAACCTGGCCCAGGTGGACCGGCCACGGGTGGACATCGA
GTGTGCAGGGAAGGGGGTGCAGTCGTCCCTGATCCACAATTAT
AAGAAGAACCCCAACTTCAACACCCTCGTCAAGTGGTTTGAAGT
GGACCTCCCAGAGAACGAGCTGCTGCACCCGCCCTTGAACATC
CGTGTGGTGGACTGCCGGGCCTTCGGTCGCTACACACTGGTGG
GCTCCCATGCCGTCAGCTCCCTGCGACGCTTCATCTACCGGCC
CCCAGACCGCTCGGCCCCCAGCTGGAACACCACGGGGGAGGT
TGTGGTGACTATGGAGCCAGAGGTACCCATCAAGAAACTGGAG
ACCATGGTGAAGCTGGACGCGACTTCTGAAGCTGTTGTCAAGGT
GGATGTGGCTGAGGAGGAGAAGGAGAAGAAGAAGAAGAAGAAG
GGCACTGCGGAGGAGCCAGAGGAGGAGGAGCCAGACGAGAGC
ATGCTGGACTGGTGGTCCAAGTACTTTGCCTCCATTGACACCAT
GAAGGAGCAACTTCGACAACAAGAGCCCTCTGGAATTGACTTGG
AGGAGAAGGAGGAAGTGGACAATACCGAGGGCCTGAAGGGGT
CAATGAAGGGCAAGGAGAAGGCAAGGGCTGCCAAAGAGGAGAA
GAAGAAGAAAACTCAGAGCTCTGGCTCTGGCCAGGGGTCCGAG
GCCCCCGAGAAGAAGAAACCCAAGATTGATGAGCTTAAGGTATA
CCCCAAAGAGCTGGAGTCCGAGTTTGATAACTTTGAGGACTGGC
TGCACACTTTCAACTTGCTTCGGGGCAAGACCGGGGATGATGA
GGATGGCTCCACCGAGGAGGAGCGCATTGTGGGACGCTTCAAG
GGCTCCCTCTGCGTGTACAAAGTGCCACTCCCAGAGGACGTGT
CCCGGGAAGCCGGCTACGACTCCACCTACGGCATGTTCCAGGG
CATCCCGAGCAATGACCCCATCAATGTGCTGGTCCGAGTCTATG
TGGTCCGGGCCACGGACCTGCACCCTGCTGACATCAACGGCAA
AGCTGACCCCTACATCGCCATCCGGCTAGGCAAGACTGACATC
CGCGACAAGGAGAACTACATCTCCAAGCAGCTCAACCCTGTCTT
TGGGAAGTCCTTTGACATCGAGGCCTCCTTCCCCATGGAATCCA
TGCTGACGGTGGCTGTGTATGACTGGGACCTGGTGGGCACTGA
TGACCTCATTGGGGAAACCAAGATCGACCTGGAGAACCGCTTCT
ACAGCAAGCACCGCGCCACCTGCGGCATCGCCCAGACCTACTC
CACACATGGCTACAATATCTGGCGGGACCCCATGAAGCCCAGC
CAGATCCTGACCCGCCTCTGCAAAGACGGCAAAGTGGACGGCC
CCCACTTTGGGCCCCCTGGGAGAGTGAAGGTGGCCAACCGCGT
CTTCACTGGGCCCTCTGAGATTGAGGACGAGAACGGTCAGAGG
AAGCCCACAGACGAGCATGTGGCGCTGTTGGCCCTGAGGCACT
GGGAGGACATCCCCCGCGCAGGCTGCCGCCTGGTGCCAGAGC
ATGTGGAGACGAGGCCGCTGCTCAACCCCGACAAGCCGGGCAT
CGAGCAGGGCCGCCTGGAGCTGTGGGTGGACATGTTCCCCATG
GACATGCCAGCCCCTGGGACGCCTCTGGACATCTCACCTCGGA
AGCCCAAGAAGTACGAGCTGCGGGTCATCATCTGGAACACAGA
TGAGGTGGTCTTGGAGGACGACGACTTCTTCACAGGGGAGAAG
TCCAGTGACATCTTCGTGAGGGGGTGGCTGAAGGGCCAGCAGG
AGGACAAGCAGGACACAGACGTCCACTACCACTCCCTCACTGG
CGAGGGCAACTTCAACTGGCGCTACCTGTTCCCCTTCGACTACC
TGGCGGCGAGGAGAAGATCGTCATCTCCAAGAAGGAGTCCAT
GTTCTCCTGGGACGAGACCCGAGTACAAGATCCCCGCGCGGCTC
ACCCTGCAGATCTGGGATGCGGACCACTTCTCCGCTGACGACTT
CCTGGGGGCCATCGAGCTGGACCTGAACCGGTTCCCGCGGGG
CGCAAAGACAGCCAAGCAGTGCACCATGGAGATGGCCACCGGG
GAGGTGGACGTGCCCCTCGTGTCCATCTTCAAGCAAAAGCGCG
TCAAAGGCTGGTGGCCCCTCCTGGCCCGCAATGAGAACGATGA
GTTTGAGCTCACGGGCAAGGTGGAGGCTGAGCTGCATTTACTG
ACAGCAGAGGAGGCAGAGAAGAACCCAGTGGGCCTGGCCCGC
AATGAACCTGACCCCCTAGAGAAACCCAACCGGCCCGACACGG
CCTTCGTCTGGTTCCTCAACCCTCTCAAGTCCATCAAGTACCTCA
TCTGCACCCGGTACAAGTGGCTCATCATCAAGATCGTGCTGGCG
CTGTTGGGGCTGCTCATGTTGGGGCTCTTCCTCTACAGCCTCCC |

TABLE 2-continued

OTOF Sequences

| SEQ ID NO. | Sequence Name | Sequence |
|---|---|---|
| | | TGGCTACATGGTCAAAAAGCTCCTTGGGGCATGAAGGCCGCCA GCTCCCGCCAGCCGCTCCCCAGCCCTGCCGCATTTCCTTTCAG TGGCTTGGACTCTTTCCCATCTCCCCTGGGGAGCCTGAGGAGC CCAGCGTCCACTCTTCATGCCTTGGGCCGAGCCTGCCTCCTGC TTGCGGGGGCCGCCTGTCCTCACTGCCCCAGGCTGCGGCTTGC CCAGTCCCGCCCCTCTGACCCCTGCCTGTGGGCTGGGGAGCCT TGGATGGGGTGGGGACCTGGAATGGGTCTCTCTTGCCCCACCT GGCTGAGGCGCCACCCTTCTTCAGGCCCAGGCTCCAGAGGAAG ACTCCTGAAACCCTCCCCAGGTCTTCCAAGTACAGGATTGAAGC TTTAGTGAAATTAACCAAGGACCATGGGTCAGTGCCCAGGGCTT TAAAAAGAATGAACGAGCAAAAGGTATCCCCGCCGTGACCCCTG CAGATAGCACCGGTCTTTGATCCGCAGCAGGGGCCAGACCCTG CCCACAAGTCCCAGCGCGGCTGCTTCTGCCACTGCTGGGCTCC ACTTGGCTCCTCTCACTTCCCAGGGGGTCGCCTGTCCTGCCTGT GGGTTTCCATGGCTTCCCAGAGCTCCCTCTGCCCCAGCCAGCG CCTCCAGGCCCAGCTGAGGAGCTGTGAGAAGCAGCAGAGGGG ACTCCCCATCCCGGGCACACCCTGTCCTCCCACCCCTGCCCCC TTGCCCTTCCAGCCCTTTCAGCTGCAGCTGGGAGCTGGCCCGT CAAGTGCTGCCCCTGCCTGTGTCTGGGTTTCTGTTGGCTGTTTT TCTTTTCTTGAGTGGTGATTTTTCTCTAAATAAAAGAAGTCAAGC ACTGAAAAAAAAAAAAAA |
| 13 | OTOF-208 transcript (NM_194322.2), human otoferlin transcript variant 3, 3924 bp, encodes the protein of SEQ ID NO: 4 | CCGTGAGTTCTGCCCAGGCCCTGTGAGCTCACCAGAGCCACAG ACTCACAGCCCAGAGGTGGCTTCTTCCTTCAGGAACTGAAGAAC CCCCATGAACACCAACATCTCCAGGTTCTGAGAACAGAACCTGG GAAATTGATGACTTCCTCATGATGACCGATACTCAGGATGGCCC TAGCGAGAGCTCCCAGATCATGAGGTCCCTCACTCCCCTGATCA ACAGGGAGGAGGCATTTGGGGAGGCTGGGGAGGCGGGGCTGT GGCCCAGCATCACCCACACTCCTGATTCACAGGAAGAAGGCCT GAACGACATACAGGAGATGATCAAAACGGAGAAGTCCTACCCTG AGCGTCGCCTGCGGGGCGTCCTGGAGGAGCTGAGCTGTGGCT GCTGCCGCTTCCTCTCCCTCGCTGACAAGGACCAGGGCCACTC ATCCCGCACCAGGCTTGACCGGGAGCGCCTCAAGTCCTGCATG AGGGAGCTGGAAAACATGGGGCAGCAGGCCAGGATGCTGCGG GCCCAGGTGAAGCGGCACACGGTGCGGGACAAGCTGAGGCTG TGCCAGAACTTCCTGCAGAAGCTGCGCTTCCTGGCGGACGAGC CCCAGCACAGCATTCCCGACATCTTCATCTGGATGATGAGCAAC AACAAGCGTGTCGCCTATGCCCGTGTGCCCTCCAAGGACCTGC TCTTCTCCATCGTGGAGGAGGAGACTGGCAAGGACTGCGCCAA GGTCAAGACGCTCTTCCTTAAGCTGCCAGGGAAGCGGGGCTTC GGCTCGGCAGGCTGGACAGTGCAGGCCAAGGTGGAGCTGTAC CTGTGGCTGGGCCTCAGCAAACAGCGCAAGGAGTTCCTGTGCG GCCTGCCCTGTGGCTTCCAGGAGGTCAAGGCAGCCCAGGGCCT GGGCCTGCATGCCTTCCCACCCCGTCAGCCTGGTCTACACCAAG AAGCAGGCGTTCCAGCTCCGAGCGCACATGTACCAGGCCCGCA GCCTCTTTGCCGCCGACAGCAGCGGACTCTCAGACCCCTTTGC CCGCGTCTTCTTCATCAATCAGAGTCAGTGCACAGAGGTGCTGA ATGAGACCCTGTGTCCCACCTGGGACCAGATGCTGGTGTTCGA CAACCTGGAGCTCTATGGTGAAGCTCATGAGCTGAGGGACGAT CCGCCCATCATTGTCATTGAAATCTATGACCAGGATTCCATGGG CAAAGCTGACTTCATGGGCCGGACCTTCGCCAAACCCCTGGTG AAGATGGCAGACGAGGCGTACTGCCCACCCCGCTTCCCACCTC AGCTCGAGTACTACCAGATCTACCGTGGCAACGCCACAGCTGG AGACCTGCTGGCGGCCTTCGAGCTGCTGCAGATTGGACCAGCA GGGAAGGCTGACCTGCCCCCCATCAATGGCCCGGTGGACGTG GACCGAGGTCCCATCATGCCCGTGCCCATGGGCATCCGGCCCG TGCTCAGCAAGTACCGAGTGGAGGTGCTGTTCTGGGGCCTACG GGACCTAAAGCGGGTGAACCTGGCCCAGGTGGACCGGCTCACG GGTGGACATCGAGTGTGCAGGGAAGGGGGTGCAGTCGTCCCT GATCCACAATTATAAGAAGAACCCCAACTTCAACACCCTCGTCAA GTGGTTTGAAGTGGACCTCCCAGAGAACGAGCTGCTGCACCCG CCCTTGAACATCCGTGTGGTGGACTGCCGGGCCTTCGGTCGCT ACACACTGGTGGGCTCCCATGCCGTCAGCTCCCTGCGACGCTT CATCTACCGGCCCCCAGACCGCTCGGCCCCCAGCTGGAACACC ACGGTCAGGCTTCTCCGGCGCTGCCGTGTGCTGTGCAATGGGG GCTCCTCCTCTCACTCCACAGGGGAGGTTGTGGTGACTATGGA GCCAGAGGTACCCATCAAGAAACTGGAGACCATGGTGAAGCTG GACGCGACTTCTGAAGCTGTTGTCAAGGTGGATGTGGCTGAGG AGGAGAAGGAGAAGAAGAAGAAGAAGGGCACTGCGGAGG AGCCAGAGGAGGAGGAGCCAGACGAGAGCATGCTGGACTGGT GGTCCAAGTACTTTGCCTCCATTGACACCATGAAGGAGCAACTT CGACAACAAGAGCCCTCTGGAATTGACTTGGAGGAGAAGGAGG AAGTGGACAATACCGAGGGCCTGAAGGGGTCAATGAAGGGCAA GGAGAAGGCAAGGGCTGCCAAAGAGGAGAAGAAGAAGAAACT CAGAGCTCTGGCTCTGGCCAGGGGTCCGAGGCCCCCGAGAAG |

TABLE 2-continued

OTOF Sequences

| SEQ ID NO. | Sequence Name | Sequence |
|---|---|---|
| | | AAGAAACCCAAGATTGATGAGCTTAAGGTATACCCCAAAGAGCT<br>GGAGTCCGAGTTTGATAACTTTGAGGACTGGCTGCACACTTTCA<br>ACTTGCTTCGGGGCAAGACCGGGGATGATGAGGATGGCTCCAC<br>CGAGGAGGAGCGCATTGTGGGACGCTTCAAGGGCTCCCTCTGC<br>GTGTACAAAGTGCCACTCCCAGAGGACGTGTCCCGGGAAGCCG<br>GCTACGACTCCACCTACGGCATGTTCCAGGGCATCCCGAGCAA<br>TGACCCCATCAATGTGCTGGTCCGAGTCTATGTGGTCCGGGCC<br>ACGGACCTGCACCCTGCTGACATCAACGGCAAAGCTGACCCCT<br>ACATCGCCATCCGGCTAGGCAAGACTGACATCCGCGACAAGGA<br>GAACTACATCTCCAAGCAGCTCAACCCTGTCTTTGGGAAGTCCT<br>TTGACATCGAGGCCTCCTTCCCCATGGAATCCATGCTGACGGTG<br>GCTGTGTATGACTGGGACCTGGTGGGCACTGATGACCTCATTG<br>GGGAAACCAAGATCGACCTGGAGAACCGCTTCTACAGCAAGCA<br>CCGCGCCACCTGCGGCATCGCCCAGACCTACTCCACACATGGC<br>TACAATATCTGGCGGGACCCCATGAAGCCCAGCCAGATCCTGA<br>CCCGCCTCTGCAAAGACGGCAAAGTGGACGGCCCCCACTTTGG<br>GCCCCCTGGGAGAGTGAAGGTGGCCAACCGCGTCTTCACTGGG<br>CCCTCTGAGATTGAGGACGAGAACGGTCAGAGGAAGCCCACAG<br>ACGAGCATGTGGCGCTGTTGGCCCTGAGGCACTGGGAGGACAT<br>CCCCCGCGCAGGCTGCCGCCTGGTGCCAGAGCATGTGGAGAC<br>GAGGCCGCTGCTCAACCCCGACAAGCCGGGCATCGAGCAGGG<br>CCGCCTGGAGCTGTGGGTGGACATGTTCCCCATGGACATGCCA<br>GCCCCTGGGACGCCTCTGGACATCTCACCTCGGAAGCCCAAGA<br>AGTACGAGCTGCGGGTCATCATCTGGAACACAGATGAGGTGGT<br>CTTGGAGGACGACGACTTCTTCACAGGGGAGAAGTCCAGTGAC<br>ATCTTCGTGAGGGGGTGGCTGAAGGGCCAGCAGGAGGACAAG<br>CAGGACACAGACGTCCACTACCACTCCCTCACTGGCGAGGGCA<br>ACTTCAACTGGCGCTACCTGTTCCCCTTCGACTACCTGGCGGCG<br>GAGGAGAAGATCGTCATCTCCAAGAAGGAGTCCATGTTCTCCTG<br>GGACGAGACCGAGTACAAGATCCCCGCGCGGCTCACCCTGCAG<br>ATCTGGGATGCGGACCACTTCTCCGCTGACGACTTCCTGGGGG<br>CCATCGAGCTGGACCTGAACCGGTTCCCGCGGGGCGCAAAGAC<br>AGCCAAGCAGTGCACCATGGAGATGGCCACCGGGGAGGTGGA<br>CGTGCCCCTCGTGTCCATCTTCAAGCAAAAGCGCGTCAAAGGCT<br>GGTGGCCCCTCCTGGCCCGCAATGAGAACGATGAGTTTGAGCT<br>CACGGGCAAGGTGGAGGCTGAGCTGCATTTACTGACAGCAGAG<br>GAGGCAGAGAAGAACCCAGTGGGCCTGGCCCGCAATGAACCTG<br>ACCCCCTAGAGAAACCCAACCGGCCCGACACGAGCTTCATCTG<br>GTTCCTGAACCCTCTCAAGTCGGCTCGCTACTTCTTGTGGCACA<br>CGTATCGCTGGCTGCTCCTCAAACTGTTGCTGCTCCTGCTGCTG<br>CTCCTCCTCCTCGCCCTGTTCCTCTACTCTGTGCCTGGCTACCT<br>GGTCAAGAAAATCCTCGGGGCCTGAGCCCAGTGGCCTCCTGGC<br>CGGCCCGACACGGCCTTCGTCTGGTTCCTCAACCCTCTCAAGTC<br>CATCAAGTACCTCATCTGCACCCGGTACAAGTGGCTCATCATCA<br>AGATCGTGCTGGCGCTGTTGGGGCTGCTCATGTTGGGGCTCTT<br>CCTCTACAGCCTCCCTGGCTACATGGTCAAAAAGCTCCTTGGGG<br>CATGAAGGCCGCCAGCTCCCGCCAGCCGCTCCCCAGCCCTGCC<br>GCATTTCCTTTCAGTGGCTTGGACTCTTTCCCATCTCCCCTGGG<br>GAGCCTGAGGAGCCCAGCGTCCACTCTTCATGCCTTGGGCCGA<br>GCCTGCCTCCTGCTTGCGGGGCCGCCTGTCCTCACTGCCCCA<br>GGCTGCGGCTTGCCCAGTCCCGCCCCTCTGACCCCTGCCTGTG<br>GGCTGGGGAGCCTTGGATGGGGTGGGGACCTGGAATGGGTCT<br>CTCTTGCCCCACCTGGCTGAGGCGCCACCCTTCTTCAGGCCCA<br>GGCTCCAGAGGAAGACTCCTGAAACCCTCCCCAGGTCTTCCAA<br>GTACAGGATTGAAGCTTTAGTGAAATTAACCAAGGACCATGGGT<br>CAGTGCCCAGGGCTTTAAAAAGAATGAACGAGCAAAAGGTATCC<br>CCGCCGTGACCCCTGCAGATAGCACCGGTCTTTGATCCGCAGC<br>AGGGGCCAGACCCTGCCCACAAGTCCCAGCGCGGCTGCTTCTG<br>CCACTGCTGGGCTCCACTTGGCTCCTCTCACTTCCCAGGGGGT<br>CGCCTGTCCTGCCTGTGGGTTTCCATGGCTTCCCAGAGCTCCCT<br>CTGCCCCAGCCAGCGCCTCCAGGCCCAGCTGAGGAGCTGTGA<br>GAAGCAGCAGAGGGGACTCCCCATCCCGGGCACACCCTGTCCT<br>CCCACCCCTGCCCCCTTGCCCTTCCAGCCCTTTCAGCTGCAGCT<br>GGGAGCTGGCCCGTCAAGTGCTGCCCCTGCCTGTGTCTGGGTT<br>TCTGTTGGCTGTTTTCTTTTCTTGAGTGGTGATTTTTCTCTAAAT<br>AAAAGAAGTCAAGCACTGAAAAAAAAAAAAAAAA |
| 14 | OTOF-205 transcript (NM_001287489.1), human otoferlin transcript variant 5, 6937 bp, encodes the protein of SEQ ID NO: 5 | ATCGGAGGGGGTCGGGAGGAGGAGGAGGAGGCAGCGGCAG<br>AGAAGAGAGGCGTGTGAGCCGTGCTCCACCGGCTAGCTCCT<br>TCCCGCTGCTCCTGCCTGGCAGTGCCAGGCAGCCCACACCAGC<br>ATGGCCTTGCTCATCCACCTCAAGACAGTCTCGGAGCTGCGG<br>GCAGGGGCGACCGGATCGCCAAAGTGACTTTCCGAGGGCAATC<br>CTTCTACTCTCGGGTCCTGGAGAACTGTGAGGATGTGGCTGACT<br>TTGATGAGACATTTCGGTGGCCGGTGGCCAGCAGCATCGACAG<br>AAATGAGATGCTGGAGATTCAGGTTTTCAACTACAGCAAAGTCTT |

TABLE 2-continued

OTOF Sequences

| SEQ ID NO. | Sequence Name | Sequence |
|---|---|---|
| | | CAGCAACAAGCTCATCGGGACCTTCCGCATGGTGCTGCAGAAG
GTGGTAGAGGAGAGCCATGTGGAGGTGACTGACACGCTGATTG
ATGACAACAATGCTATCATCAAGACCAGCCTGTGCGTGAGGTC
CGGTATCAGGCCACTGACGGCACAGTGGGCTCCTGGGACGATG
GGGACTTCCTGGGAGATGAGTCTCTTCAAGAGGAAGAGAAGGA
CAGCCAAGAGACGGATGGACTGCTCCCAGGCTCCCGGCCCAGC
TCCCGGCCCCCAGGAGAGAAGAGCTTCCGGAGAGCCGGGAGG
AGCGTGTTCTCCGCCATGAAGCTCGGCAAAAACCGGTCTCACAA
GGAGGAGCCCCAAAGACCAGATGAACCGGCGGTGCTGGAGAT
GGAAGACCTTGACCATCTGGCCATTCGGCTAGGAGATGGACTG
GATCCCGACTCGGTGTCTCTAGCCTCAGTCACAGCTCTCACCAC
TAATGTCTCCAACAAGCGATCTAAGCCAGACATTAAGATGGAGC
CAAGTGCTGGGCGGCCCATGGATTACCAGGTCAGCATCACGGT
GATCGAGGCCCGGCAGCTGGTGGGCTTGAACATGGACCCTGTG
GTGTGCGTGGAGGTGGGTGACGACAAGAAGTACACATCCATGA
AGGAGTCCACTAACTGCCCCTATTACAACGAGTACTTCGTCTTC
GACTTCCATGTCTCTCCGGATGTCATGTTTGACAAGATCATCAAG
ATTTCGGTGATTCACTCCAAGAACCTGCTGCGCAGTGGCACCCT
GGTGGGCTCCTTCAAAATGGACGTGGGAACCGTGTACTCGCAG
CCAGAGCACCAGTTCCATCACAAGTGGGCCATCCTGTCTGACCC
CGATGACATCTCCTCGGGGCTGAAGGGCTACGTGAAGTGTGAC
GTTGCCGTGGTGGGCAAAGGGGACAACATCAAGACGCCCCACA
AGGCCAATGAGACCGACGAAGATGACATTGAGGGGAACTTGCT
GCTCCCGAGGGGGTGCCCCCCGAACGCCAGTGGGCCCGGTT
CTATGTGAAAATTTACCGAGCAGAGGGGCTGCCCCGTATGAACA
CAAGCCTCATGGCCAATGTAAAGAAGGCTTTCATCGGTGAAAAC
AAGGACCTCGTGGACCCCTACGTGCAAGTCTTCTTTGCTGGCCA
GAAGGGCAAGACTTCAGTGCAGAAGAGCAGCTATGAGCCCCTG
TGGAATGAGCAGGTCGTCTTTACAGACCTCTTCCCCCCACTCTG
CAAACGCATGAAGGTGCAGATCCGAGACTCGGACAAGGTCAAC
GACGTGGCCATCGGCACCCACTTCATTGACCTGCGCAAGATTTC
TAATGACGGAGACAAAGGCTTCCTGCCCCACACTGGGCCCAGCC
TGGGTGAACATGTACGGCTCCACACGTAACTACACGCTGCTGGA
TGAGCATCAGGACCTGAACGAGGGCCTGGGGGAGGGTGTGTC
CTTCCGGGCCCGGCTCCTGCTGGGCCTGGCTGTGGAGATCGTA
GACACCTCCAACCCTGAGCTCACCAGCTCCACAGAGGTGCAGG
TGGAGCAGGCCACGCCCATCTCGGAGAGCTGTGCAGGTAAAAT
GGAAGAATTCTTTCTCTTTGGAGCCTTCCTGGAGGCCTCAATGA
TCGACCGGAGAAACGGAGACAAGCCCATCACCTTTGAGGTCAC
CATAGGCAACTATGGGAACGAAGTTGATGGCCTGTCCCGGCCC
CAGCGGCCTCGGCCCCGGAAGGAGCCGGGGGATGAGGAAGAA
GTAGACCTGATTCAGAACGCAAGTGATGACGAGGCCGGTGATG
CCGGGGACCTGGCCTCAGTCTCCTCCACTCCACCAATGCGGCC
CCAGGTCACCGACAGGAACTACTTCCATCTGCCCTACCTGGAGC
GAAAGCCCTGCATCTACATCAAGAGCTGGTGGCCGGACCAGCG
CCGCCGCCTCTACAATGCCAACATCATGGACCACATTGCCGACA
AGCTGGAAGAAGGCCTGAACGACATACAGGAGATGATCAAAAC
GGAGAAGTCCTACCCTGAGCGTCGCCTGCGGGGCGTCCTGGA
GGAGCTGAGCTGTGGCTGCTGCCGCTTCCTCTCCCTCGCTGAC
AAGGACCAGGGCCACTCATCCCGCACCAGGCTTGACCGGGAGC
GCCTCAAGTCCTGCATGAGGGAGCTGGAAAACATGGGGCAGCA
GGCCAGGATGCTGCGGGCCCAGGTGAAGCGGCACACGGTGCG
GGACAAGCTGAGGCTGTGCCAGAACTTCCTGCAGAAGCTGCGC
TTCCTGGCGGACGAGCCCCAGCACAGCATTCCCGACATCTTCAT
CTGGATGATGAGCAACAACAAGCGTGTCGCCTATGCCCGTGTG
CCCTCCAAGGACCTGCTCTTCTCCATCGTGGAGGAGGAGACTG
GCAAGGACTGCGCCAAGGTCAAGACGCTCTTCCTTAAGCTGCC
AGGGAAGCGGGGCTTCGGCTCGGCAGGCTGGACAGTGCAGGC
CAAGGTGGAGCTGTACCTGTGGCTGGGCCTCAGCAAACAGCGC
AAGGAGTTCCTGTGCGGCCTGCCCTGTGCTTCCAGGAGGTCA
AGGCAGCCCAGGGCCTGGGCCTGCATGCCTTCCCACCCGTCAG
CCTGGTCTACACCAAGAAGCAGGCGTTCCAGCTCCGAGCGCAC
ATGTACCAGGCCCGCAGCCTCTTTGCCGCCGACAGCAGCGGAC
TCTCAGACCCCTTTGCCCGCGTCTTCTTCATCAATCAGAGTCAG
TGCACAGAGGTGCTGAATGAGACCCTGTGTCCCACCTGGGACC
AGATGCTGGTGTTCGACAACCTGGAGCTCTATGGTGAAGCTCAT
GAGCTGAGGGACGATCCGCCCATCATTGTCATTGAAATCTATGA
CCAGGATTCCATGGGCAAAGCTGACTTCATGGGCCGGACCTTC
GCCAAACCCCTGGTGAAGATGGCAGACGAGGCGTACTGCCCAC
CCCGCTTCCCACCTCAGCTCGAGTACTACCAGATCTACCGTGGC
AACGCCACAGCTGGAGACCTGCTGGCGGCCTTCGAGCTGCTGC
AGATTGGACCAGCAGGGAAGGCTGACCTGCCCCCCATCAATGG
CCCGGTGGACGTGGACCGAGGTCCCATCATGCCCGTGCCCATG
GGCATCCGGCCCGTGCTCAGCAAGTACCGAGTGGAGGTGCTGT
TCTGGGGCCTACGGGACCTAAAGCGGGTGAACCTGGCCCAGGT |

TABLE 2-continued

OTOF Sequences

| SEQ ID NO. | Sequence Name | Sequence |
|---|---|---|
| | | GGACCGGCCACGGGTGGACATCGAGTGTGCAGGGAAGGGGGT
GCAGTCGTCCCTGATCCACAATTATAAGAAGAACCCCAACTTCA
ACACCCTCGTCAAGTGGTTTGAAGTGGACCTCCCAGAGAACGA
GCTGCTGCACCCGCCCTTGAACATCCGTGTGGTGGACTGCCGG
GCCTTCGGTCGCTACACACTGGTGGGCTCCCATGCCGTCAGCT
CCCTGCGACGCTTCATCTACCGGCCCCAGACCGCTCGGCCCC
CAGCTGGAACACCACGGTCAGGCTTCTCCGGCGCTGCCGTGTG
CTGTGCAATGGGGGCTCCTCCTCTCACTCCACAGGGGAGGTTG
TGGTGACTATGGAGCCAGAGGTACCCATCAAGAAACTGGAGAC
CATGGTGAAGCTGGACGCGACTTCTGAAGCTGTTGTCAAGGTG
GATGTGGCTGAGGAGGAGAAGGAGAAGAAGAAGAAGAAGAAGG
GCACTGCGGAGGAGCCAGAGGAGGAGGAGCCAGACGAGAGCA
TGCTGGACTGGTGGTCCAAGTACTTTGCCTCCATTGACACCATG
AAGGAGCAACTTCGACAACAAGAGCCCTCTGGAATTGACTTGGA
GGAGAAGGAGGAAGTGGACAATACCGAGGGCCTGAAGGGGTC
AATGAAGGGCAAGGAGAAGGCAAGGGCTGCCAAAGAGGAGAAG
AAGAAGAAAACTCAGAGCTCTGGCTCTGGCCAGGGGTCCGAGG
CCCCCGAGAAGAAGAAACCCAAGATTGATGAGCTTAAGGTATAC
CCCAAAGAGCTGGAGTCCGAGTTTGATAACTTTGAGGACTGGCT
GCACACTTTCAACTTGCTTCGGGGCAAGACCGGGGATGATGAG
GATGGCTCCACCGAGGAGGAGCGCATTGTGGGACGCTTCAAGG
GCTCCCTCTGCGTGTACAAAGTGCCACTCCCAGAGGACGTGTC
CCGGGAAGCCGGCTACGACTCCACCTACGGCATGTTCCAGGGC
ATCCCGAGCAATGACCCCATCAATGTGCTGGTCCGAGTCTATGT
GGTCCGGGCCACGGACCTGCACCCTGCTGACATCAACGGCAAA
GCTGACCCCTACATCGCCATCCGGCTAGGCAAGACTGACATCC
GCGACAAGGAGAACTACATCTCCAAGCAGCTCAACCCTGTCTTT
GGGAAGTCCTTTGACATCGAGGCCTCCTTCCCCATGGAATCCAT
GCTGACGGTGGCTGTGTATGACTGGGACCTGGTGGGCACTGAT
GACCTCATTGGGGAAACCAAGATCGACCTGGAGAACCGCTTCTA
CAGCAAGCACCGCGCCACCTGCGGCATCGCCCAGACCTACTCC
ACACATGGCTACAATATCTGGCGGGACCCCATGAAGCCCCAGCC
AGATCCTGACCCGCCTCTGCAAAGACGGCAAAGTGGACGGCCC
CCACTTTGGGCCCCCTGGGAGAGTGAAGGTGGCCAACCGCGTC
TTCACTGGGCCCTCTGAGATTGAGGACGAGAACGGTCAGAGGA
AGCCCACAGACGAGCATGTGGCGCTGTTGGCCCTGAGGCACTG
GGAGGACATCCCCCGCGCAGGCTGCCGCCTGGTGCCAGAGCA
TGTGGAGACGAGGCCGCTGCTCAACCCCGACAAGCCGGGCATC
GAGCAGGGCCGCCTGGAGCTGTGGGTGGACATGTTCCCCATGG
ACATGCCAGCCCCTGGGACGCCTCTGGACATCTCACCTCGGAA
GCCCAAGAAGTACGAGCTGCGGGTCATCATCTGGAACACAGAT
GAGGTGGTCTTGGAGGACGACGACTTCTTCACAGGGGAGAAGT
CCAGTGACATCTTCGTGAGGGGGTGGCTGAAGGGCCAGCAGGA
GGACAAGCAGGACACAGACGTCCACTACCACTCCCTCACTGGC
GAGGGCAACTTCAACTGGCGCTACCTGTTCCCCTTCGACTACCT
GGCGGCGGAGGAGAAGATCGTCATCTCCAAGAAGGAGTCCATG
TTCTCCTGGGACGAGACCGAGTACAAGATCCCCGCGCGGCTCA
CCCTGCAGATCTGGGATGCGGACCACTTCTCCGCTGACGACTT
CCTGGGGGCCATCGAGCTGGACCTGAACCGGTTCCCGCGGGG
CGCAAAGACAGCCAAGCAGTGCACCATGGAGATGGCCACCGGG
GAGGTGGACGTGCCCCTCGTGTCCATCTTCAAGCAAAAGCGCG
TCAAAGGCTGGTGGCCCCTCCTGGCCCGCAATGAGAACGATGA
GTTTGAGCTCACGGGCAAGGTGGAGGCTGAGCTGCATTTACTG
ACAGCAGAGGAGGCAGAGAAGAACCCAGTGGGCCTGGCCCGC
AATGAACCTGACCCCCTAGAGAAACCCAACCGGCCCGACACGG
CCTTCGTCTGGTTCCTCAACCCCTCTCAAGTCCATCAAGTACCTCA
TCTGCACCCGGTACAAGTGGCTCATCATCAAGATCGTGCTGGCG
CTGTTGGGCTGCTCATGTTGGGGCTCTTCCTCTACAGCCTCCC
TGGCTACATGGTCAAAAAGCTCCTTGGGGCATGAAGGCCGCCA
GCTCCCGCCAGCCGCTCCCCAGCCCTGCCGCATTTCCTTTCAG
TGGCTTGGACTCTTTCCCATCTCCCCTGGGGAGCCTGAGGAGC
CCAGCGTCCACTCTTCATGCCTTGGGCCGAGCCTGCCTCCTGC
TTGCGGGGCCGCCTGTCCTCACTGCCCCAGGCTGCGGCTTGC
CCAGTCCGCCCCTCTGACCCCTGCCTGTGGGCTGGGGAGCCT
TGGATGGGTGGGGACCTGGAATGGGTCTCTCTTGCCCCACCT
GGCTGAGGCGCCACCCTTCTTCAGGCCCAGGCTCCAGAGGAAG
ACTCCTGAAACCCTCCCCAGGTCTTCCAAGTACAGGATTGAAGC
TTTAGTGAAATTAACCAAGGACCATGGGTCAGTGCCCAGGGCTT
TAAAAAGAATGAACGAGCAAAAGGTATCCCCGCCGTGACCCCTG
CAGATAGCACCGGTCTTTGATCCGCAGCAGGGGCCAGACCCTG
CCCACAAGTCCCAGCGCGGCTGCTTCTGCCACTGCTGGGCTCC
ACTTGGCTCCTCTCACTTCCCAGGGGTCGCCTGTCCTGCCTGT
GGGTTTCCATGGCTTCCCAGAGCTCCCTCTGCCCCAGCCAGCG
CCTCCAGGCCCAGCTGAGGAGCTGTGAGAAGCAGCAGAGGGG
ACTCCCCATCCCGGGCACACCCTGTCCTCCCACCCCTGCCCCC |

TABLE 2-continued

OTOF Sequences

| SEQ ID NO. | Sequence Name | Sequence |
|---|---|---|
| | | TTGCCCTTCCAGCCCTTTCAGCTGCAGCTGGGAGCTGGCCCGT<br>CAAGTGCTGCCCCTGCCTGTGTCTGGGTTTCTGTTGGCTGTTTT<br>TCTTTTCTTGAGTGGTGATTTTTCTCTAAATAAAAGAAGTCAAGC<br>ACTGAAAAAAAAAAAAAAAAA |
| 15 | mOTOF-201_1 transcript (NM_031875.2), mouse otoferlin transcript variant 2, 7129 bp, encodes the protein of SEQ ID NO: 6 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGAGCGGGAAG<br>GAGTGTGTTCTCGGCCATGAAACTCGGCAAAACTCGGTCCCACA<br>AAGAGGAGCCCCAAAGACAAGATGAGCCAGCAGTGCTGGAGAT<br>GGAGGACCTGGACCACCTAGCCATTCAGCTGGGGGATGGGCTG<br>GATCCTGACTCCGTGTCTCTAGCCTCGGTCACCGCTCTCACCAG<br>CAATGTCTCCAACAAACGGTCTAAGCCAGATATTAAGATGGAGC<br>CCAGTGCTGGAAGGCCCATGGATTACCAGGTCAGCATCACAGT<br>GATTGAGGCTCGGCAGCTGGTGGGCTTGAACATGGACCCTGTG<br>GTGTGTGTGGAGGTGGGTGATGACAAGAAATACACGTCAATGAA<br>GGAGTCCACAAACTGCCCTTACTACAACGAGTACTTTGTCTTCG<br>ACTTCCATGTCTCTCCTGATGTCATGTTTGACAAGATCATCAAGA<br>TCTCGGTTATCCATTCTAAGAACCTGCTTCGGAGCGGCACCCTG<br>GTGGGTTCCTTCAAAATGGATGTGGGGACTGTGTATTCCCAGCC<br>TGAACACCAGTTCCATCACAAATGGGCCATCCTGTCAGACCCCG<br>ATGACATCTCTGCTGGGTTGAAGGGTTATGTAAAGTGTGATGTC<br>GCTGTGGTGGGCAAGGGAGACAACATCAAGACACCCCACAAGG<br>CCAACGAGACGGATGAGGACGACATTGAAGGGAACTTGCTGCT<br>CCCCGAGGGCGTGCCCCCCGAACGGCAGTGGGCACGGTTCTA<br>TGTGAAAATTTACCGAGCAGAGGGACTGCCCCGGATGAACACAA<br>GCCTCATGGCCAACGTGAAGAAGGCGTTCATCGGTGAGAACAA<br>GGACCTCGTCGACCCCTATGTGCAAGTCTTCTTTGCTGGACAAA<br>AGGGCAAAACATCAGTGCAGAAGAGCAGCTATGAGCCGCTATG<br>GAATGAGCAGGTCGTCTTCACAGACTTGTTCCCCCCACTCTGCA<br>AACGCATGAAGGTGCAGATCCGGGACTCTGACAAGGTCAATGAT<br>GTGGCCATCGGCACCCACTTCATCGACCTGCGCAAGATTTCCAA<br>CGATGGAGACAAAGGCTTCCTGCCTACCCTCGGTCCAGCCTGG<br>GTGAACATGTACGGCTCCACGCGCAACTACACACTGCTGGACG<br>AGCACCAGGACTTGAATGAAGGCCTGGGGGAGGGTGTGTCCTT<br>CCGGGCCCGCCTCATGTTGGGACTAGCTGTGGAGATCCTGGAC<br>ACCTCCAACCCAGAGCTCACCAGCTCCACGGAGGTGCAGGTGG<br>AGCAGGCCACGCCTGTCTCGGAGAGCTGCACAGGGAGAATGGA<br>AGAATTTTTTCTATTTGGAGCCTTCTTGGAAGCCTCAATGATTGA<br>CCGGAAAAATGGGGACAAGCCAATTACCTTTGAGGTGACCATAG<br>GAAACTACGGCAATGAAGTCGATGGTATGTCCCGGCCCCTGAG<br>GCCTCGGCCCCGGAAAGAGCTGGGGATGAAGAAGAGGTAGA<br>CCTGATTCAGAACTCCAGTGACGATGAAGGTGACGAAGCCGGG<br>GACCTGGCCTCGGTGTCCTCCACCCCACCTATGCGGCCCCAGA<br>TCACGGACAGGAACTATTTCCACCTGCCCTACCTGGAGCGCAAG<br>CCCTGCATCTATATCAAGAGCTGGTGGCCTGACCAGAGGCGGC<br>GCCTCTACAATGCCAACATCATGGATCACATTGCTGACAAGCTG<br>GAAGAAGGCCTGAATGATGTACAGGAGATGATCAAAACGGAGAA<br>GTCCTACCCGGAGCGCCGCCTGCGGGTGTGCTAGAGGAACTC<br>AGCTGTGGCTGCCACCGCTTCCTCTCCCTCTCGGACAAGGACC<br>AGGGCCGCTCGTCCCGCACCAGGCTGGATCGAGAGCGTCTTAA<br>GTCCTGTATGAGGGAGTTGGAGAGCATGGGACAGCAGGCCAAG<br>AGCCTGAGGGCTCAGGTGAAGCGGCACACTGTTCGGGACAAGC<br>TGAGGTCATGCCAGAACTTTCTGCAGAAGCTACGCTTCCTGGCG<br>GATGAGCCCCAGCACAGCATTCCTGATGTGTTCATTTGGATGAT<br>GAGCAACAACAAACGTATCGCCTATGCCCGCGTGCCTTCCAAAG<br>ACCTGCTCTTCTCCATCGTGGAGGAGGAACTGGGCAAGGACTG<br>CGCCAAAGTCAAGACCCTCTTCCTGAAGCTGCCAGGGAAGAGG<br>GGCTTCGGCTCGGCAGGCTGGACAGTACAGGCCAAGCTGGAG<br>CTCTACCTGTGGCTGGGCCTCAGCAAGCAGCGAAAGGACTTCC<br>TGTGTGGTCTGCCCCTGTGGCTTCGAGGAGGTCAAGGCAGCCCA<br>AGGCCTGGGCCTGCATTCCTTTCCGCCCATCAGCCTAGTCTACA<br>CCAAGAAGCAAGCCTTCCAGCTCCGAGCACACATGTATCAGGC |

TABLE 2-continued

OTOF Sequences

| SEQ ID NO. | Sequence Name | Sequence |
|---|---|---|
| | | CCGAAGCCTCTTTGCTGCTGACAGCAGTGGGCTCTCTGATCCCT
TTGCCCGTGTCTTCTTCATCAACCAGAGCCAATGCACTGAGGTT
CTAAACGAGACACTGTGTCCCACCTGGGACCAGATGCTGGTATT
TGACAACCTGGAGCTGTACGGTGAAGCTCACGAGTTACGAGAT
GATCCCCCCATCATTGTCATTGAAATCTACGACCAGGACAGCAT
GGGCAAAGCCGACTTCATGGGCCGGACCTTCGCCAAGCCCCTG
GTGAAGATGGCAGATGAAGCATACTGCCCACCTCGCTTCCCGC
CGCAGCTTGAGTACTACCAGATCTACCGAGGCAGTGCCACTGC
CGGAGACCTACTGGCTGCCTTCGAGCTGCTGCAGATTGGGCCA
TCAGGGAAGGCTGACCTGCCACCCATCAATGGCCCAGTGGACA
TGGACAGAGGGCCCATCATGCCTGTGCCCGTGGGAATCCGGCC
AGTGCTCAGCAAGTACCGAGTGGAGGTGCTGTTCTGGGGCCTG
AGGGACCTAAAGAGGGTGAACCTGGCCCAGGTGGACCGACCAC
GGGTGGACATCGAGTGTGCAGGAAAGGGGGTACAATCCTCCCT
GATTCACAATTATAAGAAGAACCCCAACTTCAACACGCTGGTCAA
GTGGTTTGAAGTGGACCTCCCGGAGAATGAGCTCCTGCACCCA
CCCTTGAACATCCGAGTGGTAGATTGCCGGGCCTTTGGACGATA
CACCCTGGTGGGTTCCCACGCAGTCAGCTCACTGAGGCGCTTC
ATCTACCGACCTCCAGACCGCTCAGCCCCAACTGGAACACCA
CAGTCAGGCTGCTCCGGGGCTGCCACAGGCTGCGCAATGGGG
GCCCCTCTTCTCGCCCCACAGGGGAGGTTGTAGTAAGCATGGA
GCCTGAGGAGCCAGTTAAGAAGCTGGAGACCATGGTGAAACTG
GATGCGACTTCTGATGCTGTGGTCAAGGTGGATGTGGCTGAAG
ATGAGAAGGAAAGGAAGAAGAAGAAAAAGAAAGGCCCGTCAGA
GGAGCCAGAGGAGGAAGAGCCCGATGAGAGCATGCTGGATTG
GTGGTCCAAGTACTTCGCCTCCATCGACACAATGAAGGAGCAAC
TTCGACAACATGAGACCTCTGGAACTGACTTGGAAGAGAAGGAA
GAGATGGAAAGCGCTGAGGGCCTGAAGGGACCAATGAAGAGCA
AGGAGAAGTCCAGAGCTGCAAAGGAGGAGAAAAAGAAGAAAAA
CCAGAGCCCTGGCCCTGGCCAGGGATCGGAGGCTCCTGAGAA
GAAGAAAGCCAAGATCGATGAGCTTAAGGTGTACCCCAAGGAG
CTGGAATCGGAGTTTGACAGCTTTGAGGACTGGCTGCACACCTT
CAACCTGTTGAGGGGCAAGACGGGAGATGATGAGGATGGCTCC
ACAGAGGAGGAGCGCATAGTAGGCCGATTCAAGGGCTCCCTCT
GTGTGTACAAAGTGCCACTCCCAGAAGATGTATCTCGAGAAGCT
GGCTATGATCCCACCTATGGAATGTTCCAGGGCATCCCAAGCAA
TGACCCCATCAATGTGCTGGTCCGAATCTATGTGGTCCGGGCCA
CAGACCTGCACCCGGCCGACATCAATGGCAAAGCTGACCCCTA
TATTGCCATCAAGTTAGGCAAGACCGACATCCGAGACAAGGAGA
ACTACATCTCCAAGCAGCTCAACCCTGTGTTTGGGAAGTCCTTT
GACATTGAGGCCTCCTTCCCCATGGAGTCCATGTTGACAGTGGC
CGTGTACGACTGGGATCTGGTGGGCACTGATGACCTCATCGGA
GAAACCAAGATTGACCTGGAAAACCGCTTCTACAGCAAGCATCG
CGCCACCTGCGGCATCGCACAGACCTATTCCATACATGGCTACA
ATATCTGGAGGGACCCCATGAAGCCCAGCCAGATCCTGACACG
CCTCTGTAAAGAGGGCAAAGTGGACGGCCCCCACTTTGGTCCC
CATGGGAGAGTGAGGGTTGCCAACCGTGTCTTCACGGGGCCTT
CAGAAATAGAGGATGAGAATGGTCAGAGGAAGCCCACAGATGA
GCACGTGGCACTGTCTGCTCTGAGACACTGGGAGGACATCCCC
CGGGTGGGCTGCCGCCTTGTGCCGGAACACGTGGAGACCAGG
CCGCTGCTCAACCCTGACAAGCCAGGCATTGAGCAGGGCCGCC
TGGAGCTGTGGGTGGACATGTTCCCCATGGACATGCCAGCCCC
TGGGACACCTCTGGATATATCCCCCAGGAAACCCAAGAAGTACG
AGCTGCGGGTCATCGTGTGGAACACAGACGAGGTGGTCCTGGA
AGACGATGATTTCTTCACGGGAGAGAAGTCCAGTGACATTTTTG
TGAGGGGGTGGCTGAAGGGCCAGCAGGAGGACAAACAGGACA
CAGATGTCCACTATCACTCCCTCACGGGGGAGGGCAACTTCAAC
TGGAGATACCTCTTCCCCTTCGACTACCTAGCGGCCGAAGAGAA
GATCGTTATGTCCAAAAAGGAGTCTATGTTCTCCTGGGATGAGA
CGGAGTACAAGATCCCTGCGCGGCTCACCCTGCAGATCTGGGA
CGCTGACCACTTCTCGGCTGACGACTTCCTGGGGGCTATCGAG
CTGGACCTGAACCGGTTCCCGAGGGGCGCTAAGACAGCCAAGC
AGTGCACCATGGAGATGGCCACCGGGGAGGTGGACGTACCCCT
GGTTTCCATCTTTAAACAGAAACGTGTCAAAGGCTGGTGGCCCC
TCCTGGCCCGCAATGAGAATGATGAGTTTGAGCTCACAGGCAAA
GTGGAGGCGGAGCTACACCTACTCACGGCAGAGGAGGCAGAG
AAGAACCCGTGGGCCTGGCTCGCAATGAACCTGATCCCCTAG
AAAAACCCAATCGGCCGGACACAAGCTTCATCTGGTTCTTGAAC
CCTCTCAAGTCTGCCCGCTACTTCCTGTGGCATACCTACCGCTG
GCTACTCCTCAAATTCCTGCTGCTCTTCCTCCTGCTGCTGCTCTT
CGCCCTGTTTCTCTACTCTCTGCCTGGCTACCTGGCCAAGAAGA
TCCTTGGGGCCTGAGCCCTGCAGTCGCCTAGGCCTGCCGGCCT
GACACGGCATTCGTCTGGTTCCTGAACCCACTCAAATCTATCAA
GTACCTCATCTGCACCCGGTACAAGTGGCTGATCATCAAGATCG
TGCTGGCGCTGCTGGGGCTGCTCATGCTGGCCCTCTTCCTTTAC |

TABLE 2-continued

OTOF Sequences

| SEQ ID NO. | Sequence Name | Sequence |
|---|---|---|
| | | AGCCTCCCAGGCTACATGGTCAAGAAGCTCCTAGGGGCCTGAA<br>GTGTGCCCCACCCCAGCCCGCTCCAGCATCCCTCCAGGGGCTG<br>CTGCGTATTTTGCCTTCCCTCACCTGGACTCTCTCCCAACTCCCT<br>GAGGAGCCCTCCCACGCCTGCCAGCCTTGAGCAAGACACCTGC<br>TTGCTGGACTTCATCCCCACCCCACACCCAAACTGTTGCTTGCC<br>TGATCTTGTCCCAGGCCTGCCTGGGGTTTGGGGCACAGTTGGC<br>CTCCAAAACCAGATACCCTCTTGTCTAAAGTACCAGGTTCCTCTG<br>CCCAACCCCAAGAGTGGTAGTGGCCCAACCCTCCCTGTGCTTTC<br>CAAATCTTGTCTTAAGGCACCAGTGAAATTAACCAAGAAACGCG<br>GAGCAATGCCCAAGGCTCTGATGAGTAGGAACACGTGGAAAGC<br>ACCAGGAATGCCAGCAGAGGCGAGGCGGCACACCTCTCTGCAG<br>AGCATCCAGGCCGAGCGGCGGGCAGCGGCCAGCTGCTTCTGC<br>GCATGCTCTCCTCTTGGCTCTGCTTCTTTCTCACAGTCACAGTCA<br>CTTCACAGCTTAGCCTTGGGCTTCCCATCACTTCCAGGGGTGCC<br>TCTGCCTTGGCCAGTGTGTGTCAGCTAGTACACAAGCTCCAAGT<br>GTGAATCAGGTGTACTGGCCGTCCTGAAGACTGACTGCCCTGTC<br>CTTCCTGCCGACAGCCACACCCGAGTGTACACTTAAAGCGGTG<br>CCCTTCTGCCTCTGTGGGCCTGCTGGCTGCTGTTCCTTTCTTGA<br>GTGTGATTTTTTTTTCTCTCCCTCAATAAAATAAATCAAACTCTG<br>AGAC |
| 16 | mOTOF-201_2 transcript (NM_001286421.1), mouse otoferlin transcript variant 3, 7129 bp, encodes the protein of SEQ ID NO: 7 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>TGATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGAGCGGGAAG<br>GAGTGTGTTCTCGGCCATGAAAACTCGGCAAAACTCGGTCCCACA<br>AAGAGGAGCCCCAAAGACAAGATGAGCCAGCAGTGCTGGAGAT<br>GGAGGACCTGGACCACCTAGCCATTCAGCTGGGGGATGGGCTG<br>GATCCTGACTCCGTGTCTCTAGCCTCGGTCACCGCTCTCACCAG<br>CAATGTCTCCAACAAACGGTCTAAGCCAGATATTAAGATGGAGC<br>CCAGTGCTGGAAGGCCCATGGATTACCAGGTCAGCATCACAGT<br>GATTGAGGCTCGGCAGCTGGTGGGCTTGAACATGGACCCTGTG<br>GTGTGTGTGGAGGTGGGTGATGACAAGAAATACACGTCAATGAA<br>GGAGTCCACAAACTGCCCTTACTACAACGAGTACTTTGTCTTCG<br>ACTTCCATGTCTCTCCTGATGTCATGTTTGACAAGATCATCAAGA<br>TCTCGGTTATCCATTCTAAGAACCTGCTTCGGAGCGGCACCCTG<br>GTGGGTTCCTTCAAAATGGATGTGGGGACTGTGTATTCCCAGCC<br>TGAACACCAGTTCCATCACAAATGGGCCATCCTGTCAGACCCCG<br>ATGACATCTCTGCTGGGTTGAAGGGTTATGTAAAGTGTGATGTC<br>GCTGTGGTGGGCAAGGGAGACAACATCAAGACACCCCACAAGG<br>CCAACGAGACGGATGAGGACGACATTGAAGGGAACTTGCTGCT<br>CCCCGAGGGCGTGCCCCCCGAACGGCAGTGGGCACGGTTCTA<br>TGTGAAAATTTACCGAGCAGAGGGACTGCCCCGGATGAACACAA<br>GCCTCATGGCCAACGTGAAGAAGGCGTTCATCGGTGAGAACAA<br>GGACCTCGTCGACCCCTATGTGCAAGTCTTCTTTGCTGGACAAA<br>AGGGCAAAACATCAGTGCAGAAGAGCAGCTATGAGCCGCTATG<br>GAATGAGCAGGTCGTCTTCACAGACTTGTTCCCCCCACTCTGCA<br>AACGCATGAAGGTGCAGATCCGGGACTCTGACAAGGTCAATGAT<br>GTGGCCATCGGCACCCACTTCATCGACCTGCGCAAGATTTCCAA<br>CGATGGAGACAAAGGCTTCCTGCCTACCCCTGGTCCAGCCTGG<br>GTGAACATGTACGGCTCCACGCGCAACTACACACTGCTGGACG<br>AGCACCAGGACTTGAATGAAGGCCTGGGGGAGGGTGTGTCCTT<br>CCGGGCCCGCCTCATGTTGGGACTAGCTGTGGAGATCCTGGAC<br>ACCTCCAACCCAGAGCTCACCAGCTCCACGGAGGTGCAGGTGG<br>AGCAGGCCACGCCTGTCTCGGAGAGCTGCACAGGGAGAATGGA<br>AGAATTTTTTCTATTTGGAGCCTTCTTGGAAGCCTCAATGATTGA<br>CCGGAAAAATGGGGACAAGCCAATTACCTTTGAGGTGACCATAG<br>GAAACTACGGCAATGAAGTCGATGGTATGTCCCGGCCCCTGAG<br>GCCTCGGCCCCGGAAAGAGCCTGGGGATGAAGAAGAGGTAGA<br>CCTGATTCAGAACTCCAGTGACGATGAAGGTGACGAAGCCGGG<br>GACCTGGCCTCGGTGTCCTCCACCCCACCTATGCGGCCCCAGA<br>TCACGGACAGGAACTATTTCCACCTGCCCTACCTGGAGCGCAAG<br>CCCTGCATCTATATCAAGAGCTGGTGGCCTGACCAGAGGCGGC<br>GCCTCTACAATGCCAACATCATGGATCACATTGCTGACAAGCTG |

TABLE 2-continued

OTOF Sequences

| SEQ ID NO. | Sequence Name | Sequence |
|---|---|---|
| | | GAAGAAGGCCTGAATGATGTACAGGAGATGATCAAAACGGAGAA
GTCCTACCCGGAGCGCCGCCTGCGGGTGTGCTAGAGGAACTC
AGCTGTGGCTGCCACCGCTTCCTCTCCCTCTCGGACAAGGACC
AGGGCCGCTCGTCCCGCACCAGGCTGGATCGAGAGCGTCTTAA
GTCCTGTATGAGGGAGTTGGAGAGCATGGGACAGCAGGCCAAG
AGCCTGAGGGCTCAGGTGAAGCGGCACACTGTTCGGGACAAGC
TGAGGTCATGCCAGAACTTTCTGCAGAAGCTACGCTTCCTGGCG
GATGAGCCCCAGCACAGCATTCCTGATGTGTTCATTTGGATGAT
GAGCAACAACAAACGTATCGCCTATGCCCGCGTGCCTTCCAAAG
ACCTGCTCTTCTCCATCGTGGAGGAGGAACTGGGCAAGGACTG
CGCCAAAGTCAAGACCCTCTTCCTGAAGCTGCCAGGGAAGAGG
GGCTTCGGCTCGGCAGGCTGGACAGTACAGGCCAAGCTGGAG
CTCTACCTGTGGCTGGGCCTCAGCAAGCAGCGAAAGGACTTCC
TGTGTGGTCTGCCCTGTGGCTTCGAGGAGGTCAAGGCAGCCCA
AGGCCTGGGCCTGCATTCCTTTCCGCCCATCAGCCTAGTCTACA
CCAAGAAGCAAGCCTTCCAGCTCCGAGCACACATGTATCAGGC
CCGAAGCCTCTTTGCTGCTGACAGCAGTGGGCTCTCTGATCCCT
TTGCCCGTGTCTTCTTCATCAACCAGAGCCAATGCACTGAGGTT
CTAAACGAGACACTGTGTCCCACCTGGGACCAGATGCTGGTATT
TGACAACCTGGAGCTGTACGGTAAGCTCACGAGTTACGAGAT
GATCCCCCCATCATTGTCATTGAAATCTACGACCAGGACAGCAT
GGGCAAAGCCGACTTCATGGGCCGGACCTTCGCCAAGCCCCTG
GTGAAGATGGCAGATGAAGCATACTGCCCACCTCGCTTCCCGC
CGCAGCTTGAGTACTACCAGATCTACCGAGGCAGTGCCACTGC
CGGAGACCTACTGGCTGCCTTCGAGCTGCTGCAGATTGGGCCA
TCAGGGAAGGCTGACCTGCCACCCATCAATGGCCCAGTGGACA
TGGACAGAGGGCCCATCATGCCTGTGCCCGTGGGAATCCGGCC
AGTGCTCAGCAAGTACCGAGTGGAGGTGCTGTTCTGGGGCCTG
AGGGACCTAAAGAGGGTGAACCTGGCCCAGGTGGACCGACCAC
GGGTGGACATCGAGTGTGCAGGAAAGGGGGGTACAATCCTCCCT
GATTCACAATTATAAGAAGAACCCCAACTTCAACACGCTGGTCAA
GTGGTTTGAAGTGGACCTCCCGGAGAATGAGCTCCTGCACCCA
CCCTTGAACATCCGAGTGGTAGATTGCCGGGCCTTTGGACGATA
CACCCTGGTGGGTTCCCACGCAGTCAGCTCACTGAGGCGCTTC
ATCTACCGACCTCCAGACCGCTCAGCCCCCAACTGGAACACCA
CAGGGGAGGTTGTAGTAAGCATGGAGCCTGAGGAGCCAGTTAA
GAAGCTGGAGACCATGGTGAAACTGGATGCGACTTCTGATGCT
GTGGTCAAGGTGGATGTGGCTGAAGATGAGAAGGAAAGGAAGA
AGAAGAAAAAGAAAGGCCCGTCAGAGGAGCCAGAGGAGGAAGA
GCCCGATGAGAGCATGCTGGATTGGTGGTCCAAGTACTTCGCC
TCCATCGACACAATGAAGGAGCAACTTCGACAACATGAGACCTC
TGGAACTGACTTGGAAGAGAAGGAAGAGATGGAAAGCGCTGAG
GGCCTGAAGGGACCAATGAAGAGCAAGGAGAAGTCCAGAGCTG
CAAAGGAGGAGAAAAAGAAGAAAAACCAGAGCCCTGGCCCTGG
CCAGGGATCGGAGGCTCCTGAGAAGAAGAAAGCCAAGATCGAT
GAGCTTAAGGTGTACCCCAAGGAGCTGGAATCGGAGTTTGACA
GCTTTGAGGACTGGCTGCACACCTTCAACCTGTTGAGGGGCAA
GACGGGAGATGATGAGGATGGCTCCACAGAGGAGGAGCGCATA
GTAGGCCGATTCAAGGGCTCCCTCTGTGTGTACAAAGTGCCACT
CCCAGAAGATGTATCTCGAGAAGCTGGCTATGATCCCACCTATG
GAATGTTCCAGGGCATCCCAAGCAATGACCCCATCAATGTGCTG
GTCCGAATCTATGTGGTCCGGGCCACAGACCTGCACCCGGCCG
ACATCAATGGCAAAGCTGACCCCTATATTGCCATCAAGTTAGGC
AAGACCGACATCCGAGACAAGGAGAACTACATCTCCAAGCAGCT
CAACCCTGTGTTTGGGAAGTCCTTTGACATTGAGGCCTCCTTCC
CCATGGAGTCCATGTTGACAGTGGCCGTGTACGACTGGGATCT
GGTGGGCACTGATGACCTCATCGGAGAAACCAAGATTGACCTG
GAAAACCGCTTCTACAGCAAGCATCGCGCCACCTGCGGCATCG
CACAGACCTATTCCATACATGGCTACAATATCTGGAGGGACCCC
ATGAAGCCCAGCCAGATCCTGACACGCCTCTGTAAAGAGGGCA
AAGTGGACGGCCCCCACTTTGGTCCCCATGGGAGAGTGAGGGT
TGCCAACCGTGTCTTCACGGGGCCTTCAGAAATAGAGGATGAGA
ATGGTCAGAGGAAGCCCACAGATGAGCACGTGGCACTGTCTGC
TCTGAGACACTGGGAGGACATCCCCGGGTGGGCTGCCGCCTT
GTGCCGGAACACGTGGAGACCAGGCCGCTGCTCAACCCTGACA
AGCCAGGCATTGAGCAGGGCCGCCTGGAGCTGTGGGTGGACAT
GTTCCCCATGGACATGCCAGCCCCTGGGACACCTCTGGATATAT
CCCCCAGGAAACCCAAGAAGTACGAGCTGCGGGTCATCGTGTG
GAACACAGACGAGGTGGTCCTGGAAGACGATGATTTCTTCACG
GGAGAGAAGTCCAGTGACATTTTTGTGAGGGGGTGGCTGAAGG
GCCAGCAGGAGGACAAACAGGACACAGATGTCCACTATCACTC
CCTCACGGGGGAGGGCAACTTCAACTGGAGATACCTCTTCCCC
TTCGACTACCTAGCGGCCGAAGAGAAGATCGTTATGTCCAAAAA
GGGAGTCTATGTTCTCCTGGGATGAGACGGAGTACAAGATCCCTG
CGCGGCTCACCCTGCAGATCTGGGACGCTGACCACTTCTCGGC |

TABLE 2-continued

OTOF Sequences

| SEQ ID NO. | Sequence Name | Sequence |
|---|---|---|
| | | TGACGACTTCCTGGGGGCTATCGAGCTGGACCTGAACCGGTTC<br>CCGAGGGGCGCTAAGACAGCCAAGCAGTGCACCATGGAGATGG<br>CCACCGGGGAGGTGGACGTACCCCTGGTTTCCATCTTTAAACAG<br>AAACGTGTCAAAGGCTGGTGGCCCCTCCTGGCCCGCAATGAGA<br>ATGATGAGTTTGAGCTCACAGGCAAAGTGGAGGCGGAGCTACA<br>CCTACTCACGGCAGAGGAGGCAGAGAAGAACCCTGTGGGCCTG<br>GCTCGCAATGAACCTGATCCCCTAGAAAAACCCAATCGGCCGGA<br>CACAAGCTTCATCTGGTTCTTGAACCCTCTCAAGTCTGCCCGCT<br>ACTTCCTGTGGCATACCTACCGCTGGCTACTCCTCAAATTCCTG<br>CTGCTCTTCCTCCTGCTGCTGCTCTTCGCCCTGTTTCTCTACTCT<br>CTGCCTGGCTACCTGGCCAAGAAGATCCTTGGGGCCTGAGCCC<br>TGCAGTCGCCTAGGCCTGCCGGCCTGACACGGCATTCGTCTGG<br>TTCCTGAACCCACTCAAATCTATCAAGTACCTCATCTGCACCCG<br>GTACAAGTGGCTGATCATCAAGATCGTGCTGGCGCTGCTGGGG<br>CTGCTCATGCTGGCCCTCTTCCTTTACAGCCTCCCAGGCTACAT<br>GGTCAAGAAGCTCCTAGGGGCCTGAAGTGTGCCCCACCCCAGC<br>CCGCTCCAGCATCCCTCCAGGGGCTGCTGCGTATTTTGCCTTCC<br>CTCACCTGGACTCTCTCCCAACTCCCTGAGGAGCCCTCCCACG<br>CCTGCCAGCCTTGAGCAAGACACCTGCTTGCTGGACTTCATCCC<br>CACCCCACACCCAAACTGTTGCTTGCCTGATCTTGTCCCAGGCC<br>TGCCTGGGGTTTGGGGCACAGTTGGCCTCCAAAACCAGATACC<br>CTCTTGTCTAAAGTACCAGGTTCCTCTGCCCAACCCCAAGAGTG<br>GTAGTGGCCCAACCCTCCCTGTGCTTTCCAAATCTTGTCTTAAG<br>GCACCAGTGAAATTAACCAAGAAACGCGGAGCAATGCCCAAGG<br>CTCTGATGAGTAGGAACACGTGGAAAGCACCAGGAATGCCAGC<br>AGAGGCGAGGCGGCACACCTCTCTGCAGAGCATCCAGGCCGA<br>GCGGCGGGCAGCGGCCAGCTGCTTCTGCGCATGCTCTCCTCTT<br>GGCTCTGCTTCTTTCTCACAGTCACAGTCACTTCACAGCTTAGC<br>CTTGGGCTTCCCATCACTTCCAGGGGTGCCTCTGCCTTGGCCA<br>GTGTGTGTCAGCTAGTACACAAGCTCCAAGTGTGAATCAGGTGT<br>ACTGGCCGTCCTGAAGACTGACTGCCCTGTCCTTCCTGCCGACA<br>GCCACACCCGAGTGTACACTTAAAGCGGTGCCCTTCTGCCTCTG<br>TGGGCCTGCTGGCTGCTGTTCCTTTCTTGAGTGTGATTTTTTTTT<br>TCTCTCCCTCAATAAAATAAATCAAACTCTGAGAC |
| 17 | mOTOF-202_1<br>transcript<br>(NM_001100395.1),<br>mouse otoferlin<br>transcript variant 1,<br>6881 bp, encodes<br>the protein of SEQ<br>ID NO: 8 | TTGGTTGCCTTGGTCTCTGTGGGCAGCAGCAGGAGGAGGCGGC<br>AGCAGCCAGAGAAGAGGGAGGCGTGTGAGCCACACTCCACCAG<br>CGAGCTTCTTCCCGCTGCTCTGGAACTGCCCAGGCTCTCCCCA<br>CCAGCATGGCCCTGATTGTTCACCTCAAGACTGTCTCAGAGCTC<br>CGAGGCAAAGGTGACCGGATTGCCAAAGTCACTTTCCGAGGGC<br>AGTCTTTCTACTCCCGGGTCCTGGAGAACTGCGAGGGTGTGGC<br>TGACTTTGATGAGACGTTCCGGTGGCCAGTGGCCAGCAGCATC<br>GACCGGAATGAAGTGTTGGAGATTCAGATTTTCAACTACAGCAA<br>AGTCTTCAGCAACAAGCTGATAGGGACCTTCTGCATGGTGCTGC<br>AGAAAGTGGTGGAGGAGAATCGGGTAGAGGTGACCGACACGCT<br>GATGGATGACAGCAATGCTATCATCAAGACCAGCCTGAGCATGG<br>AGGTCCGGTATCAGGCCACAGATGGCACTGTGGGCCCCTGGGA<br>TGATGGAGACTTCCTGGGAGATGAATCCCTCCAGGAGGAGAAG<br>GACAGCCAGGAGACAGATGGGCTGCTACCTGGTTCCCGACCCA<br>GCACCCGGATATCTGGCGAGAAGAGCTTTCGCAGCAAAGGCAG<br>AGAGAAGACCAAGGGAGGCAGAGATGGCGAGCACAAAGCGGG<br>AAGGAGTGTGTTCTCGGCCATGAAACTCGGCAAAACTCGGTCCC<br>ACAAAGAGGAGCCCCAAAGACAAGATGAGCCAGCAGTGCTGGA<br>GATGGAGGACCTGGACCACCTAGCCATTCAGCTGGGGGATGGG<br>CTGGATCCTGACTCCGTGTCTCTAGCCTCGGTCACCGCTCTCAC<br>CAGCAATGTCTCCAACAAACGGTCTAAGCCAGATATTAAGATGG<br>AGCCCAGTGCTGGAAGGCCCATGGATTACCAGGTCAGCATCAC<br>AGTGATTGAGGCTCGGCAGCTGGTGGGCTTGAACATGGACCCT<br>GTGGTGTGTGTGGAGGTGGGTGATGACAAGAAATACACGTCAAT<br>GAAGGAGTCCACAAACTGCCCTTACTACAACGAGTACTTTGTCT<br>TCGACTTCCATGTCTCTCCTGATGTCATGTTTGACAAGATCATCA<br>AGATCTCGGTTATCCATTCTAAGAACCTGCTTCGGAGCGGCACC<br>CTGGTGGGTTCCTTCAAAATGGATGTGGGGACTGTGTATTCCCA<br>GCCTGAACACCAGTTCCATCACAAATGGGCCATCCTGTCAGACC<br>CCGATGACATCTCTGCTGGGTTGAAGGGTTATGTAAAGTGTGAT<br>GTCGCTGTGGTGGGCAAGGGAGACAACATCAAGACACCCCACA<br>AGGCCAACGAGACGGATGAGGACGACATTGAAGGGAACTTGCT<br>GCTCCCCGAGGGCGTGCCCCCGAACGGCAGTGGGCACGGTT<br>CTATGTGAAAATTTACCGAGCAGAGGGACTGCCCCGGATGAACA<br>CAAGCCTCATGGCCAACGTGAAGAAGGCGTTCATCGGTGAGAA<br>CAAGGACCTCGTCGACCCCTATGTGCAAGTCTTCTTTGCTGGAC<br>AAAAGGGCAAAACATCAGTGCAGAAGAGCAGCTATGAGCCGCT<br>ATGGAATGAGCAGGTCGTCTTCACAGACTTGTTCCCCCCACTCT<br>GCAAACGCATGAAGGTGCAGATCCGGGACTCTGACAAGGTCAA<br>TGATGTGGCCATCGGCACCCACTTCATCGACCTGCGCAAGATTT |

TABLE 2-continued

| OTOF Sequences | | |
|---|---|---|
| SEQ ID NO. | Sequence Name | Sequence |
| | | CCAACGATGGAGACAAAGGCTTCCTGCCTACCCTCGGTCCAGC
CTGGGTGAACATGTACGGCTCCACGCGCAACTACACACTGCTG
GACGAGCACCAGGACTTGAATGAAGGCCTGGGGGAGGGTGTGT
CCTTCCGGGCCCGCCTCATGTTGGGACTAGCTGTGGAGATCCT
GGACACCTCCAACCCAGAGCTCACCAGCTCCACGGAGGTGCAG
GTGGAGCAGGCCACGCCTGTCTCGGAGAGCTGCACAGGGAGA
ATGGAAGAATTTTTTCTATTTGGAGCCTTCTTGGAAGCCTCAATG
ATTGACCGGAAAAATGGGGACAAGCCAATTACCTTTGAGGTGAC
CATAGGAAACTACGGCAATGAAGTCGATGGTATGTCCCGGCCC
CTGAGGCCTCGGCCCCGGAAAGAGCCTGGGGATGAAGAAGAG
GTAGACCTGATTCAGAACTCCAGTGACGATGAAGGTGACGAAGC
CGGGGACCTGGCCTCGGTGTCCTCCACCCCACCTATGCGGCCC
CAGATCACGGACAGGAACTATTTCCACCTGCCCTACCTGGAGCG
CAAGCCCTGCATCTATATCAAGAGCTGGTGGCCTGACCAGAGG
CGGCGCCTCTACAATGCCAACATCATGGATCACATTGCTGACAA
GCTGGAAGAAGGCCTGAATGATGTACAGGAGATGATCAAAACG
GAGAAGTCCTACCCGGAGCGCCGCCTGCGGGGTGTGCTAGAG
GAACTCAGCTGTGGCTGCCACCGCTTCCTCTCCCTCTCGGACAA
GGACCAGGGCCGCTCGTCCCGCACCAGGCTGGATCGAGAGCG
TCTTAAGTCCTGTATGAGGGAGTTGGAGAGCATGGGACAGCAG
GCCAAGAGCCTGAGGGCTCAGGTGAAGCGGCACACTGTTCGGG
ACAAGCTGAGGTCATGCCAGAACTTTCTGCAGAAGCTACGCTTC
CTGGCGGATGAGCCCCAGCACAGCATTCCTGATGTGTTCATTTG
GATGATGAGCAACAACAAACGTATCGCCTATGCCCGCGTGCCTT
CCAAAGACCTGCTCTTCTCCATCGTGGAGGAGGAACTGGGCAA
GGACTGCGCCAAAGTCAAGACCCTCTTCCTGAAGCTGCCAGGG
AAGAGGGGCTTCGGCTCGGCAGGCTGGACAGTACAGGCCAAG
CTGGAGCTCTACCTGTGGCTGGGCCTCAGCAAGCAGCGAAAGG
ACTTCCTGTGTGGTCTGCCCTGTGGCTTCGAGGAGGTCAAGGC
AGCCCAAGGCCTGGGCCTGCATTCCTTTCCGCCCATCAGCCTA
GTCTACACCAAGAAGCAAGCCTTCCAGCTCCGAGCACACATGTA
TCAGGCCCGAAGCCTCTTTGCTGCTGACAGCAGTGGGCTCTCT
GATCCCTTTGCCCGTGTCTTCTTCATCAACCAGAGCCAATGCAC
TGAGGTTCTAAACGAGACACTGTGTCCCACCTGGGACCAGATGC
TGGTATTTGACAACCTGGAGCTGTACGGTGAAGCTCACGAGTTA
CGAGATGATCCCCCCATCATTGTCATTGAAATCTACGACCAGGA
CAGCATGGGCAAAGCCGACTTCATGGGCCGGACCTTCGCCAAG
CCCCTGGTGAAGATGGCAGATGAAGCATACTGCCCACCTCGCTT
CCCGCCGCAGCTTGAGTACTACCAGATCTACCGAGGCAGTGCC
ACTGCCGGAGACCTACTGGCTGCCTTCGAGCTGCTGCAGATTG
GGCCATCAGGGAAGGCTGACCTGCCACCCATCAATGGCCCAGT
GGACATGGACAGAGGGCCCATCATGCCTGTGCCCGTGGGAATC
CGGCCAGTGCTCAGCAAGTACCGAGTGGAGGTGCTGTTCTGGG
GCCTGAGGGACCTAAAGAGGGTGAACCTGGCCCAGGTGGACC
GACCACGGGTGGACATCGAGTGTGCAGGAAAGGGGGTACAATC
CTCCCTGATTCACAATTATAAGAAGAACCCCAACTTCAACACGCT
GGTCAAGTGGTTTGAAGTGGACCTCCCGGAGAATGAGCTCCTG
CACCCACCCTTGAACATCCGAGTGGTAGATTGCCGGGCCTTTG
GACGATACACCCTGGTGGGTTCCCACGCAGTCAGCTCACTGAG
GCGCTTCATCTACCGACCTCCAGACCGCTCAGCCCCCAACTGG
AACACCACAGGGGAGGTTGTAGTAAGCATGGAGCCTGAGGAGC
CAGTTAAGAAGCTGGAGACCATGGTGAAACTGGATGCGACTTCT
GATGCTGTGGTCAAGGTGGATGTGGCTGAAGATGAGAAGGAAA
GGAAGAAGAAGAAAAAGAAAGGCCCGTCAGAGGAGCCAGAGGA
GGAAGAGCCCGATGAGAGCATGCTGGATTGGTGGTCCAAGTAC
TTCGCCTCCATCGACACAATGAAGGAGCAACTTCGACAACATGA
GACCTCTGGAACTGACTTGGAAGAGAAGGAAGAGATGGAAAGC
GCTGAGGGCCTGAAGGGACCAATGAAGAGCAAGGAGAAGTCCA
GAGCTGCAAAGGAGGAGAAAAAGAAGAAAAACCAGAGCCCTGG
CCCTGGCCAGGGATCGGAGGCTCCTGAGAAGAAGAAAGCCAAG
ATCGATGAGCTTAAGGTGTACCCCAAGGAGCTGGAATCGGAGTT
TGACAGCTTTGAGGACTGGCTGCACACCTTCAACCTGTTGAGGG
GCAAGACGGGAGATGATGAGGATGGCTCCACAGAGGAGGAGC
GCATAGTAGGCCGATTCAAGGGCTCCCTCTGTGTGTACAAAGTG
CCACTCCCAGAAGATGTATCTCGAGAAGCTGGCTATGATCCCAC
CTATGGAATGTTCCAGGGCATCCCAAGCAATGACCCCATCAATG
TGCTGGTCCGAATCTATGTGGTCCGGGCCACAGACCTGCACCC
GGCCGACATCAATGGCAAAGCTGACCCCTATATTGCCATCAAGT
TAGGCAAGACCGACATCCGAGACAAGGAGAACTACATCTCCAAG
CAGCTCAACCCTGTGTTTGGGAAGTCCTTTGACATTGAGGCCTC
CTTCCCCATGGAGTCCATGTTGACAGTGGCCGTGTACGACTGG
GATCTGGTGGGCACTGATGACCTCATCGGAGAAACCAAGATTGA
CCTGGAAAACCGCTTCTACAGCAAGCATCGCGCCACCTGCGGC
ATCGCACAGACCTATTCCATACATGGCTACAATATCTGGAGGGA
CCCCATGAAGCCCAGCCAGATCCTGACACGCCTCTGTAAAGAG |

TABLE 2-continued

OTOF Sequences

| SEQ ID NO. | Sequence Name | Sequence |
|---|---|---|
| | | GGCAAAGTGGACGGCCCCCACTTTGGTCCCCATGGGAGAGTGA
GGGTTGCCAACCGTGTCTTCACGGGGCCTTCAGAAATAGAGGA
TGAGAATGGTCAGAGGAAGCCCACAGATGAGCACGTGGCACTG
TCTGCTCTGAGACACTGGGAGGACATCCCCCGGGTGGGCTGCC
GCCTTGTGCCGGAACACGTGGAGACCAGGCCGCTGCTCAACCC
TGACAAGCCAGGCATTGAGCAGGGCCGCCTGGAGCTGTGGGTG
GACATGTTCCCCATGGACATGCCAGCCCCTGGGACACCTCTGG
ATATATCCCCCAGGAAACCCAAGAAGTACGAGCTGCGGGTCATC
GTGTGGAACACAGACGAGGTGGTCCTGGAAGACGATGATTTCTT
CACGGGAGAGAAGTCCAGTGACATTTTTGTGAGGGGGTGGCTG
AAGGGCCAGCAGGAGGACAAACAGGACACAGATGTCCACTATC
ACTCCCTCACGGGGGAGGGCAACTTCAACTGGAGATACCTCTTC
CCCTTCGACTACCTAGCGGCCGAAGAGAAGATCGTTATGTCCAA
AAAGGAGTCTATGTTCTCCTGGGATGAGACGGAGTACAAGATCC
CTGCGCGGCTCACCCTGCAGATCTGGGACGCTGACCACTTCTC
GGCTGACGACTTCCTGGGGGCTATCGAGCTGGACCTGAACCGG
TTCCCGAGGGGCGCTAAGACAGCCAAGCAGTGCACCATGGAGA
TGGCCACCGGGGAGGTGGACGTACCCCTGGTTTCCATCTTTAAA
CAGAAACGTGTCAAAGGCTGGTGGCCCCTCCTGGCCCGCAATG
AGAATGATGAGTTTGAGCTCACAGGCAAAGTGGAGGCGGAGCT
ACACCTACTCACGGCAGAGGAGGCAGAGAAGAACCCTGTGGGC
CTGGCTCGCAATGAACCTGATCCCCTAGAAAAACCCAACCGGCC
TGACACGGCATTCGTCTGGTTCCTGAACCCACTCAAATCTATCA
AGTACCTCATCTGCACCCGGTACAAGTGGCTGATCATCAAGATC
GTGCTGGCGCTGCTGGGGCTGCTCATGCTGGCCCTCTTCCTTT
ACAGCCTCCCAGGCTACATGGTCAAGAAGCTCCTAGGGGCCTG
AAGTGTGCCCCACCCCAGCCCGCTCCAGCATCCCTCCAGGGGC
TGCTGCGTATTTTGCCTTCCCTCACCTGGACTCTCTCCCAACTC
CCTGAGGAGCCCTCCCACGCCTGCCAGCCTTGAGCAAGACACC
TGCTTGCTGGACTTCATCCCCACCCCACACCCAAACTGTTGCTT
GCCTGATCTTGTCCCAGGCCTGCCTGGGGTTTGGGGCACAGTT
GGCCTCCAAAACCAGATACCCTCTTGTCTAAAGTACCAGGTTCC
TCTGCCCAACCCCAAGAGTGGTAGTGGCCCAACCCTCCCTGTG
CTTTCCAAATCTTGTCTTAAGGCACCAGTGAAATTAACCAAGAAA
CGCGGAGCAATGCCCAAGGCTCTGATGAGTAGGAACACGTGGA
AAGCACCAGGAATGCCAGCAGAGGCGAGGCGGCACACCTCTCT
GCAGAGCATCCAGGCCGAGCGGCGGGCAGCGGCCAGCTGCTT
CTGCGCATGCTCTCCTCTTGGCTCTGCTTCTTTCTCACAGTCACA
GTCACTTCACAGCTTAGCCTTGGGCTTCCCATCACTTCCAGGGG
TGCCTCTGCCTTGGCCAGTGTGTGTCAGCTAGTACACAAGCT
CCAAGTGTGAATCAGGTGTACTGGCCGTCCTGAAGACTGACTGC
CCTGTCCTTCCTGCCGACAGCCACACCCGAGTGTACACTTAAAG
CGGTGCCCTTCTGCCTCTGTGGGCCTGCTGGCTGCTGTTCCTTT
CTTGAGTGTGATTTTTTTTTTTCTCTCCCTCAATAAAATAAATCAAA
CTCTGAGAC |
| 18 | mOTOF-202_2 transcript (NM_001313767.1), mouse otoferlin transcript variant 4, 6881 bp, encodes the protein of SEQ ID NO: 9 | TTGGTTGCCTTGGTCTCTGTGGGCAGCAGCAGGAGGAGGCGGC
AGCAGCCAGAGAAGAGGGAGGCGTGTGAGCCACACTCCACCAG
CGAGCTTCTTCCCGCTGCTGCTCTGGAACTGCCCAGGCTCTCCCA
CCAGCATGGCCCTGATTGTTCACCTCAAGACTGTCTCAGAGCTC
CGAGGCAAAGGTGACCGGATTGCCAAAGTCACTTTCCGAGGGC
AGTCTTTCTACTCCCGGGTCCTGGAGAACTGCGAGGGTGTGGC
TGACTTTGATGAGACGTTCCGGTGGCCAGTGGCCAGCAGCATC
GACCGGAATGAAGTGTTGGAGATTCAGATTTTCAACTACAGCAA
AGTCTTCAGCAACAAGCTGATAGGGACCTTCTGCATGGTGCTGC
AGAAAGTGGTGGAGGAGAATCGGGTAGAGGTGACCGACACGCT
GATGGATGACAGCAATGCTATCATCAAGACCAGCCTGAGCATGG
AGGTCCGGTATCAGGCCACAGATGGCACTGTGGGCCCCTGGGA
TGATGGAGACTTCCTGGGAGATGAATCCCTCCAGGAGGAGAAG
GACAGCCAGGAGACAGATGGGCTGCTACCTGGTTCCCGACCCA
GCACCCGGATATCTGGCGAGAAGAGCTTTCGCAGAGCGGGAAG
GAGTGTGTTCTCGGCCATGAAACTCGGCAAAACTCGGTCCCACA
AAGAGGAGCCCCAAAGACAAGATGAGCCAGCAGTGCTGGAGAT
GGAGGACCTGGACCACCTAGCCATTCAGCTGGGGATGGGCTG
GATCCTGACTCCGTGTCTCTAGCCTCGGTCACCGCTCTCACCAG
CAATGTCTCCAACAAACGGTCTAAGCCAGATATTAAGATGGAGC
CCAGTGCTGGAAGGCCCATGGATTACCAGGTCAGCATCACAGT
GATTGAGGCTCGGCAGCTGGTGGGCTTGAACATGGACCCTGTG
GTGTGTGTGGAGGTGGGTGATGACAAGAAATACACGTCAATGAA
GGAGTCCACAAACTGCCCTTACTACAACGAGTACTTTGTCTTCG
ACTTCCATGTCTCTCCTGATGTCATGTTTGACAAGATCATCAAGA
TCTCGGTTATCCATTCTAAGAACCTGCTTCGGAGCGGCACCCTG
GTGGGTTCCTTCAAAATGGATGTGGGGACTGTGTATTCCCAGCC
TGAACACCAGTTCCATCACAAATGGGCCATCCTGTCAGACCCCG
ATGACATCTCTGCTGGGTTGAAGGGTTATGTAAAGTGTGATGTC |

TABLE 2-continued

OTOF Sequences

| SEQ ID NO. | Sequence Name | Sequence |
|---|---|---|
| | | GCTGTGGTGGGCAAGGGAGACAACATCAAGACACCCCACAAGG<br>CCAACGAGACGGATGAGGACGACATTGAAGGGAACTTGCTGCT<br>CCCCGAGGGCGTGCCCCCCGAACGGCAGTGGGCACGGTTCTA<br>TGTGAAAATTTACCGAGCAGAGGGACTGCCCCGGATGAACACAA<br>GCCTCATGGCCAACGTGAAGAAGGCGTTCATCGGTGAGAACAA<br>GGACCTCGTCGACCCCTATGTGCAAGTCTTCTTTGCTGGACAAA<br>AGGGCAAAACATCAGTGCAGAAGAGCAGCTATGAGCCGCTATG<br>GAATGAGCAGGTCGTCTTCACAGACTTGTTCCCCCCACTCTGCA<br>AACGCATGAAGGTGCAGATCCGGGACTCTGACAAGGTCAATGAT<br>GTGGCCATCGGCACCCACTTCATCGACCTGCGCAAGATTTCCAA<br>CGATGGAGACAAAGGCTTCCTGCCTACCCTCGGTCCAGCCTGG<br>GTGAACATGTACGGCTCCACGCGCAACTACACACTGCTGGACG<br>AGCACCAGGACTTGAATGAAGGCCTGGGGGAGGGTGTGTCCTT<br>CCGGGCCCGCCTCATGTTGGGACTAGCTGTGGAGATCCTGGAC<br>ACCTCCAACCCAGAGCTCACCAGCTCCACGGAGGTGCAGGTGG<br>AGCAGGCCACGCCTGTCTCGGAGAGCTGCACAGGGAGAATGGA<br>AGAATTTTTTCTATTTGGAGCCTTCTTGGAAGCCTCAATGATTGA<br>CCGGAAAAATGGGGACAAGCCAATTACCTTTGAGGTGACCATAG<br>GAAACTACGGCAATGAAGTCGATGGTATGTCCCGGCCCCTGAG<br>GCCTCGGCCCCGGAAAGAGCCTGGGGATGAAGAAGAGGTAGA<br>CCTGATTCAGAACTCCAGTGACGATGAAGGTGACGAAGCCGGG<br>GACCTGGCCTCGGTGTCCTCCACCCCACCTATGCGGCCCCAGA<br>TCACGGACAGGAACTATTTCCACCTGCCCTACCTGGAGCGCAAG<br>CCCTGCATCTATATCAAGAGCTGGTGGCCTGACCAGAGGCGGC<br>GCCTCTACAATGCCAACATCATGGATCACATTGCTGACAAGCTG<br>GAAGAAGGCCTGAATGATGTACAGGAGATGATCAAAACGGAGAA<br>GTCCTACCCGGAGCGCCGCCTGCGGGTGTGCTAGAGGAACTC<br>AGCTGTGGCTGCCACCGCTTCCTCTCCCTCTCGGACAAGGACC<br>AGGGCCGCTCGTCCCGCACCAGGCTGGATCGAGAGCGTCTTAA<br>GTCCTGTATGAGGGAGTTGGAGAGCATGGGACAGCAGGCCAAG<br>AGCCTGAGGGCTCAGGTGAAGCGGCACACTGTTCGGGACAAGC<br>TGAGGTCATGCCAGAACTTTCTGCAGAAGCTACGCTTCCTGGCG<br>GATGAGCCCCAGCACAGCATTCCTGATGTGTTCATTTGGATGAT<br>GAGCAACAACAAACGTATCGCCTATGCCCGCGTGCCTTCCAAAG<br>ACCTGCTCTTCTCCATCGTGGAGGAGGAACTGGGCAAGGACTG<br>CGCCAAAGTCAAGACCCTCTTCCTGAAGCTGCCAGGGAAGAGG<br>GGCTTCGGCTCGGCAGGCTGGACAGTACAGGCCAAGCTGGAG<br>CTCTACCTGTGGCTGGGCCTCAGCAAGCAGCGAAAGGACTTCC<br>TGTGTGGTCTGCCCTGTGGCTTCGAGGAGGTCAAGGCAGCCCA<br>AGGCCTGGGCCTGCATTCCTTTCCGCCCATCAGCCTAGTCTACA<br>CCAAGAAGCAAGCCTTCCAGCTCCGAGCACACATGTATCAGGC<br>CCGAAGCCTCTTTGCTGCTGACAGCAGTGGGCTCTCTGATCCCT<br>TTGCCCGTGTCTTCTTCATCAACCAGAGCCAATGCACTGAGGTT<br>CTAAACGAGACACTGTGTCCCACCTGGGACCAGATGCTGGTATT<br>TGACAACCTGGAGCTGTACGGTGAAGCTCACGAGTTACGAGAT<br>GATCCCCCCATCATTGTCATTGAAATCTACGACCAGGACAGCAT<br>GGGCAAAGCCGACTTCATGGGCCGGACCTTCGCCAAGCCCCTG<br>GTGAAGATGGCAGATGAAGCATACTGCCCACCTCGCTTCCCGC<br>CGCAGCTTGAGTACTACCAGATCTACCGAGGCAGTGCCACTGC<br>CGGAGACCTACTGGCTGCCTTCGAGCTGCTGCAGATTGGGCCA<br>TCAGGGAAGGCTGACCTGCCACCCATCAATGGCCCAGTGGACA<br>TGGACAGAGGGCCCATCATGCCTGTGCCCGTGGGAATCCGGCC<br>AGTGCTCAGCAAGTACCGAGTGGAGGTGCTGTTCTGGGGCCTG<br>AGGGACCTAAAGAGGGTGAACCTGGCCCAGGTGGACCGACCAC<br>GGGTGGACATCGAGTGTGCAGGAAAGGGGGTACAATCCTCCCT<br>GATTCACAATTATAAGAAGAACCCCAACTTCAACACGCTGGTCAA<br>GTGGTTTGAAGTGGACCTCCCCGGAGAATGAGCTCCTGCACCCA<br>CCCTTGAACATCCGAGTGGTAGATTGCCGGGCCTTTGGACGATA<br>CACCCTGGTGGGTTCCCACGCAGTCAGCTCACTGAGGCGCTTC<br>ATCTACCGACCTCCAGACCGCTCAGCCCCCAACTGGAACACCA<br>CAGGGGAGGTTGTAGTAAGCATGGAGCCTGAGGAGCCAGTTAA<br>GAAGCTGGAGACCATGGTGAAACTGGATGCGACTTCTGATGCT<br>GTGGTCAAGGTGGATGTGGCTGAAGATGAGAAGGAAAGGAAGA<br>AGAAGAAAAAGAAAGGCCCGTCAGAGGGAGCCAGAGGAGGAAGA<br>GCCCGATGAGAGCATGCTGGATTGGTGGTCCAAGTACTTCGCC<br>TCCATCGACACAATGAAGGAGCAACTTCGACAACATGAGACCTC<br>TGGAACTGACTTGGAAGAGAAGGAAGAGATGGAAAGCGCTGAG<br>GGCCTGAAGGGACCAATGAAGAGCAAGGAGAAGTCCAGAGCTG<br>CAAAGGAGGAGAAAAAGAAGAAAAACCAGAGCCCTGGCCCTGG<br>CCAGGGATCGGAGGCTCCTGAGAAGAAGAAGCCAAGATCGAT<br>GAGCTTAAGGTGTACCCCAAGGAGCTGGAATCGGAGTTTGACA<br>GCTTTGAGGACTGGCTGCACACCTTCAACCTGTTGAGGGGCAA<br>GACGGGAGATGATGAGGATGGCTCCACAGAGGAGGAGCGCATA<br>GTAGGCCGATTCAAGGGCTCCCTCTGTGTGTACAAAGTGCCACT<br>CCCAGAAGATGTATCTCGAGAAGCTGGCTATGATCCCACCTATG |

TABLE 2-continued

OTOF Sequences

| SEQ ID NO. | Sequence Name | Sequence |
|---|---|---|
| | | GAATGTTCCAGGGCATCCCAAGCAATGACCCCATCAATGTGCTG
GTCCGAATCTATGTGGTCCGGGCCACAGACCTGCACCCGGCCG
ACATCAATGGCAAAGCTGACCCCTATATTGCCATCAAGTTAGGC
AAGACCGACATCCGAGACAAGGAGAACTACATCTCCAAGCAGCT
CAACCCTGTGTTTGGGAAGTCCTTTGACATTGAGGCCTCCTTCC
CCATGGAGTCCATGTTGACAGTGGCCGTGTACGACTGGGATCT
GGTGGGCACTGATGACCTCATCGGAGAAACCAAGATTGACCTG
GAAAACCGCTTCTACAGCAAGCATCGCGCCACCTGCGGCATCG
CACAGACCTATTCCATACATGGCTACAATATCTGGAGGGACCCC
ATGAAGCCCAGCCAGATCCTGACACGCCTCTGTAAAGAGGGCA
AAGTGGACGGCCCCCACTTTGGTCCCCATGGGAGAGTGAGGGT
TGCCAACCGTGTCTTCACGGGGCCTTCAGAAATAGAGGATGAGA
ATGGTCAGAGGAAGCCCACAGATGAGCACGTGGCACTGTCTGC
TCTGAGACACTGGGAGGACATCCCCCGGGTGGGCTGCCGCCTT
GTGCCGGAACACGTGGAGACCAGGCCGCTGCTCAACCCTGACA
AGCCAGGCATTGAGCAGGGCCGCCTGGAGCTGTGGGTGGACAT
GTTCCCCATGGACATGCCAGCCCCTGGGACACCTCTGGATATAT
CCCCCAGGAAACCCAAGAAGTACGAGCTGCGGGTCATCGTGTG
GAACACAGACGAGGTGGTCCTGGAAGACGATGATTTCTTCACG
GGAGAGAAGTCCAGTGACATTTTTGTGAGGGGGTGGCTGAAGG
GCCAGCAGGAGGACAAACAGGACACAGATGTCCACTATCACTC
CCTCACGGGGGAGGGCAACTTCAACTGGAGATACCTCTTCCCC
TTCGACTACCTAGCGGCCGAAGAGAAGATCGTTATGTCCAAAAA
GGAGTCTATGTTCTCCTGGGATGAGACGGAGTACAAGATCCCTG
CGCGGCTCACCCTGCAGATCTGGGACGCTGACCACTTCTCGGC
TGACGACTTCCTGGGGGCTATCGAGCTGGACCTGAACCGGTTC
CCGAGGGGCGCTAAGACAGCCAAGCAGTGCACCATGGAGATGG
CCACCGGGGAGGTGGACGTACCCCTGGTTTCCATCTTTAAACAG
AAACGTGTCAAAGGCTGGTGGCCCCTCCTGGCCCGCAATGAGA
ATGATGAGTTTGAGCTCACAGGCAAAGTGGAGGCGGAGCTACA
CCTACTCACGGCAGAGGAGGCAGAGAAGAACCCTGTGGGCCTG
GCTCGCAATGAACCTGATCCCCTAGAAAAACCCAACCGGCCTGA
CACGGCATTCGTCTGGTTCCTGAACCCACTCAAATCTATCAAGT
ACCTCATCTGCACCCGGTACAAGTGGCTGATCATCAAGATCGTG
CTGGCGCTGCTGGGGCTGCTCATGCTGGCCCTCTTCCTTTACA
GCCTCCCAGGCTACATGGTCAAGAAGCTCCTAGGGGCCTGAAG
TGTGCCCCACCCCAGCCCGCTCCAGCATCCCTCCAGGGGCTGC
TGCGTATTTTGCCTTCCCTCACCTGGACTCTCTCCCAACTCCCT
GAGGGAGCCCTCCCACGCCTGCCAGCCTTGAGCAAGACACCTGC
TTGCTGGACTTCATCCCCACCCCACACCCAAACTGTTGCTTGCC
TGATCTTGTCCCAGGCCTGCCTGGGGTTTGGGGCACAGTTGGC
CTCCAAAACCAGATACCCTCTTGTCTAAAGTACCAGGTTCCTCTG
CCCAACCCCAAGAGTGGTAGTGGCCCAACCCTCCCTGTGCTTTC
CAAATCTTGTCTTAAGGCACCAGTGAAATTAACCAAGAAACGCG
GAGCAATGCCCAAGGCTCTGATGAGTAGGAACACGTGGAAAGC
ACCAGGAATGCCAGCAGAGGCGAGGCGGCACACCTCTCTGCAG
AGCATCCAGGCCGAGCGGCGGGCAGCGGCCAGCTGCTTCTGC
GCATGCTCTCCTCTTGGCTCTGCTTCTTTCTCACAGTCACAGTCA
CTTCACAGCTTAGCCTTGGGCTTCCCATCACTTCCAGGGGTGCC
TCTGCCTTGGCCAGTGTGTGTCAGCTAGTACACAAGCTCCAAGT
GTGAATCAGGTGTACTGGCCGTCCTGAAGACTGACTGCCCTGTC
CTTCCTGCCGACAGCCACACCCGAGTGTACACTTAAAGCGGTG
CCCTTCTGCCTCTGTGGGCCTGCTGGCTGCTGTTCCTTTCTTGA
GTGTGATTTTTTTTTTCTCTCCCTCAATAAAATAAATCAAACTCTG
AGAC |

Expression of OTOF in Mammalian Cells

Mutations in OTOF have been linked to sensorineural hearing loss and auditory neuropathy. The compositions and methods described herein increase the expression of WT OTOF protein by administering a first nucleic acid vector that contains a polynucleotide encoding an N-terminal portion of an OTOF protein and a second nucleic acid vector that contains a polynucleotide encoding a C-terminal portion of an OTOF protein. In order to utilize nucleic acid vectors for therapeutic application in the treatment of sensorineural hearing loss and auditory neuropathy, they can be directed to the interior of the cell, and, in particular, to specific cell types. A wide array of methods has been established for the delivery of proteins to mammalian cells and for the stable expression of genes encoding proteins in mammalian cells.

Polynucleotides Encoding OTOF

One platform that can be used to achieve therapeutically effective intracellular concentrations of OTOF in mammalian cells is via the stable expression of the gene encoding OTOF (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

OTOF can also be introduced into a mammalian cell by targeting vectors containing portions of a gene encoding an OTOF protein to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding an OTOF protein by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode an OTOF protein downstream of a mammalian promoter (e.g., a polynucleotide that encodes an N-terminal portion of an OTOF protein downstream of a mammalian promoter). Promoters that are useful for the expression of an OTOF protein in mammalian cells include constitutive promoters, cochlear hair cell-specific promoters, and inner hair cell-specific promoters. Constitutive promoters include the CAG promoter, the cytomegalovirus (CMV) promoter, the EF1α promoter, and the PGK promoter. Cochlear hair cell-specific promoters include the Myosin 15 (Myo15) promoter, the Myosin 7A (Myo7A) promoter, the Myosin 6 (Myo6) promoter, the POU4F3 promoter, the Atonal BHLH Transcription Factor 1 (ATOH1) promoter, the LIM Homeobox 3 (LHX3) promoter, the α9 acetylcholine receptor (α9AChR) promoter, and the α10 acetylcholine receptor (α10AChR) promoter. Inner hair cell-specific promoters include the FGF8 promoter, the VGLUT3 promoter, and the OTOF promoter. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

In some embodiments, the Myo15 promoter for use in the compositions and methods described herein includes nucleic acid sequences from regions of the Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the Myo15 locus that are capable of expressing a transgene specifically in hair cells. These regions include nucleic acid sequences immediately preceding the Myo15 translation start site and an upstream regulatory element that is located over 5 kb from the Myo15 translation start site. The Myo15 promoter for use in the compositions and methods described herein can optionally include a linker operably linking the regions of the Myo15 locus that are capable of expressing a transgene specifically in hair cells, or the regions of the Myo15 locus can be joined directly without an intervening linker.

In some embodiments, the Myo15 promoter for use in the compositions and methods described herein contains a first region (an upstream regulatory element) having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the Myo15 translation start site, the sequence of which is set forth in SEQ ID NO: 24) or a functional portion or derivative thereof joined (e.g., operably linked) to a second region having at least 85% sequence identity (e.g., 85%, 90%, 95%, 96%, 97%, 98%, 99%, or more, sequence identity) to the nucleic acid sequence immediately preceding the Myo15 translation start site (nucleic acids from −1 to −1157 with respect to the Myo15 translation start site, the sequence of which is set forth in SEQ ID NO: 25) or a functional portion or derivative thereof. The functional portion of SEQ ID NO: 24 may have the sequence of nucleic acids from −7166 to −7091 with respect to the Myo15 translation start site (set forth in SEQ ID NO: 26) and/or the sequence of nucleic acids from −7077 to −6983 with respect to the Myo15 translation start site (set forth in SEQ ID NO: 27). The first region may contain the nucleic acid sequence of SEQ ID NO: 26 fused to the nucleic acid sequence of SEQ ID NO: 27 with no intervening nucleic acids, as set forth in SEQ ID NO: 28, or the first region may contain the nucleic acid sequence of SEQ ID NO: 27 fused to the nucleic acid sequence of SEQ ID NO: 26 with no intervening nucleic acids, as set forth in SEQ ID NO: 29. Alternatively, the first region may contain the sequences of SEQ ID NO: 26 and SEQ ID NO: 27 joined by the endogenous intervening nucleic acid sequence (e.g., the first region may have the sequence of nucleic acids from −7166 to −6983 with respect to the Myo15 translation start site, as set forth in SEQ ID NO: 30) or a nucleic acid linker. In a Myo15 promoter in which the first region contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26). The functional portion of SEQ ID NO: 25 may have the sequence of nucleic acids from −590 to −509 with respect to the Myo15 translation start site (set forth in SEQ ID NO: 31) and/or the sequence of nucleic acids from −266 to −161 with respect to the Myo15 translation start site (set forth in SEQ ID NO: 32). The second region may contain the nucleic acid sequence of SEQ ID NO: 31 fused to the nucleic acid sequence of SEQ ID NO: 32 with no intervening nucleic acids, as set forth in SEQ ID NO: 33, or the second region may contain the nucleic acid sequence of SEQ ID NO: 32 fused to the nucleic acid sequence of SEQ ID NO: 31 with no intervening nucleic acids, as set forth in SEQ ID NO: 34. Alternatively, the second region may contain the sequences of SEQ ID NO: 31 and SEQ ID NO: 32 joined by the endogenous intervening nucleic acid sequence (e.g., the second region may have the sequence of nucleic acids from −590 to −161 with respect to the Myo15 translation start site, as set forth in SEQ ID NO: 35) or a nucleic acid linker. In a Myo15 promoter in which the second region contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

The first region and the second region of the Myo15 promoter can be joined directly or can be joined by a nucleic acid linker. For example, the Myo15 promoter can contain the sequence of SEQ ID NO: 24 or a functional portion or derivative thereof (e.g., any one or more of SEQ ID NOs: 26-30, e.g., SEQ ID NOs 26 and 27) fused to the sequence of SEQ ID NO: 25 or a functional portion or derivative thereof (e.g., any one or more of SEQ ID NOs: 31-35, e.g., SEQ ID NOs 31 and 32) with no intervening nucleic acids. For example, the nucleic acid sequence of the Myo15 promoter that results from direct fusion of SEQ ID NO: 24 to SEQ ID NO: 25 is set forth in SEQ ID NO: 36. Alternatively, a linker can be used to join the sequence of SEQ ID NO: 24 or a functional portion or derivative thereof (e.g., any one or more of SEQ ID NOs: 26-30, e.g., SEQ ID NOs 26 and 27) to the sequence of SEQ ID NO: 25 or a functional portion or derivative thereof (e.g., any one or more of SEQ ID NOs: 31-35, e.g., SEQ ID NOs 31 and 32).

The length of a nucleic acid linker for use in a Myo15 promoter described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the Myo15 promoter described herein do not disrupt the ability of the Myo15 promoter of the invention to induce transgene expression in hair cells.

In some embodiments, the sequence of SEQ ID NO: 24 or a functional portion or derivative thereof (e.g., any one or more of SEQ ID NOs: 26-30, e.g., SEQ ID NOs 26 and 27) is joined (e.g., operably linked) to the sequence of SEQ ID NO: 25 or a functional portion or derivative thereof (e.g., any one or more of SEQ ID NOs: 31-35, e.g., SEQ ID NOs 31 and 32), and, in some embodiments, the order of the regions is reversed (e.g., the sequence of SEQ ID NO: 25 or a functional portion or derivative thereof (e.g., any one or more of SEQ ID NOs: 31-35, e.g., SEQ ID NOs 31 and 32) is joined (e.g., operably linked) to the sequence of SEQ ID NO: 24 or a functional portion or derivative thereof (e.g., any one or more of SEQ ID NOs: 26-30, e.g., SEQ ID NOs 26 and 27)). For example, the nucleic acid sequence of the Myo15 promoter that results from direct fusion of SEQ ID NO: 25 to SEQ ID NO: 24 is set forth in SEQ ID NO: 37. Regardless of order, the sequence of SEQ ID NO: 24 or a functional portion or derivative thereof and the sequence of SEQ ID NO: 25 or a functional portion or derivative thereof can be joined by direct fusion or a nucleic acid linker, as described above.

In some embodiments, the Myo15 promoter for use in the compositions and methods described herein contains a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the Myo15 translation start site, the sequence of which is set forth in SEQ ID NO: 24) or a functional portion or derivative thereof. The functional portion of SEQ ID NO: 24 may have the sequence of nucleic acids from −7166 to −7091 with respect to the Myo15 translation start site (set forth in SEQ ID NO: 26) and/or the sequence of nucleic acids from −7077 to −6983 with respect to the Myo15 translation start site (set forth in SEQ ID NO: 27). The Myo15 promoter may contain the nucleic acid sequence of SEQ ID NO: 26 fused to the nucleic acid sequence of SEQ ID NO: 27 with no intervening nucleic acids, as set forth in SEQ ID NO: 28, or the Myo15 promoter may contain the nucleic acid sequence of SEQ ID NO: 27 fused to the nucleic acid sequence of SEQ ID NO: 26 with no intervening nucleic acids, as set forth in SEQ ID NO: 29. Alternatively, the Myo15 promoter may contain the sequences of SEQ ID NO: 26 and SEQ ID NO: 27 joined by the endogenous intervening nucleic acid sequence (e.g., the first region may have the sequence of nucleic acids from −7166 to −6983 with respect to the Myo15 translation start site, as set forth in SEQ ID NO: 30) or a nucleic acid linker. In a Myo15 promoter that contains both SEQ ID NO: 26 and SEQ ID NO: 27, the two sequences can be included in any order (e.g., SEQ ID NO: 26 may be joined to (e.g., precede) SEQ ID NO: 27, or SEQ ID NO: 27 may be joined to (e.g., precede) SEQ ID NO: 26).

In some embodiments, the Myo15 promoter for use in the compositions and methods described herein contains a region having at least 85% sequence identity (e.g., 85%, 90%, 95%, 96%, 97%, 98%, 99%, or more, sequence identity) to the nucleic acid sequence immediately upstream of the Myo15 translation start site (nucleic acids from −1 to −1157 with respect to the Myo15 translation start site, the sequence of which is set forth in SEQ ID NO: 25) or a functional portion or derivative thereof. The functional portion of SEQ ID NO: 25 may have the sequence of nucleic acids from −590 to −509 with respect to the Myo15 translation start site (set forth in SEQ ID NO: 31) and/or the sequence of nucleic acids from −266 to −161 with respect to the Myo15 translation start site (set forth in SEQ ID NO: 32). The Myo15 promoter may contain the nucleic acid sequence of SEQ ID NO: 31 fused to the nucleic acid sequence of SEQ ID NO: 32 with no intervening nucleic acids, as set forth in SEQ ID NO: 33, or the Myo15 promoter may contain the nucleic acid sequence of SEQ ID NO: 32 fused to the nucleic acid sequence of SEQ ID NO: 31 with no intervening nucleic acids, as set forth in SEQ ID NO: 34. Alternatively, the Myo15 promoter may contain the sequences of SEQ ID NO: 31 and SEQ ID NO: 32 joined by the endogenous intervening nucleic acid sequence (e.g., the second region may have the sequence of nucleic acids from −590 to −161 with respect to the Myo15 translation start site, as set forth in SEQ ID NO: 35) or a nucleic acid linker. In a Myo15 promoter that contains both SEQ ID NO: 31 and SEQ ID NO: 32, the two sequences can be included in any order (e.g., SEQ ID NO: 31 may be joined to (e.g., precede) SEQ ID NO: 32, or SEQ ID NO: 32 may be joined to (e.g., precede) SEQ ID NO: 31).

The foregoing Myo15 promoter sequences are summarized in Table 3, below.

TABLE 3

Exemplary nucleotide sequences for use in the Myo15 promoter described herein

| SEQ ID NO. | Description of nucleic acid sequence | Nucleic Acid Sequence |
|---|---|---|
| 24 | Region containing non-coding exon 1 of Myo15 (-6755 to -7209) | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTAT |
| 25 | Region immediately preceding the translation start site of Myo15 (-1 to -1157) | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT GCTAACCCTGACCAAGCTACCTATTACTTACCCTCCTCTTTCT CCTCCTCCTCTTTCTCCTTCTCCTGCTTCCCCTCTTCCTTCTC CCTCCCTTCCTCTCCCTCCTCCCCCTCCTTGGCTGTGATCAG ATCCAGAGCCTGAATGAGCCTCCTGACCCCACACCCCCACTA GCATGGGCCTGCAAGTGCCCAGAAGTCCCTCCTGCCTCCTA AACTGCCCAGCCGATCCATTAGCTCTTCCTTCTTCCCAGTGA AGAAGCAGGCACAGCCTGTCCCTCCCGTTCTACAGAAAGG AAGCTACAGCACAGGGAGGGCCAAAGGCCTTCCTGGGACTA GACAGTTGATCAACAGCAGGACTGGAGAGCTGGGCTCCATTT TTGTTCCTTGGTGCCCTGCCCCTCCCCATGACCTGCAGAGAC ATTCAGCCTGCCAGGCTTTATGAGGTGGGAGCTGGGCTCTC CCTGATGTATTATTCAGCTCCCTGGAGTTGGCCAGCTCCTGT TACACTGGCCACAGCCCTGGGCATCCGCTTCTCACTTCTAGT TTCCCCTCCAAGGTAATGTGGTGGGTCATGATCATTCTATCCT GGCTTCAGGGACCTGACTCCACTTTGGGGCCATTCGAGGGG TCTAGGGTAGATGATGTCCCCCTGTGGGGATTAATGTCCTGC TCTGTAAAACTGAGCTAGCTGAGATCCAGGAGGGCTTGGCCA GAGACAGCAAGTTGTTGCCATGGTGACTTTAAAGCCAGGTTG CTGCCCCAGCACAGGCCTCCCAGTCTACCCTCACTAGAAAAC AACACCCAGGCACTTTCCACCACCTCTCAAAGGTGAAACCCA AGGCTGGTCTAGAGAATGAATTATGGATCCTCGCTGTCCGTG CCACCCAGCTAGTCCCAGCGGCTCAGACACTGAGGAGAGAC TGTAGGTTCAGCTACAAGCAAAAAGACCTAGCTGGTCTCCAA GCAGTGTCTCCAAGTCCCTGAACCTGTGACACCTGCCCCAG GCATCATCAGGCACAGAGGGCCACC |
| 26 | Portion of SEQ ID NO: 24 (-7166 to -7091) | CCCATGTCAGCTGCTTGTGCTTTCCAGAGACAAAACAGGAAT AATAGATGTCATTAAATATACATTGGGCCCCAGG |
| 27 | Portion of SEQ ID NO: 24 (-7077 to -6983) | AGCCTGAGCCTCCTTTCCATCTCTGTGGAGGCAGACATAGGA CCCCAACAAACAGCATGCAGGTTGGGAGCCAGCCACAGGA CCCAGGTAAGGG |
| 28 | Portion of SEQ ID NO: 24 (SEQ ID NO: 26 fused to SEQ ID NO: 27) | CCCATGTCAGCTGCTTGTGCTTTCCAGAGACAAAACAGGAAT AATAGATGTCATTAAATATACATTGGGCCCCAGGAGCCTGAG CCTCCTTTCCATCTCTGTGGAGGCAGACATAGGACCCCCAAC AAACAGCATGCAGGTTGGGAGCCAGCCACAGGACCCAGGTA AGGG |
| 29 | Portion of SEQ ID NO: 24 (SEQ ID NO: 27 fused to SEQ ID NO: 26) | AGCCTGAGCCTCCTTTCCATCTCTGTGGAGGCAGACATAGGA CCCCAACAAACAGCATGCAGGTTGGGAGCCAGCCACAGGA CCCAGGTAAGGGCCCATGTCAGCTGCTTGTGCTTTCCAGAGA CAAAACAGGAATAATAGATGTCATTAAATATACATTGGGCCCC AGG |
| 30 | Portion of SEQ ID NO: 24 (-7166 to -6983) | CCCATGTCAGCTGCTTGTGCTTTCCAGAGACAAAACAGGAAT AATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGG |
| 31 | Portion of SEQ ID NO: 25 (-590 to -509) | TGAGGTGGGAGCTGGGCTCTCCCTGATGTATTATTCAGCTCC CTGGAGTTGGCCAGCTCCTGTTACACTGGCCACAGCCCTG |

TABLE 3-continued

Exemplary nucleotide sequences for use
in the Myo15 promoter described herein

| SEQ ID NO. | Description of nucleic acid sequence | Nucleic Acid Sequence |
|---|---|---|
| 32 | Portion of SEQ ID NO: 25 (-266 to -161) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 33 | Portion of SEQ ID NO: 25 (SEQ ID NO: 31 fused to SEQ ID NO: 32) | TGAGGTGGGAGCTGGGCTCTCCCTGATGTATTATTCAGCTCC CTGGAGTTGGCCAGCTCCTGTTACACTGGCCACAGCCCTG CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCT |
| 34 | Portion of SEQ ID NO: 25 (SEQ ID NO: 32 fused to SEQ ID NO: 31) | CACAGGCCTCCCAGTCTACCCTCACTAGAAAACAACACCCAG GCACTTTCCACCACCTCTCAAAGGTGAAACCCAAGGCTGGTC TAGAGAATGAATTATGGATCCTTGAGGTGGGAGCTGGGCTCT CCCTGATGTATTATTCAGCTCCCTGGAGTTGGCCAGCTCCTG TTACACTGGCCACAGCCCTG |
| 35 | Portion of SEQ ID NO: 25 (-590 to -161) | TGAGGTGGGAGCTGGGCTCTCCCTGATGTATTATTCAGCTCC CTGGAGTTGGCCAGCTCCTGTTACACTGGCCACAGCCCTGG GCATCCGCTTCTCACTTCTAGTTTCCCCTCCAAGGTAATGTG GTGGGTCATGATCATTCTATCCTGGCTTCAGGGACCTGACTC CACTTTGGGGCCATTCGAGGGGTCTAGGGTAGATGATGTCC CCCTGTGGGGATTAATGTCCTGCTCTGTAAAACTGAGCTAGC TGAGATCCAGGAGGGCTTGGCCAGAGACAGCAAGTTGTTGC CATGGTGACTTTAAAGCCAGGTTGCTGCCCCAGCACAGGCCT CCCAGTCTACCCTCACTAGAAAACAACACCCAGGCACTTTCC ACCACCTCTCAAAGGTGAAACCCAAGGCTGGTCTAGAGAATG AATTATGGATCCT |
| 36 | SEQ ID NO: 24 fused to SEQ ID NO: 25 | CTGCAGCTCAGCCTACTACTTGCTTTCCAGGCTGTTCCTAGT TCCCATGTCAGCTGCTTGTGCTTTCCAGAGACAAAACAGGAA TAATAGATGTCATTAAATATACATTGGGCCCCAGGCGGTCAAT GTGGCAGCCTGAGCCTCCTTTCCATCTCTGTGGAGGCAGAC ATAGGACCCCCAACAAACAGCATGCAGGTTGGGAGCCAGCC ACAGGACCCAGGTAAGGGGCCCTGGGTCCTTAAGCTTCTGC CACTGGCTCCGGCATTGCAGAGAGAAGAGAAGGGGCGGCA GAGCTGAACCTTAGCCTTGCCTTCCTGGGTACCCTTCTGAGC CTCACTGTCTTCTGTGAGATGGGCAAAGTGCGGGTGTGACTC CTTGGCAACGGTGTTACACCAGGGCAGGTAAAGTTGTAGTTA TTTGTGGGGTACACCAGGACTGTTAAAGGTGTAACTATGGTC TCACCCAGCATTTTCACTTCTAATAAGTTCAAATGTGATACGG CACCTTTCTAAAAATTAGTTTTCAGGGAAATAGGGTTCAAAAC TGGTAGTGGTAGGGTCCATTCTCACGACCCCCAGGCCTGCT AACCCTGACCAAGCTACCTATTACTTACCCTCCTCTTTCTCCT CCTCCTCTTTCTCCTTCTCCTGCTTCCCCTCTTCCTTCTCCCT CCCTTCCTCTCCCTCCTCCCCCTCCTTGGCTGTGATCAGATC CAGAGCCTGAATGAGCCTCCTGACCCCACACCCCCACTAGC ATGGGCCTGCAAGTGCCCAGAAGTCCCTCCTGCCTCCTAAAC TGCCCAGCCGATCCATTAGCTCTTCCTTCTTCCCAGTGAAAG AAGCAGGCACAGCCTGTCCCTCCCGTTCTACAGAAAGGAAG CTACAGCACAGGGAGGGCCAAAGGCCTTCCTGGGACTAGAC AGTTGATCAACAGCAGGACTGGAGAGCTGGGCTCCATTTTTG TTCCTTGGTGCCCTGCCCCTCCCCATGACCTGCAGAGACATT CAGCCTGCCAGGCTTTATGAGGTGGGAGCTGGGCTCTCCCT GATGTATTATTCAGCTCCCTGGAGTTGGCCAGCTCCTGTTAC ACTGGCCACAGCCCTGGGCATCCGCTTCTCACTTCTAGTTTC CCCTCCAAGGTAATGTGGTGGGTCATGATCATTCTATCCTGG CTTCAGGGACCTGACTCCACTTTGGGGCCATTCGAGGGGTC TAGGGTAGATGATGTCCCCCTGTGGGGATTAATGTCCTGCTC TGTAAAACTGAGCTAGCTGAGATCCAGGAGGGCTTGGCCAG AGACAGCAAGTTGTTGCCATGGTGACTTTAAAGCCAGGTTGC TGCCCCAGCACAGGCCTCCCAGTCTACCCTCACTAGAAAACA ACACCCAGGCACTTTCCACCACCTCTCAAAGGTGAAACCCAA GGCTGGTCTAGAGAATGAATTATGGATCCTCGCTGTCCGTGC CACCCAGCTAGTCCCAGCGGCTCAGACACTGAGGAGAGACT GTAGGTTCAGCTACAAGCAAAAAGACCTAGCTGGTCTCCAAG CAGTGTCTCCAAGTCCCTGAACCTGTGACACCTGCCCCAGG CATCATCAGGCACAGAGGGCCACC |
| 37 | SEQ ID NO: 25 fused to SEQ ID NO: 24 | GGTCTCACCCAGCATTTTCACTTCTAATAAGTTCAAATGTGAT ACGGCACCTTTCTAAAAATTAGTTTTCAGGGAAATAGGGTTCA AAACTGGTAGTGGTAGGGTCCATTCTCACGACCCCCAGGCCT GCTAACCCTGACCAAGCTACCTATTACTTACCCTCCTCTTTCT CCTCCTCCTCTTTCTCCTTCTCCTGCTTCCCCTCTTCCTTCTC CCTCCCTTCCTCTCCCTCCTCCCCCTCCTTGGCTGTGATCAG |

TABLE 3-continued

Exemplary nucleotide sequences for use
in the Myo15 promoter described herein

| SEQ ID NO. | Description of nucleic acid sequence | Nucleic Acid Sequence |
|---|---|---|
| | | ATCCAGAGCCTGAATGAGCCTCCTGACCCCACACCCCCACTA
GCATGGGCCTGCAAGTGCCCAGAAGTCCCTCCTGCCTCCTA
AACTGCCCAGCCGATCCATTAGCTCTTCCTTCTTCCCAGTGA
AAGAAGCAGGCACAGCCTGTCCCTCCCGTTCTACAGAAAGG
AAGCTACAGCACAGGGAGGGCCAAAGGCCTTCCTGGGACTA
GACAGTTGATCAACAGCAGGACTGGAGAGCTGGGCTCCATTT
TTGTTCCTTGGTGCCCTGCCCCTCCCCATGACCTGCAGAGAC
ATTCAGCCTGCCAGGCTTTATGAGGTGGGAGCTGGGCTCTC
CCTGATGTATTATTCAGCTCCCTGGAGTTGGCCAGCTCCTGT
TACACTGGCCACAGCCCTGGGCATCCGCTTCTCACTTCTAGT
TTCCCCTCCAAGGTAATGTGGTGGGTCATGATCATTCTATCCT
GGCTTCAGGGACCTGACTCCACTTTGGGGCCATTCGAGGGG
TCTAGGGTAGATGATGTCCCCCTGTGGGGATTAATGTCCTGC
TCTGTAAAACTGAGCTAGCTGAGATCCAGGAGGGCTTGGCCA
GAGACAGCAAGTTGTTGCCATGGTGACTTTAAAGCCAGGTTG
CTGCCCCAGCACAGGCCTCCCAGTCTACCCTCACTAGAAAAC
AACACCCAGGCACTTTCCACCACCTCTCAAAGGTGAAACCCA
AGGCTGGTCTAGAGAATGAATTATGGATCCTCGCTGTCCGTG
CCACCCAGCTAGTCCCAGCGGCTCAGACACTGAGGAGAGAC
TGTAGGTTCAGCTACAAGCAAAAAGACCTAGCTGGTCTCCAA
GCAGTGTCTCCAAGTCCCTGAACCTGTGACACCTGCCCCAG
GCATCATCAGGCACAGAGGGCCACCCTGCAGCTCAGCCTAC
TACTTGCTTTCCAGGCTGTTCCTAGTTCCCATGTCAGCTGCTT
GTGCTTTCCAGAGACAAAACAGGAATAATAGATGTCATTAAAT
ATACATTGGGCCCCAGGCGGTCAATGTGGCAGCCTGAGCCT
CCTTTCCATCTCTGTGGAGGCAGACATAGGACCCCCAACAAA
CAGCATGCAGGTTGGGAGCCAGCCACAGGACCCAGGTAAGG
GGCCCTGGGTCCTTAAGCTTCTGCCACTGGCTCCGGCATTG
CAGAGAGAAGAGAAGGGGCGGCAGAGCTGAACCTTAGCCTT
GCCTTCCTGGGTACCCTTCTGAGCCTCACTGTCTTCTGTGAG
ATGGGCAAAGTGCGGGTGTGACTCCTTGGCAACGGTGTTAC
ACCAGGGCAGGTAAAGTTGTAGTTATTTGTGGGGTACACCAG
GACTGTTAAAGGTGTAACTAT |

Additional Myo15 promoters useful in conjunction with the compositions and methods described herein include nucleic acid molecules that have at least 85% sequence identity (e.g., 85%, 90%, 95%, 96%, 97%, 98%, 99%, or more, sequence identity) to the nucleic acid sequences set forth in Table 3, as well as functional portions or derivatives of the nucleic acid sequences set forth in Table 3. The Myo15 promoters listed in Table 3 are characterized in U.S. Provisional Application 62/663,679, which is incorporated herein by reference.

Once a polynucleotide encoding OTOF has been incorporated into the nuclear DNA of a mammalian cell or stabilized in an episomal monomer or concatemer, the transcription of this polynucleotide can be induced by methods known in the art. For example expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies®, Carlsbad, Calif.) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode an OTOF protein and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding an OTOF protein, for example, at a position 5' or 3' to this gene. In a preferred orientation, the enhancer is positioned at the 5' side of the promoter, which in turn is located 5' relative to the polynucleotide encoding an OTOF protein.

The nucleic acid vectors described herein may include a Woodchuck Posttranscriptional Regulatory Element (WPRE). The WPRE acts at the mRNA level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo. The WPRE can be located in the second nucleic acid vector between the polynucleotide encoding a C-terminal portion of an OTOF protein and the poly(A) sequence. In the compositions and methods described herein, the WPRE can have the sequence:

(SEQ ID NO: 23)
GATCCAATCAACCTCTGGATTACAAAATTTGTGAAAGATTGACTGGTAT

TCTTAACTATGTTGCTCCTTTTACGCTATGTGGATACGCTGCTTTAATG

CCTTTGTATCATGCTATTGCTTCCCGTATGGCTTTCATTTTCTCCTCCT

TGTATAAATCCTGGTTGCTGTCTCTTTATGAGGAGTTGTGGCCCGTTGT

CAGGCAACGTGGCGTGGTGTGCACTGTGTTTGCTGACGCAACCCCCACT

GGTTGGGGCATTGCCACCACCTGTCAGCTCCTTTCCGGGACTTTCGCTT

TCCCCCTCCCTATTGCCACGGCGGAACTCATCGCCGCCTGCCTTGCCCG

CTGCTGGACAGGGGCTCGGCTGTTGGGCACTGACAATTCCGTGGTGTTG

TCGGGGAAATCATCGTCCTTTCCTTGGCTGCTCGCCTGTGTTGCCACCT

GGATTCTGCGCGGGACGTCCTTCTGCTACGTCCCTTCGGCCCTCAATCC

AGCGGACCTTCCTTCCCGCGGCCTGCTGCCGGCTCTGCGGCCTCTTCCG

CGTCTTCGA.

The WPRE can also have the sequence:

(SEQ ID NO: 38)
AATCAACCTCTGGATTACAAAATTTGTGAAAGATTGACTGGTATTCTTA

ACTATGTTGCTCCTTTTACGCTATGTGGATACGCTGCTTAATGCCTTT

GTATCATGCTATTGCTTCCCGTATGGCTTTCATTTTCTCCTCCTTGTAT

AAATCCTGGTTAGTTCTTGCCACGGCGGAACTCATCGCCGCCTGCCTTG

CCCGCTGCTGGACAGGGGCTCGGCTGTTGGGCACTGACAATTCCGTGGT

GTTTATTTGTGAAATTTGTGATGCTATTGCTTTATTTGTAACCATCTAG

CTTTATTTGTGAAATTTGTGATGCTATTGCTTTATTTGTAACCATTATA

AGCTGCAATAAACAAGTTAACAACAACAATTGCATTCATTTTATGTTTC

AGGTTCAGGGGGAGATGTGGGAGGTTTTTAAA

In some embodiments, the nucleic acid vectors for use in the compositions and methods described herein include a reporter sequence, which can be useful in verifying OTOF gene expression, for example, in specific cells and tissues (e.g., in cochlear hair cells). Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Overlapping Dual Vectors

One approach for expressing large proteins in mammalian cells involves the use of overlapping dual vectors. This approach is based on the use of two nucleic acid vectors, each of which contains a portion of a polynucleotide that encodes a protein of interest and has a defined region of sequence overlap with the other polynucleotide. Homologous recombination can occur at the region of overlap and lead to the formation of a single nucleic acid molecule that encodes the full-length protein of interest.

Overlapping dual vectors for use in the methods and compositions described herein contain at least one kilobase (kb) of overlapping sequence (e.g., 1 kb, 1.5 kb, 2 kb, 2.5 kb, 3 kb or more of overlapping sequence). The nucleic acid vectors are designed such that the overlapping region is centered at an OTOF exon boundary, with an equal amount of overlap on either side of the boundary. The boundaries are chosen based on the size of the promoter and the locations of the portions of the polynucleotide that encode OTOF C2 domains. Overlapping regions are centered on exon boundaries that occur outside of the portion of the polynucleotide that encodes the C2C domain (e.g., after the portion of the polynucleotide that encodes the C2C domain). Exon boundaries within the portion of the polynucleotide that encodes the C2D domain can be selected as the center of the overlapping region, or exon boundaries located after the portion of the polynucleotide that encodes the C2D domain and before the portion of the polynucleotide that encodes the C2E domain can serve as the center of an overlapping region. The nucleic acid vectors for use in the methods and compositions described herein are also designed such that approximately half of the OTOF gene is contained within each vector (e.g., each vector contains a polynucleotide that encodes approximately half of the OTOF protein).

One exemplary overlapping dual vector system includes a first nucleic acid vector containing a CAG promoter operably linked to exons 1-28 and the 500 kb immediately 3' of the exon 28/29 boundary of a polynucleotide encoding an OTOF protein (e.g., human OTOF, e.g., SEQ ID NO: 1, or mouse OTOF, e.g., SEQ ID NO: 6); and a second nucleic acid vector containing the 500 kb immediately 5' of the exon 28/29 boundary and exons 29-48 of a polynucleotide encoding an OTOF protein (e.g., human OTOF, e.g., SEQ ID NO: 1, or mouse OTOF, e.g., SEQ ID NO: 6) and a poly(A) sequence (e.g., a bovine growth hormone (bGH) poly(A) signal sequence). In this overlapping dual vector system, the overlapping sequence is centered at the exon 28/29 boundary, which is after the portion of the polynucleotide that encodes the C2D domain. Another exemplary overlapping dual vector system includes a first nucleic acid vector containing a CAG promoter operably linked to exons 1-24 and the 500 kb immediately 3' of the exon 24/25 boundary of a polynucleotide encoding an OTOF protein (e.g., human OTOF, e.g., SEQ ID NO: 1, or mouse OTOF, e.g., SEQ ID NO: 6); and a second nucleic acid vector containing the 500 kb immediately 5' of the exon 24/25 boundary and exons 25-48 of a polynucleotide encoding an OTOF protein (e.g., human OTOF, e.g., SEQ ID NO: 1, or mouse OTOF, e.g., SEQ ID NO: 6) and a poly(A) sequence (e.g., a bGH poly(A) signal sequence). In this overlapping dual vector system, the overlapping sequence is centered at the exon 24/25 boundary, which is within the portion of the polynucleotide that encodes the C2D domain. The two exon boundaries described above can be used with any promoter that is a similar size to the CAG promoter (e.g., the CMV promoter), such as promoters that are 1 kb or shorter (e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter). For example, in either of the foregoing dual vector systems, the CMV promoter can be used in the place of the CAG promoter. A Myo15 promoter having a sequence that is 1 kb or shorter (e.g., a Myo15 promoter described hereinabove) can also be used in place of the CAG promoter. Alternatively, a different exon boundary can be chosen that is within or after the portion of the polynucleotide that encodes the C2D domain and before the portion of the polynucleotide that encodes the C2E domain. The nucleic acid vectors containing promoters of this size can optionally contain OTOF UTRs. For example, in the foregoing overlapping dual vector system in which the overlapping region is centered at the exon 28/29 boundary of OTOF, the second nucleic acid vector can contain the full-length OTOF 3' UTR (e.g., the 1035 bp human OTOF 3' UTR in dual vector systems encoding human OTOF, or the 1001 bp mouse OTOF 3' UTR in dual vector systems encoding mouse OTOF). In the foregoing overlapping dual vector system in which the overlapping region is centered at the exon 24/25 boundary of OTOF, neither the first nor the second nucleic acid vector contains an OTOF UTR.

In some embodiments, the first nucleic acid vector in the overlapping dual vector system contains a long promoter (e.g., a promoter that is longer than 1 kb, e.g., 1.1 kb, 1.25 kb, 1.5 kb, 1.75 kb, 2 kb, 2.5 kb, 3 kb or longer). In such overlapping dual vector systems, the overlapping region is centered at an exon boundary that is located after the portion of the polynucleotide that encodes the C2C domain and before the portion of the polynucleotide that encodes the C2D domain. For example, an overlapping dual vector system for use in the methods and compositions described herein includes a first nucleic acid vector containing a Myo15 promoter that is longer than 1 kb (e.g., SEQ ID NO: 36) operably linked to exons 1-21 and the 500 kb immediately 3' of the exon 21/22 boundary of a polynucleotide encoding an OTOF protein (e.g., human OTOF, e.g., SEQ ID NO: 1); and a second nucleic acid vector containing the 500 kb immediately 5' of the exon 21/22 boundary and exons 22-48 of a polynucleotide encoding an OTOF protein (e.g., human OTOF, e.g., SEQ ID NO: 1) and a poly(A) sequence (e.g., a bGH poly(A) signal sequence). In this overlapping dual vector system, neither the first nor the second nucleic acid vector includes an OTOF UTR. A short promoter (e.g., a CMV promoter, CAG promoter, or a Myo15 promoter having a sequence that is 1 kb or shorter) can also be used in this dual vector system (e.g., a dual vector system in which the overlapping region is centered at the exon 21/22 boundary). If a short promoter is used, additional elements, such as a 5' OTOF UTR, can be included in the first vector (e.g., the vector containing exons 1-21 and the 500 kb immediately 3' of the exon 21/22 boundary of a polynucleotide encoding an OTOF protein).

Trans-Splicing Dual Vectors

A second approach for expressing large proteins in mammalian cells involves the use of trans-splicing dual vectors. In this approach, two nucleic acid vectors are used that contain distinct nucleic acid sequences, and the polynucleotide encoding the N-terminal portion of the protein of interest and the polynucleotide encoding the C-terminal portion of the protein of interest do not overlap. Instead, the first nucleic acid vector includes a splice donor sequence 3' of the polynucleotide encoding the N-terminal portion of the protein of interest, and the second nucleic acid vector includes a splice acceptor sequence 5' of the polynucleotide encoding the C-terminal portion of the protein of interest. When the first and second nucleic acids are present in the same cell, their ITRs can concatemerize, forming a single nucleic acid structure in which the concatemerized ITRs are positioned between the splice donor and splice acceptor. Trans-splicing then occurs during transcription, producing a nucleic acid molecule in which the polynucleotides encoding the N-terminal and C-terminal portions of the protein of interest are contiguous, thereby forming the full-length coding sequence.

Trans-splicing dual vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the trans-splicing dual vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as a CAG promoter, a CMV promoter, or a Myo15 promoter having a sequence that is 1 kb or shorter (e.g., a Myo15 promoter described hereinabove), the OTOF polynucleotide sequence is divided between the two nucleic acid vectors at an exon boundary that occurs after the portion of the polynucleotide that encodes the C2D domain and before the portion of the polynucleotide that encodes the C2E domain, for example, the exon 26/27 boundary. The nucleic acid vectors containing promoters of this size can optionally contain OTOF UTRs (e.g., both the 5' and 3' OTOF UTRs, e.g., full-length UTRs). When a long promoter is used in the trans-splicing dual vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, CAG promoter, or a Myo15 promoter having a sequence that is 1 kb or shorter) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary trans-splicing dual vector system that uses a short promoter includes a first nucleic acid vector containing a CAG promoter operably linked to exons 1-26 of a polynucleotide encoding an OTOF protein (e.g., human OTOF, e.g., SEQ ID NO: 1) and a splice donor sequence 3' of the polynucleotide sequence; and a second nucleic acid vector containing a splice acceptor sequence 5' of exons 27-48 of a polynucleotide encoding an OTOF protein (e.g., human OTOF, e.g., SEQ ID NO: 1) and a poly(A) sequence (e.g., a bGH poly(A) signal sequence). An alternative trans-splicing dual vector system includes a first nucleic acid vector containing a CAG promoter operably linked to exons 1-28 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 29-48 of a polynucleotide encoding an OTOF protein (e.g., mouse OTOF, e.g., SEQ ID NO: 6) and a poly(A) sequence (e.g., a bGH poly(A) signal sequence). The CMV promoter or a Myo15 promoter having a sequence that is 1 kb or shorter (e.g., a Myo15 promoter described hereinabove) can be used in place of the CAG promoter either of the foregoing dual vector systems. These nucleic acid vectors can also contain full-length 5' and 3' OTOF UTRs in the first and second nucleic acid vectors, respectively (e.g., the first nucleic acid vector can contain the 5' human OTOF UTR (127 bp) in dual vector systems encoding human OTOF, or the 5' mouse UTR (134 bp) in dual vector systems encoding mouse OTOF; and the second nucleic acid vector can contain the 3' human OTOF UTR (1035 bp) in dual vector systems encoding human OTOF, or the 3' mouse OTOF UTR (1001 bp) in dual vector systems encoding mouse OTOF).

An exemplary trans-splicing dual vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1) and a splice donor sequence 3' of the polynucleotide sequence; and a second nucleic acid vector containing a splice acceptor sequence 5' of exons 20-48 of a polynucleotide encoding an OTOF protein (e.g., human OTOF, e.g., SEQ ID NO: 1) and a poly(A) sequence (e.g., a bGH poly(A) signal sequence). Alternatively, the trans-splicing dual vector system can include a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6) and a splice donor sequence 3' of the polynucleotide sequence; and a second nucleic acid vector containing a splice acceptor sequence 5' of exons 21-48 of a polynucleotide encoding an OTOF protein (e.g., mouse OTOF, e.g., SEQ ID NO: 6) and a poly(A) sequence (e.g., a bGH poly(A) signal sequence). Neither the first nor the second nucleic acid vector in either of the foregoing Myo15 promoter trans-splicing dual vector systems contains an OTOF UTR. A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a trans-splicing dual vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1) and a splice donor sequence 3' of the polynucleotide sequence; and the second nucleic acid vector contains a splice acceptor sequence 5' of exons 26-48 of a polynucleotide encoding an OTOF protein (e.g., human OTOF, e.g., SEQ ID NO: 1) and a poly(A) sequence (e.g., a bGH poly(A) signal sequence), the second nucleic acid can also contain a full-length OTOF 3' UTR (e.g., the 1035 bp human OTOF 3' UTR). For mouse OTOF, the trans-splicing dual vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6) and a splice donor sequence 3' of the polynucleotide sequence; and the second nucleic acid vector contains a splice acceptor sequence 5' of exons 25-48 of a polynucleotide encoding an OTOF protein (e.g., mouse OTOF, e.g., SEQ ID NO: 6) and a poly(A) sequence (e.g., a bGH poly(A) signal sequence). In this dual vector system, the second nucleic acid can also contain a full-length OTOF 3' UTR (e.g., the 1001 bp mouse OTOF 3' UTR). A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

Dual Hybrid Vectors

A third approach for expressing large proteins in mammalian cells involves the use of dual hybrid vectors. This approach combines elements of the overlapping dual vector strategy and the trans-splicing strategy in that it features both an overlapping region at which homologous recombination can occur and splice donor and splice acceptor sequences. In dual hybrid vector systems, the overlapping region is a recombinogenic region that is contained in both the first and second nucleic acid vectors, rather than a portion of the polynucleotide sequence encoding the protein of interest—the polynucleotide encoding the N-terminal portion of the protein of interest and the polynucleotide encoding the C-terminal portion of the protein of interest do not overlap in this approach. The recombinogenic region is 3' of the splice donor sequence in the first nucleic acid vector and 5' of the splice acceptor sequence in the second nucleic acid sequence. The first and second nucleic acid sequences can then join to form a single sequence based on one of two mechanisms: 1) recombination at the overlapping region, or 2) concatemerization of the ITRs. The remaining recombinogenic region(s) and/or the concatemerized ITRs can be removed by splicing, leading to the formation of a contiguous polynucleotide sequence that encodes the full-length protein of interest.

Recombinogenic regions that can be used in the compositions and methods described herein include the F1 phage AK gene having a sequence of: GGGATTTTGCCGATTCGGCCTATTGGTTAA AAAATGAGCTGATTTAAC-AAAAATTTAACGCGAATTTTAACAAAAT (SEQ ID NO: 19) and alkaline phosphatase (AP) gene fragments as described in U.S. Pat. No. 8,236,557, which are incorporated herein by reference. In some embodiments, the AP gene fragment has the sequence of:

```
(SEQ ID NO: 39)
CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTCCGTATAG
```

GAGGACCGTGTAGGCCTTCCTGTCCCGGGCCTTGCCAGCGGCCAGCCCG

ATGAAGGAGCTCCCTCGCAGGGGGTAGCCTCCGAAGGAGAAGACGTGGG

AGTGGTCGGCAGTGACGAGGCTCAGCGTGTCCTCCTCGCTGGTGAGCTG

GCCCGCCCTCTCAATGGCGTCGTCGAACATGATCGTCTCAGTCAGTGCC

CGGTAAGCCCTGCTTTCATGATGACCATGGTCGATGCGACCACCCTCCA

CGAAGAGGAAGAAGCCGCGGGGGTGTCTGCTCAGCAGGCGCAGGGCAGC

CTCTGTCATCTCCATCAGGGAGGGGTCCAGTGTGGAGTCTCGGTGGATC

TCGTATTTCATGTCTCCAGGCTCAAAGAGACCCATGAGATGGGTCACAG

ACGGGTCCAGGGAAGCCTGCATGAGCTCAGTGCGGTTCCACACGTACCG

GGCACCCTGGCGTTCGCCGAGCCATTCCTGCACCAGATTCTTCCCGTCC

AGCCTGGTCCCACCTTGGCTGTAGTCATCTGGGTACTCAGGGTCTGGGG

TTCCCATGCGAAACATGTACTTTCGGCCTCCA.

In some embodiments, the AP gene fragment has the sequence of:

(SEQ ID NO: 40)
CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTCCGTATAG

GAGGACCGTGTAGGCCTTCCTGTCCCGGGCCTTGCCAGCGGCCAGCCCG

ATGAAGGAGCTCCCTCGCAGGGGGTAGCCTCCGAAGGAGAAGACGTGGG

AGTGGTCGGCAGTGACGAGGCTCAGCGTGTCCTCCTCGCTGGTGA.

In some embodiments, the AP gene fragment has the sequence of:

(SEQ ID NO: 41)
GCTGGCCCGCCCTCTCAATGGCGTCGTCGAACATGATCGTCTCAGTCAG

TGCCCGGTAAGCCCTGCTTTCATGATGACCATGGTCGATGCGACCACCC

TCCACGAAGAGGAAGAAGCCGCGGGGGTGTCTGCTCAGCAGGCGCAGGG

CAGCCTCTGTCATCTCCATCAGGGAGGGGTCCAGTGTGGAGTCTCGGTG

GATCTCGTATTTCATGTCTCCAGGCTCAAAGAGACCCATGAGATGGGTC

ACAGACGGGTCCAGGGAAGCCTGCATGAGCTCAGTGCGGTTCCACACGT

ACCGGGCACCCTGGCGTTCGCCGAGCCATTCCTGCACCAGATTCTTCCC

GTCCAGCCTGGTCCCACCTTGGCTGTAGTCATCTGGGTACTCAGGGTCT

GGGGTTCCCATGCGAAACATGTACTTTCGGCCTCCA.

In some embodiments, the AP gene fragment has the sequence of:

(SEQ ID NO: 42)
CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTC

In some embodiments, the AP gene fragment has the sequence of:

(SEQ ID NO: 43)
CGTATAGGAGGACCGTGTAGGCCTTCCTGTCCCGGGCCTTGCCAGCGGC

CAGCCCGATGAAGGAGCTCCCTCGCAGGGGGTAGCCTCCGAAGGAGAAG

ACGTGGGAGTGGTCGGCAGTGACGAGGCTCAGCGTGTCCTCCTCGCTGG

TGAGCTGGCCCGCCCTCTCAATGGCGTCGTCGAACATGATCGTCTCAGT

CAGTGCCCGGTAAGCCCTGCTTTCATGATGACCATGGTCGATGCGACCA

CCCTCCACGAAGAGGAAGAAGCCGCGGGGGTGTCTGCTCAGCAGG.

In some embodiments, the AP gene fragment has the sequence of:

(SEQ ID NO: 44)
CGCAGGGCAGCCTCTGTCATCTCCATCAGGGAGGGGTCCAGTGTGGAGT

CTCGGTGGATCTCGTATTTCATGTCTCCAGGCTCAAAGAGACCCATGAG

ATGGGTCACAGACGGGTCCAGGGAAGCCTGCATGAGCTCAGTGCGGTTC

CACACGTACCGGGCACCCTGGCGTTCGCCGAGCCATTCCTGCACCAGAT

TCTTCCCGTCCAGCCTGGTCCCACCTTGGCTGTAGTCATCTGGGTACTC

AGGGTCTGGGGTTCCCATGCGAAACATGTACTTTCGGCCTCCA.

An exemplary splice donor sequence for use in the methods and compositions described herein (e.g., in trans-splicing and dual hybrid approaches) has the sequence: GTAAGTATCAAGGTTACAAGAC AGGTTTAAGGA-GACCAATAGAAACTGGGCTTGTCGAGACAGAGAA-GACTCTTGCGTTTCT (SEQ ID NO: 20). An exemplary splice acceptor sequence for use in the methods and compositions described herein (e.g., in trans-splicing and dual hybrid approaches) has the sequence: GATAGGCACCTAT-TGG TCTTACTGACATCCACTTTGCCTTTCTCTC-CACAG (SEQ ID NO: 21). Additional examples of splice donor and splice acceptor sequences are known in the art.

Dual hybrid vectors for use in the methods and compositions described herein are designed such that approximately half of the OTOF gene is contained within each vector (e.g., each vector contains a polynucleotide that encodes approximately half of the OTOF protein). The determination of how to split the polynucleotide sequence between the two nucleic acid vectors is made based on the size of the promoter and the locations of the portions of the polynucleotide that encode the OTOF C2 domains. When a short promoter is used in the dual hybrid vector system (e.g., a promoter that is 1 kb or shorter, e.g., approximately 1 kb, 950 bp, 900 bp, 850 bp, 800 bp, 750 bp, 700 bp, 650 bp, 600 bp, 550 bp 500 bp, 450 bp, 400 bp, 350 bp, 300 bp or shorter), such as CAG, CMV, or a Myo15 promoter having a sequence that is 1 kb or shorter (e.g., a Myo15 promoter described hereinabove), the OTOF polynucleotide sequence is divided between the two nucleic acid vectors at an exon boundary that occurs after the portion of the polynucleotide that encodes the C2D domain and before the portion of the polynucleotide that encodes C2E domain, for example, the exon 26/27 boundary. The nucleic acid vectors containing promoters of this size can optionally contain OTOF UTRs (e.g., full-length 5' and 3' UTRs). When a long promoter is used in the trans-splicing dual vector system (e.g., a promoter that is longer than 1 kb, e.g., 1.1 kb, 1.25 kb, 1.5 kb, 1.75 kb, 2 kb, 2.5 kb, 3 kb or longer), such as a Myo15 promoter that is longer than 1 kb (e.g., SEQ ID NO: 36), the OTOF polynucleotide sequence will be divided between the two nucleic acid vectors at an exon boundary that occurs after the portion of the polynucleotide that encodes the C2C domain, and either before the portion of the polynucleotide that encodes the C2D domain, such as the exon 19/20 boundary, or within the portion of the polynucleotide that encodes the C2D domain, such as the exon 25/26 boundary. A short promoter (e.g., a CMV promoter, CAG promoter, or a Myo15 promoter having a sequence that is 1 kb or shorter) can also be used in the dual vector systems designed for large promoters, in which case additional elements (e.g., OTOF UTR sequences) may be included in the first vector (e.g., the vector containing the portion of the polynucleotide the encodes the C2C domain).

One exemplary dual hybrid vector system that uses a short promoter includes a first nucleic acid vector containing a CAG promoter operably linked to exons 1-26 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 27-48 of a polynucleotide encoding an OTOF protein (e.g., human OTOF, e.g., SEQ ID NO: 1), and a poly(A) sequence (e.g., a bGH poly(A) signal sequence). The first and second nucleic acid vectors can also contain the full-length 5' and 3' OTOF UTRs, respectively (e.g., the 127 bp human OTOF 5' UTR can be included in the first nucleic acid vector, and the 1035 bp human OTOF 3' UTR can be included in the second nucleic acid vector). Another exemplary dual hybrid vector system that uses a short promoter includes a first nucleic acid vector containing a CAG promoter operably linked to exons 1-28 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 29-48 of a polynucleotide encoding an OTOF protein (e.g., mouse OTOF, e.g., SEQ ID NO: 6), and a poly(A) sequence (e.g., a bGH poly(A) signal sequence). The first and second nucleic acid vectors can also contain the full-length 5' and 3' OTOF UTRs, respectively (e.g., the 134 bp mouse OTOF 5' UTR can be included in the first nucleic acid vector, and the 1001 bp mouse OTOF 3' UTR can be included in the second nucleic acid vector). The CMV promoter or a Myo15 promoter having a sequence that is 1 kb or shorter (e.g., a Myo15 promoter described hereinabove) can be used in place of the CAG promoter either of the foregoing dual vector systems.

An exemplary dual hybrid vector system that uses a long promoter includes a first nucleic acid vector containing a Myo15 promoter that is longer than 1 kb (e.g., SEQ ID NO: 36) operably linked to exons 1-19 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 20-48 of a polynucleotide encoding an OTOF protein (e.g., human OTOF, e.g., SEQ ID NO: 1), and a poly(A) sequence (e.g., a bGH poly(A) signal sequence). Another exemplary dual hybrid vector system that uses a long promoter includes a first nucleic acid vector containing a Myo15 promoter that is longer than 1 kb (e.g., SEQ ID NO: 36) operably linked to exons 1-20 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and a second nucleic acid vector containing a recombinogenic region, a splice acceptor sequence 3' of the recombinogenic region, a polynucleotide 3' of the splice acceptor sequence that contains exons 21-48 of a polynucleotide encoding an OTOF protein (e.g., mouse OTOF, e.g., SEQ ID NO: 6), and a poly(A) sequence (e.g., a bGH poly(A) signal sequence). Neither the first nor the second nucleic acid vector in either of the foregoing Myo15 promoter dual hybrid vector systems contains an OTOF UTR. A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

To accommodate an OTOF UTR, the OTOF coding sequence can be divided in a different position. For example, in a dual hybrid vector system in which the first nucleic acid vector contains a Myo15 promoter that is longer than 1 kb (e.g., SEQ ID NO: 36) operably linked to exons 1-25 of a polynucleotide encoding an OTOF protein (e.g., human OTOF, e.g., SEQ ID NO: 1), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 26-48 of a polynucleotide encoding an OTOF protein (e.g., human OTOF, e.g., SEQ ID NO: 1), and a poly(A) sequence (e.g., a bGH poly(A) signal sequence), the second nucleic acid can also contain a full-length OTOF 3' UTR (e.g., the 1035 bp human OTOF UTR). For mouse OTOF, the dual hybrid vector system can contain a 3' UTR if the first nucleic acid vector contains a Myo15 promoter that is longer than 1 kb (e.g., SEQ ID NO: 36) operably linked to exons 1-24 of a polynucleotide encoding an OTOF protein (e.g., mouse OTOF, e.g., SEQ ID NO: 6), a splice donor sequence 3' of the polynucleotide sequence, and a recombinogenic region 3' of the splice donor sequence; and the second nucleic acid vector contains a recombinogenic region, a splice acceptor sequence 3' of the recombinogenic region, a polynucleotide 3' of the splice acceptor sequence that contains exons 25-48 of a polynucleotide encoding an OTOF protein (e.g., human OTOF, e.g., SEQ ID NO: 1), and a poly(A) sequence (e.g., a bGH poly(A) signal sequence). In this dual hybrid vector system, the second nucleic acid can also contain a full-length OTOF 3' UTR (e.g., the 1001 bp mouse OTOF UTR). A short promoter (e.g., a CMV promoter, CAG promoter, or a Myo15 promoter having a sequence that is 1 kb or shorter) can also be used in the foregoing dual vector systems designed for large promoters. If these dual vector systems contain a short promoter, they may also include a 5' OTOF UTR in the first vector.

The dual hybrid vectors used in the methods and compositions described herein can optionally include a degradation signal sequence in both the first and second nucleic acid vectors. The degradation signal sequence can be included to prevent or reduce the expression of portions of the OTOF protein from polynucleotides that failed to recombine and/or undergo splicing. The degradation signal sequence is positioned 3' of the recombinogenic region in the first nucleic acid vector, and is positioned between the recombinogenic region and the splice acceptor in the second nucleic acid vector. A degradation signal sequence that can be used in the compositions and methods described herein has the sequence of:

(SEQ ID NO: 22)
GCCTGCAAGAACTGGTTCAGCAGCCTGAGCCACTTCGTGATCCACCTG.

Exemplary pairs of overlapping, trans-splicing, and dual hybrid vectors are described in Table 4 below.

TABLE 4

Exemplary pairs of overlapping, trans-splicing, and hybrid dual vectors for use in the methods and compositions described herein

| Vector Pair Number | Vector Type | Vector Pair |
|---|---|---|
| 1 | Overlapping | First nucleic acid vector contains: CAG promoter operably linked to exons 1-24 and the 500 kb 3' of the exon 24/25 boundary of a polynucleotide encoding a human OTOF protein<br>Second nucleic acid vector contains: the 500 kb 5' of the exon 24/25 boundary and exons 25-48 of a polynucleotide encoding a human OTOF protein and a bGH poly(A) sequence |
| 2 | Overlapping | First nucleic acid vector contains: CAG promoter operably linked to exons 1-28 and the 500 kb 3' of the exon 28/29 boundary of a polynucleotide encoding a human OTOF protein<br>Second nucleic acid vector contains: the 500 kb 5' of the exon 28/29 boundary and exons 29-48 of a polynucleotide encoding a human OTOF protein and a bGH poly(A) sequence |
| 3 | Overlapping | First nucleic acid vector contains: Myo15 promoter operably linked to exons 1-21 and the 500 kb 3' of the exon 21/22 boundary of a polynucleotide encoding a human OTOF protein<br>Second nucleic acid vector contains: the 500 kb 5' of the exon 21/22 boundary and exons 22-48 of a polynucleotide encoding a human OTOF protein and a bGH poly(A) sequence |
| 4 | Trans-splicing | First nucleic acid vector contains: CAG promoter operably linked to exons 1-26 of a polynucleotide encoding a human OTOF protein and a splice donor sequence 3' of the polynucleotide<br>Second nucleic acid vector contains: a splice acceptor sequence 5' of exons 27-48 of a polynucleotide encoding a human OTOF protein and a bGH poly(A) sequence |
| 5 | Trans-splicing | First nucleic acid vector contains: Myo15 promoter operably linked to exons 1-19 of a polynucleotide encoding a human OTOF protein and a splice donor sequence 3' of the polynucleotide<br>Second nucleic acid vector contains: a splice acceptor sequence 5' of exons 20-48 of a polynucleotide encoding a human OTOF protein and a bGH poly(A) sequence |
| 6 | Trans-splicing | First nucleic acid vector contains: Myo15 promoter operably linked to exons 1-25 of a polynucleotide encoding a human OTOF protein and a splice donor sequence 3' of the polynucleotide<br>Second nucleic acid vector contains: a splice acceptor sequence 5' of exons 26-48 of a polynucleotide encoding a human OTOF protein and a bGH poly(A) sequence |
| 7 | Hybrid | First nucleic acid vector contains: CAG promoter operably linked to exons 1-26 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 27-48 of a polynucleotide encoding a human OTOF protein 3' of the splice acceptor sequence, and a bGH poly(A) sequence |
| 8 | Hybrid | First nucleic acid vector contains: Myo15 promoter operably linked to exons 1-19 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 20-48 of a polynucleotide encoding a human OTOF protein 3' of the splice acceptor sequence, and a bGH poly(A) sequence |
| 9 | Hybrid | First nucleic acid vector contains: Myo15 promoter operably linked to exons 1-25 of a polynucleotide encoding a human OTOF protein, a splice donor sequence 3' of the polynucleotide, and a recombinogenic region 3' of the splice donor sequence<br>Second nucleic acid vector contains: a recombinogenic region, a splice acceptor sequence 3' of the recombinogenic region, exons 26-48 of a polynucleotide encoding a human OTOF protein 3' of the splice acceptor sequence, and a bGH poly(A) sequence |

Vectors for the Expression of OTOF

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a polynucleotide sequence that encodes a portion of OTOF, as well as, e.g., additional sequence elements used for the expression of these agents and/or the integration of these polynucleotide sequences into the genome of a mammalian cell. Certain vectors that can be used for the expression of OTOF include plasmids that contain regulatory sequences, such as promoter and enhancer regions, which direct gene transcription. Other useful vectors for expression of OTOF contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

AA V Vectors for Nucleic Acid Delivery

In some embodiments, nucleic acids of the compositions and methods described herein are incorporated into recombinant AAV (rAAV) vectors and/or virions in order to facilitate their introduction into a cell. rAAV vectors useful in the compositions and methods described herein are recombinant nucleic acid constructs that include (1) a heterologous sequence to be expressed (e.g., a polynucleotide encoding an N-terminal or C-terminal portion of an OTOF protein) and (2) viral sequences that facilitate stability and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. For use in the methods and compositions described herein, the ITRs can be AAV2 ITRs. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The nucleic acids and vectors described herein can be incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S. For targeting cochlear hair cells, AAV1, AAV2, AAV6, AAV9, Anc80, Anc80L65, DJ/9, 7m8, and PHP.B may be particularly useful. Serotypes evolved for transduction of the retina may also be used in the methods and compositions described herein. The first and second nucleic acid vectors in the compositions and methods described herein may have the same serotype or different serotypes. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Pharmaceutical Compositions

The nucleic acid vectors described herein may be incorporated into a vehicle for administration into a patient, such as a human patient suffering from sensorineural hearing loss or auditory neuropathy, as described herein. Pharmaceutical compositions containing vectors, such as viral vectors, that contain a polynucleotide encoding a portion of an OTOF protein can be prepared using methods known in the art. For example, such compositions can be prepared using, e.g., physiologically acceptable carriers, excipients or stabilizers (Remington's Pharmaceutical Sciences 16th edition, Osol, A. Ed. (1980); incorporated herein by reference), and in a desired form, e.g., in the form of lyophilized formulations or aqueous solutions.

Mixtures of the nucleic acid vectors (e.g., viral vectors) described herein may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466, 468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. For local administration to the inner ear, the composition may be formulated to contain a synthetic perilymph solution. An exemplary synthetic perilymph solution includes 20-200 mM NaCl, 1-5 mM KCl, 0.1-10 mM $CaCl_2$), 1-10 mM glucose, and 2-50 mM HEPEs, with a pH between about 6 and 9 and an osmolality of about 300 mOsm/kg. The person responsible for administration will, in any event, determine the appropriate dose for the individual subject. Moreover, for human administration, preparations may meet sterility, pyrogenicity, general safety, and purity standards as required by FDA Office of Biologics standards.

Methods of Treatment

The compositions described herein may be administered to a subject with sensorineural hearing loss or auditory neuropathy by a variety of routes, such as local administration to the inner ear (e.g., administration into the perilymph or endolymph, e.g., through the oval window, round window, or horizontal canal, e.g., administration to a cochlear hair cell), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bi-monthly, monthly, or bi-weekly). In some embodiments, the first and second nucleic acid vectors are administered simultaneously (e.g., in one composition). In some embodiments, the first and second nucleic acid vectors are administered sequentially (e.g., the second nucleic acid vector is administered immediately after the first nucleic acid vector, or 5 minutes, 10 minutes, 15 minutes, 20 minutes, 25 minutes, 30 minutes, 45 minutes, 1 hour, 2 hours, 8 hours, 12 hours, 1 day, 2 days, 7 days, two weeks, 1 month or more after the first nucleic acid vector). The first and second nucleic acid vector can have the same serotype or different serotypes (e.g., AAV serotypes).

Subjects that may be treated as described herein are subjects having or at risk of developing sensorineural hearing loss or auditory neuropathy. The compositions and methods described herein can be used to treat subjects having a mutation in OTOF (e.g., a mutation that reduces OTOF function or expression, or an OTOF mutation associated with sensorineural hearing loss), subjects having a family history of autosomal recessive sensorineural hearing loss or deafness (e.g., a family history of OTOF-related hearing loss), or subjects whose OTOF mutational status and/or OTOF activity level is unknown. The methods described herein may include a step of screening a subject for a mutation in OTOF prior to treatment with or administration of the compositions described herein. A subject can be screened for an OTOF mutation using standard methods known to those of skill in the art (e.g., genetic testing). The methods described herein may also include a step of assessing hearing in a subject prior to treatment with or administration of the compositions described herein. Hearing can be assessed using standard tests, such as audiometry, ABR, electrochleography (ECOG), and otoacoustic emissions. The compositions and methods described herein may also be administered as a preventative treatment to patients at risk of developing hearing loss or auditory neuropathy, e.g., patients who have a family history of inherited hearing loss or patients carrying an OTOF mutation who do not yet exhibit hearing loss or impairment.

Treatment may include administration of a composition containing the nucleic acid vectors (e.g., AAV viral vectors) described herein in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may include continuous infusion over a set period of time. Dosing may be performed using a syringe pump to control infusion rate in order to minimize damage to the cochlea. In cases in which the nucleic acid vectors are AAV vectors (e.g., AAV1, AAV2, AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, or PHP.S vectors), the viral vectors may be administered to the patient at a dose of, for example, from about $1\times10^{10}$ vector genomes (VG) to $1\times10^{15}$ VG (e.g., $1\times10^{10}$ VG, $2\times10^{10}$ VG, $3\times10^{10}$ VG, $4\times10^{10}$ VG, $5\times10^{10}$ VG, $6\times10^{10}$ VG, $7\times10^{10}$ VG, $8\times10^{10}$ VG, $9\times10^{10}$ VG, $1\times10^{11}$ VG, $2\times10^{11}$ VG, $3\times10^{11}$ VG, $4\times10^{11}$ VG, $5\times10^{11}$ VG, $6\times10^{11}$ VG, $7\times10^{11}$ VG, $8\times10^{11}$ VG, $9\times10^{11}$ VG, $1\times10^{12}$ VG, $2\times10^{12}$ VG, $3\times10^{12}$ VG, $4\times10^{12}$ VG, $5\times10^{12}$ VG, $6\times10^{12}$ VG, $7\times10^{12}$ VG, $8\times10^{12}$ VG, $9\times10^{12}$ VG, $1\times10^{13}$ VG, $2\times10^{13}$ VG, $3\times10^{13}$ VG, $4\times10^{13}$ VG, $5\times10^{13}$ VG, $6\times10^{13}$ VG, $7\times10^{13}$ VG, $8\times10^{13}$ VG, $9\times10^{13}$ VG, $1\times10^{14}$ VG, $2\times10^{14}$ VG, $3\times10^{14}$ VG, $4\times10^{14}$ VG, $5\times10^{14}$ VG, $6\times10^{14}$ VG, $7\times10^{14}$ VG, $8\times10^{14}$ VG, $9\times10^{14}$ VG, $1\times10^{15}$ VG) in a volume of 1 µL to 200 µL (e.g., 1, 2, 3, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 µL).

The compositions described herein are administered in an amount sufficient to improve hearing, increase WT OTOF expression (e.g., expression in a cochlear hair cell, e.g., an inner hair cell), or increase OTOF function. Hearing may be evaluated using standard hearing tests (e.g., audiometry, ABR, electrochleography (ECOG), and otoacoustic emissions) and may be improved by 5% or more (e.g., 5%, 10%, 15%, 20%, 30%, 40%, 50%, 60%, 70%, 80%, 90%, 100% or more) compared to hearing measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss or auditory neuropathy (e.g., in subjects who carry a mutation in OTOF or have a family history of autosomal recessive hearing loss but do not exhibit hearing impairment, or in subjects exhibiting mild to moderate hearing loss). OTOF expression may be evaluated using immunohistochemistry, Western blot analysis, quantitative real-time PCR, or other methods known in the art for detection protein or mRNA, and may be increased by 5% or more (e.g., 5%, 10%, 15%, 20%, 30%, 40%, 50%, 60%, 70%, 80%, 90%, 100% or more) compared to OTOF expression prior to administration of the compositions described herein. OTOF function may be evaluated directly (e.g., using electrophysiological methods or imaging methods to assess exocytosis) or indirectly based on hearing tests, and may be increased by 5% or more (e.g., 5%, 10%, 15%, 20%, 30%, 40%, 50%, 60%, 70%, 80%, 90%, 100% or more) compared to OTOF function prior to administration of the compositions described herein. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Kits

The compositions described herein can be provided in a kit for use in treating sensorineural hearing loss or auditory neuropathy (e.g., hearing loss associated with a mutation in OTOF). Compositions may include nucleic acid vectors described herein (e.g., a first nucleic acid vector containing a polynucleotide that encodes and N-terminal portion of an OTOF protein and a second nucleic acid vector containing a polynucleotide that encodes a C-terminal portion of an OTOF protein), optionally packaged in an AAV virus capsid (e.g., AAV1, AAV9, Anc80L65, DJ/9, or 7m8). The kit can further include a package insert that instructs a user of the kit, such as a physician, to perform the methods described herein. The kit may optionally include a syringe or other device for administering the composition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Generation of Nucleic Acid Vectors that Recombine to Produce Full-Length OTOF Gene fragments were synthesized and sub-cloned into an AAV2/cis-plasmid using restriction enzyme sites. Plasmids were maxi prepped to generate 1 mg of transfection grade plasmid. Inner ear-derived HEI-OC1 cells were seeded into a 12-well tissue culture dish 24 hours before plasmid transfection at a density of 200,000 cells/well. One microgram of each plasmid was transfected using Lipofectamine® 3000 according to standard manufacturer's protocol. For wells that received both 5' and 3' plasmids, 1 µg of each was transfected for a total of 2 µg of DNA. As a positive control, full-length Otoferlin cDNA was also transfected. Cells were incubated with plasmid for 48 hours.

For PCR to check for recombination at the DNA level, genomic DNA was extracted from each well using the Qiagen®, DNeasy® Blood and Tissue kit, according to standard manufacturer's protocol. PCR primers were designed to anneal to the plasmid outside of the region of overlap or splicing to generate an amplicon of ~1200 bp. PCR was performed using MyTaq® 2x mastermix according to manufacturer's recommendations: annealing temperature of 58° C., elongation step of 30 seconds, and cycle number of 35x. Ten microliters of PCR product was run on a pre-cast 1.2% agarose E-gel and imaged on a Bio-Rad® gel doc imaging station. Both dual hybrid vectors (FIG. 20A) and overlapping vectors (FIG. 20B) showed evidence of recombination when the 5' and 3' plasmids were transfected together.

For immunofluorescence to check for recombination and generation of protein, cells were fixed with cold 4% PFA for 20 minutes at room temperature. Cells were washed three times with PBS and then permeabilized in a blocking solution of PBS with 10% normal donkey serum and 0.01% TritonX100. Cells were incubated in primary antibody overnight (mouse-anti-Otoferlin, Abcam® ab53233) at a concentration of 1:1000 at 4° C. Cells were washed three times with PBS and incubated in secondary antibody for three hours at room temperature (donkey-anti-mouse Alexa Fluor® 647, Thermo Fisher Scientific® A-31571). Cells were washed three times in PBS and stained with DAPI for 15 minutes at room temperature. Cells were imaged using a Zeiss® inverted Apotome® microscope. Increased staining was observed in cells transfected with both 5' and 3' plasmids compared to transfection of the 5' or 3' plasmid alone, indicating that the dual hybrid vector (FIG. 21A), trans-splicing vector (FIG. 21B), and overlapping vector (FIG. 21C) systems recombined in HEI-OC1 cells and generated OTOF protein.

Example 2: Administration of a Composition Containing Overlapping Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-21 of a polynucleotide encoding an OTOF protein (e.g., human OTOF, e.g., SEQ ID NO: 1) and the 500 kb immediately 3' of the exon 21/22 boundary, and a second AAV vector (e.g., AAV1 or AAV9) containing the 500 kb immediately 5' of the exon 21/22 boundary and exons 22-48 of a polynucleotide encoding an OTOF protein (e.g., human OTOF, e.g., SEQ ID NO: 1) and a bGH poly(A) sequence. The composition containing the overlapping dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrochocleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 3: Administration of a Composition Containing Trans-Splicing Dual Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-19 of a polynucleotide encoding an OTOF protein (e.g., human OTOF, e.g., SEQ ID NO: 1) and a splice donor sequence (e.g., SEQ ID NO: 20) 3' of the polynucleotide sequence, and a second AAV vector (e.g., AAV1 or AAV9) containing a splice acceptor sequence (e.g., SEQ ID NO: 21) 5' of exons 20-48 of a polynucleotide encoding an OTOF protein (e.g., human OTOF, e.g., SEQ ID NO: 1) and a bGH poly(A) sequence. The composition containing the trans-splicing dual AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrochocleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 4: Administration of a Composition Containing Dual Hybrid Vectors that Express OTOF to a Subject with Sensorineural Hearing Loss According to the methods disclosed herein, a physician of skill in the art can treat a patient, such as a human patient, with sensorineural hearing loss (e.g., sensorineural hearing loss associated with a mutation in OTOF) so as to improve or restore hearing. To this end, a physician of skill in the art can administer to the human patient a composition containing a first AAV vector (e.g., AAV1 or AAV9) containing a Myo15 promoter (e.g., SEQ ID NO: 36) operably linked to exons 1-19 of a polynucleotide encoding an OTOF protein (e.g., human OTOF, e.g., SEQ ID NO: 1), a splice donor sequence (e.g., SEQ ID NO: 20) 3' of the polynucleotide sequence, and an F1 phage recombinogenic region (e.g., an F1 phage AK gene, SEQ ID NO: 19) 3' of the splice donor sequence, and a second nucleic acid vector containing an F1 phage recombinogenic region (e.g., an F1 phage AK gene, SEQ ID NO: 19), a splice acceptor sequence (e.g., SEQ ID NO: 21) 3' of the recombinogenic region, a polynucleotide 3' of the splice acceptor sequence that contains exons 20-48 of a polynucleotide encoding an OTOF protein (e.g., human OTOF, e.g., SEQ ID NO: 1), and a bGH poly(A) sequence. The first and second dual hybrid AAV vectors can optionally include a degradation signal sequence (e.g., SEQ ID NO: 22) positioned 3' of the recombinogenic region in the first nucleic acid vector, and positioned between the recombinogenic region and the splice acceptor sequence in the second nucleic acid vector. The composition containing the dual hybrid AAV vectors may be administered to the patient, for example, by local administration to the inner ear (e.g., injection into the perilymph), to treat sensorineural hearing loss.

Following administration of the composition to a patient, a practitioner of skill in the art can monitor the expression of OTOF, and the patient's improvement in response to the therapy, by a variety of methods. For example, a physician can monitor the patient's hearing by performing standard tests, such as audiometry, ABR, electrochocleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

The invention claimed is:

1. A composition comprising:
   a first nucleic acid vector comprising a myosin 15 (Myo15) promoter having at least 98% sequence identity to the sequence of SEQ ID NO: 36 operably linked to a first coding polynucleotide that encodes an N-terminal portion of an otoferlin (OTOF) protein; and
   a second nucleic acid vector comprising a second coding polynucleotide that encodes a C-terminal portion of an OTOF protein and a polyadenylation (poly(A)) sequence positioned at a 3' end of the second coding polynucleotide,
   wherein neither the first nor second nucleic acid vector encodes a full-length OTOF protein, and, when introduced into a mammalian cell, the first and second nucleic acid vectors undergo homologous recombination or concatemerization to form a recombined nucleic acid that encodes a full-length OTOF protein.

2. The composition of claim 1, wherein
   the first nucleic acid vector further comprises a splice donor signal sequence positioned at a 3' end of the first coding polynucleotide; and
   the second nucleic acid vector further comprises a splice acceptor signal sequence, wherein the second coding polynucleotide that encodes a C-terminal portion of an OTOF protein is positioned at a 3' end of the splice acceptor signal sequence,
   wherein the first coding polynucleotide and the second coding polynucleotide do not overlap.

3. The composition of claim 1, wherein
   the first nucleic acid vector further comprises a splice donor signal sequence positioned at a 3' end of the first coding polynucleotide and a first recombinogenic region positioned 3' of the splice donor signal sequence; and
   the second nucleic acid vector further comprises a second recombinogenic region and a splice acceptor signal sequence positioned 3' of the second recombinogenic region, wherein the second coding polynucleotide that encodes a C-terminal portion of an OTOF protein is positioned at a 3' end of the splice acceptor signal sequence,
   wherein the first coding polynucleotide and the second coding polynucleotide do not overlap.

4. The composition of claim 3, wherein the first and second recombinogenic regions have the same nucleic acid sequence.

5. The composition of claim 3, wherein the first nucleic acid vector further comprises a degradation signal sequence positioned 3' of the recombinogenic region; and wherein the second nucleic acid vector further comprises a degradation signal sequence positioned between the recombinogenic region and the splice acceptor signal sequence.

6. The composition of claim 2, wherein the division between the first and second coding polynucleotides is at an OTOF exon boundary.

7. The composition of claim 1, wherein the first and second nucleic acid vectors are adeno-associated virus (AAV) vectors.

8. The composition of claim 1, wherein the first and second coding polynucleotides that encode the OTOF protein do not comprise introns.

9. The composition of claim 1, wherein the first and second nucleic acid vectors comprise an inverted terminal repeat (ITR) at each end of the nucleic acid sequence.

10. The composition of claim 1, wherein the second nucleic acid vector comprises a Woodchuck Hepatitis Virus Posttranscriptional Regulatory Element (WPRE).

11. The composition of claim 1, wherein the Myo15 promoter comprises the sequence of SEQ ID NO: 36.

* * * * *